United States Patent
Wilson et al.

(10) Patent No.: US 11,578,341 B2
(45) Date of Patent: Feb. 14, 2023

(54) COMPOSITIONS USEFUL IN TREATMENT OF SPINAL MUSCULAR ATROPHY

(71) Applicant: The Trustees of the University of Pennsylvania, Philadelphia, PA (US)

(72) Inventors: James M. Wilson, Philadelphia, PA (US); Christian Hinderer, Philadelphia, PA (US); Nathan Katz, Stamford, CT (US); Qiang Wang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 299 days.

(21) Appl. No.: 16/487,690

(22) PCT Filed: Feb. 27, 2018

(86) PCT No.: PCT/US2018/019996
§ 371 (c)(1),
(2) Date: Aug. 21, 2019

(87) PCT Pub. No.: WO2018/160585
PCT Pub. Date: Sep. 7, 2018

(65) Prior Publication Data
US 2020/0056205 A1 Feb. 20, 2020

Related U.S. Application Data

(60) Provisional application No. 62/464,756, filed on Feb. 28, 2017, provisional application No. 62/515,902, filed on Jun. 6, 2017, provisional application No. 62/618,437, filed on Jan. 17, 2018.

(51) Int. Cl.
*A61K 48/00* (2006.01)
*C12N 15/86* (2006.01)
*C07K 14/47* (2006.01)
*C12N 15/864* (2006.01)
*A61K 45/06* (2006.01)

(52) U.S. Cl.
CPC .......... *C12N 15/8645* (2013.01); *C07K 14/47* (2013.01); *C12N 15/864* (2013.01); *A61K 45/06* (2013.01); *C12N 2750/14143* (2013.01); *C12N 2800/22* (2013.01)

(58) Field of Classification Search
CPC ...... A61K 48/00; A61K 48/05; A61K 48/066; C12N 15/86; C12N 15/864; C12N 15/8645; C12N 2750/14143; C12N 2800/22; C07K 14/47
See application file for complete search history.

(56) References Cited

U.S. PATENT DOCUMENTS

| | | |
|---|---|---|
| 4,816,567 A | 3/1989 | Cabilly et al. |
| 5,139,941 A | 8/1992 | Muzyczka et al. |
| 5,478,745 A | 12/1995 | Samulski et al. |
| 5,741,683 A | 4/1998 | Zhou et al. |
| 5,811,524 A | 9/1998 | Brams et al. |
| 5,830,462 A | 11/1998 | Crabtree et al. |
| 5,834,266 A | 11/1998 | Crabtree et al. |
| 5,869,337 A | 2/1999 | Crabtree et al. |
| 5,871,753 A | 2/1999 | Crabtree et al. |
| 6,011,018 A | 1/2000 | Crabtree et al. |
| 6,015,709 A | 1/2000 | Natesan |
| 6,043,082 A | 3/2000 | Crabtree et al. |
| 6,046,047 A | 4/2000 | Crabtree et al. |
| 6,057,152 A | 5/2000 | Samulski et al. |
| 6,063,625 A | 5/2000 | Crabtree et al. |
| 6,117,680 A | 9/2000 | Natesan et al. |
| 6,127,521 A | 10/2000 | Berlin et al. |
| 6,133,456 A | 10/2000 | Holt et al. |
| 6,140,120 A | 10/2000 | Crabtree et al. |
| 6,150,137 A | 11/2000 | Berlin et al. |
| 6,150,527 A | 11/2000 | Holt et al. |
| 6,165,787 A | 12/2000 | Crabtree et al. |
| 6,166,197 A | 12/2000 | Cook et al. |
| 6,187,757 B1 | 2/2001 | Clackson et al. |
| 6,200,560 B1 | 3/2001 | Couto et al. |
| 6,204,059 B1 | 3/2001 | Samulski et al. |
| 6,221,349 B1 | 4/2001 | Couto et al. |
| 6,258,603 B1 | 7/2001 | Carlson et al. |
| 6,258,823 B1 | 7/2001 | Holt et al. |

(Continued)

FOREIGN PATENT DOCUMENTS

| | | |
|---|---|---|
| EP | 1310571 | 5/2003 |
| EP | 2296700 A2 | 3/2011 |

(Continued)

OTHER PUBLICATIONS

Armbruster et al, Molecular Therapy 3: 16060; doi:10.1038/mtm.2016.60; published online Sep. 14, 2016.*
Favaro et al, Human Gene Therapy 22: 843-852, 2011.*
Armbruster et al, Molecular Therapy—Methods & Clinical Developments 3: 16060; doi:10.1038/mtm.2016.60; available online Sep. 14, 2016.*
GenBank AAS99264, 2004.*
Van Vliet et al, J. Virological Methods 159: 167-177, 2009.*
Hinderer et al, Molecular Therapy—Methods & Clinical Development 1, 14051; 9 pages, doi: 10.1038/mtm.2014.51; 2014.*

(Continued)

*Primary Examiner* — Kevin K Hill
(74) *Attorney, Agent, or Firm* — Howson & Howson; Cathy A. Kodroff

(57) ABSTRACT

A rAAV vector is described herein which has an AAVhu68 capsid and at least one expression cassette in the capsid. The at least one expression cassette comprises nucleic acid sequences encoding a functional SMN protein and expression control sequences that direct expression of the SMN sequences in a host cell. Also provided are compositions containing this rAAVhu68.SMN vector and methods of using same for spinal muscular atrophy in a patient.

14 Claims, 39 Drawing Sheets

Specification includes a Sequence Listing.

(56) References Cited

U.S. PATENT DOCUMENTS

| | | |
|---|---|---|
| 6,268,213 B1 | 7/2001 | Samulski et al. |
| 6,326,166 B1 | 12/2001 | Pomerantz et al. |
| 6,464,374 B2 | 10/2002 | Akiyama et al. |
| 6,464,974 B1 | 10/2002 | Berlin et al. |
| 6,476,200 B1 | 11/2002 | Sabatini et al. |
| 6,479,653 B1 | 11/2002 | Natesan et al. |
| 6,491,907 B1 | 12/2002 | Rabinowitz et al. |
| 6,506,379 B1 | 1/2003 | Clackson et al. |
| 6,509,152 B1 | 1/2003 | Berlin et al. |
| 6,596,535 B1 | 7/2003 | Carter |
| 6,649,595 B2 | 11/2003 | Clackson et al. |
| 6,660,514 B1 | 12/2003 | Zolotukhin et al. |
| 6,693,189 B2 | 2/2004 | Holt et al. |
| 6,780,639 B1 | 8/2004 | Chtarto et al. |
| 6,951,753 B2 | 10/2005 | Shenk et al. |
| 6,972,193 B1 | 12/2005 | Crabtree et al. |
| 6,984,635 B1 | 1/2006 | Schreiber et al. |
| 7,008,780 B2 | 3/2006 | Pomerantz et al. |
| 7,045,315 B2 | 5/2006 | Evans et al. |
| 7,067,526 B1 | 6/2006 | Yang et al. |
| 7,091,038 B2 | 8/2006 | Palli et al. |
| 7,094,604 B2 | 8/2006 | Snyder et al. |
| 7,109,317 B1 | 9/2006 | Clemons et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,442,373 B2 | 10/2008 | Morrow et al. |
| 7,456,683 B2 | 11/2008 | Takano et al. |
| 7,485,441 B2 | 2/2009 | Pomerantz et al. |
| 7,588,772 B2 | 9/2009 | Kay et al. |
| 7,785,888 B2 | 8/2010 | Carter |
| 7,790,449 B2 | 9/2010 | Gao et al. |
| 7,838,657 B2 | 11/2010 | Singh et al. |
| 7,846,729 B2 | 12/2010 | Carter |
| 7,906,111 B2 | 3/2011 | Wison et al. |
| 7,985,565 B2 | 7/2011 | Mayer et al. |
| 8,008,005 B2 | 8/2011 | Belshaw et al. |
| 8,093,054 B2 | 1/2012 | Carter |
| 8,110,560 B2 | 2/2012 | Singh et al. |
| 8,114,402 B2 | 2/2012 | Grandea et al. |
| 8,124,092 B2 | 2/2012 | Lanzavecchia |
| 8,211,631 B2 | 7/2012 | Svendsen et al. |
| 8,361,977 B2 | 1/2013 | Baker et al. |
| 8,734,809 B2 | 5/2014 | Gao et al. |
| 8,852,595 B2 | 10/2014 | Vogels et al. |
| 8,927,514 B2 | 1/2015 | Chatterjee et al. |
| 8,961,978 B2 | 2/2015 | Kwaks et al. |
| 8,980,853 B2 | 3/2015 | Bennett et al. |
| 9,034,836 B2 | 5/2015 | Dodge et al. |
| 9,061,059 B2 * | 6/2015 | Chakraborty .... C07K 14/43595 |
| 9,340,603 B2 | 5/2016 | Lanzavecchia |
| 9,719,106 B2 | 8/2017 | Wilson et al. |
| 10,265,417 B2 | 4/2019 | Wilson et al. |
| 10,370,435 B2 | 8/2019 | Brandenburg et al. |
| 10,485,883 B2 | 11/2019 | Wilson et al. |
| 10,695,441 B2 | 6/2020 | Wilson et al. |
| 10,722,598 B2 | 7/2020 | Wilson et al. |
| 10,786,568 B2 | 9/2020 | Limberis et al. |
| 10,973,928 B2 | 4/2021 | Wilson et al. |
| 2002/0110861 A1 | 8/2002 | Dhadialla et al. |
| 2002/0173474 A1 | 11/2002 | Schreiber et al. |
| 2004/0033600 A1 | 2/2004 | Palli et al. |
| 2004/0096942 A1 | 5/2004 | Kapitskaya et al. |
| 2005/0266457 A1 | 12/2005 | Palli et al. |
| 2006/0014711 A1 | 1/2006 | Evans et al. |
| 2006/0100416 A1 | 5/2006 | Palli et al. |
| 2006/0136184 A1 | 6/2006 | Gustafsson et al. |
| 2007/0036760 A1 | 2/2007 | Wilson et al. |
| 2007/0161086 A1 | 7/2007 | Palli et al. |
| 2008/0292593 A1 | 11/2008 | Passini et al. |
| 2009/0197338 A1 | 8/2009 | Vandenberghe et al. |
| 2009/0275107 A1 | 11/2009 | Lock et al. |
| 2009/0286857 A1 | 11/2009 | O'Riordan et al. |
| 2010/0080813 A1 | 4/2010 | Lanzavecchia |
| 2010/0267812 A1 | 10/2010 | Dodge et al. |
| 2011/0076265 A1 | 3/2011 | Burioni et al. |
| 2011/0150904 A1 | 6/2011 | Schiltz et al. |
| 2011/0236353 A1 | 9/2011 | Wilson et al. |
| 2011/0274702 A1 | 11/2011 | Lanzavecchia |
| 2012/0232133 A1 | 9/2012 | Balazs et al. |
| 2012/0282695 A1 | 11/2012 | Blain et al. |
| 2013/0045186 A1 | 2/2013 | Gao et al. |
| 2013/0243792 A1 | 9/2013 | Vogels et al. |
| 2013/0287736 A1 | 10/2013 | Passini et al. |
| 2014/0032186 A1 | 1/2014 | Gustafsson et al. |
| 2014/0037637 A1 | 2/2014 | McNally et al. |
| 2014/0065666 A1 | 3/2014 | Simpson et al. |
| 2014/0094392 A1 | 4/2014 | Bowers et al. |
| 2014/0127749 A1 | 5/2014 | Mason et al. |
| 2015/0344911 A1 | 12/2015 | Chatterjee et al. |
| 2016/0074474 A1 * | 3/2016 | Passini .................. A61P 21/00 514/44 R |
| 2016/0243260 A1 | 8/2016 | Blits |
| 2017/0028082 A1 | 2/2017 | Wilson et al. |
| 2017/0043035 A1 | 2/2017 | Wilson et al. |
| 2017/0081392 A1 | 3/2017 | Wilson et al. |
| 2017/0101458 A1 | 4/2017 | Wilson et al. |
| 2017/0159027 A1 | 6/2017 | Wilson et al. |
| 2017/0292132 A1 | 10/2017 | Wilson et al. |
| 2018/0243416 A1 | 8/2018 | Limberis et al. |
| 2018/0353624 A1 | 12/2018 | Wilson et al. |
| 2019/0015527 A1 | 1/2019 | Wilson et al. |
| 2019/0054188 A1 | 2/2019 | Wilson et al. |
| 2019/0216841 A1 | 7/2019 | Wilson et al. |
| 2020/0056159 A1 | 2/2020 | Wilson et al. |
| 2020/0155704 A1 | 5/2020 | Wilson et al. |
| 2021/0170050 A1 | 6/2021 | Wilson et al. |

FOREIGN PATENT DOCUMENTS

| | | |
|---|---|---|
| WO | WO 1994/18347 | 8/1994 |
| WO | WO 1995/33052 | 12/1995 |
| WO | WO 1996/06097 | 2/1996 |
| WO | WO 1996/009378 | 3/1996 |
| WO | WO 1996/020951 | 7/1996 |
| WO | WO 1996/41865 | 12/1996 |
| WO | WO 1997/31898 | 9/1997 |
| WO | WO 1998/02441 | 1/1998 |
| WO | WO 1999/10508 | 3/1999 |
| WO | WO 1999/10510 | 3/1999 |
| WO | WO 1999/36553 | 7/1999 |
| WO | WO 1999/41258 | 8/1999 |
| WO | WO 2001/114387 | 3/2001 |
| WO | WO 2001/70816 | 9/2001 |
| WO | WO 2002/29075 | 4/2002 |
| WO | WO 2002/066612 | 8/2002 |
| WO | WO 2002/066613 | 8/2002 |
| WO | WO 2002/066614 | 8/2002 |
| WO | WO 2002/066615 | 8/2002 |
| WO | WO 2003/042397 | 5/2003 |
| WO | WO 2005/033321 | 4/2005 |
| WO | WO 2005/108617 | 11/2005 |
| WO | WO 2006/110689 | 10/2006 |
| WO | WO 2007/127264 | 11/2007 |
| WO | WO 2008/156763 | 12/2008 |
| WO | WO 2009/079259 A2 | 6/2009 |
| WO | WO 2009/115972 | 9/2009 |
| WO | WO 2009/121004 A2 | 10/2009 |
| WO | WO 2010/010466 | 1/2010 |
| WO | WO 2010/044921 A2 | 4/2010 |
| WO | WO 2010/053572 | 5/2010 |
| WO | WO 2010/130636 | 11/2010 |
| WO | WO 2010/140114 | 12/2010 |
| WO | WO 2010/151673 | 12/2010 |
| WO | WO 2011/126808 | 3/2011 |
| WO | WO 2012/145572 | 10/2012 |
| WO | WO 2012/170930 | 12/2012 |
| WO | WO 2013/007770 | 1/2013 |
| WO | WO 2013/049493 | 4/2013 |
| WO | WO 2013/114885 | 8/2013 |
| WO | WO 2013/132007 | 9/2013 |

(56) References Cited

FOREIGN PATENT DOCUMENTS

| | | |
|---|---|---|
| WO | WO 2013/155222 | 10/2013 |
| WO | WO 2013/158879 | 10/2013 |
| WO | WO 2013/182683 | 12/2013 |
| WO | WO 2013/190059 | 12/2013 |
| WO | WO 2015/012924 | 1/2015 |
| WO | WO 2015/013148 | 1/2015 |
| WO | WO 2015/127136 | 8/2015 |
| WO | WO 2015/164757 | 10/2015 |
| WO | WO 2015/168666 | 11/2015 |
| WO | WO 2016/049230 | 3/2016 |
| WO | WO 2016/054598 | 4/2016 |
| WO | WO 2016/124768 | 8/2016 |
| WO | WO 2016/200543 | 12/2016 |
| WO | WO 2017/075119 | 5/2017 |
| WO | WO 2017/100674 | 6/2017 |
| WO | WO 2017/100676 | 6/2017 |
| WO | WO 2017/100704 | 6/2017 |
| WO | WO 2017/106244 | 6/2017 |
| WO | WO 2017/106326 | 6/2017 |
| WO | WO 2017/106354 | 6/2017 |
| WO | WO 2017/136500 | 8/2017 |
| WO | WO 2017/160360 | 9/2017 |
| WO | WO 2018/035059 | 2/2018 |
| WO | WO 2018/057916 | 3/2018 |

OTHER PUBLICATIONS

Body and brain weight by animal, https://mste.illinois.edu/malcz/DATA/BIOLOGY/Animals.html; last accessed Jan. 26, 2022.*

Armbruster et al. Efficacy and biodistribution analysis of intracerebroventricular administration of an optimized scAAV9-SMN1 vector in a mouse model of spinal muscular atrophy, Mol Ther Methods Clin Dev. Sep. 14, 2016;3:16060.

Aschauer et el., Analysis of transduction efficiency, tropism and axonal transport of AAV serotypes 1, 2, 5, 6, 8 and 9 in the mouse brain. PLoS One. Sep. 27, 2013;8(9):e76310.

Bell et al., An optimized protocol for detection of E. coli beta-galactosidase in lung tissue following gene transfer. Histochem Cell Biol. Jul. 2005;124(1):77-85. Epub Jun. 10, 2005.

Bell et al., Analysis of Tumors Arising in Male B6C3F1 Mice with and without AAV Vector Delivery to Liver. Mol Ther. Jul. 2006;14(1):34-44. Epub May 6, 2006.

Bell et al., Identification of the galactose binding domain of the adeno-associated virus serotype 9 capsid. J Virol. Jul. 2012;86(13):7326-33. Epub Apr. 18, 2012.

Bell et al., No. Evidence for Tumorigenesis of AAV Vectors in a Large-Scale Study in Mice. Mol Ther. Aug. 2005;12(2):299-306.

Bell et al., The AAV9 receptor and its modification to improve in vivo lung gene transfer in mice. J Clin Invest. Jun. 2011;121(6):2427-35. Epub May 16, 2011.

Bell P et al., Motor neuron transduction after intracisternal delivery of AAV9 in a cynomolgus macaque. Hum Gene Ther Methods. Apr. 2015;26(2):43-4.

Bendell et al., Central nervous system metastases in women who receive trastuzumab-based therapy for metastatic breast carcinoma. Cancer. Jun. 15, 2003;97(12):2972-7.

Benkhelifa-Ziyyat et al., Intramuscular scAAV9-SMN injection mediates widespread gene delivery to the spinal cord and decreases disease severity in SMA mice. Mol Ther. Feb. 2013;21(2):282-90. Epub Jan. 8, 2013.

Bergman et al., Pharmacokinetics of IgG and IgM anti-ganglioside antibodies in rats and monkeys after intrathecal administration. J Pharmacol Exp Ther. Jan. 1998;284(1):111-5.

Bevan et al., Early heart failure in the SMNDelta7 model of spinal muscular atrophy and correction by postnatal ScAAV9-SMN delivery. Hum Mol Genet. Oct. 15, 2010;19(20):3895-905. Epub Jul. 16, 2010.

Bousquet et al., Intrathecal Trastuzumab Halts Progression of CNS Metastases in Breast Cancer. J Clin Oncol. 34(16):e151-155. Epub Dec. 29, 2014.

Brantly et al., Sustained transgene expression despite T lymphocyte responses in a clinical trial of rAAV1-AAT gene therapy. Proc Natl Acad Sci U S A. Sep. 22, 2009;106(38):16363-8. Epub Aug. 1, 2009.

Bryant et al., Lessons learned from the clinical development and market authorization of Glybera. Hum Gene Ther Clin Dev. Jun. 2013;24(2):55-64. Epub Jun. 29, 2013.

Bucher et al., Intracisternal delivery of AAV9 results in oligodendrocyte and motor neuron transduction in the whole central nervous system of cats. Gene Ther. May 2014;21(5):522-8. Epub Feb. 27, 2014.

Buning et al., Recent developments in adeno-associated virus vector technology, J Gene Med. Jul. 2008;10(7):717-33.

Bussaglia et al., A frame-shift deletion in the survival motor neuron gene in Spanish spinal muscular atrophy patients. Nat Genet. Nov. 1995;11(3):335-7.

Calcedo et al., Worldwide epidemiology of neutralizing antibodies to adeno-associated viruses. J Infect Dis. Feb. 1, 2009;199(3):381-90.

Cao et al., Distance, Depth and Puncture Angle for Cisterna Magna in Chinese Adults as Read from Magnetic Resonance Imaging. Chin Med J (Engl). Jun. 20, 2015;128(12):1683-5.

Castle et al., Adeno-associated virus serotypes 1, 8, and 9 share conserved mechanisms for anterograde and retrograde axonal transport. Hum Gene Ther. Aug. 2014;25(8):705-20. Epub May 2, 2014.

Castle et al., Long-distance axonal transport of AAV9 is driven by dynein and kinesin-2 and is trafficked in a highly motile Rab7-positive compartment. Mol Ther. Mar. 2014;22(3):554-566. Epub Oct. 8, 2013.

Cearley et al., Expanded repertoire of AAV vector serotypes mediate unique patterns of transduction in mouse brain. Mol Ther. Oct. 2008;16(10):1710-8. Epub Aug. 19, 2008.

Chandler et al., Vector design influences hepatic genotoxicity after adeno-associated virus gene therapy. J Clin Invest. Feb. 2015;125(2):870-80. Epub Jan. 20, 2015.

Chen et al., Prevalence and risk factors for feeding and swallowing difficulties in spinal muscular atrophy types II and III. J Pediatr. Mar. 2012;160(3):447-451.e1. Epub Sep. 1, 2011.

Cho and Dreyfuss, A degron created by SMN2 exon 7 skipping is a principal contributor to spinal muscular atrophy severity. Genes Dev. Mar. 1, 2010;24(5):438-42.

Ciesielska, et al. Cerebral infusion of AAV9 vector-encoding non-self proteins can elicit cell-mediated immune responses. Mol Ther. Jan. 2013;21(1):158-66. Epub Aug. 28, 2012.

Cobleigh, et al, Multinational study of the efficacy and safety of humanized anti-HER2 monoclonal antibody in women who have HER2-overexpressing metastatic breast cancer that has progressed after chemotherapy for metastatic disease. J. Clin. Oncol. 17, 2639-2648 (1999).

Colle, et al. Efficient intracerebral delivery of AAV5 vector encoding human ARSA in non-human primate. Hum Mol Genet. Jan. 1, 2010;19(1):147-58.

Coovert et al., The survival motor neuron protein in spinal muscular atrophy. Human Molecular Genetics. 1997;6(8):1205-14.

Crawford & Pardo. The neurobiology of childhood spinal muscular atrophy. Neurobiol Dis. Apr. 1996;3(2):97-110.

Crawford et al., Evaluation of SMN protein, transcript, and copy number in the biomarkers for spinal muscular atrophy (BforSMA) clinical study. PLoS One. 2012;7(4):e33572. Epub Apr. 27, 2012.

David et al., Recombinant adeno-associated virus-mediated in utero gene transfer gives therapeutic transgene expression in the sheep., Hum Gene Ther. Apr. 2011;22(4):419-26. Epub Feb. 2, 2011.

Dekaban, Changes in brain weights during the span of human life: relation of brain weights to body heights and body weights. Ann Neurol. Oct. 1978;4(4):345-56.

Delzor et al., Restricted transgene expression in the brain with cell-type specific neuronal promoters. Human Gene Therapy Methods. Hum Gene Ther Methods. Aug. 2012;23(4):242-54. Epub Aug. 30, 2012.

Deverman et al., Cre-dependent selection yields AAV variants for widespread gene transfer to the adult brain. Nat Biotechnol. Feb. 2016;34(2):204-9. Epub Feb. 1, 2016.

(56) References Cited

OTHER PUBLICATIONS

Didonato et al., Cloning, characterization, and copy number of the murine survival motor neuron gene: homolog of the spinal muscular atrophy-determining gene. Genome Res. Apr. 1997;7(4):339-52.

Dimattia et al., Structural insight into the unique properties of adeno-associated virus serotype 9. J Virol. Jun. 2012;86(12):6947-58. Epub Apr. 11, 2012.

Dirren et al., Intracerebroventricular Injection of Adeno-Associated Virus 6 and 9 Vectors for Cell Type-Specific Transgene Expression in the Spinal Cord. Hum Gene Ther. Feb. 2014;25(2):109-20. Epub Jan. 15, 2014.

Dominguez et al., Intravenous scAAV9 delivery of a codon-optimized SMN1 sequence rescues SMA mice. Hum Mol Genet. Hum Mol Genet. Feb. 15, 2011;20(4):681-93. Epub Nov. 30, 2010.

Donsante et al., Observed incidence of tumorigenesis in long-term rodent studies of rAAV vectors. Gene Ther. Sep. 2001;8(17):1343-6.

Dubowitz, Very severe spinal muscular atrophy (SMA type 0): an expanding clinical phenotype. Eur J Paediatr Neurol. 1999;3(2):49-51.

Duque et al., A large animal model of spinal muscular atrophy and correction of phenotype. Ann Neurol. Mar. 2015;77(3):399-414. Epub Feb. 9, 2015.

Duque et al., Intravenous administration of self-complementary AAV9 enables transgene delivery to adult motor neurons. Mol Ther. Jul. 2009;17(7):1187-96. Epub Apr. 14, 2009.

El-Khodor et al., Identification of a battery of tests for drug candidate evaluation in the SMNΔ7 neonate model of spinal muscular atrophy. Exp Neurol. Jul. 2008;212(1):29-43. Epub Mar. 18, 2008.

Ellinwood et al. Safe, Efficient, and Reproducible Gene Therapy of the Brain in the Dog Models of Sanfilippo and Hurler Syndromes. Mol Ther. Feb. 2011;19(2): 251-259.

Fang et al. Molecular characterization and copy number of SMN1, SMN2 and NAIP in Chinese patients with spinal muscular atrophy and unrelated healthy controls. BMC Musculoskelet Disord. 2015; 16(1): 11.

Faravelli, et al. Spinal muscular atrophy—recent therapeutic advances for an old challenge. Nat Rev Neurol. Jun. 2015;11(6):351-9. Epub May 19, 2015.

Federici et al., Robust spinal motor neuron transduction following intrathecal delivery of AAV9 in pigs. Gene Ther. Aug. 2012;19(8):852-9. Epub Sep. 15, 2011.

Feldkotter et al., Quantitative analyses of SMN1 and SMN2 based on real-time lightCycler PCR: fast and highly reliable carrier testing and prediction of severity of spinal muscular atrophy. Am J Hum Genet. Feb. 2002;70(2):358-68. Epub Dec. 21, 2001.

Finkel et al. 209th ENMC International Workshop: Outcome Measures and Clinical Trial Readiness in Spinal Muscular Atrophy Nov. 7-9, 2014, Heemskerk, The Netherlands. Neuromuscul Disord. Jul. 2015;25(7):593-602. Epub Apr. 28, 2015.

Finkel et al., Nusinersen versus Sham Control in Infantile-Onset Spinal Muscular Atrophy. N Engl J Med. Nov. 2, 2017;377(18):1723-1732.

Finkel et al., Observational study of spinal muscular atrophy type I and implications for clinical trials. Neurology. Aug. 26, 2014;83(9):810-7. Epub Jul. 30, 2014.

Finkel, Electrophysiological and motor function scale association in a pre-symptomatic infant with spinal muscular atrophy type I. Neuromuscul Disord. Feb. 2013;23(2):112-5. Epub Nov. 10, 2012.

Fisher et al., Transduction with recombinant adeno-associated virus for gene therapy is limited by leading-strand synthesis. J Virol. Jan. 1996;70(1):520-32.

Foust et al., Intravascular AAV9 preferentially targets neonatal neurons and adult astrocytes, Nat Biotechnol. Jan. 2009;27(1):59-65. Epub Dec. 21, 2008.

Friedmann, Gene therapy for spinomuscular atrophy: a biomedical advance, a missed opportunity for more equitable drug pricing. Gene Ther. Sep. 2017;24(9):503-505. Epub Jun. 22, 2017.

Ganey et al., Role of the coagulation system in acetaminophen-induced hepatotoxicity in mice. Hepatology. Oct. 2007;46(4):1177-86.

Gao et al., Adeno-associated viruses undergo substantial evolution in primates during natural infections. Proc Natl Acad Sci U S A. May 13, 2003;100(10):6081-6. Epub Apr. 25, 2003.

Gao et al., Clades of Adeno-associated viruses are widely disseminated in human tissues. J Virol. Jun. 2004;78(12):6381-8.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., Purification of recombinant adeno-associated virus vectors by column chromatography and its performance in vivo. Hum Gene Ther. Oct. 10, 2000;11(15):2079-91.

Garcia et al., Peripheral motor and sensory nerve conduction studies in normal infants and children. Clin Neurophysiol. Mar. 2000;111(3):513-20.

GenBank Accession AAS99264.1, capsid protein VP1 [Adeno-associated virus 9], Jun. 2004.

GenBank Accession AY530553.1, Adeno-associated virus isolate pi.1 capsid protein VP1 (cap) gene, complete cds, Jun. 2004.

GenBank Accession AY530629, Adeno-associated virus isolate hu.9 capsid protein VP1 (cap) gene, complete cds, Jun. 2004.

GenBank Accession K03104.1, Human cytomegalovirus major immediate-early gene, enhancer, Aug. 1993.

GenBank Accession NC_001401.2, Adeno-associated virus—2, complete genome, Dec. 2014.

GenBank Accession NM_000344.3, *Homo sapiens* survival of motor neuron 1, telomeric (SMN1), transcript variant d, mRNA, Jan. 22, 2018.

GenBank Accession NM_001297715.1, *Homo sapiens* survival of motor neuron 1, telomeric (SMN1), transcript variant a, mRNA, Sep. 2016.

GenBank Accession NM_022874.2, *Homo sapiens* survival of motor neuron 1, telomeric (SMN1), transcript variant b, mRNA, Sep. 2016.

GenBank Accession NP_000335.1, survival motor neuron protein isoform d [*Homo sapiens*], Apr. 22, 2016.

GenBank Accession NP_001284644.1, survival motor neuron protein isoform a [*Homo sapiens*], Sep. 2016.

GenBank Accession NP_075012.1, survival motor neuron protein isoform b [*Homo sapiens*], Sep. 2016.

GenBank Accession V00882.1, Rabbit (*O. cuniculus*) gene for beta-globin, Nov. 2006.

GenBank Accession X00182.1, Gallus gallus cytoplasmic beta-actin, Nov. 2006.

George et al., Hemophilia B Gene Therapy with a High-Specific-Activity Factor IX Variant. N Engl J Med. Dec. 7, 2017;377(23):2215-2227.

Giles et al., Deamidation of Amino Acids on the Surface of Adeno-Associated Virus Capsids Leads to Charge Heterogeneity and Altered Vector Function. Mol Ther. Dec. 5, 2018;26(12):2848-2862. Epub Oct. 18, 2018.

Gil-Farina et al., Recombinant AAV Integration Is Not Associated With Hepatic Genotoxicity in Nonhuman Primates and Patients. Mol Ther. Jun. 2016;24(6):1100-1105. Epub Mar. 7, 2016.

Gordeeva et al., Improved PCR-based gene synthesis method and its application to the Citrobacter freundii phytase gene codon modification. J Microbiol Methods. May 2010;81(2):147-52. Epub Mar. 10, 2010.

Graham et al., Characteristics of a human cell line transformed by DNA from human adenovirus type 5. J Gen Virol. Jul. 1977;36(1):59-74.

Gray et al., Global CNS gene delivery and evasion of anti-AAV-neutralizing antibodies by intrathecal AAV administration in non-human primates. Gene Ther. Apr. 2013;20(4):450-9. Epub Jan. 10, 2013.

Gray et al., Preclinical differences of intravascular AAV9 delivery to neurons and glia: a comparative study of adult mice and nonhuman primates. Mol Ther. Jun. 2011;19(6):1058-69. Epub Apr. 12, 2011.

Gregoretti et al., Survival of patients with spinal muscular atrophy type 1. Pediatrics. May 2013;131(5):e1509-14. Epub Apr. 22, 2013.

(56) References Cited

OTHER PUBLICATIONS

Greig et al., Intramuscular Injection of AAV8 in Mice and Macaques Is Associated with Substantial Hepatic Targeting and Transgene Expression, PLoS One. Nov. 13, 2014;9(11):e112268. doi: 10.1371/journal.pone.0112268. eCollection 2014.

Grieger & Samulski, Adeno-associated virus as a gene therapy vector: Vector development, production and clinical applications, Adv. Biochem. Engin/Biotechnol. 2005;99: 119-145.

Grimm et al., Titration of AAV-2 particles via a novel capsid ELISA: packaging of genomes can limit production of recombinant AAV-2. Gene Ther. Jul. 1999;6(7):1322-30.

Haaker and Fujak, Proximal spinal muscular atrophy: current orthopedic perspective. Appl Clin Genet. Nov. 14, 2013;6(11):113-20.

Haurigot et al., Whole body correction of mucopolysaccharidosis IIIA by intracerebrospinal fluid gene therapy. J Clin Invest. Jul. 1, 2013. pii: 66778.

Helmken et al., Evidence for a modifying pathway in SMA discordant families: reduced SMN level decreases the amount of its interacting partners and Htra2-beta1. Hum Genet. Dec. 2003;114(1):11-21. Epub Oct. 1, 2003.

Hinderer et al., Neonatal tolerance induction enables accurate evaluation of gene therapy for MPS I in a canine model. Mol Genet Metab. Sep. 2016;119(1-2):124-30. Epub Jun. 8, 2016.

Hinderer et al., Widespread gene transfer in the central nervous system of cynomolgus macaques following delivery of AAV9 into the cisterna magna. Mol Ther Methods Clin Dev. Dec. 10, 2014;1:14051.

Hinderer, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.

Hinderer, et al. Intrathecal gene therapy corrects CNS pathology in a feline model of mucopolysaccharidosis I. Mol Ther. Dec. 2014;22(12):2018-27. Epub Jul. 16, 2014.

Hinderer, et al. Severe Toxicity in Nonhuman Primates and Piglets Following High-Dose Intravenous Administration of an Adeno-Associated Virus Vector Expressing Human SMN.Hum Gene Ther. Mar. 2018;29(3):285-298. Epub Feb. 12, 2018.

Hioki et al., Efficient gene transduction of neurons by lentivirus with enhanced neuron-specific promoters. Gene Ther. Jun. 2007;14(11):872-82. Epub Mar. 15, 2007.

Hordeaux et al., The Neurotropic Properties of AAV-PHP.B Are Limited to C57BL/6J Mice. Mol Ther. Mar. 7, 2018;26(3):664-668. Epub Feb. 2, 2018.

Hu et al., RH10 provides superior transgene expression in mice when compared with natural AAV serotypes for neonatal gene therapy. J Gene Med. Sep. 2010;12(9):766-78.

Hua et al., Antisense masking of an hnRNP A1/A2 intronic splicing silencer corrects SMN2 splicing in transgenic mice. Am J Hum Genet. Apr. 2008;82(4):834-48. Epub Mar. 27, 2008.

Hua et al., Peripheral SMN restoration is essential for long-term rescue of a severe spinal muscular atrophy mouse model. Nature. Oct. 5, 2011;478(7367):123-6.

Iliff et al., A paravascular pathway facilitates CSF flow through the brain parenchyma and the clearance of interstitial solutes, including amyloid β. Sci Transl Med. Aug. 15, 2012;4(147):147ra111.

Iliff et al., Cerebral arterial pulsation drives paravascular CSF-interstitial fluid exchange in the murine brain. J Neurosci. Nov. 13, 2013;33(46):18190-9.

James et al., Predictors of outcome after acetaminophen poisoning in children and adolescents. J Pediatr. May 2002;140(5):522-6.

Janson, et al. Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Jedrzejowska et al., Incidence of spinal muscular atrophy in Poland—more frequent than predicted? Neuroepidemiology. 2010;34(3):152-7. Epub Jan. 15, 2010.

Jin et al., Direct Liquid Chromatography/Mass Spectrometry Analysis for Complete Characterization of Recombinant Adeno-Associated Virus Capsid Proteins. Hum Gene Ther Methods. Oct. 2017;28(5):255-267. Epub Jun. 16, 2017.

Kaplitt et al., Safety and tolerability of gene therapy with an adeno-associated virus (AAV) borne GAD gene for Parkinson's disease: an open label, phase I trial.Lancet. Lancet. Jun. 23, 2007;369(9579):2097-105.

Kashima et al., An intronic element contributes to splicing repression in spinal muscular atrophy. Proc Natl Acad Sci U S A. Feb. 27, 2007;104(9):3426-31. Epub Feb. 16, 2007.

Kay et al., Evidence for gene transfer and expression of factor IX in haemophilia B patients treated with an AAV vector. Nat Genet. Mar. 2000;24(3):257-61.

Kerr, New insights into haemostasis in liver failure. Blood Coagul Fibrinolysis. Jun. 2003;14 Suppl 1:S43-5.

Khan et al., Mitigation of septic shock in mice and rhesus monkeys by human chorionic gonadotrophin-related oligopeptides. Clin Exp Immunol. Jun. 2010;160(3):466-78. Epub Mar. 16, 2010.

Kim et al., Intracerebroventricular viral injection of the neonatal mouse brain for persistent and widespread neuronal transduction. Journal of Visualized Experiments, J Vis Exp. Sep. 15, 2014;(91):51863.

Kolb & Kissel, Spinal Muscular Atrophy. Neurol Clin. Nov. 2015;33(4):831-46.

Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. Epub Feb. 9, 2005.

Lefebvre et al., Correlation between severity and SMN protein level in spinal muscular atrophy. Nat Genet. Jul. 1997;16(3):265-9.

Lefebvre et al., Identification and characterization of a spinal muscular atrophy-determining gene. Cell. Jan. 13, 1995;80(1):155-65.

Li et al., Adeno-associated virus capsid antigen presentation is dependent on endosomal escape. J Clin Invest. Mar. 2013;123(3):1390-401. Epub Feb. 1, 2013.

Li et al., Assessing the potential for AAV vector genotoxicity in a murine model. Blood. Mar. 24, 2011;117(12):3311-9. Epub Nov. 24, 2010.

Lock et al., Absolute determination of single-stranded and self-complementary adeno-associated viral vector genome titers by droplet digital PCR. Hum Gene Ther Methods. Apr. 2014;25(2):115-25. Epub Feb. 14, 2014.

Lock et al., Characterization of a recombinant adeno-associated virus type 2 Reference Standard Material. Hum Gene Ther. Oct. 2010;21(10):1273-85.

Lock et al., Rapid, simple, and versatile manufacturing of recombinant adeno-associated viral vectors at scale. Hum Gene Ther. Oct. 2010;21(10):1259-71.

Luo et al., Adeno-associated virus-mediated cancer gene therapy: current status. Cancer Lett. Jan. 28, 2015;356(2 Pt B):347-56. Epub Nov. 10, 2014.

MacLaren et al., Retinal gene therapy in patients with choroideremia: initial findings from a phase 1/2 clinical trial. Lancet. Mar. 29, 2014;383(9923):1129-37. Epub Jan. 16, 2014.

MacLeod et al., Prenatal onset spinal muscular atrophy. Eur J Paediatr Neurol. 1999;3(2):65-72.

Maguire et al., Safety and efficacy of gene transfer for Leber's congenital amaurosis. N Engl J Med. May 22, 2008;358(21):2240-8. Epub Apr. 27, 2008.

Malkova et al., Longitudinal magnetic resonance imaging study of rhesus monkey brain development. Eur J Neurosci. Dec. 2006;24(11):3204-12.

Manno et al., Successful transduction of liver in hemophilia by AAV-Factor IX and limitations imposed by the host immune response. Nat Med. Mar. 2006;12(3):342-7. Epub Feb. 12, 2006.

Martino et al., Engineered AAV vector minimizes in vivo targeting of transduced hepatocytes by capsid-specific CD8+ T cells. Blood. Mar. 21, 2013;121(12):2224-33. Epub Jan. 16, 2013.

Mayer, et al. Respiratory inductance plethysmography in healthy 3- to 5-year-old children. Chest. Nov. 2003;124(5):1812-9.

Mazzone, et al. Assessing upper limb function in nonambulant SMA patients: development of a new module. Neuromuscul Disord. Jun. 2011;21(6):406-12. Epub Mar. 21, 2011.

(56) References Cited

OTHER PUBLICATIONS

McAndrew et al., Identification of proximal spinal muscular atrophy carriers and patients by analysis of SMNT and SMNC gene copy number. Am J Hum Genet. Jun. 1997;60(6):1411-22.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
Meister et al., SMN-mediated assembly of RNPs: a complex story. Trends Cell Biol. Oct. 2002;12(10):472-8.
Melnick et al., Association of 20-Millimicron Particles with Adenoviruses. J Bacteriol. Jul. 1965;90(1):271-4.
Mendell et al., Abstract: AVXS-101 Phase 1 Gene Therapy Clinical Trial in SMA Type 1: Event Free Survival and Achievement of developmental milestones (CT.003). Neurology. Apr. 2017;88(16 Supplement).
Mendell et al., Single-Dose Gene-Replacement Therapy for Spinal Muscular Atrophy. N Engl J Med. Nov. 2, 2017;377(18):1713-22.
Mercuri et al., Childhood spinal muscular atrophy: controversies and challenges. Lancet Neurol. May 2012;11(5):443-52.
Mercuri et al., Efficacy and safety of nusinersen in children with later-onset spinal muscular atrophy (SMA): end of study results from the phase 3 CHERISH study. Oct. 2017, vol. 27, Supplement 2, p. S210.
Mercuri et al., Nusinersen versus Sham Control in Later-Onset Spinal Muscular Atrophy. N Engl J Med. Feb. 15, 2018;378(7):625-635.
Mercuri et al., Patterns of disease progression in type 2 and 3 SMA: Implications for clinical trials. Neuromuscul Disord. Feb. 2016;26(2):126-31. Epub Dec. 3, 2015.
Meyer et al., Improving single injection CSF delivery of AAV9-mediated gene therapy for SMA: a dose-response study in mice and nonhuman primates. Mol Ther. Mar. 2015;23(3):477-87. Epub Oct. 31, 2014.
Miller, Glybera and the future of gene therapy in the European Union. Nat Rev Drug Discov. May 2012;11(5):419.
Mittermeyer et al., Long-term evaluation of a phase 1 study of AADC gene therapy for Parkinson's disease. Hum Gene Ther. Apr. 2012;23(4):377-81. Epub Apr. 10, 2012.
Mizukami et al., A Protocol for AAV vector production and purification. Diss. Division of Genetic Therapeutics, Center for Molecular Medicine, 1998.
Monani et al., A single nucleotide difference that alters splicing patterns distinguishes the SMA gene SMN1 from the copy gene SMN2. Hum Mol Genet. Jul. 1999;8(7):1177-83.
Monani et al., The human centromeric survival motor neuron gene (SMN2) rescues embryonic lethality in Smn(-/-) mice and results in a mouse with spinal muscular atrophy. Hum Mol Genet. Feb. 12, 2000;9(3):333-9.
Morford et al., Preclinical safety evaluations supporting pediatric drug development with biopharmaceuticals: strategy, challenges, current practices. Birth Defects Res B Dev Reprod Toxicol. Aug. 2011;92(4):359-80. Epub Jul. 18, 2011.
Mueller et al., Human Treg responses allow sustained recombinant adeno-associated virus-mediated transgene expression. J Clin Invest. Dec. 2013;123(12):5310-8. Epub Nov. 15, 2013.
Muraszko et al., Pharmacokinetics and toxicology of immunotoxins administered into the subarachnoid space in nonhuman primates and rodents. Cancer Res. Aug. 15, 1993;53(16):3752-7.
Nathwani et al., Adenovirus-associated virus vector-mediated gene transfer in hemophilia B. N Engl J Med. Dec. 22, 2011;365(25):2357-65. Epub Dec. 10, 2011.
Neubert et al., Connectivity reveals relationship of brain areas for reward-guided learning and decision making in human and monkey frontal cortex. Proc Natl Acad Sci U S A. May 19, 2015;112(20):E2695-704. Epub May 6, 2015.
Ogino et al., New insights on the evolution of the SMN1 and SMN2 region: simulation and meta-analysis for allele and haplotype frequency calculations. Eur J Hum Genet. Dec. 2004;12(12):1015-23.

Ogino et al., Spinal muscular atrophy: molecular genetics and diagnostics. Expert Rev Mol Diagn. Jan. 2004;4(1):15-29.
O'Hagen et al., An expanded version of the Hammersmith Functional Motor Scale for SMA II and III patients. Neuromuscul Disord. Oct. 2007;17(9-10):693-7. Epub Jul. 19, 2007.
Oshio et al., Reduced cerebrospinal fluid production and intracranial pressure in mice lacking choroid plexus water channel Aquaporin-1. FASEB J. Jan. 2005;19(1):76-8. Epub Nov. 8, 2004.
Park et al., Spinal muscular atrophy: new and emerging insights from model mice. Curr Neurol Neurosci Rep. Mar. 2010;10(2):108-17.
Parsons et al., An 11 Base Pair Duplication in Exon 6 of the SMN Gene Produces a Type I Spinal Muscular Atrophy (SMA) Phenotype: Further Evidence For SMN as the Primary SMA-Determining Gene. Human Molecular Genetics. Nov. 1996;5(11):1727-32.
Passini et al., Antisense Oligonucleotides Delivered to the Mouse CNS Ameliorate Symptoms of Severe Spinal Muscular Atrophy. Sci Transl Med. Mar. 2, 2011;3(72):72ra18.
Passini et al., CNS-targeted gene therapy improves survival and motor function in a mouse model of spinal muscular atrophy. J Clin Invest. Apr. 2010;120(4):1253-64. Epub Mar. 15, 2010.
Passini et al., Translational fidelity of intrathecal delivery of self-complementary AAV9-survival motor neuron 1 for spinal muscular atrophy. Hum Gene Ther. Jul. 2014;25(7):619-30. Epub Apr. 28, 2014.
Patrizi et al. SMN protein analysis in fibroblast, amniocyte and CVS cultures from spinal muscular atrophy patients and its relevance for diagnosis. Eur J Hum Genet. Apr. 1999;7(3):301-9.
Payen et al., Prothrombin time prolongation in paracetamol poisoning: a relevant marker of hepatic failure? Hum Exp Toxicol. Nov. 2003;22(11):617-21.
Pellizzoni et al., A novel function for SMN, the spinal muscular atrophy disease gene product, in pre-mRNA splicing. Cell. Nov. 25, 1998;95(5):615-24.
Pellizzoni et al., Essential role for the SMN complex in the specificity of snRNP assembly. Science. Nov. 29, 2002;298(5599):1775-9.
Pellizzoni et al., The survival of motor neurons (SMN) protein interacts with the snoRNP proteins fibrillarin and GAR1. Curr Biol. Jul. 24, 2001;11(14):1079-88.
Petrone et al., Noninvasive ventilation in children with spinal muscular atrophy types 1 and 2. Am J Phys Med Rehabil. Mar. 2007;86(3):216-21.
Petrosyan et al., Transduction efficiency of neurons and glial cells by AAV-1, -5, -9, -rh10 and -hu11 serotypes in rat spinal cord following contusion injury. Gene Ther. Dec. 2014;21(12):991-1000. Epub Aug. 14, 2014.
Prior and Finanger, Spinal Muscular Atrophy, Feb. 24, 2000 [Updated Dec. 22, 2016]. In: Adam MP, Ardinger HH, Pagon RA, et al., editors. GeneReviews® [Internet]. Seattle (WA): University of Washington, Seattle; 1993-2019.
Prior et al., Homozygous SMN1 deletions in unaffected family members and modification of the phenotype by SMN2. Am J Med Genet A. Oct. 15, 2004;130A(3):307-10.
Prior et al., Spinal muscular atrophy: newborn and carrier screening. Obstet Gynecol Clin North Am. Mar. 2010;37(1):23-36.
Prior, Perspectives and diagnostic considerations in spinal muscular atrophy. Genet Med. Mar. 2010;12(3):145-52.
Pulicherla et al., Engineering liver-detargeted AAV9 vectors for cardiac and musculoskeletal gene transfer. Mol Ther. Jun. 2011;19(6):1070-8. pub Mar. 1, 2011.
Roderick et al., Genetic and phenotypic variation in weight of brain and spinal cord between inbred strains of mice. Brain Res. Dec. 21, 1973;64:345-53.
Rosas et al., Patterns of scAAV vector insertion associated with oncogenic events in a mouse model for genotoxicity. Mol Ther. Nov. 2012;20(11):2098-110. Epub Sep. 18, 2012.
Royo et al., Specific AAV serotypes stably transduce primary hippocampal and cortical cultures with high efficiency and low toxicity. Brain Res. Jan. 23, 2008;1190:15-22. Epub Nov. 17, 2007.
Rudnik-Schoneborn et al., The predictive value of achieved motor milestones assessed in 441 patients with infantile spinal muscular atrophy types II and III. Eur Neurol. 2001;45(3):174-81.

(56) References Cited

OTHER PUBLICATIONS

Russman, Spinal muscular atrophy: clinical classification and disease heterogeneity. J Child Neurol. Aug. 2007;22(8):946-51.
Sahashi et al., Pathological impact of SMN2 mis-splicing in adult SMA mice. EMBO Mol Med. Oct. 2013;5(10):1586-601. Epub Sep. 9, 2013.
Saunders and Riordan, Cisternal or Suboccipital Puncture: A Report of 2019 Punctures. The New England Journal of Medicine, 1929;201(4):168-8.
Schrank et al., Inactivation of the survival motor neuron gene, a candidate gene for human spinal muscular atrophy, leads to massive cell death in early mouse embryos. Proc Natl Acad Sci U S A. Sep. 2, 1997;94(18):9920-5.
Sivo et al. Upper limb module in non-ambulant patients with spinal muscular atrophy: 12 month changes. Neuromuscul Disord. Mar. 2015;25(3):212-5. Epub Nov. 22, 2014.
Sleigh et al., The contribution of mouse models to understanding the pathogenesis of spinal muscular atrophy. Dis Model Mech. Jul. 2011;4(4):457-67.
Snyder et al., Comparison of Adeno-Associated Viral Vector Serotypes for Spinal Cord and Motor Neuron Gene Delivery. Hum Gene Ther. Sep. 2011;22(9):1129-35. Epub Jul. 25, 2011.
Sommer et al., Quantification of adeno-associated virus particles and empty capsids by optical density measurement. Mol Ther. Jan. 2003;7(1):122-8.
Staropoli et al., Rescue of gene-expression changes in an induced mouse model of spinal muscular atrophy by an antisense oligonucleotide that promotes inclusion of SMN2 exon 7. Genomics. Apr. 2015;105(4):220-8. Epub Jan. 31, 2015.
Stetefeld et al., Dynamic light scattering: a practical guide and applications in biomedical sciences. Biophys Rev. Dec. 2016;8(4):409-427. Epub Oct. 6, 2016.
Su et al., In vitro and in vivo mRNA delivery using lipid-enveloped pH-responsive polymer nanoparticles. Mol Pharm. Jun. 6, 2011;8(3):774-87. Epub Apr. 1, 2011.
Sugarman et al., Pan-ethnic carrier screening and prenatal diagnosis for spinal muscular atrophy: clinical laboratory analysis of >72,400 specimens.
Swoboda et al., Natural history of denervation in SMA: relation to age, SMN2 copy number, and function. Ann Neurol. May 2005;57(5):704-12.
Swoboda et al., SMA CARNI-VAL trial part I: double-blind, randomized, placebo-controlled trial of L-carnitine and valproic acid in spinal muscular atrophy. PLoS One. Aug. 19, 2010;5(8):e12140.
Talbot et al., Characterization of a gene encoding survival motor neuron (SMN)-related protein, a constituent of the spliceosome complex. Hum Mol Genet. Dec. 1998;7(13):2149-56.
Tanguy et al., Systemic AAVrh10 provides higher transgene expression than AAV9 in the brain and the spinal cord of neonatal mice. Front Mol Neurosci. Jul. 28, 2015;8:36.
Tardieu et al., Intracerebral administration of adeno-associated viral vector serotype rh. 10 carrying human SGSH and SUMF1 cDNAs in children with mucopolysaccharidosis type IIIA disease: results of a phase I/II trial. Hum Gene Ther. Jun. 2014;25(6):506-16. Epub May 5, 2014.
Thompson et al., A comprehensive comparison of multiple sequence alignment programs. Nucleic Acids Res. Jul. 1, 1999;27(13):2682-90.
U.S. Department of Health and Human Services Food and Drug Administration Center for Biologies Evaluation and Research, Guidance for Industry Preclinical Assessment of Investigational Cellular and Gene Therapy Products, Nov. 2013.
Vincent-Lacaze et al., Structure of Adeno-Associated Virus Vector DNA following Transduction of the Skeletal Muscle. J Virol. Mar. 1999;73(3):1949-55.
Viollet et al., cDNA isolation, expression, and chromosomal localization of the mouse survival motor neuron gene (Smn). Genomics. Feb. 15, 1997;40(1):185-8.
Vite et al., Effective gene therapy for an inherited CNS disease in a large animal model. Ann Neurol. Mar. 2005;57(3):355-64.
Wang and Lunn, Spinal muscular atrophy: advances in research and consensus on care of patients. Curr Treat Options Neurol. Nov. 2008;10(6):420-8.
Wang et al., Consensus statement for standard of care in spinal muscular atrophy. J Child Neurol. Aug. 2007;22(8):1027-49.
Wang et al., Impact of pre-existing immunity on gene transfer to nonhuman primate liver with adeno-associated virus 8 vectors. Hum Gene Ther. Nov. 2011;22(11):1389-401. Epub Jun. 8, 2011.
Wang et al., The pleiotropic effects of natural AAV infections on liver-directed gene transfer in macaques. Mol Ther. Jan. 2010;18(1):126-34. Epub Nov. 3, 2009.
Wirth, Mildly affected patients with spinal muscular atrophy are partially protected by an increased SMN2 copy number. Hum Genet. May 2006;119(4):422-8. Epub Mar. 1, 2006.
Wobus et al., Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93.
Worgall et al., Treatment of late infantile neuronal ceroid lipofuscinosis by CNS administration of a serotype 2 adeno-associated virus expressing CLN2 cDNA. Hum Gene Ther. May 2008;19(5):463-74.
Wright, Product-Related Impurities in Clinical-Grade Recombinant AAV Vectors: Characterization and Risk Assessment, Biomedicines. Mar. 3, 2014;2(1):80-97.
Yang et al., Evaluating glymphatic pathway function utilizing clinically relevant intrathecal infusion of CSF tracer. J Transl Med. May 1, 2013;11:107.
Young and Dong, Two-step total gene synthesis method. Nucleic Acids Res. Apr. 15, 2004;32(7):e59.
Young et al., The relationship between SMN, the spinal muscular atrophy protein, and nuclear coiled bodies in differentiated tissues and cultured cells. Exp Cell Res. May 1, 2000;256(2):365-74.
Yu et al. Recent patents on oligonucleotide synthesis and gene synthesis. Recent Pat DNA Gene Seq. Apr. 2012;6(1):10-21.
Zanta-Boussif et al., Validation of a mutated PRE sequence allowing high and sustained transgene expression while abrogating WHV-X protein synthesis: application to the gene therapy of WAS. Gene Ther. May 2009;16(5):605-19. Epub Mar. 5, 2009.
Zerres & Rudnik-Schoneborn, Natural history in proximal spinal muscular atrophy. Clinical analysis of 445 patients and suggestions for a modification of existing classifications. Arch Neurol. May 1995;52(5):518-23.
Zhang et al., Adenovirus-adeno-associated virus hybrid for large-scale recombinant adeno-associated virus production. Hum Gene Ther. Sep. 2009;20(9):922-9.
Zolgensma Package Insert, May 2019.
International Search Report and Written Opinion issued in International Patent Application No. PCT/US2018/019996, dated Sep. 21, 2018.
International Search Report and Written Opinion issued in International Patent Application No. PCT/US2018/019992, dated Jun. 25, 2018.
Substantive Examination Report dated Sep. 21, 2020 issued in corresponding Chilean Patent Application No. 2019-2473.
Saraiva et al., Gene therapy for the CNS using AAVs: The impact of systemic delivery by AAV9, Journal of Controlled Release, vol. 241:94-109, Nov. 2016.
Lukashchuk et al., AAV9-mediated central nervous system-targeted gene delivery via cisterna magna route in mice, Molecular Therapy—Methods & Clinical Development, vol. 3:1-10, Feb. 2016.
Duan, Systemic delivery of adeno-associated viral vectors, Current Opinion in Virology, vol. 21:16-25, Dec. 2016.
Choudhury et al., Widespread Central Nervous System Gene Transfer and Silencing After Systemic Delivery of Novel AAV-AS Vector, The American Society of Gene & Cell Therapy, vol. 24 (4):726-735, Apr. 2016.
Substantive Examination Report dated Jun. 17, 2021 issued in corresponding Chilean Patent Application No. 2019-2473.
Examination Report dated Jul. 26, 2021 issued in corresponding Colombian Patent Application No. NC2019/0009522.
Communication Pursuant to Article 94(3) EPC dated Nov. 3, 2020 issued in corresponding European Patent Application No. EP 18 713 745.0 with Response.

(56) References Cited

OTHER PUBLICATIONS

Communication Pursuant to Article 94(3) EPC dated Aug. 30, 2021 issued in corresponding European Patent Application No. EP 18 713 745.0.
Substantive Examination Report dated Sep. 8, 2021 issued in corresponding Chilean Patent Application No. 2019-002474.
Examination Report dated Jul. 23, 2021 issued in corresponding Colombian Patent Application No. NC2019/0009525.
Communication Pursuant to Rule 164(2)(b) and Article 94(3) EPC dated Mar. 1, 2021 issued in corresponding European Patent Application No. EP 18 711 202.4 with Response.
Adam VS et al., Adeno-associated virus 9-mediated airway expression of antibody protects old and immunodeficient mice against influenza virus. Clin. Vaccine Immunol., 21(11):1528-33, Nov. 2014. (Epub Sep. 10, 2014).
Afonine PV et al., Towards automated crystallographic structure refinement with phenix.refine, Acta Crystallogr. D Biol. Crystallogr., 68(Pt 4):352-67, Apr. 2012. (Epub Mar. 16, 2012).
Alexander MC et al., Insulin stimulates glyceraldehyde-3-phosphate dehydrogenase gene expression through cis-acting DNA sequences, Proc Natl Acad Sci U S A, 85(14):5092-6, Jul. 1988.
Ali MY, Histology of the Human Nasopharyngeal Mucosa, J. Anat., 99(3):657-672, 1965.
Almond B. and Schenborn ET, A Comparison of pCI-neo Vector and pcDNA4/HisMax Vector, Promega Corporation Website, Updated 2000, Available from: http://www.promega.com/resources/pubhub/enotes/a-comparison-of-pcineo-vector-and-pcdna4hismax-vector/.
Amara JF et al., A versatile synthetic dimerizer for the regulation of protein-protein interactions, Proc. Natl. Acad. Sci. USA, 94(20):10618-23, Sep. 1997.
An W et al., Active retrotransposition by a synthetic L1 element in mice, Proc Natl Acad Sci U S A, 103(49):18662-7, Dec. 5, 2006. (Epub Nov. 21, 2006).
Andersson R et al, An atlas of active enhancers across human cell types and tissues, Nature, 507(7493):455-61, Mar. 27, 2014.
Aquino TL et al., Influenza Outbreak in a Vaccinated Population—USS Ardent, Feb. 2014. MMWR Morb Mortal Wkly Rep, 63(42):947-9, Oct. 24, 2014.
Arkblad et al., A population-based study of genotypic and phenotypic variability in children with spinal muscular atrophy. Acta Paediatr. May 2009;98(5):865-72. Epub Jan. 20, 2009.
Arnold et al., Spinal muscular atrophy: diagnosis and management in a new therapeutic era. Muscle Nerve. Feb. 2015;51(2):157-67. Epub Dec. 16, 2014.
Ashkenazi A et al., Immunoadhesins, International reviews of immunology, 10(2):219-227, 1993.
Balazs AB et al., Antibody-based protection against HIV infection by vectored immunoprophylaxis, Nature, 481(7379):81-4, Nov. 30, 2011.
Ballay A et al., In vitro and in vivo synthesis of the hepatitis B virus surface antigen and of the receptor for polymerized human serum albumin from recombinant human adenoviruses, EMBO J., 4(13B):3861-5, Dec. 30, 1985.
Bankiewicz et al., Long-term clinical improvement in MPTP-lesioned primates after gene therapy with AAV-hAADC. Mol Ther. Oct. 2006;14(4):564-70. Epub Jul. 7, 2006.
Bartus et al., Parkinson's Disease Gene Therapy: Success by Design Meets Failure by Efficacy. Mol Ther. Mar. 2014; 22(3): 487-497.
Berezov A et al., Disabling erbB receptors with rationally designed exocyclic mimetics of antibodies: structure-function analysis, J. Med. Chem., 44(16):2565-74, Aug. 2001.
Beyer WE et al., Cochrane re-arranged: support for policies to vaccinate elderly people against influenza, Vaccine, 31(50):6030-3, Dec. 2013. (Epub Oct. 3, 2013).
Boyer JL et al., 853. Persistent expression of single chain antibodies mediated by AAV5 and AAVrh.10 vectors. Molecular Therapy, 11(Supp. 1):331-2, May 2005.
Brinster et al., Regulation of metallothionein-thymidine kinase fusion plasmids injected into mouse eggs, Nature, 296:39-42, Mar. 4, 1982.
Carragher B et al., Leginon: an automated system for acquisition of images from vitreous ice specimens, J. Struct. Biol., 132(1):33-45, Oct. 2000.
Carter BJ, Chapter 10: The Growth Cycle of Adeno-associated Virus, in CRC Handbook of Parvoviruses, ed. P. Tijsser, CRC Press, p. 155-68, 1990.
Center for Disease Control and Prevention, "Types of Influenza Viruses" Web page <https://www.cdc.gov/flu/about/viruses/types.htm>, 2 pages, Apr. 4, 2016, page last updated Aug. 19, 2014, retrieved from Internet Archive Wayback Machine <https://web.archive.org/web/20160404144120/https://www.cdc.gov/flu/about/viruses/types.htm> on May 11, 2018.
Centers for Disease Control and Prevention, Estimates of deaths associated with seasonal influenza: United States, 1976-2007, available in MMWR Morb. Mortal. Wkly. Rep. 59:1057-1062, Aug. 27, 2010.
Chamow SM and Ashkenazi, Immunoadhesins: principles and applications, Trends in biotechnology, 14(2):52-60, Feb. 1996.
Chen H et al., Avian flu: H5N1 virus outbreak in migratory waterfowl. Nature, 436(7048): 191-2, Jul. 14, 2005.
Ch'ng JL et al., Antisense RNA complementary to 3' coding and noncoding sequences of creatine kinase is a potent inhibitor of translation in vivo, Proc. Natl. Acad. Sci. USA, 86(24):10006-10, Dec. 1989.
Corti D et al., A neutralizing antibody selected from plasma cells that binds to group 1 and group 2 influenza A hemagglutinins, Science, 333:850-6, Aug. 12, 2011. (Epub Jul. 28, 2011).
Cox F et al., Protection against H5N1 influenza virus induced by matrix-M adjuvanted seasonal virosomal vaccine in mice requires both antibodies and T cells, PLoS One, 10(12):e0145243, Dec. 22, 2015.
Crosariol M, et al., Effective AAV9 Vector Delivery to Nasal Mucosa for Protection Against Airborne Challenge With Influenza A and B, Abstract 699, Molecular Therapy, 24(Supp. 1):S276, May 2016.
Davidson E et al., Mechanism of Binding to Ebola Virus Glycoprotein by the ZMapp, ZMAb, and MB-003 Cocktail Antibodies, 89(21):10982-92, Nov. 2015. (Epub Aug. 26, 2015).
Dawood FS et al., Estimated global mortality associated with the first 12 months of 2009 pandemic influenza A H1N1 virus circulation: a modelling study, Lancet Infect Dis, 12(9):687-95, Sep. 2012. (Epub Jun. 26, 2012).
De BP et al, Rapid/ Sustained Anti-anthrax Passive Immunity Mediated by co-administration od Ad/AAV, Molecular Therapy, 6(1):203-9, Jan. 2008.
De BP et al., High levels of persistent expression of alpha 1—antitrypsin mediated by the nonhuman primate serotype rh.10 adeno-associated virus despite preexisting immunity to common human adeno-associated viruses, Mol. Ther., 13(1):67-76, Jan. 2006.
Deuschle U et al., Tetracycline-Reversible Silencing of Eukaryotic Promoters, Mol Cell Biol., 15(4):1907-14, Apr. 1995.
Dhuria SV et al., Intranasal Delivery to the Central Nervous System: Mechanisms and Experimental Considerations, Journal of Pharmaceutical Sciences, 99(4):1654-73, Apr. 2010. (Epub Oct. 29, 2009).
Dilillo DJ et al., Broadly neutralizing anti-influenza antibodies require Fc receptor engagement for in vivo protection, J. Clin. Invest., 126(2):605-10, Feb. 2016. (Epub Jan. 5, 2016).
Djupesland PG, Nasal drug delivery devices: characteristics and performance in a clinical perspective—a review, Drug Deliv Transl Res, 3(1):42-62, Feb. 2013. (Epub Oct. 18, 2012).
Donnelly MLL et al., The cleavage activities of aphthovirus and cardiovirus 2A proteins, J. Gen. Virol., 78(Pt 1):13-21, Jan. 1997.
Dreyfus C et al., Highly conserved protective epitopes on influenza B viruses, Science, 337:1343-8, Sep. 14, 2012. (Epub Aug. 9, 2012).
Du L et al., Intranasal vaccination of recombinant adeno-associated virus encoding receptor-binding domain of severe acute respiratory syndrome coronavirus (SARS-CoV) spike protein induces strong mucosal immune responses and provides long-term protection against SARS-CoV infection, J Immunology, 180(2):948-956, Jan. 2008.
Ekiert DC et al., A highly conserved neutralizing epitope on group 2 influenza A viruses, Science, 333(6044):843-50, Aug. 12, 2011. (Epub Jul. 7, 2011).

(56) References Cited

OTHER PUBLICATIONS

Ekiert DC et al., Antibody recognition of a highly conserved influenza virus epitope, Science, 324(5924):246-51, Apr. 10, 2009. (Epub Feb. 26, 2009).

Ekiert DC et al., Cross-neutralization of influenza A viruses mediated by a single antibody loop, Nature, 489(7417):526-32, Sep. 27, 2012. (Epub Sep. 16, 2012).

Emsley P et al., Cowtan, Features and development of Coot, Acta Crystallogr. D Biol. Crystallogr., 66(Pt 4):486-501, Apr. 2010. (Epub Mar. 24, 2010).

Ercolani L et al., Isolation and complete sequence of a functional human glyceraldehyde-3-phosphate dehydrogenase gene, J Biol Chem, 263(30):15335-41, Oct. 25, 1988.

Fang J et al., An antibody delivery system for regulated expression of therapeutic levels of monoclonal antibodies in vivo, Mol. Ther., 15(6);1153-9, Jun. 2007. (Epub Mar. 20, 2007).

Flotte and Buning, Severe Toxicity in Nonhuman Primates and Piglets with Systemic High-Dose Administration of Adeno-Associated Virus Serotype 9-Like Vectors: Putting Patients First. Hum Gene Ther. Mar. 2018;29(3):283-284. Epub Feb. 7, 2018.

Flotte TR et al., Stable in vivo expression of the cystic fibrosis transmembrane conductance regulator with an adeno-associated virus vector. Proc Natl Acad Sci U S A. 90(22):10613-7, Nov. 15, 1993.

Forsman A et al., Llama antibody fragments with cross-subtype human immunodeficiency virus type 1 (HIV-1)-neutralizing properties and high affinity for HIV-1 gp120. J. Virol., 82(24):12069-81, Dec. 2008. (Epub Oct. 8, 2008).

Foster et al., Codon and mRNA sequence optimization for microdystrophin transgenes improves expression and physiological outcome in dystrophic mdx mice following AAV2/8 gene transfer. Mol. Ther. 2008; 16:1825-32 and Supplementary Material, Figure S1 and S2. Epub Sep. 2, 2008.

Furler S et al., Recombinant AAV vectors containing the foot and mouth disease virus 2A sequence confer efficient bicistronic gene expression in cultured cells and rat substantia nigra neurons, Gene Ther., 8(11):864-73, Jun. 2001.

Gamblin SJ et al., Influenza hemagglutinin and neuraminidase membrane glycoproteins, Journal of Biological Chemistry, 285(37):28403-9, Sep. 10, 2010. (Epub Jun. 10, 2010).

Gao R et al., Human infection with a novel avian-origin influenza A (H7N9) virus. N. Engl. J. Med., 368:1888-97, May 16, 2013. (Epub Apr. 11, 2013).

GenBank Accession NM_000344.2, *Homo sapiens* survival of motor neuron 1, telomeric (SMN1), transcript variant d, mRNA, Oct. 8, 2008.

GenBank: AAB86861.1, Web page <https://www.ncbi.nlm.nih.gov/protein/AAB86861.1>, 1 page, retrieved from Internet on May 11, 2018.

GenBank: ACJ71709.1, Web page <https://www.ncbi.nlm.nih.gov/protein/ACJ71709.1>, 2 pages, retrieved from Internet on May 11, 2018.

GenBank: AEL31303.1, Web page <https://www.ncbi.nlm.nih.gov/protein/AEL31303.1>, 2 pages, retrieved from Internet on May 11, 2018.

GenBank: AFP87542.1, Web page <https://www.ncbi.nlm.nih.gov/protein/AFP87542.1>, 2 pages, retrieved from Internet on May 11, 2018.

GenBank: AGH70219.1, Web page <https://www.ncbi.nlm.nih.gov/protein/AGH70219.1>, 1 page, retrieved from Internet on May 11, 2018.

GenBank: BAF64540.1, Web page <https://www.ncbi.nlm.nih.gov/protein/BAF64540.1>, 2 pages, retrieved from Internet on May 11, 2018.

GenBank: CAA24362.1, Web page <https://www.ncbi.nlm.nih.gov/protein/AGH70219.1>, 1 page, retrieved from Internet on May 11, 2018.

Glaven RH et al., Linking Single Domain Antibodies that Recognize Different Epitopes on the Same Target, Biosensors (Basel), 2(1):43-56, Feb. 1, 2012.

Glezen WP et al., The burden of influenza B: a structured literature review, Am J Public Health, 103(3):e43-51, Mar. 2013. (Epub Jan. 17, 2013).

Gossen M and Bujard H, Tight control of gene expression in mammalian cells by tetracycline-responsive promoters, Proc. Natl. Acad. Sci. USA, 89:5547-51, Jun. 1992.

Gossen M et al., Transcriptional activation by tetracyclines in mammalian cells, Science 268(5218):1766-9, Jun. 23, 1995.

Gupta P, Preclinical pharmacokinetics of MHAA4549A, a human monoclonal antibody to influenza A virus, and the prediction of its efficacious clinical dose for the treatment of patients hospitalized with influenza A, Mabs, 8(5):991-7, Jul. 2016. (Epub Mar. 31, 2016).

Gurda et al., Evaluation of AAV-mediated Gene Therapy for Central Nervous System Disease in Canine Mucopolysaccharidosis VII. Mol Ther. Feb. 2016;24(2):206-216. Epub Oct. 8, 2015.

Harris A et al., Influenza virus pleiomorphy characterized by cryoelectron tomograph, Proc. Natl. Acad. Sci. U.S.A., 103(50)19123-7, Dec. 12, 2006. (Epub Dec. 4, 2006).

Hessell AJ et al., Fc receptor but not complement binding is important in antibody protection against HIV, Nature, 449(7158):101-104, Sep. 6, 2007.

Hinderer et al., Neonatal Systemic AAV Induces Tolerance to CNS Gene Therapy in MPS I Dogs and Nonhuman Primates. Mol Ther. Aug. 2015; 23(8):1298-1307, Prepublished online May 29, 2015, Published online Jun. 30, 2015.

Hohn M et al., SPARX, a new environment for Cryo-EM image processing, J. Struct. Biol., 157(1):47-55, Jan. 2007. (Epub Jul. 16, 2006).

Holehonnur et al., Adeno-associated viral serotypes produce differing titers and differentially transduce neurons within the rat basal and lateral amygdala. BMC Neurosci. Feb. 18, 2014;15:28.

Hoogenboom HR et al, By-passing immunisation: Human antibodies from synthetic repertoires of germline VH gene segments rearranged in vitro, J. Mil. Biol., 227(2):381-8, Sep. 1992.

Hynes et al., Hormone-responsive expression of an endogenous proviral gene of mouse mammary tumor virus after molecular cloning and gene transfer into cultured cells, Proc. Natl. Acad. Sci. USA, 78(4):2038-42, Apr. 1981.

Irani V et al., Molecular properties of human IgG subclasses and their implications for designing therapeutic monoclonal antibodies against infectious diseases, Molecular immunology, 67(2):171-82, Oct. 2015. (Epub Apr. 18, 2015).

Israel DI and Kaufman RJ, Highly inducible expression from vectors containing multiple GRE's in CHO cells overexpressing the glucocorticoid receptor, Nucl. Acids Res., 17(12):2589-2604, Nov. 12, 1989.

Jegaskanda PC et al., Influenza-specific antibody-dependent cellular cytotoxicity: toward a universal influenza vaccine, J. Immunol. 193(2):469-75, Jul. 15, 2014.

Johnson PR et al., Vector-mediated gene transfer engenders long-lived neutralizing activity and protection against SIV infection in monkeys, Nat Med., 15(8):901-6, Aug. 2009. (Epub May 17, 2009).

Jones PT et al., Replacing the complementarity-determining regions in a human antibody with those from a mouse, Nature, 321(6069):522-5, May 1986.

Julien JP et al., Structural insights into key sites of vulnerability on HIV-1 Env and influenza HA, Immunol. Rev., 250(1):180-98, Nov. 2012.

Kabsch W, XDS, Acta Crystallogr. D Biol. Crystallogr., 66(Pt 2):125-32, Feb. 2010. (Epub Jan. 22, 2010).

Kaplitt MG, et al. Long-term gene expression and phenotypic correction using adeno-associated virus vectors in the mammalian brain. Nat Genet., 8(2):148-54, Oct. 1, 1994.

Kashyap AK et al., Combinatorial antibody libraries from survivors of the Turkish H5N1 avian influenza outbreak reveal virus neutralization strategies, Proc. Natl. Acad. Sci. U.S.A., 105(16):5986-91, Apr. 22, 2008. (Epub Apr. 14, 2008).

Kelly S et al., Splicing of many human genes involves sites embedded within introns, Nucleic Acids Research, 43(9):4721-32, May 19, 2015. (Epub Apr. 20, 2015).

(56) References Cited

OTHER PUBLICATIONS

Klein C et al., Progress in overcoming the chain association issue in bispecific heterodimeric IgG antibodies, mAbs, 4(6):653-63, Nov.-Dec. 2012. (Epub Aug. 27, 2012).

Klock G et al., Oestrogen and glucocorticoid responsive elements are closely related but distinct, Nature, 329(6141):734-6, Oct. 22-28, 1987.

Klump H et al., Retroviral vector-mediated expression of HoxB4 in hematopoietic cells using a novel coexpression strategy, Gene Ther., 8(10):811-7, May 2001.

Kohler et al., Continuous cultures of fused cells secreting antibody of predefined specificity, Nature, 256(5517):495-7, Aug. 1975.

Kortt AA et al., Recombinant anti-sialidase single-chain variable fragment antibody. Characterization, formation of dimer and higher-molecular-mass multimers and the solution of the crystal structure of the single-chain variable fragment/sialidase complex, Eur. J. Biochem., 221(1):151-7, Apr. 1994.

Kramer RA et al., The human antibody repertoire specific for rabies virus glycoprotein as selected from immune libraries, Eur. J. Immunol., 35(7):2131-45, Jul. 2005.

Krause et al., Human Monoclonal Antibodies to Pandemic 1957 H2N2 and Pandemic 1968 H3N2 Influenze Viruses, Journal of Virology, 86(11):6334-6340, Jun. 2012.

Kuo TT et al., Neonatal Fc Receptor and IgG-Based Therapeutics, mAbs, 3(5):422-30, Sep.-Oct. 2011, (Epub Sep. 1, 2011).

Labrijn et al., Efficient generation of stable bispecific IgG1 by controlled Fab-arm exchange, Proc Natl Acad Sci USA, 110(13):5145-50, Mar. 26, 2013. (Epub Mar. 11, 2013).

Lai et al., Antisense RNA complimentary to 3' coding and noncoding sequences of creatine kinase is a potent inhibitor of translation in vivo, Proc. Natl. Acad. Sci. USA, vol. 86(24):10006-10 (Dec. 1989).

Lander et al., Appion: an integrated, database-driven pipeline to facilitate EM image processing, J. Struct. Biol., 166(1):95-102, Apr. 2009.

Laursen S and Wilson IA, Broadly neutralizing antibodies against influenza viruses, Antiviral. Res. 98(3):476-83, Jun. 2013. (Epub Apr. 9, 2013).

Lee F et al., Glucocorticoids regulate expression of dihydrofolate reductase cDNA in mouse mammary tumour virus chimaeric plasmids, Nature 294(5838):228-32, Nov. 19, 1981.

Lee PS et al., Heterosubtypic antibody recognition of the influenza virus hemagglutinin receptor binding site enhanced by avidity. Proc. Natl. Acad. Sci. U.S.A. 109(42):17040-5, Oct. 16, 2012. (Epub Oct. 1, 2012).

Levitt N et al., Definition of an efficient synthetic poly(A) site, Genes Dev., 3(7):1019-25, Jul. 1989.

Limberis et al., Vectored expression of the broadly neutralizing antibody FI6 in mouse airway provides partial protection against a new avian influenza A virus, H7N9., Clin Vaccine Immunol, 20(12):1836-7. Dec. 2013. (Epub Oct. 16, 2013).

Limberis MP and Wilson JM, Adeno-associated virus serotype 9 vectors transduce murine alveolar and nasal epithelia and can be readministered 2006, Proc Natl Acad Sci USA, 103(35):12993-8, Aug. 29, 2006. (Epub Aug. 22, 2006).

Limberis MP et al., Adeno-Associated Virus Serotype 9-Expressed ZMapp in Mice Confers Protection Against Systemic and Airway-Acquired Ebola Virus Infection, J Infect Dis., 214(12):1975-79, Dec. 2016. (Epub Sep. 28, 2016).

Limberis MP et al., Transduction efficiencies of novel AAV vectors in mouse airway epithelium in vivo and human ciliated airway epithelium in vitro, Mol. Ther., 17(2):294-301, Feb. 2009. (Epub Dec. 9, 2008).

Limberis MP, AAV Vectors for Rapid and Effective Prophylaxis against Airborne Viruses, presented on Feb. 14, 2018 at 2018 ASM Biothreats meeting in Baltimore, Maryland, pp. 1-34.

Ljungman P, Vaccination of immunocompromised patients, Clin Microbiol Infect,18 Suppl 5:93-9, Oct. 2012.

Lobner E et al., Engineered IgG1-Fc-one fragment to bind them all, Immunological reviews, 270(1):113-131, Mar. 2016. (Epub Feb. 10, 2016).

Marks JD et al., By-passing immunization. Human antibodies from V-gene libraries displayed on phage, J. Mol. Biol., 222(3):381-97, Dec. 1991.

Mayo KE et al. The mouse metallothionein-I gene is transcriptionally regulated by cadmium following transfection into human or mouse cells, Cell, 29(1):99-108, May 1982.

McCoy AJ et al., Likelihood-enhanced fast translation functions. Acta Crystallogr. D Biol. Crystallogr. 61(Pt 4):458-64, Apr. 2005. (Epub Mar. 24, 2005).

McLellan JS et al., Structure of respiratory syncytial virus fusion glycoprotein in the postfusion conformation reveals preservation of neutralizing epitopes, J Virol., 85(15):7788-96, Aug. 2011. (Epub May 25, 2011).

Medina RA, Influenza A viruses: new research developments, Nat Rev Microbiol., 9(8):590-603, Jul. 11, 2011.

Miller AD et al., Expression of a retrovirus encoding human HPRT in mice, Science, 225(4662):630-2, Aug. 10, 1984.

Molinari N-A M et al., The annual impact of seasonal influenza in the US: measuring disease burden and costs, Vaccine, 25(27):5086-96, Jun. 28, 2007. (Epub Apr. 20, 2007).

Mouquet H et al., Enhanced HIV-1 neutralization by antibody heteroligation, Proc. Natl. Acad. Sci. U.S.A., 109(3):875-80, Jan. 17, 2012. (Epub Jan. 4, 2012).

Murshudov GN et al., Refinement of macromolecular structures by the maximum-likelihood method, Acta Crystallogr. D Biol. Crystallogr., 53(Pt 3):240-55, May 1, 1997.

Nakamura G et al., An in vivo human-plasmablast enrichment technique allows rapid identification of therapeutic A antibodies. Cell Host Microbe, 14(1):93-103, Jul. 17, 2013.

Ng S-Y et al., Regulation of the human beta-actin promoter by upstream and intron domains, Nuc. Nucleic Acids Res., 17(2):601-615, Jan. 25, 1989.

Nieto K et al., Combined prophylactic and therapeutic intranasal vaccination against human papillomavirus type-16 using different adeno-associated virus serotype vectors, Antiviral Ther., 14(8):1125-37, 2009.

Ogura T et al., Topology representing network enables highly accurate classification of protein images taken by cryo electron-microscope without masking, J. Struct. Biol., 143(3):185-200, Sep. 2003.

Oliveira EC et al., Influenza in the intensive care unit. J Intensive Care Med, 18(2):80-91, Mar.-Apr. 2003. (First Published Mar. 1, 2003 ).

Osterholm MT et al., Efficacy and effectiveness of influenza vaccines: a systematic review and meta-analysis. Lancet Infect Dis. 12(1):36-44, Jan. 2012. (Epub Oct. 25, 2011).

Ostrowski LE et al., Targeting expression of a transgene to the airway surface epithelium using a ciliated cell-specific promoter, Molecular Therapy, 8(4):637-45, Oct. 2003.

PDB: 2J6E_A, Web page <https://www.ncbi.nlm.nih.gov/protein/2J6E_A>, 2 pages, retrieved from Internet on May 11, 2018.

PDB: 4FQL_H, Web page <https://www.ncbi.nlm.nih.gov/protein/4FQL_H>, 3 pages, retrieved from Internet on May 11, 2018.

Pettersen EF et al., UCSF Chimera—a visualization system for exploratory research and analysis, J. Comput. Chem., 25(13):1605-12, Oct. 2004.

Quitschke WW et al., The beta actin promoter, High levels of transcription depend upon a CCAAT binding factor, 264(16):9539-46, Jun. 5, 1989.

Radcliffe PA et al., Multiple gene products from a single vector: 'self-cleaving' 2A peptides, Gene Therapy, 11(23):1673-4, 2004. (Published Oct. 26, 2004).

Rath T et al., Fc-fusion proteins and FcRn: structural insights for longer-lasting and more effective therapeutics, Critical reviews in biotechnology, 35(2):235-54, Jun. 2015. (Epub Oct. 24, 2013).

Riechmann L et al., Reshaping human antibodies for therapy, Nature, 332(6162):323-7, Mar. 1988.

Roscilli G et al., Long-Term and Tight Control of Gene Expression in Mouse Skeletal Muscle by a New Hybrid Human Transcription Factor, Mol. Ther., 6(5):653-63, Nov. 2002.

(56) References Cited

OTHER PUBLICATIONS

Roseman AM, FindEM—a fast, efficient program for automatic selection of particles from electron micrographs, J. Struct. Biol., 145(1-2):91-9, Jan.-Feb. 2004.
Sanner MF et al., Reduced surface: an efficient way to compute molecular surfaces, Biopolymers, 38(3):305-20, Mar. 1996.
Scharfmann R et al., Long-term in vivo expression of retrovirus-mediated gene transfer in mouse fibroblast implants, Proc. Natl. Acad. Sci. USA, 88(11):4626-30, Jun. 1, 1991.
Scheres SH, A Bayesian view on cryo-EM structure determination, J. Mol. Biol., 415(2):406-18, Jan. 13, 2012. (Epub Nov. 12, 2011).
Schillinger KJ et al., Regulatable atrial natriuretic peptide gene therapy for hypertension, Proc. Natl. Acad. Sci. USA., 102(39):13789-94, Sep. 27, 2005. (Epub Sep. 14, 2005).
Searle et al., Building a Metal-Responsive Promoter with Synthetic Regulatory Elements, Mol. Cell. Biol., 5(6):1480-9, Jun. 1985.
Shapshak P et al., The Influenza Pandemic of 2009: Lessons and Implications, Mol Diagn Ther., 15(2):63-81, Apr. 1, 2011.
Shepelev V and Fedorov A. Advances in the Exon-Intron Database. Briefings in Bioinformatics, 7(2):178-85, Jun. 2006. (Epub Mar. 9, 2006).
Skaricic D et al., Genetic delivery of an anti-RSV antibody to protect against pulmonary infection with RSV, Virology, 378(1):79-85, Aug. 2008.
Slamon et al., Use of Chemotherapy plus a Monoclonal Antibody against HER2 for Metastatic Breast Cancer That Overexpresses HER2. N Engl J Med. Mar. 15, 2001;344(11):783-92.
Stratford-Perricaudet LD et al., Evaluation of the transfer and expression in mice of an enzyme-encoding gene using a human adenovirus vector, Hum Gene Ther., 1(3):241-56, 1990.
Strohl WR, Optimization of Fc-Mediated Effector Functions of Monoclonal Antibodies, Current Opinion in Biotechnology, 20(6):685-91, Dec. 2009. (Epub Nov. 4, 2009).
Sui J et al., Structural and functional bases for broad-spectrum neutralization of avian and human influenza A viruses, Nature structural & molecular biology, 16(3):265-73. (Epub Feb. 22, 2009).
Tan GS et al., A pan-H1 anti-hemagglutinin monoclonal antibody with potent broad-spectrum efficacy in vivo, 86(11):6179-88, Jun. 2012. (Epub Apr. 4, 2012).
Tang G et al., EMAN2: an extensible image processing suite for electron microscopy, J. Struct. Biol., 157(1):38-46, Jan. 2007. (Epub Jun. 8, 2006).
Tillib et al., Formatted single-domain antibodies can protect mice against infection with influenza virus (H5N2), Antiviral Research. 97(3):245-54, Mar. 2013. (Epub Dec. 25, 2012).
UniProtKB—P60568 (IL2_HUMAN), Web page http://www.uniprot.org/uniprot/P60568, 9 pages, retrieved from Internet on May 11, 2018.
Vafa O et al., An engineered Fc variant of an IgG eliminates all immune effector functions via structural perturbations, Methods, 65(1):114-26, Jan. 1, 2014. (Epub Jul. 17, 2013).
Vanlandschoot P et al., Nanobodies: new ammunition to battle viruses, Antiviral Res., 92(3):389-407, Dec. 2011. (Epub Sep. 10, 2011).
Verhoeyen M et al., Reshaping human antibodies: grafting an antilysozyme activity, Science, 239(4847):1534-6, Mar. 1988.
Wang Y et al., A regulatory system for use in gene transfer, Proc. Natl. Acad. Sci. USA., 91(17):8180-4, Aug. 1994.
Ward et al., Codon optimization of human factor VIII cDNA leads to high-level expression, Blood, Jan. 20, 2011; 117(3):798-807. DOI: 10.1182/blood-2010-05-282707 Epub Nov. 1, 2010.
Willey R et al., Neutralizing antibody titers conferring protection to macaques from a simian/human immunodeficiency virus challenge using the TZM-bl assay, AIDS research and human retroviruses, 26(1):89-98, Jan. 10, 2010.
Williams DA et al., Introduction of new genetic material into pluripotent haematopoietic stem cells of the mouse, Nature, 310(5977):476-80, Aug. 9, 1984.
Wu Z et al., Effect of genome size on AAV vector packaging, Mol Ther, 18(1):80-6, Jan. 2010. (Epub Nov. 10, 2009).
Xia H et al., siRNA-mediated gene silencing in vitro and in vivo, Nat Biotechnol, 20(10):1006-10, Oct. 2002. (Epub Sep. 16, 2002).
Xie H et al., H3N2 Mismatch of 2014-15 Northern Hemisphere Influenza Vaccines and Head-to-head Comparison between Human and Ferret Antisera derived Antigenic Maps, Sci. Rep., 5:15279, Oct. 16, 2015.
Xin K-Q et al., A novel recombinant adeno-associated virus vaccine induces a long-term humoral immune response to human immunodeficiency virus, Human Gene Ther., 12(9):1047-61, Jun. 2001.
Xiong et al., PCR-based accurate synthesis of long DNA sequences. Nat Protoc. 2006;1(2):791-7.
Xu R et al., Structural basis of preexisting immunity to the 2009 H1N1 pandemic influenza virus, Science, 328(5976):357-60, Apr. 16, 2010. (Epub Mar. 25, 2010).
Yang Z et al., Iterative stable alignment and clustering of 2D transmission electron microscope images, Structure, 20(2):237-47, Feb. 8, 2012.
Yoshida R et al., Cross-protective potential of a novel monoclonal antibody directed against antigenic site B of the hemagglutinin of influenza A viruses, PLoS Pathog., 5(3):e1000350, Mar. 2009. (Epub Mar. 20, 2009).
Zagouri et al., Intrathecal administration of trastuzumab for the treatment of meningeal carcinomatosis in HER2-positive metastatic breast cancer: a systematic review and pooled analysis. Breast Cancer Res Treat. May 2013;139(1):13-22.
Zhang L et al., Alteration in the IL-2 signal peptide affects secretion of proteins in vitro and in vivo, J Gene Med., 7(3):354-65, Mar. 2005. (Published online Dec. 23, 2004 )WHO Manual on Animal Influenza Diagnosis and Surveillance, Geneva: World Health Organisation, 2002, version 2002.5.
Substantive Examination Report issued in corresponding Saudi Arabian Patent Application No. 519402565, dated Oct. 31, 2021, with unofficial English translation.
Substantive Examination Report issued in corresponding Saudi Arabian Patent Application No. 519402566, dated Dec. 27, 2021, with unofficial English translation.
Office Action issued in corresponding Eurasian Patent Application No. 201992032, dated Mar. 14, 2022, with unofficial English translation.
Armbruster et al., Efficacy and biodistribution analysis of intracerebroventricular administration of an optimized scAAV9-SMN1 vector in a mouse model of spinal muscular atrophy, Molecular Therapy—Methods & Clinical Development, vol. 14, No. 3, (Published online Sep. 14, 2016) pp. 16060 [Online pp. 1-8], doi:10.1038/mtm.2016.60.
Aschauer et el., Analysis of transduction efficiency, tropism and axonal transport of AAV serotypes 1, 2, 5, 6, 8 and 9 in the mouse brain, PLoS One, vol. 8, No. 9, (Published online Sep. 27, 2013, p. e76310 [Online pp. 1-16], doi: 10.1371/journal.pone.0076310,.
Brandenburg B et al., Mechanisms of hemagglutinin targeted influenza virus neutralization, PLoS One, vol. 8, No. 12), (Published online Dec. 11, 2013), p. e80034 [Online pp. 1-14], doi: 10.1371/journal.pone.0080034.
Daley, J., Severe Toxicity Reported in High-Dose AAV Gene Therapy in Animals, The Scientist, p. 1-2, (Published online Jan. 31, 2018) [retrieved on Aug. 4, 2022], [PDF] Retrieved from the internet <https://www.the-scientist.com/the-nutshell/severe-toxicity-reported-in-high-dose-aav-gene-therapy-in-animals-30348>.
De BP et al, Abstract 611—Induction of Persistent Passive Immunity Against Anthrax Toxin by an Adeno-Associated Virus Type rh10 Vector Expressing Anti-Protective Antigen Antibody, Molecular Therapy, vol. 13, Suppl. 1), (Published online Jan. 1, 2006) pp. S236, doi: https://doi.org/10.1016/j.ymthe.2006.08.685.
European Medicines Agency, Guideline on Development, Production, Characterization and Specifications for Monoclonal Antibodies and Related Products (EMEA/CHMP/BWP/532517/2008), pp. 1-13 [online], (Published online Jul. 21, 2016), [retrieved on Aug. 4, 2022], [PDF], Retrieved from the Internet <https://www.ema.europa.eu/en/development-production-characterisation-specifications-monoclonal-antibodies-related-products>.

(56) References Cited

OTHER PUBLICATIONS

Friesen RH et al., A common solution to group 2 influenza virus neutralization. PNAS U.S.A., vol. 111, No. 1), pp. 445-450, Jan. 7, 2014. (Published online Dec. 11, 2013), doi: 10.1073/pnas. 1319058110.

Hufton SE et al. The breadth of cross sub-type neutralisation activity of a single domain antibody to influenza hemagglutinin can be increased by antibody valency, PLoS One, vol. 9, No. 8), (Published online Aug. 1, 2014), p. e103294 [Online pp. 1-19], doi: 10.1371/journal.pone.0103294.

Hultberg A et al., Llama-derived single domain antibodies to build multivalent, superpotent and broadened neutralizing anti-viral molecules, PLoS One, vol. 6, No. 4, (Published online Apr. 1, 2011), p. e17665 [Online pp. 1-12], https://doi.org/10.1371/journal.pone. 0017665.

Invivogen, IgG-Fc Engineering for Therapeutic Use, (Published online Apr./May 2006), pp. 1-4 [Online], [retrieved on Aug. 4, 2022], [PDF], Retrieved from the Internet <www.invivogen.com/docs/Insight200605.pdf>.

Juno J et al., Immunogenetic Factors Associated with Severe Respiratory Illness Caused by Zoonotic H1N1 and H5N1 Influenza Viruses, Clinical and Developmental Immunology, vol. 2012, p. 797180 [Online pp. 1-9], (Published online Nov. 3, 2011), doi: 10.1155/2012/797180.

Kashyap AK et al., Combinatorial antibody libraries from survivors of the Turkish H5N1 avian influenza outbreak reveal vims neutralization strategies, PNAS U.S.A., vol. 105, No. 16, (Published online Apr. 14, 2008), pp. 5986-5991, https://doi.org/10.1073/pnas. 0801367105.

Krah S et al., Single-domain antibodies for biomedical applications, Immunopharmacol. Immunotoxicol., vol. 38, No. 1, (Published online Nov. 9, 2015), pp. 21-28, doi: 10.3109/08923973.2015. 1102934.

Kramer RA et al., A novel helper phage that improves phage display selection efficiency by preventing the amplification of phages without recombinant protein, Nucleic Acids Res., vol. 31, No. 11, (Published online Jun. 1, 2003), p. e59 [Online pp. 1-9], doi: 10.1093/nar/gng058.

Laube et al., The expanding role of aerosols in systemic drug delivery, gene therapy and vaccination: an update, Transl. Respir. Med., vol. 2, (Published online Jan. 13, 2014) p. 3 [Online pp. 1-12], doi: 10.1186/2213-0802-2-3,.

Limberis MP et al., Establishment of a New AAV Clinical Candidate for Prophylaxis Against Influenza A and B (Abstract 398), Poster presented at American Society of Gene & Cell Therapy 2017 Annual Meeting on May 11, 2017.

Limberis MP et al., Intranasal Antibody Gene Transfer in Mice and Ferrets Elicits Broad Protection Against Pandemic Influenza, Science Translational Medicine, vol. 5, No. 187, (Published online May 29, 2013), pp. 187ra72 [Online pp. 1-19], doi: 10.1126/scitranslmed.3 006299.

Liu J et al., Highly pathogenic H5N1 influenza virus infection in migratory birds, Science, vol. 309, No. 5738, (Published online Jul. 6, 2005), p. 1206 [Online p. 1], DOI: 10.1126/science.1115273.

McBride JM et al., Phase 2 Randomized Trial of the Safety and Efficacy of MHAA4549A, a Broadly Neutralizing Monoclonal Antibody, in a Human Influenza A Virus Challenge Model, Antimicrob Agents Chemother, vol. 61, No. 11, (Accepted manuscript published online Aug. 14, 2017), pp. e01154-17, doi: 10.1128/AAC.01154-17.

Merrifield, Solid Phase Peptide Synthesis I. The Synthesis of a Tetrapepide, J. Am. Chem. Soc., vol. 85, No. 14, (Jul. 1, 1963), pp. 2149-2154, https://doi.org/10.1021/ja00897a025.

Miller MA et al., Visualization of murine intranasal dosing efficiency using luminescent Francisella tularensis: effect of instillation volume and form of anesthesia. PLoS One, vol. 7, No. 2, (Published online Feb. 24, 2012), p. e31359 [Online pp. 1-8], doi: 10.1371/journal.pone.0031359.

Sawada-Hirai et al., Human anti-anthrax protective antigen neutralizing monoclonal antibodies derived from donors vaccinated with anthrax vaccine adsorbed, Journal of Immune Based Therapy Vaccines, vol. 2, No. 1, (Published May 12, 2004), p. 5 [Online pp. 1-15] doi: 10.1186/1476-8518-2-5.

Saxena A and Wu D, Advances in therapeutic Fc engineering-modulation of IgG-Associated effector functions and serum half-life, Frontiers in Immunology, vol. 7, (Published online Dec. 12, 2016), p. 580 [Online pp. 1-11], doi: 10.3389/fimmu.2016.00580.

Shapiro RJ, The Potential American Market for Generic Biological Treatments and the Associated Cost Savings, Sonecon, (Feb. 2008), pp.. 1-20, , [retrieved on Aug. 4, 2022], [PDF], Retrieved from the Internet <http://www.sonecon.com/docs/studies/0208_ GenericBiologicsStudy.pdf>.

Throsby M et al., Heterosubtypic neutralizing monoclonal antibodies cross-protective against H5N1 and H1N1 recovered from human IgM+ memory B cells, PLoS One, vol. 3, No. 12, (Published online Dec. 16, 2008), p. e3942 [Online pp. 1-15), doi: 10.1371/journal. pone.0003 942.

Tsibane et al., Influenza human monoclonal antibody 1F1 interacts with three major antigenic sites and residues mediating human receptor specificity in H1N1 viruses, PLoS Pathog., vol. 8, No. 12, (Published online Dec. 6, 2012), p. el003 067 [Online pp. 1-15], doi: 10.1371/journal.ppat.1003067.

Tycko J et al., 701. Intranasal Delivery of Neutralizing Antibodies by AAV9 to Protect Mice Against RSV Infection. Molecular Therapy: Vaccines and Immunotherapy, vol. 22, No. 1, (Published online May 1, 2014), pp. S271, Abstract, DOI:https://doi.org/10.1016/S1525-0016(16)35714-8.

U.S. Department of Health and Human Services, Food and Drug Administration, Center for Biologies Evaluation, "Research Points to Consider in the Manufacture and Testing of Monoclonal Ab Products for Human Use," Center for Biologies Evaluation and Research, Center for Drug Evaluation and Research, (Published Feb. 1997), [retrieved on Aug. 4, 2022], [PDF], Retrieved from the Internet <https://www.fda.gov/regulatory-information/search-fda-guidance-documents/points-consider-manufacture-and-testing-monoclonal-antibody-products-human-use>.

Urrutia R., KRAB-containing zinc-finger repressor proteins, Genome Biol., vol. 4, No. 10, (Published online Sep. 23, 2003), p. 231 [Online pp. 1-8], doi: 10.1186/GB-2003-4-10-231.

Wang TT et al., Broadly protective monoclonal antibodies against H3 influenza viruses following sequential immunization with different hemagglutinins, PLoS Pathogens, vol. 6, No. 2, (Published online Feb. 26, 2010), p. e1000796 [Online pp. 1-9], https://doi.org/10.1371/journal.ppat.1000796.

WHO Manual on Animal Influenza Diagnosis and Surveillance, Geneva: World Health Organization, (2002), Version 2002.5, pp. 1-105, [retrieved on Aug. 4, 2022], [PDF], Retrieved from the Internet <https://apps.who.int/iris/handle/10665/68026>.

Wu Y et al., A potent broad-spectrum protective human monoclonal antibody crosslinking two haemagglutinin monomers of influenza A virus, Nat. Commun., vol. 6 (Published online Jul. 21, 2015), 7708 [Online pp. 1-11], doi: 10.103 8/ncomms8708.

* cited by examiner

FIG 1A

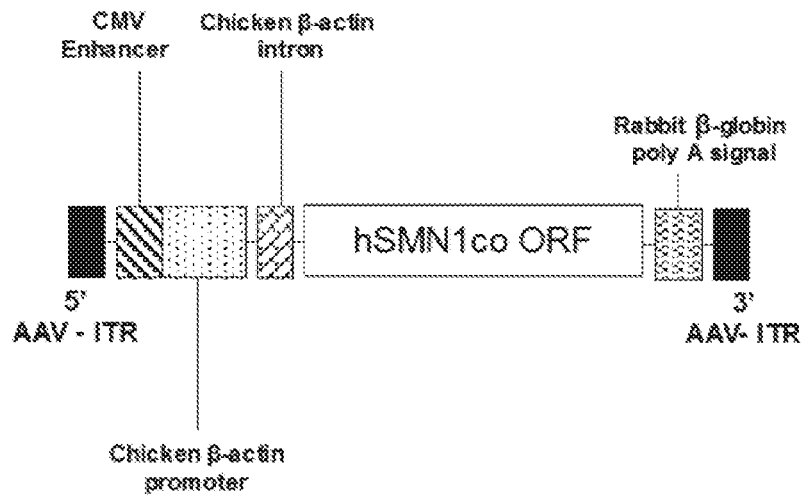

FIG 1B

```
Query   1    ATGGCGATGAGCAGCGGCGGCAGTGGTGGCGGCGTCCCGGAGCAGGAGGATTCCGTGCTG   60
             ||||| |||   || || |||||||| || || || || || ||||| |||||||||||
Sbjct   1    ATGGCCATGTCGAGTGGGGGCAGTGGAGGGGGAGTGCCAGAACAGGAAGATTCCGTGCTG   60

Query   61   TTCCGGCGCGGCACAGGCCAGAGCGATGATTCTGACATTTGGGATGATACAGCACTGATA   120
             ||| |||| || || || ||||| || || ||      ||||||||| || || |||||
Sbjct   61   TTCAGGCGAGGAACCGGGCAGAGTGACGACAGTGACATTTGGGACGACACGGCCCTGATC   120

Query   121  AAAGCATATGATAAAGCTGTGGCTTCATTTAAGCATGCTCTAAAGAATGGTGACATTTGT   180
             || || ||||| ||||| ||||| ||  ||||||||| || |||||| || ||||||| 
Sbjct   121  AAGGCCTATGACAAAGCCGTGGCCTCCTTCAAGCACGCGCTGAAGAACGGCGACATTTGC   180

Query   181  GAAACTTCGGGtaaaccaaaaaccacccctaaagaaaactgctaagaagaataaaagc    240
             |||||   ||  || || || || ||||| || ||| ||  ||||| ||||||   |
Sbjct   181  GAAACCAGCGGCAAGCCTAAGACCACCCCTAAACGGAAGCCCGCCAAGAAAAATAAGTCC   240
```

FIG 1C

```
Query  241  caaaagaagaaTACTGCAGCTTCCTTACAACAGTGGAAAGTTGGGGACAAATGTTCTGCC  300
            || || |||||| || || ||    | || || ||||| || ||||| || || || ||
Sbjct  241  CAGAAAAGAACACAGCCGCAAGTCTTCAGCAATGGAAGGTGGGGGATAAGTGCTCCGCG   300

Query  301  ATTTGGTCAGAAGACGGTTGCATTTACCCAGCTACCATTGCTTCAATTGATTTTAAGAGA  360
            || |||   ||||||||  ||||| || || || || || ||||| ||   || || || |
Sbjct  301  ATATGGAGTGAAGACGGGTGCATCTATCCTGCCACCATCGCCAGCATAGACTTCAAGCGC  360

Query  361  GAAACCTGTGTTGTGGTTTACACTGGATATGGAAATAGAGAGGAGCAAAATCTGTCCGAT  420
            |||||||| || ||||| |||||||||| || || | |||||||| || ||| |||
Sbjct  361  GAAACCTGCGTGGTGGTGTACACTGGATACGGGAACCGGGAGGAGCAGAACCTGAGCGAC  420

Query  421  CTACTTTCCCCAATCTGTGAAGTAGCTAATAATATAGAACAAAATGCTCAAGAGAATGAA  480
            || |   ||| || || |||||  || || || || || || || || ||||| ||||| |||||
Sbjct  421  CTGTTGAGCCCTATTTGTGAGGTGGCCAACAACATCGAGCAGAATGCGCAAGAAAATGAA  480

Query  481  AATGAAAGCCAAGTTTCAACAGATGAAAGTGAGAACTCCAGGTCTCCTGGAAATAAATCA  540
            || || ||  || || || || || || |||| |||| |||    |||   || || || |||||
Sbjct  481  AACGAGAGTCAGGTGTCCACCGATGAGAGTGAAAACAGTAGGAGCCCCGGCAACAAATCC  540

Query  541  GATAACATCAAGCCCAAATCTGCTCCATGGAACTCTTTTCTCCCTCCACCACCCCCCATG  600
            || || ||||||||||||    || || ||||    || || || || || ||||| |||
Sbjct  541  GACAATATCAAGCCCAAAAGCGCACCCTGGAATAGCTTCCTTCCACCCCCCCCCCAATG  600

Query  601  CCAGGGCCAAGACTGGGACCAGGAAAG  627
            || || ||  ||||||| || ||||||
Sbjct  601  CCCGGACCTCGACTGGGCCCCGGAAAG  627
```

|  | GC/pup (1.5g pup) | KO + PBS (n=8) | KO + 3e10 (n=7) | KO + 8.76e10 (n=10) |
|---|---|---|---|---|
| hu68.CB.hSMN | Median Survival (day) | 15 | 37 | 23 | weight at P15 weight at P30

```
         1                                                                                                  100
AAV9     (1)   MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF
hu.68.VP1(1)   MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF
hu.31    (1)   MAADGYLPDWLEDTLSEGIRBWWMKLKPGPPPPKPAERHKDDSRGLVLPGYKYLGPGNGLDKGEPVNEADAAALEHDKAYDQQLKAGDNPYLKYNHADAEF
hu.32    (1)   MAADGYLPDWLEDTLSEGIRBWWMKLKPGPPPPKPAERHKDDSRGLVLPGYKYLGPGNGLDKGEPVNAADAAALEHDKAYDQQLKAGDNPYLKYNHADAEF 101                                                                                                200
AAV9     (101) QERLKEDTSFGGNLGRAVFQAKKRRLLEPLGLVEEAAKTAPGKKRPVEQSPQEPDSSAGIGKSGAQPAKKRLNFGQTGDTESVPDPQPIGEPPAAPSGVGS
hu.68.VP1(101) QERLKEDTSFGGNLGRAVFQAKKRRLLEPLGLVEEAAKTAPGKKRPVEQSPQEPDSSVGIGKSGAQPAKKRLNFGQTGDTESVPDPQPIGEPPAAPSGVGS
hu.31    (101) QERLKEDTSFGGNLGRAVFQAKKRRLLEPLGLVEEAAKTAPGKKRPVEQSPQEPDSSAGIGKSGSQPAKKKLNFGQTGDTESVPDPQPIGEPPAAPSGVGS
hu.32    (101) QERLKEDTSFGGNLGRAVFQAKKRRLLEPLGLVEEAAKTAPGKKRPVEQSPQEPDSSAGIGKSGSQPAKKKLNFGQTGDTESVPDPQPIGEPPAAPSGVGS 201                                                                                                300
AAV9     (201) LTMASGGGAPVADNNEGADGVGSSSGNWHCDSQWLGDRVITSTRTWALPTYNNHLYKQISNSTSGGSSNDNAYFGYSTPWGYFDFNRFHCHFSPRDWQR
hu.68.VP1(201) LTMASGGGAPVADNNEGADGVGSSSGNWHCDSQWLGDRVITSTRTWALPTYNNHLYKQISNSTSGGSSNDNAYFGYSTPWGYFDFNRFHCHFSPRDWQR
hu.31    (201) LTMASGGGAPVADNNEGADGVGSSSGNWHCDSQWLGDRVITSTRTWALPTYNNHLYKQISNSTSGGSSNDNAYFGYSTPWGYFDFNRFHCHFSPRDWQR
hu.32    (201) LTMASGGGAPVADNNEGADGVGSSSGNWHCDSQWLGDRVITSTRTWALPTYNNHLYKQISNSTSGGSSNDNAYFGYSTPWGYFDFNRFHCHFSPRDWQR 301                                                                                                400
AAV9     (301) LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF
hu.68.VP1(301) LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF
hu.31    (301) LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF
hu.32    (301) LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF 401                                                                                                500
AAV9     (401) PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE
hu.68.VP1(401) PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE
hu.31    (401) PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE
hu.32    (401) PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE
```

FIG. 8A

```
         501                                                                                  600
AAV9     (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG
hu.68.VP1(501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG
hu.31    (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG
hu.32    (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG 601                                                                                  700
AAV9     (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ
hu.68.VP1(601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ
hu.31    (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ
hu.32    (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ 701                                    736
AAV9     (701) YTSNYYKSNNVEFAVNTEGVYSEPRPIGTRYLTRNL
hu.68.VP1(701) YTSNYYKSNNVEFAVNTEGVYSEPRPIGTRYLTRNL
hu.31    (701) YTSNYYKSNNVEFAVSTEGVYSEPRPIGTRYLTRNL
hu.32    (701) YTSNYYKSNNVEFAVNTEGVYSEPRPIGTRYLTRNL
```

```
            901  CTCATCAACAACAACTGGGGATTCCGGCCTAAGCGACTCAACTTCAAGTCTCTTCAAACATTCAGGTCAAAGAGGTTACGGACAACAATGGAGTCAAGACCA
AAV9       (901) CTCATCAACAACAACTGGGGATTCCGGCCTAAGCGACTCAACTTCAAGTCTCTTCAAACATTCAGGTCAAAGAGGTTACGGACAACAATGGAGTCAAGACCA
hu.68.VP1  (901) CTCATCAACAACAACTGGGGATTCCGGCCTAAGCGACTCAACTTCAAGTCTCTTCAAACATTCAGGTCAAAGAGGTTACGGACAACAATGGAGTCAAGACCA
hu.31      (901) CTCATCAACAACAACTGGGGATTCCGGCCTAAGCGACTCAACTTCAAGTCTCTTCAAACATTCAGGTCAAAGAGGTTACGGACAACAATGGAGTCAAGACCA
hu.32      (901) CTCATCAACAACAACTGGGGATTCCGGCCTAAGCGACTCAACTTCAAGTCTCTTCAAACATTCAGGTCAAAGAGGTTACGGACAACAATGGAGTCAAGACCA

1001  TCGCCAATAACCTTACCAGCACGGTCCAGGTCTTCACGGACTCAGATATCAGCTCCCGTACGTGCTCGGGTCGGCTCAGGGGCTGCCTCCCGCCGTT
AAV9      (1001) TCGCCAATAACCTTACCAGCACGGTCCAGGTCTTCACGGACTCAGATATCAGCTCCCGTACGTGCTCGGGTCGGCTCAGGGGCTGCCTCCCGCCGTT
hu.68.VP1 (1001) TCGCTAATAACCTTACCAGCACGGTCCAGGTCTTCACGGACTCAGATATCAGCTCCCGTACGTGCTCGGGTCGGCTCAGGGGCTGCCTCCCGCCGTT
hu.31     (1001) TCGCCAATAACCTTACCAGCACGGTCCAGGTCTTCACGGACTCAGATATCAGCTCCCGTACGTGCTCGGGTCGGCTCAGGGGCTGCCTCCCGCCGTT
hu.32     (1001) TCGCCAATAACCTTACCAGCACGGTCCAGGTCTTCACGGACTCAGATATCAGCTCCCGTACGTGCTCGGGTCGGCTCAGGGGCTGCCTCCCGCCGTT

1101  CCCAGCGGACGTTTCATGATTCCTCAGTACGGGTATCTGACGCTTAATGATGGAAGCCAGGCCGTCGTTCGTCGTTCGTCCTTTACTGCCTGCCTATATTC
AAV9      (1101) CCCAGCGGACGTTTCATGATTCCTCAGTACGGGTATCTGACGCTTAATGATGGAAGCCAGGCCGTCGTTCGTCGTTCGTCCTTTACTGCCTGCCTATATTC
hu.68.VP1 (1101) CCCAGCGGACGTTTCATGATTCCTCAGTACGGGTATCTACGCTTAATGATGATGGAAGCCAGGCCGTCGTTCGTCGTTCGTCCTTTACTGCCTGCCTATATTC
hu.31     (1101) CCCAGCGGACGTTTCATGATTCCTCAGTACGGGTATCTGACGCTTAATGATGGAGGCCAGGCCGTCGTTCGTCGTTCGTCCTTTACTGCCTGCCTATATTC
hu.32     (1101) CCCAGCGGACGTTTCATGATTCCTCAGTACGGGTATCTGACGCTTAATGATGGAGGCCAGGCCGTCGTTCGTCGTTCGTCCTTTACTGCCTGCCTATATTC

1201  CCGTGCGCAAATGCTAAGAACGGGTAACAACTTCAGTTCAGTCAGTTTGAGAACGTACCTTCCATAGCAGCTACGCTACGCTACGCTCACAGCCAAAGCCTGGACC
AAV9      (1201) CCGTGCGCAAATGCTAAGAACGGGTAACAACTTCAGTTCAGTCAGTTTGAGAACGTACCTTCCATAGCAGCTACGCTACGCTACGCTCACAGCCAAAGCCTGGACC
hu.68.VP1 (1201) CCGTCGCAAATGCTAAGAACGGGTAACAACTTCAGTTCAGTCAGTTTGAGAACGTACCTTCCATAGCAGCTACGCTACGCTACGCTCACAGCCAAAGCCTGGACC
hu.31     (1201) CCGTCGCAAATGCTAAGAACGGGTAACAACTTCAGTTCAGTCAGTTTGAGAACGTACCTTCCATAGCAGCTAGCAGCTACGCTACGCTCACAGCCAAAGCCTGGACC
hu.32     (1201) CCGTCGCAAATGCTAAGAACGGGTAACAACTTCAGTTCAGTCAGTTTGAGAACGTACCTTCCATAGCAGCTACGCTACGCTACGCTCACAGCCAAAGCCTGGACC

1301  GACTAATGAATCCACTCATCGACCAATACTGTACTATCTCTCAAAGACTATTAACGGTTCTGGACAGAATCAACAAACGCTAAAATTCAGTGTGGCCGG
AAV9      (1301) GACTAATGAATCCACTCATCGACCAATACTGTACTATCTCTCAAAGACTATTAACGGTTCTGGACAGAATCAACAAACGCTAAAATTCAGTGTGGCCGG
hu.68.VP1 (1301) GACTCATGAATCCACTCATCGACCAATACTGTACTATCTCTCAAAGACTATTAACGGTTCTGGACAGAATCAACAAACGCTAAAATTCAGTGTGGCCGG
hu.31     (1301) GACTAATGAATCCACTCATCGACCAATACTGTACTATCTCTCAAAGACTATTAACGGTTCTGGACAGAATCAACAAACGCTAAAATTCAGTGTGGCCGG
hu.32     (1301) GACTAATGAATCCACTCATCGACCAATACTGTACTATCTCTCAAAGACTATTAACGGTTCTGGACAGAATCAACAAACGCTAAAATTCAGGGTGGCCGG
```

FIG. 8E

```
              1401                                                                                   1500
AAV9     (1401) ACCCAGCAACATGGCTGTCTCCAGGGAAGAAGAAACTACATACCTGGACCCAGCTACCGACAACAACGTGTCTCAACCACTGTGACTCAAAACAACAACAGCGAA
hu.68.VP1(1401) ACCCAGCAACATGGCTGTCTCCAGGGAAGAAGAAACTACATACCTGGACCCAGCTACCGACAACAACGTGTCTCAACCACTGTGACTCAAAACAACAACAGCGAA
hu.31    (1401) ACCCAGCAACATGGCTGTCTCCAGGGAAGAAGAAACTACATACCTGGACCCAGCTACCGACAACAACGTGTCTCAACCACTGTGACTCAAAACAACAACAGCGAA
hu.32    (1401) ACCAGCAACATGGCTGTCTCCAGGGAAGAAGAAACTACATACCTGGACCCAGCTACCGACAACAACGTGTCTCAACCACTGTGACTCAAAACAACAACAGCGAA 1501                                                                                   1600
AAV9     (1501) TTTGCTTGGGCTGGAGCTTCTCTTGGGCTCTCAATGGACGTAATAGCTTGATGAATCCTGGACCTGCTATGGCCAGCACAAAGAAGGAGAGGACCGTT
hu.68.VP1(1501) TTTGCTTGGGCTGGAGCTTCTCTTGGGCTCTCAATGGACGTAATAGCTTGATGAATCCTGGACCTGCTATGGCCAGCACAAAGAAGGAGAGGACCGTT
hu.31    (1501) TTTGCTTGGGCTGGAGCTTCTCTTGGGCTCTCAATGGACGTAATAGCTTGATGAATCCTGGACCTGCTATGGCCAGCACAAAGAAGGAGAGGACCGTT
hu.32    (1501) TTTGCTTGGGCTGGAGCTTCTCTTGGGCTCTCAATGGACGTAATAGCTTGATGAATCCTGGACCTGCTATGGCCAGCACAAAGAAGGAGAGGACCGTT 1601                                                                                   1700
AAV9     (1601) TCTTTCCTTTGTCTCGGATCTTTAATTTTTGGCAAACAAGGAACTGGAAGAGACAACGTGGATGCGGACAAAGTCATGATAACCAACGAAGAAGAAATTAA
hu.68.VP1(1601) TCTTTCCTTTGTCTCGGATCTTTAATTTTTGGCAAACAAGGAACTGGAAGAGACAACGTGGATGCGGACAAAGTCATGATAACCAACGAAGAAGAAATTAA
hu.31    (1601) TCTTTCCTTTGTCTC GGATCTTTAATTTTTGGCAAACAAGGAACTGGAAGAGACAACGTGGATGCGGACAAAGTCATGATAACCAACGAAGAAGAAATTAA
hu.32    (1601) TCTTTCCTTTGTCTCGGATCTTTAATTTTTGGCAAACAAGGAACTGGAAGAGACAACGTGGATGCGGACAAAGTCATGATAACCAACGAAGAAGAAATTAA 1701                                                                                   1800
AAV9     (1701) AACTACTAACCCGGTAGCAACGGAGTCCTATGGACAAGTGGCCACAAACCAGAGTGCCCAAGCACAGGCGAGACCGGCTGGGTTCAAAACCAAGGA
hu.68.VP1(1701) AACTAC AACC A AACCCGGTAGCAACGGAGTCCTATGGACAAGTGGCCACAAACCAGAGTGCCCAAGCACAGGCGAGACCGGCTGGGTTCAAAACCAAGGA
hu.31    (1701) AACTACTAACCCGGTAGCAACGGAGTCCTATGGACAAGTGGCCACAAACCAGAGTGCCCAAGCACAGGCGAGACCGGCTGGGTTCAAAACCAAGGA
hu.32    (1701) AACTACTAACCCGGTAGCAACGGAGTCCTATGGACAAGTGGCCACAAACCAGAGTGCCCAAGCACAGGCGAGACCGGCTGGGTTCAAAACCAAGGA
```

FIG.8F

```
                 1801                                                                        1900
AAV9     (1801)  ATACTTCCGGGTATGGTTTGGCAGGAGGACAGAGATGTGTACCTGCAAGGACCCATTTGGGCCAACTTTCACCCTTCTCCGC
hu.68.VP1(1801)  ATACTTCCGGGTATGGTTTGGCAGGAGGACAGAGATGTGTACCTGCAAGGACCCATTTGGGCCAACTTTCACCCTTCTCCGC
hu.31    (1801)  ATACTTCCGGGTATGGTTTGGCAGGAGGACAGAGATGTGTACCTGCAAGGACCCATTTGGGCCAACTTTCACCCTTCTCCGC
hu.32    (1801)  ATACTTCCGGGTATGGTTTGGCAGGAGGACAGAGATGTGTACCTGCAAGGACCCATTTGGGCCAACTTTCACCCTTCTCCGC 1901                                                                        2000
AAV9     (1901)  TGATGGGAGGGGTTTGGAATGAAGCACCCGCCTCCTCAGATCCTCATCAAAAACACACCTGTACCTGCGGATCCTCCAACGGCTTCAACAAGGACAAGCT
hu.68.VP1(1901)  TGATGGGAGGGGTTTGGAATGAAGCACCCGCCTCCTCAGATCCTCATCAAAAACACACCTGTACCTGCGGATCCTCCAACGGCTTCAACAAGGACAAGCT
hu.31    (1901)  TAATGGGAGGGGTTTGGAATGAAGCACCCGCCTCCTCAGATCCTCATCAAAAACACACCTGTACCTGCGGATCCTCCAACGGCTTTCAATAAGGACAAGCT
hu.32    (1901)  TAATGGGAGGGGTTTGGAATGAAGCACCCGCCTCCTCAGATCCTCATCAAAAACACACCTGTACCTGCGGATCCTCCAACGGCTTTCAATAAGGACAAGCT 2001                                                                        2100
AAV9     (2001)  GAACTCTTTCATCACCCAGTATTCTACTGGCCAAGTCAGCGTGGAGATCGAGTGGGAGCTGCAGAAGGAAAACAGCAAGCGCTGAACCCGGAGATCCAG
hu.68.VP1(2001)  GAACTCTTTCATCACCCAGTATTCTACTGGCCAAGTCAGCGTGGAGATCGAGTGGGAGCTGCAGAAGGAAAACAGCAAGCGCTGAACCCGGAGATCCAG
hu.31    (2001)  GAACTCTTTCATCACCCAGTATTCTACTGGCCAAGTCAGCGTGGAGATTGAGTGGGAGCTGCAGAAGGAAAACAGCAAGCGCTGAACCCGGAGATCCAG
hu.32    (2001)  GAACTCTTTCATCACCCAGTATTCTACTGGCCAAGTCAGCGTGGAGATTGAGTGGGAGCTGCAGAAGGAAAACAGCAAGCGCTGAACCCGGAGATCCAG 2101                                                                        2200
AAV9     (2101)  TACACTTCCAACTATTACAAGTCTAATAATGTTGAATTTGCTGTTAATACTGAAGGTGTATATAGTGAACCCGCCCCATTGGCACCAGATACCTGACTC
hu.68.VP1(2101)  TACACTTCCAACTATTACAAGTCTAATAATGTTGAATTTGCTGTTAATACTGAAGGTGTTTATTGTGAACCCGCCCCATTGGCACCAGATACCTGACTC
hu.31    (2101)  TACACTTCCAACTATTACAAGTCTAATAATGTTGAATTTGCTGTTAATACTGAAGGTGTATATAGTGAACCCGCCCCATTGGCACCAGATACCTGACTC
hu.32    (2101)  TACACTTCCAACTATTACAAGTCTAATAATGTTGAATTTGCTGTTAATACTGAAGGTGTATATAGTGAACCCGCCCCATTGGCACCAGATACCTGACTC 2201 2211
AAV9     (2201)  GTAATCTGTAA
hu.68.VP1(2201)  GTAATCTGTAA
hu.31    (2201)  GTAATCTGTAA
hu.32    (2201)  GTAATCTGTAA
```

FIG. 8G

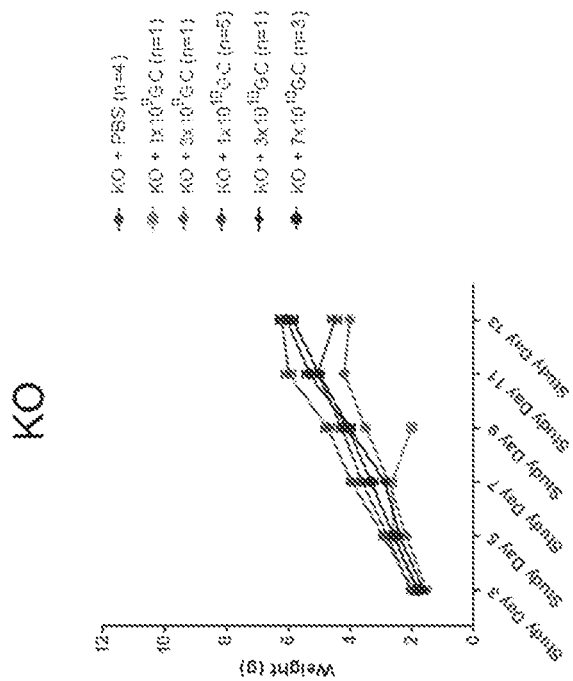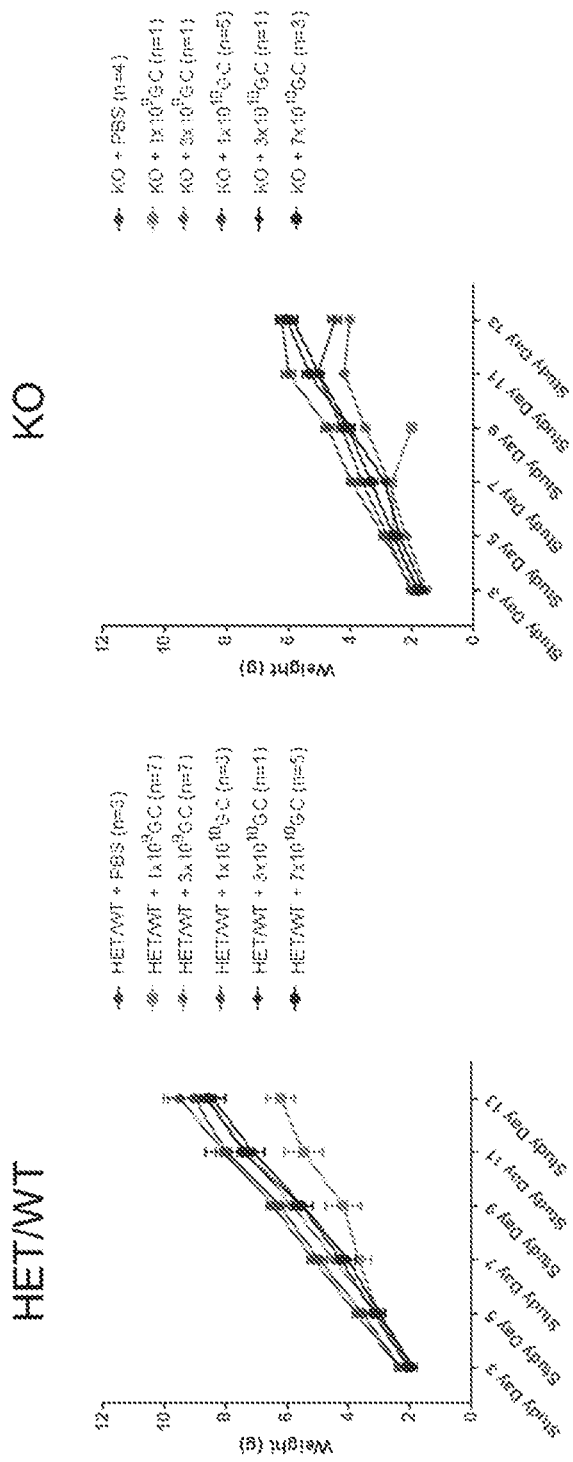

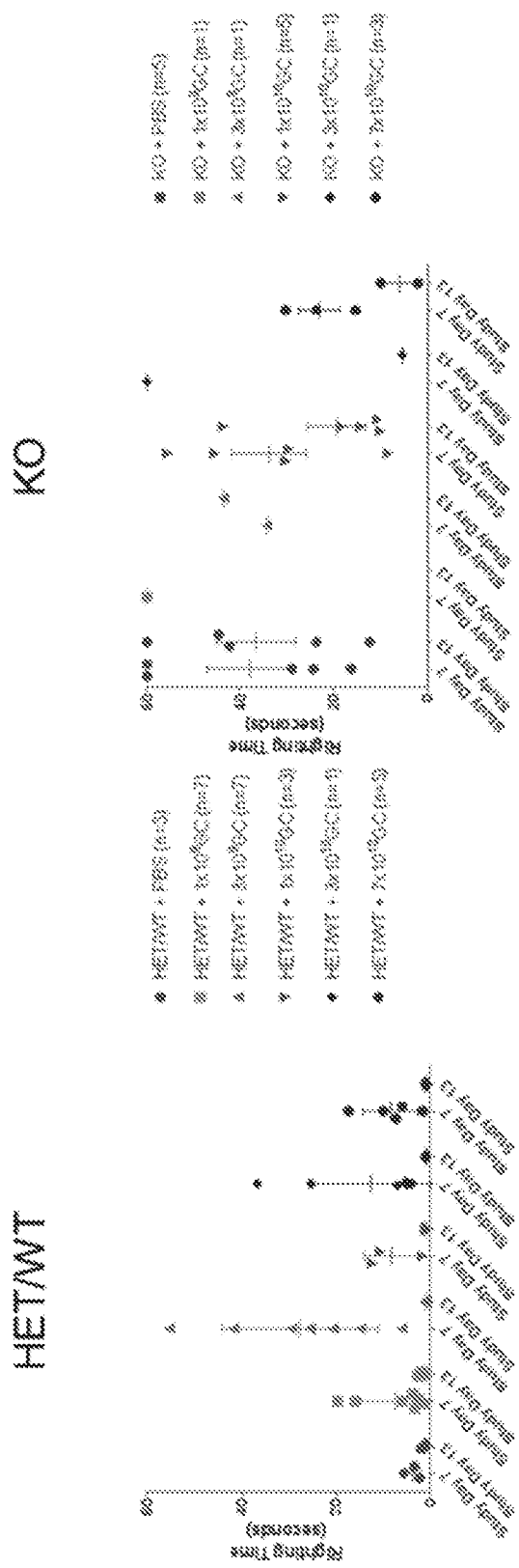

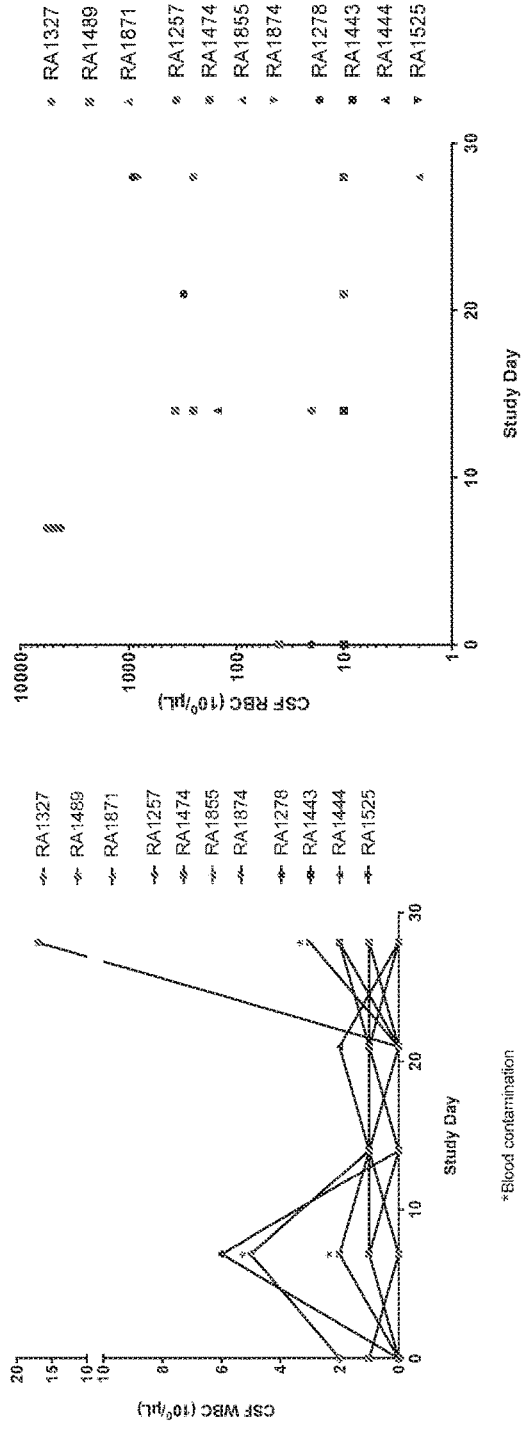
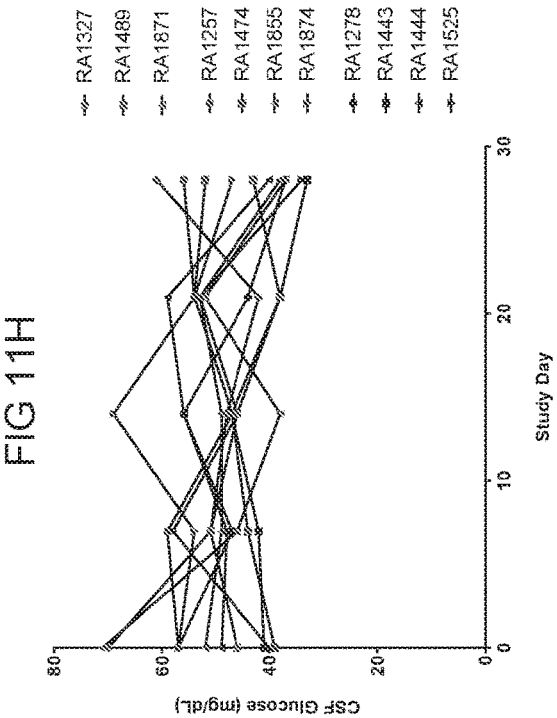
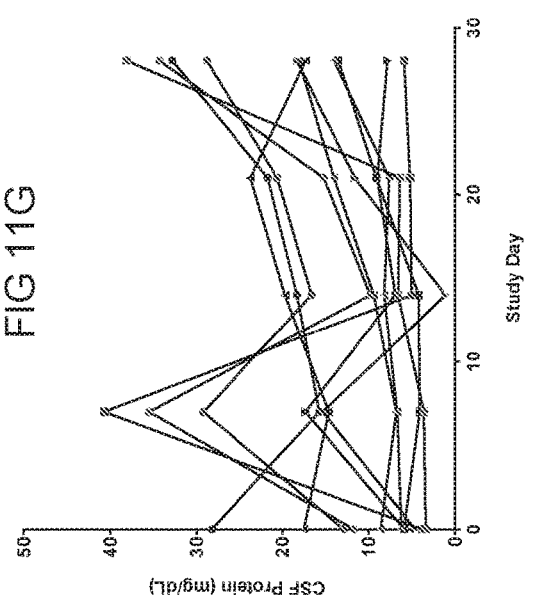

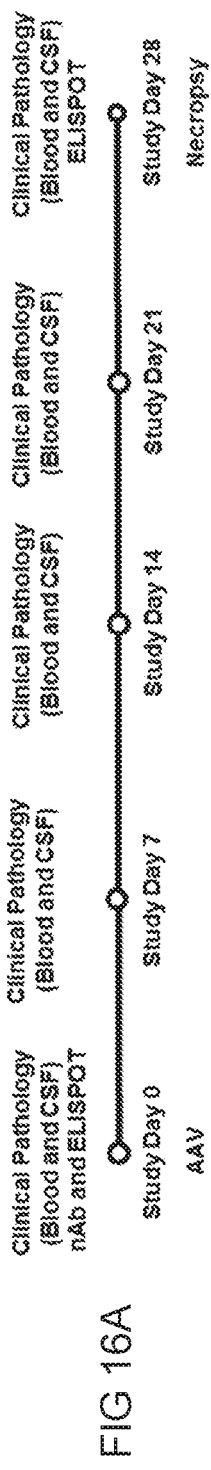
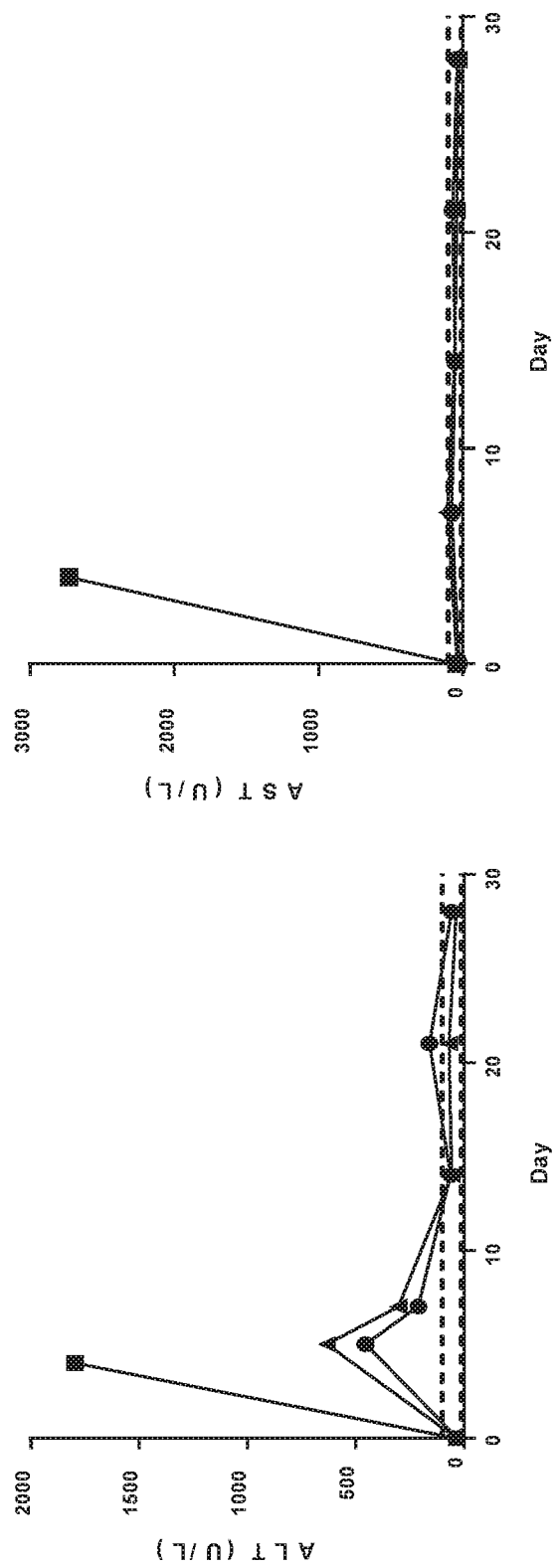

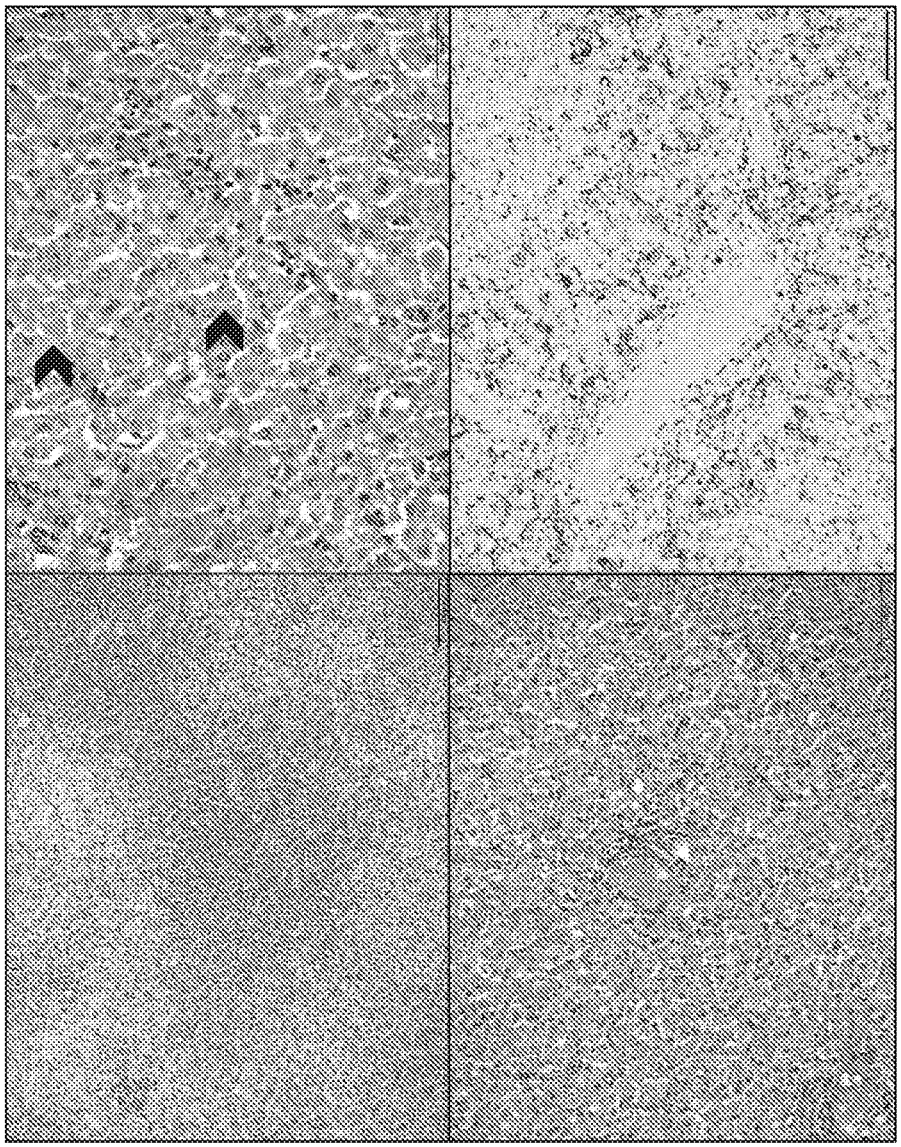

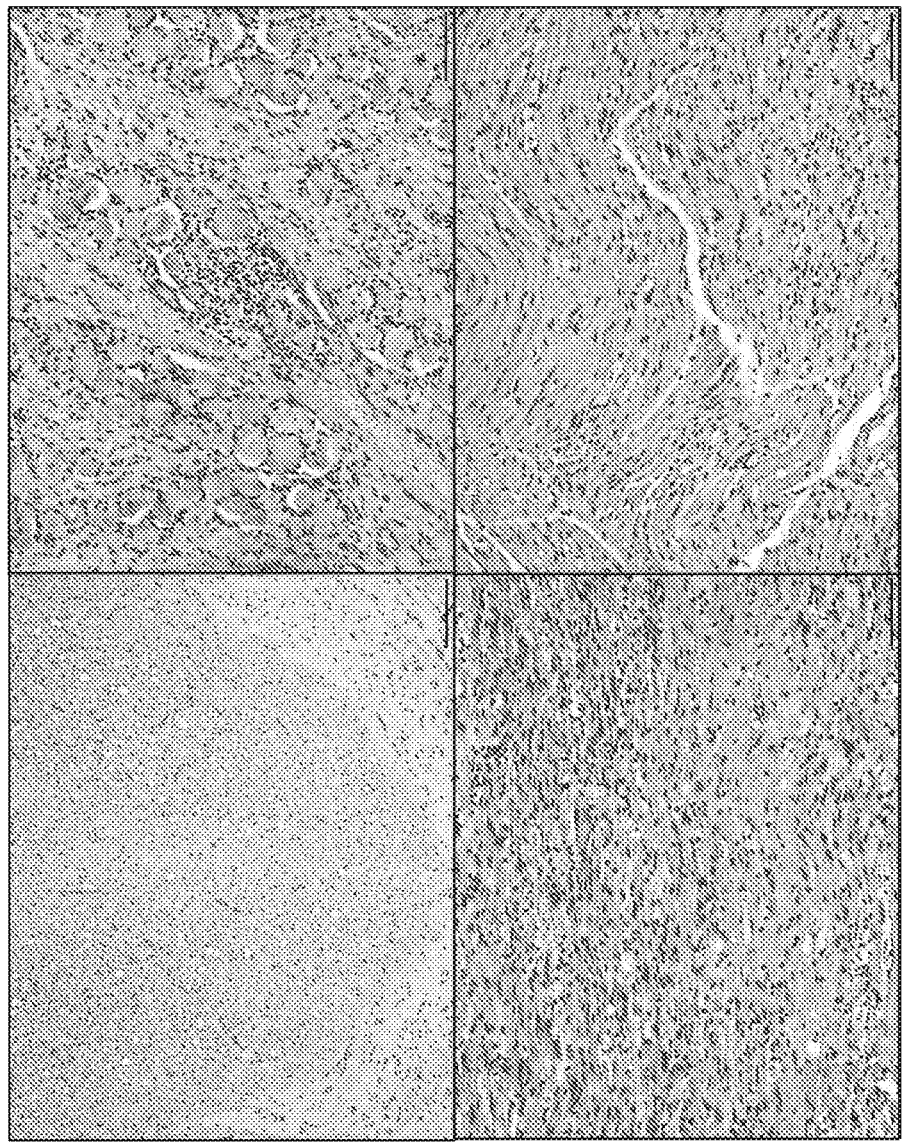

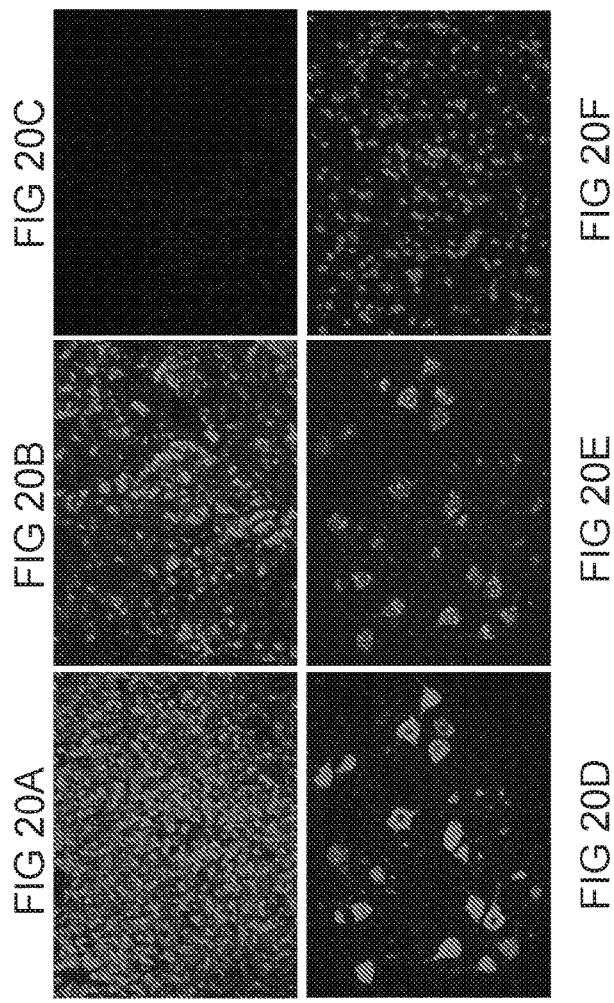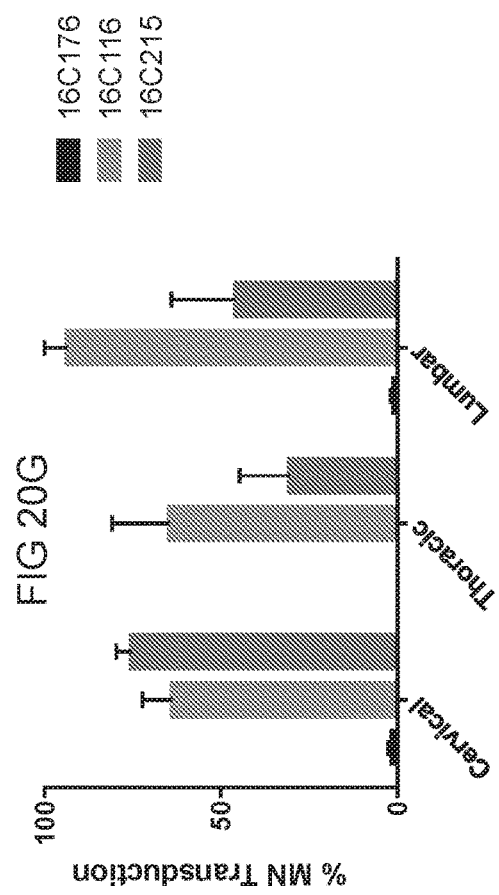

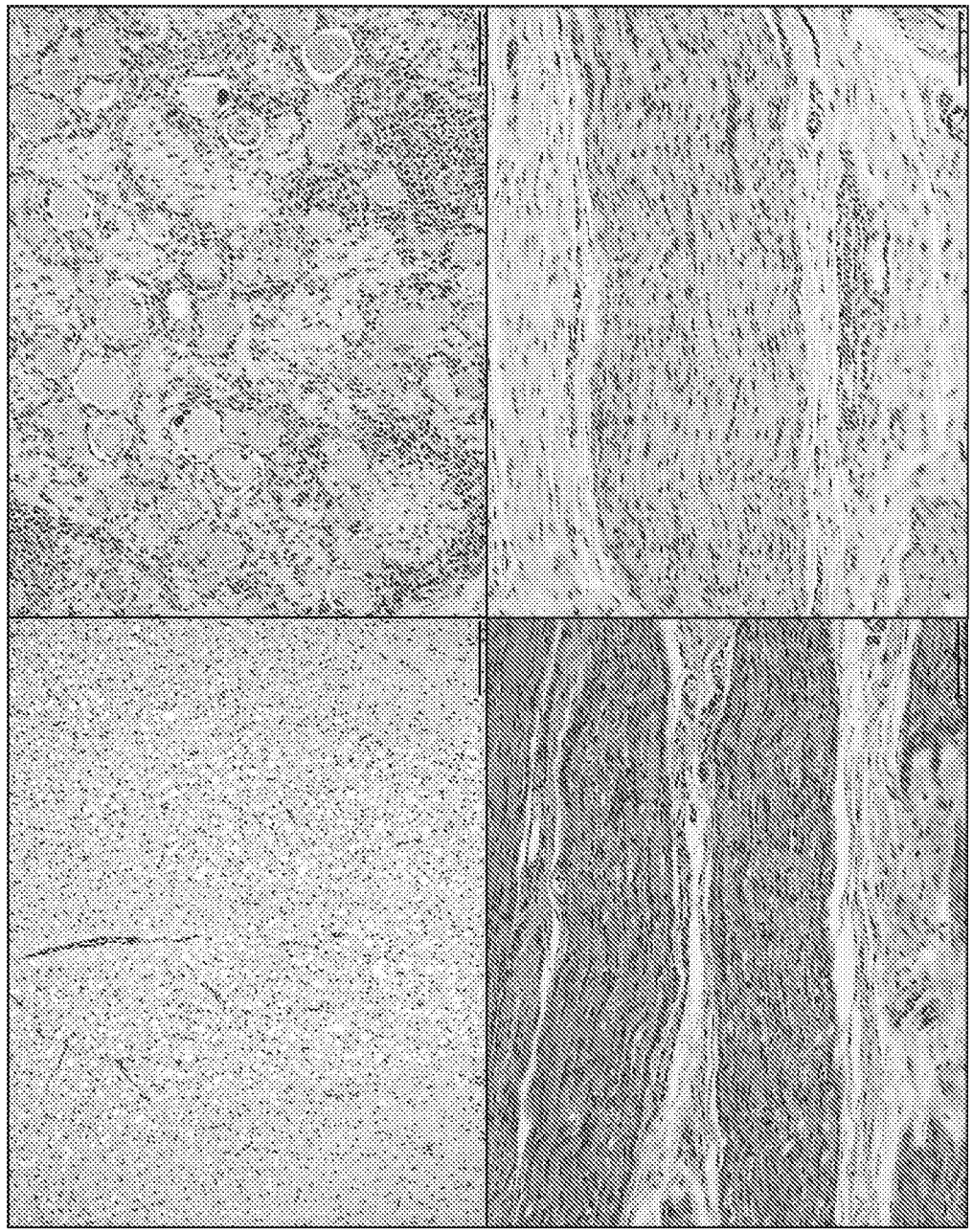

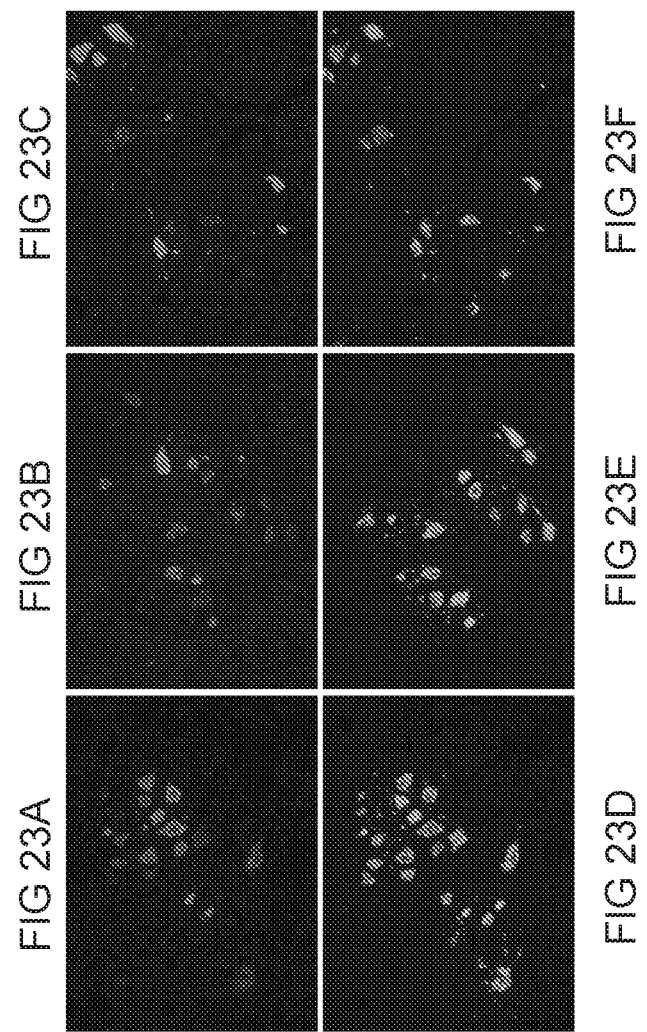

COMPOSITIONS USEFUL IN TREATMENT OF SPINAL MUSCULAR ATROPHY

BACKGROUND OF THE INVENTION

Spinal muscular atrophy (SMA) is neuromuscular disease caused by mutations in telomeric SMN1, a gene encoding a ubiquitously expressed protein (survival of motor neuron—SMN) involved in splicesome biogenesis. SMA is an autosomal recessive disorder caused by mutations or deletion of the SMN1 gene. Provision of a functioning SMN1 gene has been shown to rescue the phenotype. See, e.g., Tanguy et al, Systemic AAVrh10 provides higher transgene expression than AAV9 in the brain and the spinal cord of neonatal mice, Frontiers in Molecular Neuroscience, 8(36) (July 2015).

The International SMA Consortium classification defines several degrees of severity in the SMA phenotype, depending on the age of onset and motor development milestones. SMA 0 designation is proposed to reflect prenatal onset and severe joint contractures, facial diplegia, and respiratory failure. Type 1 (or I) SMA, Werdnig-Hoffmann I disease, is the most severe post-natal form with onset within 6 months of birth. Patients are unable to sit up and have serious respiratory dysfunction. Type 2 (or II) SMA is the intermediate form with onset within the first 2 years; children can sit up but are unable to walk. The clinical course is variable. Type 3 (or III) (also called Kugelberg-Welander disease) begins after 2 years of age and usually has a chronic evolution. Children can stand and walk unaided at least in infancy. Adult form (type 4 or IV) is the mildest, with onset after 30 years of age; few cases have been reported and its prevalence is not accurately known.

Many inherited and acquired neuromuscular diseases involve degeneration of lower motor neurons. One of the most common and devastating examples is spinal muscular atrophy (SMA), an inherited deficiency of the survival of motor neuron (SMN) protein characterized by selective death of lower motor neurons, progressive weakness, and often death in early childhood. For unclear reasons SMN deficiency results in selective toxicity to lower motor neurons, resulting in progressive neuron loss and muscle weakness. The severity of the disease is modified by the copy number of a centromeric duplication of the homologous gene (SMN2), which carries a splice site mutation that results in production of only small amounts of the full length SMN transcript. Patients who carry 1-2 copies of SMN2 present with the severe form of SMA, characterized by onset in the first few months of life and rapid progression to respiratory failure. Patients with 3 copies of SMN2 generally exhibit an attenuated form of the disease, typically presenting after six months of age. Though many never gain the ability to walk, they rarely progress to respiratory failure, and often live into adulthood. Patients with four SMN2 copies may not present until adulthood with gradual onset of muscle weakness. There is no current treatment for SMA other than palliative care.

The clear correlation between SMN expression and disease severity as well as the relatively small number of affected cells make SMA an excellent target for gene therapy. Previous studies have demonstrated that the SMA phenotype can be rescued in transgenic mouse models using systemic injection of AAV vector serotypes with the ability to cross the blood-brain barrier. See, e.g., Tanguy et al, Systemic AAVrh10 provides higher transgene expression than AAV9 in the brain and the spinal cord of neonatal mice, Frontiers in Molecular Neuroscience, 8(36) (July 2015). Passini et al, HGT, 2014 reported a dose dependent increase in survival up to 200 days in SMN$\Delta$7 mice using an scAAV9.GusB.SMN1 vector. Meyer et al, Molecular Therapy, 2014 reported a dose dependent increase in survival up to 450 days using a scAAV9.CBA.SMN1 vector at dosages of $2.7 \times 10^9$ GC/pup to $3.3 \times 10^{10}$ GC/pup. However, the lower dosages showed very little improvement. See also, Passini et al, JCI, 2010 and Passini et al, Sci Trans Med, 2011. Each of these documents is incorporated herein by reference.

Effective treatments for SMA are still needed.

SUMMARY OF THE INVENTION

In one aspect, a recombinant adeno-associated viral (rAAV) vector comprising an AAVhu68 capsid and at least one expression cassette is provided, wherein the at least one expression cassette comprises nucleic acid sequences encoding a functional SMN protein and expression control sequences that direct expression of the SMN sequences in a host cell, wherein the AAVhu68 capsid comprises a population of AAVhu68vp1 capsid proteins having an amino acid sequence independently selected from an proteins produced encoded by SEQ ID NO: 7 or having the amino acid sequence of SEQ ID NO: 8. In certain embodiments, the AAVhu68 capsid has a heterogenous population of vp1 proteins. In certain embodiments the AAVhu68 capsid has a heterogenous population of vp2 proteins. In certain embodiments the AAVhu68 capsid has a heterogenous population of vp3 proteins. In one embodiment, the AAVhu68 capsid protein coding sequence has the sequence of SEQ ID NO: 7. In one embodiment, the SMA coding sequence has the sequence of SEQ ID NO: 1.

An rAAV vector is further provided comprising an AAVhu68 capsid which has packaged therein a nucleic acid molecule comprising an AAV 5' ITR, a CB7 promoter, an intron, nucleic acid sequences of SEQ ID NO:1, a polyA, and an AAV 3' inverted terminal repeat sequence, wherein the AAVhu68 capsid comprises a population of vp1 proteins, a population of vp2 and a population of vp3 proteins, wherein the AAVhu68 capsid proteins have amino acid sequences independently selected from proteins produced by SEQ ID NO: 7 capsid proteins having the amino acid sequence of the vp1, vp2 and/or vp3 of SEQ ID NO: 8. In certain embodiments, the AAVhu68 capsid has a heterogenous population of vp1 proteins. In certain embodiments the AAVhu68 capsid has a heterogenous population of vp2 proteins. In certain embodiments the AAVhu68 capsid has a heterogenous population of vp3 proteins.

A pharmaceutical composition is provided which contains an AAVhu68 vector such as described above. In addition to at least one vector stock, the composition further contains at least one of a pharmaceutically acceptable carrier, excipient and/or preservative.

Further provided is a method for treating spinal muscular atrophy in a subject in need thereof, using a rAAVhu68.SMA vector or another delivery vehicle for the engineered hSMN provided herein. In certain embodiments, the compositions provided herein may be administered intrathecally.

In certain embodiments, a rAAVhu68.SMN1 is provided as described herein or a composition for use in treating spinal muscular atrophy in a patient, optionally in a co-therapy. In certain embodiments, the patient has SMA type 3. In certain embodiments, the composition is formulated for intrathecal delivery.

Use of an rAAVhu68.SMA as described herein, or a composition containing same, for treating a patient with SMA is provided, optionally in a co-therapeutic regimen. Such a composition may be formulated for intrathecal delivery.

Other aspects and advantages of the invention will be readily apparent from the following detailed description of the invention.

BRIEF DESCRIPTION OF THE DRAWINGS

FIG. 1A is a Schematic representation of the AAVhu68.CB7.CI.hSMN1co.RBG vector genome. ITR represents an AAV2 inverted terminal repeat. CB7 represents a chicken beta actin promoter with cytomegalovirus enhancer. RBG PolyA represents a rabbit beta globin polyadenylation signal.

FIGS. 1B-1C are an alignment of native hSMN1, variant D (Accession no. NM_000344.3) (SEQ ID NO: 3) vs. the codon optimized sequence described herein (SEQ ID NO: 1).

FIG. 8A to 8B provides an alignment showing the amino acid sequence of the vp1 capsid sequences encoded by the nucleic acid sequences of FIGS. 8B-8D. The alignment includes the vp1 protein of AAVhu68 [SEQ ID NO: 8], with AAV9 [SEQ ID NO: 16], AAVhu31 (labelled hu.31 in alignment) [SEQ ID NO: 18] and AAVhu32 (labelled hu.32 in alignment) [SEQ ID NO: 19]. Compared to AAV9, AAVhu31 and AAVhu32, two mutations (A67E and A157V) were found critical in AAVhu68 and are circled in the figure.

FIGS. 8C to 8G provide an alignment of the nucleic acid sequence encoding the vp1 capsid of AAVhu68 [SEQ ID NO: 7], with AAV9 [SEQ ID NO: 22], AAVhu31 [SEQ ID NO: 20] and AAVhu32 [SEQ ID NO: 21].

FIGS. 9A-9B are graphs showing weight monitoring results in adult wild-type mice (HET/WT, FIG. 9A) or SMNΔ7 mice (KO, FIG. 9B) treated ICV with AAVhu68.CB7.CI.hSMN1.RBG at various doses ($1 \times 10^9$ GC, WT, n=7, KO, n=1; $3 \times 10^9$ GC, WT, n=7, KO, n=1; $1 \times 10^{10}$ GC, WT, n=3, KO, n=5; $3 \times 10^{10}$ GC, WT, n=1, KO, n=1; or $7 \times 10^{10}$ GC, WT, n=5, KO, n=3). PBS injected animal (WT, n=3; KO, n=4) were provided as control.

FIGS. 10A-10B are graphs showing righting reflex results in adult wild-type mice (HET/WT, FIG. 10A) or SMNΔ7 mice (KO, FIG. 10B) treated ICV with AAVhu68.CB7.CI.hSMN1.RBG at various doses ($1 \times 10^9$ GC, WT, n=7, KO, n=1; $3 \times 10^9$ GC, WT, n=7, KO, n=1; $1 \times 10^{10}$ GC, WT, n=3, KO, n=5; $3 \times 10^{10}$ GC, WT, n=1, KO, n=1; or $7 \times 10^{10}$ GC, WT, n=5, KO, n=3). PBS injected animal (WT, n=3; KO, n=5) were provided as control.

FIGS. 11A-11H are graphs showing clinical pathology, CSF Chemistry, and CSF cytology in adult Rhesus Macaques treated intrathecally with AAVhu68.CB7.CI.hSMN1co.RBG as described in Example 10.

FIG. 14A provides weight monitoring results in female subjects. FIG. 14B provides weight monitoring results in male subjects.

FIGS. 16A-16E provide graphs showing acute transaminase elevations following intravenous administration of an AAV vector expressing human SMN to nonhuman primates. FIG. 16A provides the study design as described in Example 14. FIG. 16B provides a plot of serum ALT. FIG. 16C provides a plot of serum AST. FIG. 16D provides a plot of serum alkaline phosphatase. FIG. 16E provides a plot of serum total bilirubin. Unscheduled laboratory assessments were performed for all animals on study day 5 after animal 16C176 developed acute liver failure requiring euthanasia. AST was not performed on study day 5 for animals 16C116 and 16C215. Dashed lines indicate laboratory reference range.

FIGS. 17A-17D provide representative IHC images showing liver histopathologic findings for animal 16C176. Massive acute hepatocellular necrosis (FIG. 17A) with sinusoidal fibrin deposition (FIG. 17B, arrowheads) and acute fibrin thrombi (FIG. 17C) in portal veins (Hematoxylin and eosin; Scale bar=10 µm (FIGS. 17A and 17C), 50 µm (FIG. 17B)) Immunohistochemistry for fibrinogen depicts prominent periportal sinusoidal fibrin deposition (FIG. 17D) (Fibrinogen IHC, Scale bar represents 100 µm (FIG. 17D)).

FIGS. 18A-18D provide representative nervous system histopathologic findings in infant NHPs treated with intravenous (IV) AAVhu68 expressing human SMN 28 days post injection. Both animals had an axonopathy of the dorsal white matter tracts of the spinal cord (FIG. 18A). The dorsal axonopathy was typically bilateral and characterized by dilated myelin sheaths with and without myelomacrophages, consistent with axonal degeneration. The dorsal root ganglia of the spinal cord (FIG. 18B) exhibited minimal to mild neuronal cell body degeneration characterized by central chromatolysis, satellitosis and mononuclear cell infiltrates that surrounded and invaded neuronal cell bodies (neuronophagia). A similar axonopathy was observed in the peripheral nerves of the hindlimb (sciatic nerve, FIG. 18C) and forelimb (median nerve, FIG. 18D). The animal (16C176) that was euthanized at Day 5 for acute liver failure had no findings in the nervous system. (Hematoxylin and eosin staining; Scale bar=200 µm (FIG. 18A), 100 µm (FIGS. 18B-18D))

FIGS. 20A-20G show SMN expression in rhesus macaques, Human SMN RNA was detected by ISH in liver (FIG. 20A). Liver was stained with control probes for albumin (FIG. 20B) and GFP (FIG. 20C). SMN expressing cells were identified by ISH in spinal cord (FIG. 20D). Motor neurons were identified by ChAT ISH (FIG. 20E). Rare patches of transduced neurons were detected by SMN ISH in the brain (FIG. 20F, DAPI nuclear stain). The percentage of ChAT+ motor neurons transduced at each level of spinal cord was quantified (FIG. 20G). Error bars=SEM.

FIGS. 21A-21D provide representative histopathologic findings of piglets treated with intravenous AAVhu68 expressing human SMN at 7 and 30 days of age. Throughout both groups, an axonopathy of the dorsal white matter tracts of the spinal cord was observed (FIG. 21A). The dorsal axonopathy was bilateral and characterized by dilated myelin sheaths with and without myelomacrophages, consistent with axonal degeneration. The dorsal root ganglia of the spinal cord (FIG. 21B) exhibited varying degrees of neuronal cell body degeneration characterized by central chromatolysis, satellitosis and mononuclear cell infiltrates that surrounded and invaded neuronal cell bodies (neuronophagia). A similar axonopathy was observed to varying degrees in the peripheral nerves of the hindlimb (sciatic nerve, FIG. 21C) and forelimb (median nerve, FIG. 21D) in the majority of piglets. (Hematoxylin and eosin; Scale bar=200 µm (FIG. 21A), 100 µm (FIGS. 21B-21D))

FIGS. 23A-23F provide representative images showing SMN expression in spinal cord of piglets. Human SMN RNA was detected by ISH in cervical (FIG. 23A) thoracic (FIG. 23B) and lumbar (FIG. 23C) spinal cord segments. Motor neurons were identified by ChAT ISH in corresponding sections (FIGS. 23D-23F). Representative images are shown.

DETAILED DESCRIPTION OF THE INVENTION

Figure 2:
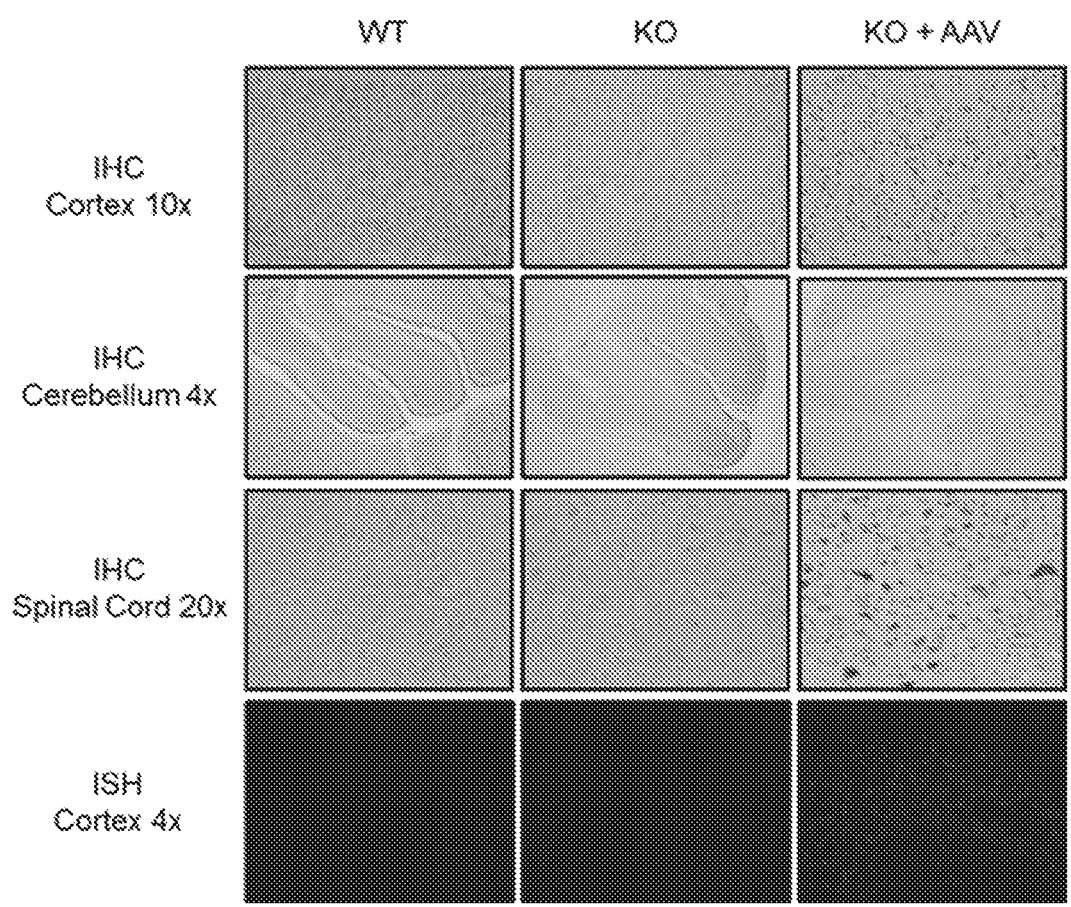
FIG. 2 is an assessment of transduction in brain and spinal cord by immunohistochemistry (IHC) and in situ hybridization (ISH) Immunohistochemistry of SMN1 was performed on cortex, cerebellum and spinal cord sections and representative images are displayed in the top three panels. ISH for the codon-optimized hSMN1 ribonucleic acid (RNA) was conducted in the cortex sections and representative results are shown in the bottom panel. Samples were collected from SMNΔ7 (KO) mice treated with or without $3 \times 10^{10}$ GC of AAVhu68.CB7.CI.hSMN1.RBG per pup. Wild-type (WT) and heterozygous (Het) littermates served as positive controls.

A recombinant AAVhu68 vector having a AAVhu68 capsid and nucleic acid encoding a survival of motor neuron (SMN) gene under control of regulatory sequences directing expression thereof in patients in need thereof is provided herein. The rAAVhu68 capsid contains proteins independently having the amino acid sequence produced from SEQ ID NO: 7 and/or having the amino acid sequence of SEQ ID NO: 8. Compositions containing these vectors are provided, as are use of these vectors in compositions for treatment of SMA patients. Although the examples focus on treatment of SMA 3(sometimes called Kugelberg-Welander disease), use of these rAAV vectors alone or in combination with other co-therapies is contemplated for SMA types 1, 2, or 4. SMA may be diagnosed using a blood test for a deletion mutation in the SMN1 gene on chromosome 5. Further muscle tests such as electromyogram or muscle biopsy may be used to assist in diagnosis.

I. AAV

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, J Virol, 2004 June; 78(10: 6381-6388, which identifies Clades A, B, C, D, E and F, and provides nucleic acid sequences of novel AAV, GenBank Accession Numbers AY530553 to AY530629. See, also, WO 2005/033321.

As used herein, an "AAV9 capsid" is a self-assembled AAV capsid composed of multiple AAV9 vp proteins. The AAV9 vp proteins are typically expressed as alternative splice variants encoded by a nucleic acid sequence of SEQ ID NO: 22 or a sequence at least 70%, at least 75%, at least 80%, at least 85%, at least 90%, at least 95%, at least 97%, at least 99% thereto, which encodes the vp1 amino acid sequence of SEQ ID NO: 16 (GenBank accession: AAS99264). These splice variants result in proteins of different length of SEQ ID NO: 16. In certain embodiments, "AAV9 capsid" includes an AAV having an amino acid sequence which is 99% identical to AAS99264 or 99% identical to SEQ ID NO: 16. See, also, U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809.

A rAAVhu68 is composed of an AAVhu68 capsid and a vector genome. An AAVhu68 capsid is an assembly of a heterogenous population of vp1, a heterogenous population of vp2, and a heterogenous population of vp3 proteins. As used herein when used to refer to vp capsid proteins, the term "heterogenous" or any grammatical variation thereof, refers to a population consisting of elements that are not the same, for example, having vp1, vp2 or vp3 monomers (proteins) with different modified amino acid sequences. SEQ ID NO: 8 provides the encoded amino acid sequence of the AAVhu68 vp1 protein. See, also, U.S. Provisional Patent Applications Nos. 62/614,002, 62/591,002 and 62/464,748, each of which is entitled "Novel Adeno-Associated Virus (AAV) Clade F Vector and Uses Therefor", and which are incorporated herein by reference in its entirety.

The AAVhu68 capsid contains subpopulations within the vp1 proteins, within the vp2 proteins and within the vp3 proteins which have modifications from the predicted amino acid residues in SEQ ID NO:8. These subpopulations include, at a minimum, certain deamidated asparagine (N or Asn) residues. For example, certain subpopulations comprise at least one, two, three or four highly deamidated asparagines (N) positions in asparagine-glycine pairs in SEQ ID NO: 8 and optionally further comprising other deamidated amino acids, wherein the deamidation results in an amino acid change and other optional modifications. SEQ ID NO: 26 provides the amino acid sequence of a modified AAVhu68 capsid, illustrating residue positions which may be deamidated or otherwise modified.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine-glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, 97%, 99%, up to about 100% deamidated at a referenced amino acid position, as compared to the predicted amino acid sequence at the reference amino acid position (e.g., at least 80% of the asparagines at amino acid 57 of SEQ ID NO:8 may be deamidated based on the total vp1 proteins or 20% of the asparagines at amino acid 409 of SEQ ID NO: 8 may be deamidated based on the total vp1, vp2 and vp3 proteins). Such percentages may be determined using 2D-gel, mass spectrometry techniques, or other suitable techniques.

Without wishing to be bound by theory, the deamidation of at least highly deamidated residues in the vp proteins in the AAVhu68 capsid is believed to be primarily non-enzymatic in nature, being caused by functional groups within the capsid protein which deamidate selected asparagines, and to a lesser extent, glutamine residues. Efficient capsid assembly of the majority of deamidation vp1 proteins indicates that either these events occur following capsid assembly or that deamidation in individual monomers (vp1, vp2 or vp3) is well-tolerated structurally and largely does not affect assembly dynamics. Extensive deamidation in the VP1-unique (VP1-u) region (~aa 1-137), generally considered to be located internally prior to cellular entry, suggests that VP deamidation may occur prior to capsid assembly.

Without wishing to be bound by theory, the deamidation of N may occur through its C-terminus residue's backbone nitrogen atom conducts a nucleophilic attack to the Asn's side chain amide group carbon atom. An intermediate ring-closed succinimide residue is believed to form. The succinimide residue then conducts fast hydrolysis to lead to the final product aspartic acid (Asp) or iso aspartic acid (IsoAsp). Therefore, in certain embodiments, the deamidation of asparagine (N or Asn) leads to an Asp or IsoAsp, which may interconvert through the succinimide intermediate e.g., as illustrated below.

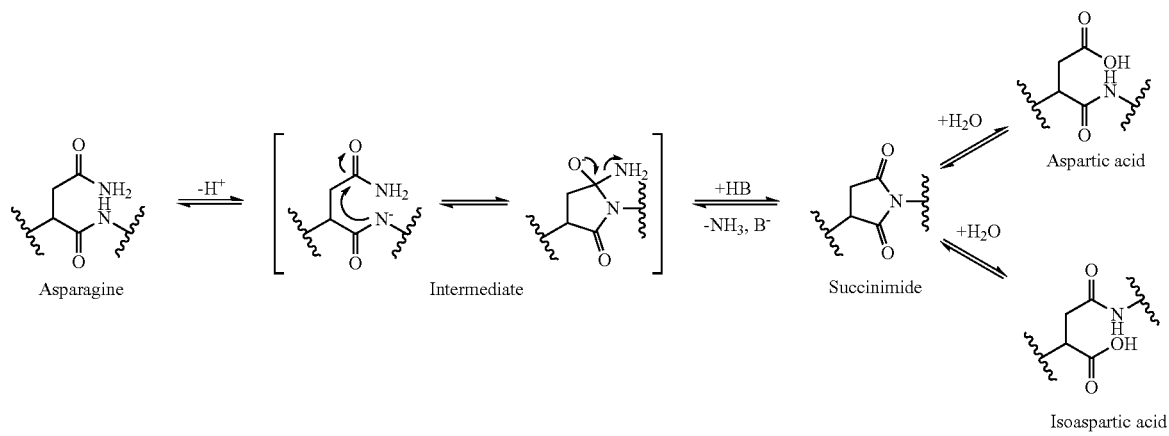

As provided herein, each deamidated N of SEQ ID NO: 8 may independently be aspartic acid (Asp), isoaspartic acid (isoAsp), aspartate, and/or an interconverting blend of Asp and isoAsp, or combinations thereof. Any suitable ratio of α- and isoaspartic acid may be present. For example, in certain embodiments, the ratio may be from 10:1 to 1:10 aspartic to isoaspartic, about 50:50 aspartic: isoaspartic, or about 1:3 aspartic: isoaspartic, or another selected ratio.

In certain embodiments, one or more glutamine (Q) in SEQ ID NO: 8 deamidates to glutamic acid (Glu), i.e., α-glutamic acid, γ-glutamic acid (Glu), or a blend of α- and γ-glutamic acid, which may interconvert through a common glutarinimide intermediate. Any suitable ratio of α- and γ-glutamic acid may be present. For example, in certain embodiments, the ratio may be from 10:1 to 1:10 α to γ, about 50:50 α:γ, or about 1:3 α:γ, or another selected ratio.

In certain embodiments, an AAVhu68 capsid contains subpopulations of vp1, vp2 and vp3 having at least 4 to at least about 25 deamidated amino acid residue positions, of which at least 1 to 10% are deamidated as compared to the encoded amino acid sequence of SEQ ID NO: 8. The majority of these may be N residues. However, Q residues may also be deamidated.

In certain embodiments, an AAV68 capsid is further characterized by one or more of the following. AAV hu68 capsid proteins comprise: AAVhu68 vp1 proteins produced by expression from a nucleic acid sequence which encodes the predicted amino acid sequence of 1 to 736 of SEQ ID NO:8, vp1 proteins produced from SEQ ID NO:7, or vp1 proteins produced from a nucleic acid sequence at least 70% identical to SEQ ID NO:7 which encodes the predicted amino acid sequence of 1 to 736 of SEQ ID NO:8; AAVhu68

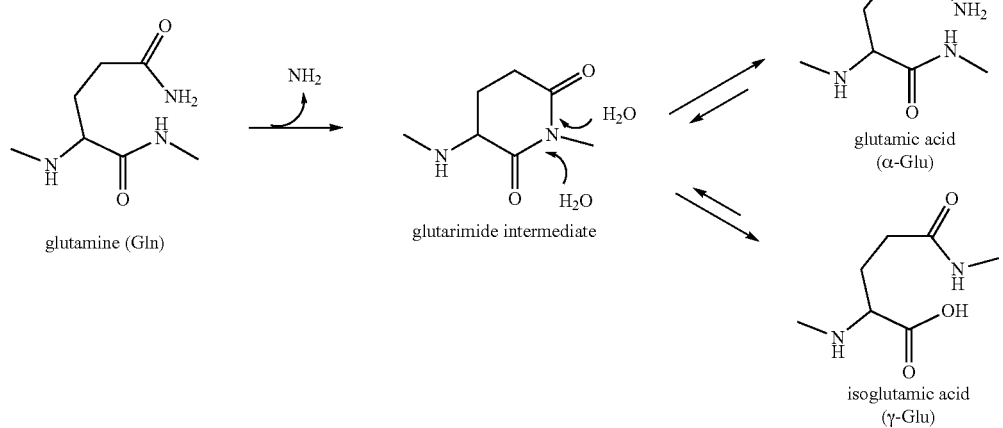

Thus, an rAAVhu68 includes subpopulations within the rAAVhu68 capsid of vp1, vp2 and/or vp3 proteins with deamidated amino acids, including at a minimum, at least one subpopulation comprising at least one highly deamidated asparagine. In addition, other modifications may include isomerization, particularly at selected aspartic acid (D or Asp) residue positions. In still other embodiments, modifications may include an amidation at an Asp position.

vp2 proteins produced by expression from a nucleic acid sequence which encodes the predicted amino acid sequence of at least about amino acids 138 to 736 of SEQ ID NO:8, vp2 proteins produced from a sequence comprising at least nucleotides 412 to 2211 of SEQ ID NO:7, or vp2 proteins produced from a nucleic acid sequence at least 70% identical to at least nucleotides 412 to 2211 of SEQ ID NO:7 which encodes the predicted amino acid sequence of at least about amino acids 138 to 736 of SEQ ID NO:8, and/or AAVhu68 vp3 proteins produced by expression from a nucleic acid sequence which encodes the predicted amino acid sequence of at least about amino acids 203 to 736 of SEQ ID NO:8, vp3 proteins produced from a sequence comprising at least nucleotides 607 to 2211 of SEQ ID NO:7, or vp3 proteins produced from a nucleic acid sequence at least 70% identical to at least nucleotides 607 to 2211 of SEQ ID NO:7 which encodes the predicted amino acid sequence of at least about amino acids 203 to 736 of SEQ ID NO:8.

Additionally or alternatively, an AAV capsid is provided which comprise a heterogenous population of vp1 proteins, a heterogenous population of vp2 proteins optionally comprising a valine at position 157, and a heterogenous population of vp3 proteins, wherein at least a subpopulation of the vp1 and vp2 proteins comprise a valine at position 157 and optionally further comprising a glutamic acid at position 67 based on the numbering of the vp1 capsid of SEQ ID NO:8. Additionally or alternatively, an AAVhu68 capsid is provided which comprises a heterogenous population of vp1 proteins which are the product of a nucleic acid sequence encoding the amino acid sequence of SEQ ID NO: 8, a heterogenous population of vp2 proteins which are the product of a nucleic acid sequence encoding the amino acid sequence of at least about amino acids 138 to 736 of SEQ ID NO: 8, and a heterogenous population of vp3 proteins which are the product of a nucleic acid sequence encoding at least amino acids 203 to 736 of SEQ ID NO: 8, wherein: the vp1, vp2 and vp3 proteins contain subpopulations with amino acid modifications The AAVhu68 vp1, vp2 and vp3 proteins are typically expressed as alternative splice variants encoded by the same nucleic acid sequence which encodes the full-length vp1 amino acid sequence of SEQ ID NO: 8 (amino acid 1 to 736). Optionally the vp1-encoding sequence is used alone to express the vp1, vp2 and vp3 proteins. Alternatively, this sequence may be co-expressed with one or more of a nucleic acid sequence which encodes the AAVhu68 vp3 amino acid sequence of SEQ ID NO: 8 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 7), or a sequence at least 70% to at least 99% (e.g., at least 85%, at least 90%, at least 95%, at least 97%, at least 98% or at least 99%) identical to SEQ ID NO: 7 which encodes aa 203 to 736 of SEQ ID NO: 8. Additionally, or alternatively, the vp1-encoding and/or the vp2-encoding sequence may be co-expressed with the nucleic acid sequence which encodes the AAVhu68 vp2 amino acid sequence of SEQ ID NO: 8 (about aa 138 to 736) without the vp1-unique region (about aa 1 to about 137), or a strand complementary thereto, the corresponding mRNA or tRNA (nt 412 to 2211 of SEQ ID NO: 7), or a sequence at least 70% to at least 99% (e.g., at least 85%, at least 90%, at least 95%, at least 97%, at least 98% or at least 99%) identical to SEQ ID NO: 7 which encodes about aa 138 to 736 of SEQ ID NO: 8.

As described herein, a rAAVhu68 has a rAAVhu68 capsid produced in a production system expressing capsids from an AAVhu68 nucleic acid which encodes the vp1 amino acid sequence of SEQ ID NO: 8, and optionally additional nucleic acid sequences, e.g., encoding a vp3 protein free of the vp1 and/or vp2-unique regions. The rAAVhu68 resulting from production using a single nucleic acid sequence vp1 produces the heterogenous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO: 8. These subpopulations include, at a minimum, deamidated asparagine (N or Asn) residues. For example, asparagines in asparagine-glycine pairs are highly deamidated.

In one embodiment, the AAVhu68 vp1 nucleic acid sequence has the sequence of SEQ ID NO: 7, or a strand complementary thereto, e.g., the corresponding mRNA or tRNA. In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 8 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 7). In certain embodiments, also provided is a nucleic acid sequence which encodes the AAVhu68 vp2 amino acid sequence of SEQ ID NO: 8 (about aa 138 to 736) without the vp1-unique region (about aa 1 to about 137), or a strand complementary thereto, the corresponding mRNA or tRNA (nt 412 to 2211 of SEQ ID NO: 7).

However, other nucleic acid sequences which encode the amino acid sequence of SEQ ID NO: 8 may be selected for use in producing rAAVhu68 capsids. In certain embodiments, the nucleic acid sequence has the nucleic acid sequence of SEQ ID NO: 7 or a sequence at least 70% to 99% identical, at least 75%, at least 80%, at least 85%, at least 90%, at least 95%, at least 97%, at least 99%, identical to SEQ ID NO: 7 which encodes SEQ ID NO: 8. In certain embodiments, the nucleic acid sequence has the nucleic acid sequence of about nt 412 to about nt 2211 of SEQ ID NO: 7 or a sequence at least 70% to 99%, at least 75%, at least 80%, at least 85%, at least 90%, at least 95%, at least 97%, at least 99%, identical to about nt 412 to about nt 2211 of SEQ ID NO: 7 which encodes the vp2 capsid protein (about aa 138 to 736) of SEQ ID NO: 8. In certain embodiments, the nucleic acid sequence has the nucleic acid sequence of about nt 607 to about nt 2211 of SEQ ID NO:7 or a sequence at least 70% to 99.%, at least 75%, at least 80%, at least 85%, at least 90%, at least 95%, at least 97%, at least 99%, identical to about nt 607 to about nt 2211 of SEQ ID NO: 7 which encodes the vp3 capsid protein (about aa 203 to 736) of SEQ ID NO: 8.

Figure 8C:
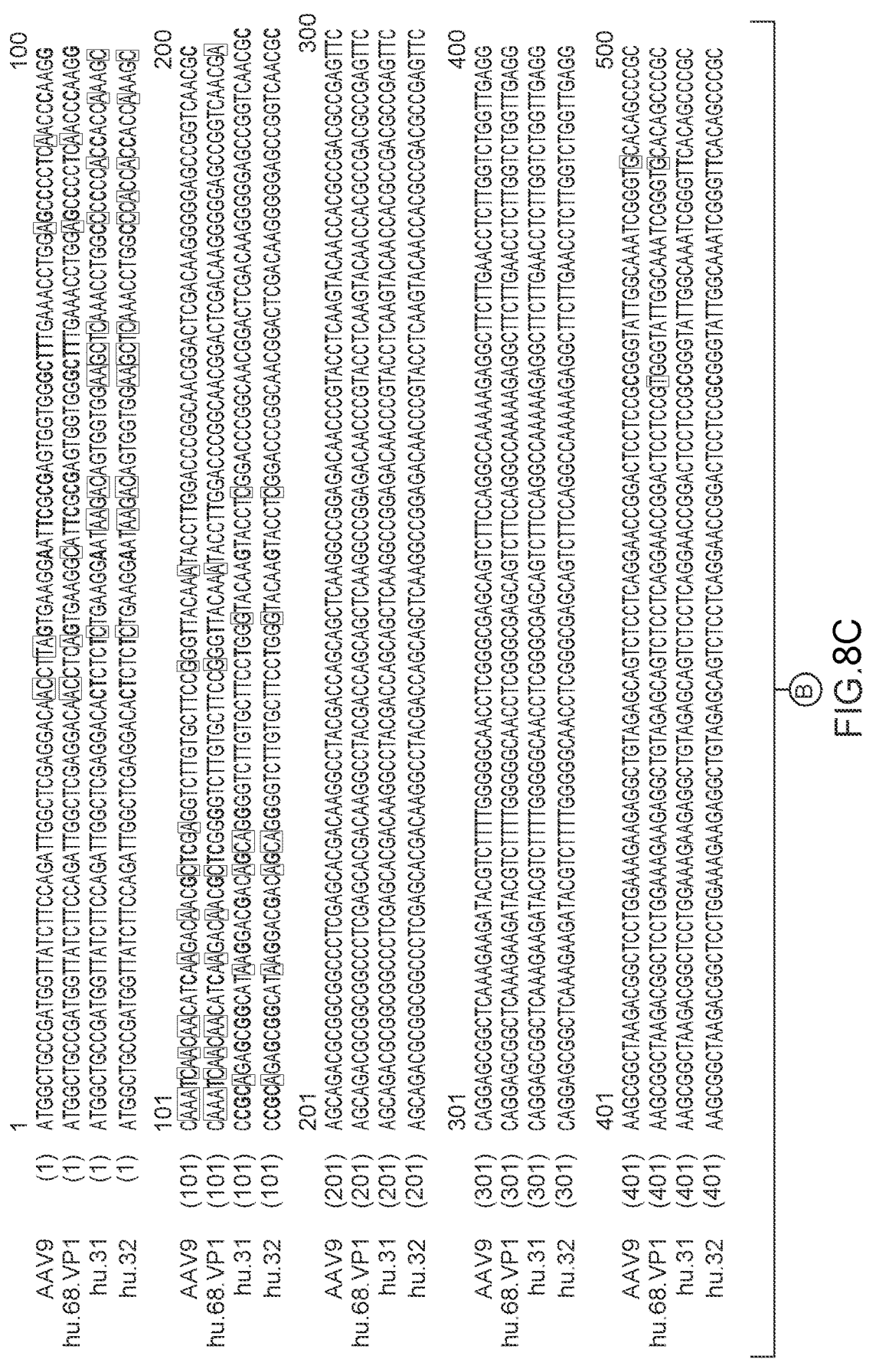
Figure 8D:
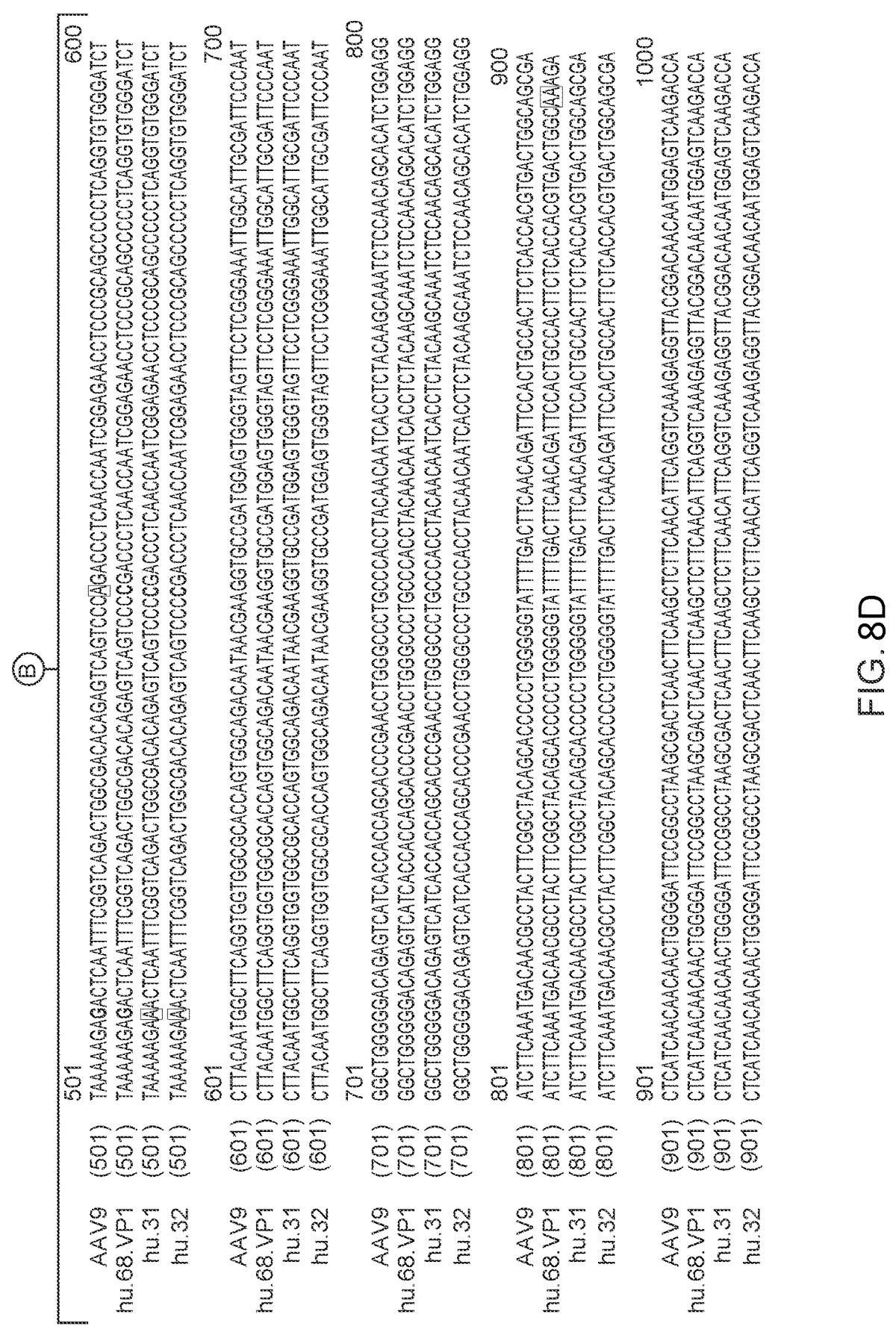

It is within the skill in the art to design nucleic acid sequences encoding this AAVhu68 capsid, including DNA (genomic or cDNA), or RNA (e.g., mRNA). In certain embodiments, the nucleic acid sequence encoding the AAVhu68 vp1 capsid protein is provided in SEQ ID NO: 7. See, also, FIGS. 8B-8D. In other embodiments, a nucleic acid sequence of 70% to 99.9% identity to SEQ ID NO: 7 may be selected to express the AAVhu68 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 7. Such nucleic acid sequences may be codon-optimized for expression in a selected system (i.e., cell type) can be designed by various methods. This optimization may be performed using methods which are available on-line (e.g., GeneArt), published methods, or a company which provides codon optimizing services, e.g., DNA2.0 (Menlo Park, Calif.). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide. A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, the asparagine (N) in N-G pairs in the AAVhu68 vp1, vp2 and vp3 proteins are highly deamidated. In certain embodiments, an AAVhu68 capsid contains subpopulations of AAV vp1, vp2 and/or vp3 capsid proteins having at least four asparagine (N) positions in the AAVhu68 capsid proteins which are highly deamidated. In certain embodiments, about 20 to 50% of the N—N pairs (exclusive of N—N—N triplets) show deamidation. In certain embodiments, the first N is deamidated. In certain embodiments, the second N is deamidated. In certain embodiments, the deamidation is between about 15% to about 25% deamidation. Deamidation at the Q at position 259 of SEQ ID NO: 8 is about 8% to about 42% of the AAVhu68 vp1, vp2 and vp3 capsid proteins of an AAVhu68 protein.

In certain embodiments, the rAAVhu68 capsid is further characterized by an amidation in D297 the vp1, vp2 and vp3 proteins. In certain embodiments, about 70% to about 75% of the D at position 297 of the vp1, vp2 and/or vp3 proteins in a AAVhu68 capsid are amidated, based on the numbering of SEQ ID NO: 8.

In certain embodiments, at least one Asp in the vp1, vp2 and/or vp3 of the capsid is isomerized to D-Asp. Such isomers are generally present in an amount of less than about 1% of the Asp at one or more of residue positions 97, 107, 384, based on the numbering of SEQ ID NO: 8.

In certain embodiments, a rAAVhu68 has an AAVhu68 capsid having vp1, vp2 and vp3 proteins having subpopulations comprising combinations of two, three, four or more deamidated residues at the positions set forth in the table below. Deamidation in the rAAV may be determined using 2D gel electrophoresis, and/or mass spectrometry, and/or protein modelling techniques. Online chromatography may be performed with an Acclaim PepMap column and a Thermo UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value of 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. BioPharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule +0.984 Da (the mass difference between —OH and —NH$_2$ groups). The percent deamidation of a particular peptide is determined mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It will be understood by one of skill in the art that a number of variations on these illustrative methods can be used. For example, suitable mass spectrometers may include, e.g., a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

| Deamidation Based on Predicted AAVHu68 [SEQ ID NO: 8] Deamidated | Average % Based on VP1/VP2/VP3 Proteins in AAVhu68 Capsid | |
| --- | --- | --- |
| Residue + 1 (Neighboring AA) | Broad Range of Percentages (%) | Narrow Ranges (%) |
| N57 (N-G) | 78 to 100% | 80 to 100, 85 to 97 |
| N66 (N-E) | 0 to 5 | 0, 1 to 5 |
| N94 (N-H) | 0 to 15, | 0, 1 to 15, 5 to 12, 8 |
| N113 (N-L) | 0 to 2 | 0, 1 to 2 |
| ~N253 (N-N) | 10 to 25 | 15 to 22 |
| Q259 (Q-I) | 8 to 42 | 10 to 40, 20 to 35 |
| ~N270 (N-D) | 12 to 30 | 15 to 28 |
| ~N304 (N-N) (position 303 also N) | 0 to 5 | 1 to 4 |
| N319 (N-I) | 0 to 5 | 0, 1 to 5, 1 to 3 |
| N329 * (N-G)*(position 328 also N) | 65 to 100 | 70 to 95, 85 to 95, 80 to 100, 85 to 100, |
| N336 (N-N) | 0 to 100 | 0, 1 to 10, 25 to 100, 30 to 100, 30 to 95 |
| ~N409 (N-N) | 15 to 30 | 20 to 25 |
| N452 (N-G) | 75 to 100 | 80 to 100, 90 to 100, 95 to 100, |
| N477 (N-Y) | 0 to 8 | 0, 1 to 5 |
| N512 (N-G) | 65 to 100 | 70 to 95, 85 to 95, 80 to 100, 85 to 100, |
| ~N515 (N-S) | 0 to 25 | 0, 1 to 10, 5 to 25, 15 to 25 |
| ~Q599 (Asn-Q-Gly) | 1 to 20 | 2 to 20, 5 to 15 |
| N628 (N-F) | 0 to 10 | 0, 1 to 10, 2 to 8 |
| N651 (N-T) | 0 to 3 | 0, 1 to 3 |
| N663 (N-K) | 0 to 5 | 0, 1 to 5, 2 to 4 |
| N709 (N-N) | 0 to 25 | 0, 1 to 22, 15 to 25 |
| N735 | 0 to 40 | 0. 1 to 35, 5 to 50, 20 to 35 |

In certain embodiments, the AAVhu68 capsid is characterized, by having, capsid proteins in which at least 45% of N residues are deamidated at least one of positions N57, N329, N452, and/or N512 based on the numbering of amino acid sequence of SEQ ID NO: 8. In certain embodiments, at least about 60%, at least about 70%, at least about 80%, or at least 90% of the N residues at one or more of these N-G positions (i.e., N57, N329, N452, and/or N512, based on the numbering of amino acid sequence of SEQ ID NO: 8) are deamidated. In these and other embodiments, an AAVhu68 capsid is further characterized by having a population of proteins in which about 1% to about 20% of the N residues have deamidations at one or more of positions: N94, N253, N270, N304, N409, N477, and/or Q599, based on the numbering of amino acid sequence of SEQ ID NO: 8. In certain embodiments, the AAVhu68 comprises at least a subpopulation of vp1, vp2 and/or vp3 proteins which are deamidated at one or more of positions N35, N57, N66, N94, N113, N252, N253, Q259, N270, N303, N304, N305, N319, N328, N329, N336, N409, N410, N452, N477, N515, N598, Q599, N628, N651, N663, N709, N735, based on the numbering of amino acid sequence of SEQ ID NO: 8, or combinations thereof. In certain embodiments, the capsid proteins may have one or more amidated amino acids.

Still other modifications are observed, most of which do not result in conversion of one amino acid to a different amino acid residue. Optionally, at least one Lys in the vp1, vp2 and vp3 of the capsid are acetylated. Optionally, at least one Asp in the vp1, vp2 and/or vp3 of the capsid is isomerized to D-Asp. Optionally, at least one S (Ser, Serine) in the vp1, vp2 and/or vp3 of the capsid is phosphorylated. Optionally, at least one T (Thr, threonine) in the vp1, vp2 and/or vp3 of the capsid is phosphorylated. Optionally, at least one W (trp, tryptophan) in the vp1, vp2 and/or vp3 of the capsid is oxidized. Optionally, at least one M (Met, Methionine) in the vp1, vp2 and/or vp3 of the capsid is oxidized. In certain embodiments, the capsid proteins have one or more phosphorylations. For example, certain vp1 capsid proteins may be phosphorylated at position 149.

In certain embodiments, an AAVhu68 capsid comprises a heterogenous population of vp1 proteins which are the product of a nucleic acid sequence encoding the amino acid sequence of SEQ ID NO: 8, wherein the vp1 proteins comprise a Glutamic acid (Glu) at position 67 and/or a valine (Val) at position 157; a heterogenous population of vp2 proteins optionally comprising a valine (Val) at position 157; and a heterogenous population of vp3 proteins. The AAVhu68 capsid contains at least one subpopulation in which at least 65% of asparagines (N) in asparagine-glycine pairs located at position 57 of the vp1 proteins and at least 70% of asparagines (N) in asparagine-glycine pairs at positions 329, 452 and/or 512 of the vp1, v2 and vp3 proteins are deamidated, based on the residue numbering of the amino acid sequence of SEQ ID NO: 8, wherein the deamidation results in an amino acid change. As discussed in more detail herein, the deamidated asparagines may be deamidated to aspartic acid, isoaspartic acid, an interconverting aspartic acid/isoaspartic acid pair, or combinations thereof. In certain embodiments, the rAAVhu68 are further characterized by one or more of: (a) each of the vp2 proteins is independently the product of a nucleic acid sequence encoding at least the vp2 protein of SEQ ID NO: 8; (b) each of the vp3 proteins is independently the product of a nucleic acid sequence encoding at least the vp3 protein of SEQ ID NO: 8; (c) the nucleic acid sequence encoding the vp1 proteins is SEQ ID NO: 7, or a sequence at least 70% to at least 99% (e.g., at least 85%, at least 90%, at least 95%, at least 97%, at least 98% or at least 99%) identical to SEQ ID NO: 7 which encodes the amino acid sequence of SEQ ID NO:8. Optionally that sequence is used alone to express the vp1, vp2 and vp3 proteins. Alternatively, this sequence may be co-expressed with one or more of a nucleic acid sequence which encodes the AAVhu68 vp3 amino acid sequence of SEQ ID NO: 8 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 7), or a sequence at least 70% to at least 99% (e.g., at least 85%, at least 90%, at least 95%, at least 97%, at least 98% or at least 99%) identical to SEQ ID NO: 7 which encodes aa 203 to 736 of SEQ ID NO: 8. Additionally, or alternatively, the vp1-encoding and/or the vp2-encoding sequence may be co-expressed with the nucleic acid sequence which encodes the AAVhu68 vp2 amino acid sequence of SEQ ID NO: 8 (about aa 138 to 736)

without the vp1-unique region (about aa 1 to about 137), or a strand complementary thereto, the corresponding mRNA or tRNA (nt 412 to 2211 of SEQ ID NO: 7), or a sequence at least 70% to at least 99% (e.g., at least 85%, at least 90%, at least 95%, at least 97%, at least 98% or at least 99%) identical to SEQ ID NO: 7 which encodes about aa 138 to 736 of SEQ ID NO: 8.

Additionally or alternatively, the rAAVhu68 capsid comprises at least a subpopulation of vp1, vp2 and/or vp3 proteins which are deamidated at one or more of positions N57, N66, N94, N113, N252, N253, Q259, N270, N303, N304, N305, N319, N328, N329, N336, N409, N410, N452, N477, N512, N515, N598, Q599, N628, N651, N663, N709, based on the numbering of SEQ ID NO:8, or combinations thereof; (e) rAAVhu68 capsid comprises a subpopulation of vp1, vp2 and/or vp3 proteins which comprise 1% to 20% deamidation at one or more of positions N66, N94, N113, N252, N253, Q259, N270, N303, N304, N305, N319, N328, N336, N409, N410, N477, N515, N598, Q599, N628, N651, N663, N709, based on the numbering of SEQ ID NO:8, or combinations thereof; (f) the rAAVhu68 capsid comprises a subpopulation of vp1 in which 65% to 100% of the N at position 57 of the vp1 proteins, based on the numbering of SEQ ID NO:8, are deamidated; (g) the rAAVhu68 capsid comprises subpopulation of vp1 proteins in which 75% to 100% of the N at position 57 of the vp1 proteins are deamidated; (h) the rAAVhu68 capsid comprises subpopulation of vp1 proteins, vp2 proteins, and/or vp3 proteins in which 80% to 100% of the N at position 329, based on the numbering of SEQ ID NO:8, are deamidated; (i) the rAAVhu68 capsid comprises subpopulation of vp1 proteins, vp2 proteins, and/or vp3 proteins in which 80% to 100% of the N at position 452, based on the numbering of SEQ ID NO:8, are deamidated; (j) the rAAVhu68 capsid comprises subpopulation of vp1 proteins, vp2 proteins, and/or vp3 proteins in which 80% to 100% of the N at position 512, based on the numbering of SEQ ID NO:8, are deamidated; (k) the rAAV comprises about 60 total capsid proteins in a ratio of about 1 vp1 to about 1 to 1.5 vp2 to 3 to 10 vp3 proteins; (1) the rAAV comprises about 60 total capsid proteins in a ratio of about 1 vp1 to about 1 vp2 to 3 to 9 vp3 proteins.

In certain embodiments, the AAVhu68 is modified to change the glycine in an asparagine-glycine pair, to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain amide groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAVhu68 amino acid sequence. In certain embodiments, such modifications are not made in all four of the asparagine-glycine pairs. Thus, a method for reducing deamidation of AAVhu68 and/or engineered AAVhu68 variants having lower deamidation rates. Additionally, or alternative one or more other amide amino acids may be changed to a non-amide amino acid to reduce deamidation of the AAVhu68.

These amino acid modifications may be made by conventional genetic engineering techniques. For example, a nucleic acid sequence containing modified AAVhu68 vp codons may be generated in which one to three of the codons encoding glycine at position 58, 330, 453 and/or 513 in SEQ ID NO: 8 (arginine-glycine pairs) are modified to encode an amino acid other than glycine. In certain embodiments, a nucleic acid sequence containing modified arginine codons may be engineered at one to three of the arginine-glycine pairs located at position 57, 329, 452 and/or 512 in SEQ ID NO: 8, such that the modified codon encodes an amino acid other than arginine. Each modified codon may encode a different amino acid. Alternatively, one or more of the altered codons may encode the same amino acid. In certain embodiments, these modified AAVhu68 nucleic acid sequences may be used to generate a mutant rAAVhu68 having a capsid with lower deamidation than the native hu68 capsid. Such mutant rAAVhu68 may have reduced immunogenicity and/or increase stability on storage, particularly storage in suspension form. As used herein, a "codon" refers to three nucleotides in a sequence which encodes an amino acid.

In one embodiment, a recombinant adeno-associated virus (rAAV) is provided which comprises: (A) an AAV68 capsid comprising one or more of: (1) AAV hu68 capsid proteins comprising: AAVhu68 vp1 proteins produced by expression from a nucleic acid sequence which encodes the predicted amino acid sequence of 1 to 736 of SEQ ID NO:8, vp1 proteins produced from SEQ ID NO:7, or vp1 proteins produced from a nucleic acid sequence at least 70% identical to SEQ ID NO:7 which encodes the predicted amino acid sequence of 1 to 736 of SEQ ID NO:8, AAVhu68 vp2 proteins produced by expression from a nucleic acid sequence which encodes the predicted amino acid sequence of at least about amino acids 138 to 736 of SEQ ID NO:8, vp2 proteins produced from a sequence comprising at least nucleotides 412 to 2211 of SEQ ID NO:7, or vp2 proteins produced from a nucleic acid sequence at least 70% identical to at least nucleotides 412 to 2211 of SEQ ID NO:7 which encodes the predicted amino acid sequence of at least about amino acids 138 to 736 of SEQ ID NO:8, AAVhu68 vp3 proteins produced by expression from a nucleic acid sequence which encodes the predicted amino acid sequence of at least about amino acids 203 to 736 of SEQ ID NO:8, vp3 proteins produced from a sequence comprising at least nucleotides 607 to 2211 of SEQ ID NO:7, or vp3 proteins produced from a nucleic acid sequence at least 70% identical to at least nucleotides 607 to 2211 of SEQ ID NO:7 which encodes the predicted amino acid sequence of at least about amino acids 203 to 736 of SEQ ID NO:8; and/or (2) AAV capsid proteins comprising a heterogenous population of vp1 proteins optionally comprising a valine at position 157 and/or a glutamic acid at position 67, a heterogenous population of vp2 proteins optionally comprising a valine at position 157, and a heterogenous population of vp3 proteins, wherein at least a subpopulation of the vp1 and vp2 proteins comprise a valine at position 157 and optionally further comprising a glutamic at position 67 based on the numbering of the vp1 capsid of SEQ ID NO:8; and/or (3) a heterogenous population of vp1 proteins which are the product of a nucleic acid sequence encoding the amino acid sequence of SEQ ID NO: 8, a heterogenous population of vp2 proteins which are the product of a nucleic acid sequence encoding the amino acid sequence of at least about amino acids 138 to 736 of SEQ ID NO: 8, and a heterogenous population of vp3 proteins which are the product of a nucleic acid sequence encoding at least amino acids 203 to 736 of SEQ ID NO:8, wherein: the vp1, vp2 and vp3 proteins contain subpopulations with amino acid modifications comprising at least two highly deamidated asparagines (N) in asparagine-glycine pairs in SEQ ID NO: 8 and optionally further comprising subpopulations comprising other deamidated amino acids, wherein the deamidation results in an amino acid change; and (B) a vector genome in the AAVhu68 capsid, the vector genome comprising a nucleic acid molecule comprising AAV inverted terminal repeat sequences and a non-AAV nucleic acid sequence encoding a product operably linked to sequences which direct expression of the product in a host cell. For example, four residues (N57, N329, N452, N512) routinely display high levels of deamidation. Additional residues (N94, N253, N270, N304, N409, N477 and Q599) also display deamidation levels up to ~20% across various lots.

In certain embodiments, the deamidated asparagines are deamidated to aspartic acid, isoaspartic acid, an interconverting aspartic acid/isoaspartic acid pair, or combinations thereof. In certain embodiments, the deamidated glutamine (s) are deamidated to (α)-glutamic acid, γ-glutamic acid, an interconverting (α)-glutamic acid/γ-glutamic acid pair, or combinations thereof.

In certain embodiments, the AAVhu68 capsid comprises subpopulations having one or more of: (a) at least 65% of asparagines (N) in asparagine-glycine pairs located at positions 57 of the vp1 proteins are deamidated, based on the numbering of SEQ ID NO:8; (b) at least 75% of N in asparagine-glycine pairs in position 329 of the vp1, v2 and vp3 proteins are deamidated, based on the residue numbering of the amino acid sequence of SEQ ID NO: 8; (c) at least 50% of N in asparagine-glycine pairs in position 452 of the vp1, v2 and vp3 proteins are deamidated, based on the residue numbering of the amino acid sequence of SEQ ID NO: 8; and/or (d) at least 75% of N in asparagine-glycine pairs in position 512 of the vp1, v2 and vp3 proteins are deamidated, based on the residue numbering of the amino acid sequence of SEQ ID NO: 8. In certain embodiments, the hu68 capsid comprises a subpopulation of vp1 in which 75% to 100% of the N at position 57 of the vp1 proteins are deamidated, as determined using mass spectrometry. In certain embodiments, the AAVhu68 capsid comprises subpopulation of vp1 proteins, vp2 proteins, and/or vp3 proteins in which 75% to 100% of the N at position 329, based on the numbering of SEQ ID NO:8, are deamidated as determined using mass spectrometry. In certain embodiments, the hu68 capsid comprises subpopulation of vp1 proteins, vp2 proteins, and/or vp3 proteins in which 75% to 100% of the N at position 452, based on the numbering of SEQ ID NO:8, are deamidated as determined using mass spectrometry. In certain embodiments, the hu68 capsid comprises subpopulation of vp1 proteins, vp2 proteins, and/or vp3 proteins in which 75% to 100% of the N at position 512, based on the numbering of SEQ ID NO:8, are deamidated. In certain embodiments, the nucleic acid sequence encoding the proteins is SEQ ID NO: 7, or a sequence at least 80% to at least 99% identical to SEQ ID NO: 7 which encodes the amino acid sequence of SEQ ID NO:8. In certain embodiments, the sequence is at least 80% to 97% identical to SEQ ID NO: 7. In certain embodiments, the rAAVhu68 capsid further comprises at least subpopulation of vp1, vp2 and/or vp3 proteins having amino acid modifications from SEQ ID NO: 8 comprising at least about 50% to 100% deamidation at least four positions selected from one or more of N57, 329, 452, 512, or combinations thereof. In certain embodiments, the AAVhu68 capsid comprises subpopulations of vp1, vp2 and/or vp3 proteins which further comprise 1% to about 40% deamidation in at least one or more of positions N94, N113, N252, N253, Q259, N270, N303, N304, N305, N319, N328, N336, N409, N410, N477, N515, N598, Q599, N628, N651, N663, N709, or combinations thereof. In certain embodiments, the hu68 capsid comprises subpopulations of vp1, vp2 and/or vp3 proteins which further comprise one or more modifications selected from one or more modification in one or more of the following: acetylated lysine, phosphorylated serine and/or threonine, isomerized aspartic acid, oxidized tryptophan and/or methionine, or an amidated amino acid. In certain embodiments, the rAAVhu68 comprises about 60 total capsid proteins in a ratio of about 1 vp1 to about 1 to 1.5 vp2 to 3 to 10 vp3 proteins. In certain embodiments, the AAVhu68 capsid about 60 total capsid proteins in a ratio of about 1 vp1 to about 1 vp2 to 3 to 9 vp3 proteins. In certain embodiments, the vector genome comprises AAV ITR sequences from an AAV source other than AAVhu68.

In certain embodiments, a composition is provided which comprises a mixed population of recombinant adeno-associated virus hu68 (rAAVhu68), wherein each of the rAAVhu68 is independently selected from an rAAVhu68 as described herein. In certain embodiments, the average AAVhu68 capsid comprises about 60 total capsid proteins in a ratio of about 1 vp1 to about 1 to 1.5 vp2 to 3 to 10 vp3 proteins. In certain embodiments, the average AAVhu68 capsid comprises about 60 total capsid proteins in a ratio of about 1 vp1 to about 1 vp2 to 3 to 6 vp3 proteins. In certain embodiments, the composition is formulated for intravenous delivery. In certain embodiments, the composition is formulated for intranasal or intramuscular delivery. In certain embodiments, a composition comprises at least an rAAVhu68 vector stock and an optional carrier, excipient and/or preservative.

Any suitable rAAV production system useful for producing a recombinant AAVhu68 may be used. For example, such a production system may comprise: (a) an AAVhu68 capsid nucleic acid sequence encoding the amino acid sequence of SEQ ID NO:8; (b) a nucleic acid molecule suitable for packaging into the AAVhu68 capsid, said nucleic acid molecule comprising at least one AAV inverted terminal repeat (ITR) and a non-AAV nucleic acid sequence encoding a gene product operably linked to sequences which direct expression of the product in a host cell; and (c) sufficient AAV rep functions and helper functions to permit packaging of the nucleic acid molecule into the recombinant AAVhu68 capsid. In certain embodiments, the nucleic acid sequence of (a) comprises at least SEQ ID NO: 7, or a sequence at least 70% to at least 99% identical to SEQ ID NO: 7 which encodes the amino acid sequence of SEQ ID NO:8. In certain embodiments, the system optionally further comprises a nucleic acid sequence of about nt 607 to about nt 2211 of SEQ ID NO:7 encoding the AAVhu68 vp3 of about aa 203 to about amino acid 736 of SEQ ID NO: 8. In certain embodiments, the system comprises human embryonic kidney 293 cells or a baculovirus system.

In certain embodiments, a method for reducing deamidation of an AAVhu68 capsid is provided. The method comprises producing an AAVhu68 capsid from a nucleic acid sequence containing modified AAVhu68 vp codons, the nucleic acid sequence comprising independently modified glycine codons at one to three of the arginine-glycine pairs located at position 58, 330, 453 and/or 513 in SEQ ID NO: 8, such that the modified codon encodes an amino acid other than glycine. In certain embodiments, the method comprises producing an AAVhu68 capsid from a nucleic acid sequence containing modified AAVhu68 vp codons, the nucleic acid sequence comprising independently modified arginine codons at one to three of the arginine-glycine pairs located at position 57, 329, 452 and/or 512 in SEQ ID NO: 8, such that the modified codon encodes an amino acid other than arginine. In certain embodiments, each modified codon encodes a different amino acid. In certain embodiments, two or more modified codons encode the same amino acid. In certain embodiments, a mutant AAVhu68 capsid as described herein contains a mutation in an arginine-glycine pair, such that the glycine is changed to an alanine or a serine. A mutant AAVhu68 capsid may contain one, two or three mutants where the reference AAVhu68 natively contains four NG pairs. In certain embodiments, a mutant AAVhu68 capsid contains only a single mutation in an NG pair. In certain embodiments, a mutant AAVhu68 capsid contains mutations in two different NG pairs. In certain embodiments, a mutant AAVhu68 capsid contains mutation is two different NG pairs which are located in structurally separate location in the AAVhu68 capsid. In certain embodiments, the mutation is not in the VP1-unique region. In certain embodiments, one of the mutations is in the VP1-unique region. Optionally, a mutant AAVhu68 capsid contains no modifications in the NG pairs, but contains mutations to minimize or eliminate deamidation in one or more asparagines, or a glutamine, located outside of an NG pair.

As used herein, "encoded amino acid sequence" refers to the amino acid which is predicted based on the translation of a known DNA codon of a referenced nucleic acid sequence being translated to an amino acid. The following table illustrates DNA codons and twenty common amino acids, showing both the single letter code (SLC) and three letter code (3LC).

| Amino Acid | SLC | 3 LC | DNA codons |
|---|---|---|---|
| Isoleucine | I | Ile | ATT, ATC, ATA |
| Leucine | L | Leu | CTT, CTC, CTA, CTG, TTA, TTG |
| Valine | V | Val | GTT, GTC, GTA, GTG |
| Phenylalanine | F | Phe | TTT, TTC |
| Methionine | M | Met | ATG |
| Cysteine | C | Cys | TGT, TGC |
| Alanine | A | Ala | GCT, GCC, GCA, GCG |
| Glycine | G | Gly | GGT, GGC, GGA, GGG |
| Proline | P | Pro | CCT, CCC, CCA, CCG |
| Threonine | T | Thr | ACT, ACC, ACA, ACG |
| Serine | S | Ser | TCT, TCC, TCA, TCG, AGT, AGC |
| Tyrosine | Y | Tyr | TAT, TAC |
| Tryptophan | W | Trp | TGG |
| Glutamine | Q | Gln | CAA, CAG |
| Asparagine | N | Asn | AAT, AAC |
| Histidine | H | His | CAT, CAC |
| Glutamic acid | E | Glu | GAA, GAG |
| Aspartic acid | D | Asp | GAT, GAC |
| Lysine | K | Lys | AAA, AAG |
| Arginine | R | Arg | CGT, CGC, CGA, CGG, AGA, AGG |
| Stop codons | Stop |  | TAA, TAG, TGA |

Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1. Other capsids, such as, e.g., those described in WO 2003/042397; WO 2005/033321, WO 2006/110689; U.S. Pat. No. 7,588,772 B2, which are incorporated by reference herein may be used in human subjects. In one embodiment, the invention provides an engineered molecule comprising a spacer sequence between the AAVhu68 vp1 coding sequence and the AAVhu68 rep coding sequences.

As indicated above, the AAVhu68 sequences and proteins are useful in production of rAAV. The examples below describe production of rAAV vectors having AAVhu68 or AAV9 vectors. However, in other embodiments, another AAV capsid is selected. Tissue specificity is determined by the capsid type. For example, a viral vector having an AAVhu68 is illustrated in the examples below as being useful for transducing nasal epithelial cells. The sequences of AAVhu68 are described herein. Further, methods of generating vectors having the AAV9 capsid and chimeric capsids derived from AAV9 have been described. See, e.g., U.S. Pat. No. 7,906,111, which is incorporated by reference herein. Other AAV serotypes which transduce nasal cells or another suitable target (e.g., muscle or lung) may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 (See, e.g., US Published Patent Application No. 2007-0036760-A1; US Published Patent Application No. 2009-0197338-A1; and EP 1310571). See also, WO 2003/042397 (AAV7 and other simian AAV), U.S. Pat. Nos. 7,790,449 and 7,282,199 (AAV8), WO 2005/033321 (AAV9), and WO 2006/110689, or yet to be discovered, or a recombinant AAV based thereon, may be used as a source for the AAV capsid. These documents also describe other AAV which may be selected for generating AAV and are incorporated by reference. In some embodiments, an AAV capsid (cap) for use in the viral vector can be generated by mutagenesis (i.e., by insertions, deletions, or substitutions) of one of the aforementioned AAV caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned caps.

AAVhu68 capsids may be useful in certain embodiments. For example, such capsids may be used in generating monoclonal antibodies and/or generating reagents useful in assays for monitoring AAVhu68 concentration levels in gene therapy patients. Techniques for generating useful anti-AAVhu68 antibodies, labelling such antibodies or empty capsids, and suitable assay formats are known to those of skill in the art.

More typically, the AAVhu68 capsids provided herein are useful in generating recombinant AAV vectors, in which an engineered nucleic acid sequence is packaged in the AAVhu68 capsid. These recombinant AAV vectors, termed "rAAVhu68" or "rAAVhu68 vectors", and their uses are discussed in more detail in another section of this application. These rAAVhu68 vectors are useful for generating recombinant AAV (rAAV) vectors that provide good yield and/or packaging efficiency, and providing rAAV vectors useful in transducing a number of different cell and tissue types. Such cells and tissue types include, without limitation, lung, heart, muscle, liver, pancreas, kidney, brain, hippocampus, motor cortex, cerebellum, nasal epithelial cells, cardiac muscle cells or cardiomyocytes, hepatocytes, pulmonary endothelial cells, myocytes, pulmonary epithelial cells, islet cells, acinar cells, renal cells, and/or motor neurons.

In certain embodiments, vectors having the AAVhu68 capsids provide at least a 15% increase in yield of packaged vector as compared to vectors based on AAV9. In a comparison between AAVhu68 and AAVrh10, AAVhu68 has been found to provide better transduction efficiency than AAVrh10 at low dose (e.g. about $1\times10^9$) following intracerebroventricular administration. In a further comparison between AAVhu68 and AAV9, AAVhu68 has been found to provide better transduction efficiency than AAV9 in cerebellum, motor cortex and hippocampus of brain (e.g. at about 1×10$^{11}$ GC) following intracerebroventricular administration.

A "recombinant AAV" or "rAAV" is a DNAse-resistant viral particle containing two elements, an AAV capsid and a vector genome containing at least non-AAV coding sequences packaged within the AAV capsid. In certain embodiments, the capsid contains about 60 proteins composed of vp1 proteins, vp2 proteins, and vp3 proteins, which self-assemble to form the capsid. Unless otherwise specified, "recombinant AAV" or "rAAV" may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends of the vector genome in order to allow the gene and regulatory sequences located between the ITRs to be packaged within the AAV capsid.

In general, the term "nuclease-resistant" indicates that the AAV capsid has assembled around the expression cassette which is designed to deliver a gene to a host cell and protects these packaged genomic sequences from degradation (digestion) during nuclease incubation steps designed to remove contaminating nucleic acids which may be present from the production process.

In certain embodiments, non-viral genetic elements used in manufacture of a rAAV, will be referred to as vectors (e.g., production vectors). In certain embodiments, these vectors are plasmids, but the use of other suitable genetic elements is contemplated. Such production plasmids may encode sequences expressed during rAAV production, e.g., AAV capsid or rep proteins required for production of a rAAV, which are not packaged into the rAAV. Alternatively, such a production plasmid may carry the vector genome which is packaged into the rAAV.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s), and an AAV 3' ITR. ITRs from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. Further, the vector genome contains regulatory sequences which direct expression of the gene products. Suitable components of a vector genome are discussed in more detail herein.

In certain embodiments, the term an "expression cassette" refers to a nucleic acid molecule which comprises the hSMN sequences and regulatory sequences therefore (e.g., promoter, enhancer, polyA), which cassette may be packaged into the capsid of a viral vector (e.g., a viral particle). Typically, such an expression cassette for generating a viral vector contains the hSMN sequences described herein flanked by packaging signals of the viral genome and other expression control sequences such as those described herein. For example, for an AAV viral vector, the packaging signals are the 5' inverted terminal repeat (ITR) and the 3' ITR. In certain embodiments, the term "transgene" may be used interchangeably with "expression cassette". In other embodiments, the term "transgene" refers solely to the coding sequences for a selected gene, e.g., "hSMN1".

As used herein, the term "SMN" includes any isoform of SMN which restores a desired function, reduces a symptom, or provides another desired physiologic result, when delivered a composition or method provided herein. The examples provided herein utilize the longest isoform, Isoform D, which is thought to be the predominant transcript produced by the gene is a patient unaffected by an SMN deficiency or defect. Isoform D provides a 294 amino acid protein [see, e.g., NCBI accession NM_000334/ NP_000335; ENSEMBL ID ENST00000380707], the protein sequence is reproduced in SEQ ID NO: 2 and the coding sequence is reproduced in SEQ ID NO: 3. However, another isoform may be selected. For example, Isoform B has an alternate in-frame exon in the 3' coding sequence, resulting in a protein which is shorter in length (262 amino acids) than Isoform D, but having the same N- and C-termini as that isoform. See, NCBI Accession No. NM_022874/ NP_075012; ENSEMBL ID ENST00000503079. Isoform B coding and protein sequences are reproduced in SEQ ID NO: 11 and 12, respectively. Isoform A lacks the penultimate exon, which results in an alternate translation stop codon as compared to Isoform D. Thus, Isoform A is shorter (282 amino acids) and has a distinct C-terminus compared to Isoform D. See, NCBI Accession No. NM_001297715/ NP_001284644; ENSEMBL ID ENSTL00000506163. Isoform A coding and protein sequences are reproduced in SEQ ID NOs: 13 and 14, respectively.

In certain embodiments, an engineered human (h) survival of motor neuron (SMN) cDNA is provided herein, which was designed to maximize translation as compared to the native hSMN sequence (SEQ ID NO: 3). An intron may be incorporated upstream of coding sequence to improve 5' capping and stability of mRNA. See, e.g., SEQ ID NOs: 15 and 25. These compositions may be used in methods for the treatment of spinal muscular atrophy as described herein. For comparison purposes, an alignment of native human SMN coding sequence and an engineered cDNA is illustrated in FIGS. 1B-1C.

The hSMN cDNA sequences described herein can be generated in vitro or synthetically, or by any other suitable method using techniques well known in the art. For example, the PCR-based accurate synthesis (PAS) of long DNA sequence method may be utilized, as described by Xiong et al, Nature Protocols 1, 791-797 (2006). A method combining the dual asymmetrical PCR and overlap extension PCR methods is described by Young and Dong, Two-step total gene synthesis method, Nucleic Acids Res. 2004; 32(7): e59. See also, Gordeeva et al, J Microbiol Methods. Improved PCR-based gene synthesis method and its application to the *Citrobacter freundii* phytase gene codon modification. 2010 May; 81(2):147-52. Epub 2010 Mar. 10; see, also, the following patents on oligonucleotide synthesis and gene synthesis, Gene Seq. 2012 April; 6(1):10-21; U.S. Pat. Nos. 8,008,005; and 7,985,565. Each of these documents is incorporated herein by reference. In addition, kits and protocols for generating DNA via PCR are available commercially. These include the use of polymerases including, without limitation, Taq polymerase; OneTaq® (New England Biolabs); Q5® High-Fidelity DNA Polymerase (New England Biolabs); and GoTaq® G2 Polymerase (Promega). DNA may also be generated from cells transfected with plasmids containing the hOTC sequences described herein. Kits and protocols are known and commercially available and include, without limitation, QIAGEN plasmid kits; Chargeswitch® Pro Filter Plasmid Kits (Invitrogen); and GenElute™ Plasmid Kits (Sigma Aldrich). Other techniques useful herein include sequence-specific isothermal amplification methods that eliminate the need for thermocycling. Instead of heat, these methods typically employ a strand-displacing DNA polymerase, like Bst DNA Polymerase, Large Fragment (New England Biolabs), to separate duplex DNA. DNA may also be generated from RNA molecules through amplification via the use of Reverse Transcriptases (RT), which are RNA-dependent DNA Polymerases. RTs polymerize a strand of DNA that is complimentary to the original RNA template and is referred to as cDNA. This cDNA can then be further amplified through PCR or isothermal methods as outlined above. Custom DNA can also be generated commercially from companies including, without limitation, GenScript; GENEWIZ®; GeneArt® (Life Technologies); and Integrated DNA Technologies.

Also provided herein are viral vectors which include the engineered hSMN sequences. In one embodiment, an rAAVhu68.SMN is a viral vector which consists of an external component and internal DNA genome. The external vector component is an AAVhu68 capsid as defined herein. Packaged within the capsid is a single-stranded DNA genome consisting of a human Survival of Motor Neuron (hSMN) transgene flanked by the two AAV inverted terminal repeats (ITRs). An enhancer, promoter, intron, hSMN1 coding sequence and (polyA) signal comprise the hSMN transgene. The ITRs are the genetic elements responsible for the replication and packaging of the genome during vector production and are the only viral cis elements required to generate rAAV. Expression of the hSMN coding sequence is driven by a CB7 promoter, a hybrid between a cytomegalovirus (CMV) immediate early enhancer (C4) and the chicken beta actin promoter. Transcription from this promoter is enhanced by the presence of the CI. An rBG polyA signal is included to mediate termination of human hSMN mRNA transcripts. In certain embodiment, the "hSMN" is hSMN1.

In one aspect, a coding sequence is provided which encodes a functional SMN protein. By "functional hSMN", is meant a gene which encodes an SMN protein which provides at least about 50%, at least about 75%, at least about 80%, at least about 90%, or about the same, or greater than 100% of the biological activity level of the native survival of motor neuron protein, or a natural variant or polymorph thereof which is not associated with disease. Additionally, SMN1homologue-SMN2 also encodes the SMN protein, but processes the functional protein less efficiently. Based on the copy number of SMN2, subjects lacking a functional hSMN gene demonstrate SMA to varying degrees. Thus, for some subjects, it may be desirable for the SMN protein to provide less than 100% of the biological activity of the native SMN protein. In certain embodiment, the terms "hSMN1", "hSMN" and "functional hSMN" are used interchangably.

A variety of assays exist for measuring SMN expression and activity levels in vitro. See, e.g., Tanguy et al, 2015, cited above. The methods described herein can also be combined with any other therapy for treatment of SMA or the symptoms thereof. In certain embodiments, the standard of care may include nusinersen, which is an SMN2 pre-messenger ribonucleic acid (mRNA)-targeting antisense oligonucleotide (ASO) accepted by the FDA and EMA [SPINRAZA™, Biogen]. See, e.g., U.S. Pat. Nos. 6,166,197, 6,210,892, 7,101,993; 7,838,657; 8,110,560; 8,361,977; 8,980,853. This is an SMN2-directed antisense oligonucleotide which is administered intrathecally. The recommended dosage is 12 mg (5 mL per administration). Treatment is initiated with 4 loading doses; the first three loading doses being administered at 14-day intervals, the $4^{th}$ loading dose administered 30 days after the $3^{rd}$ does, and a maintenance dose administered once every 4 months thereafter.

In one embodiment, the amino acid sequence of the functional SMN is that of SEQ ID NO: 2 or a sequence sharing 95% identity therewith. In one embodiment, a modified hSMN coding sequence is provided. Preferably, the modified hSMN coding sequence has less than about 80% identity, preferably about 75% identity or less to the full-length native hSMN coding sequence (FIGS. 1B-1C, SEQ ID NO: 3). In one embodiment, the modified hSMN coding sequence is characterized by improved translation rate as compared to native hSMN following AAV-mediated delivery (e.g., rAAV). In one embodiment, the modified hSMN coding sequence shares less than about 80%, 79%, 78%, 77%, 76%, 75%, 74%, 73%, 72%, 71%, 70%, 69%, 68%, 67%, 66%, 65%, 64%, 63%, 62%, 61% or less identity to the full length native hSMN1 coding sequence. In one embodiment, the modified hSMN coding sequence is SEQ ID NO: 1, or a sequence sharing 70%, 75%, 80%, 85%, 90%, 95% or greater identity with SEQ ID NO: 1. In other embodiments, a different SMN coding sequence is selected.

In still other embodiments, a coding sequence for an SMN isoform other than isoform D is selected. Additionally or alternatively, a composition or regimen provided herein may combine a treatment using an AAVhu68.SMN stock encoding the isoform D SMN protein in combination with a vector stock encoding a different SMN protein. This vector stock may have an AAVhu68 capsid, or a different capsid.

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Identity may be determined by preparing an alignment of the sequences and through the use of a variety of algorithms and/or computer programs known in the art or commercially available [e.g., BLAST, ExPASy; ClustalO; FASTA; using, e.g., Needleman-Wunsch algorithm, Smith-Waterman algorithm]. Alignments are performed using any of a variety of publicly or commercially available Multiple Sequence Alignment Programs. Sequence alignment programs are available for amino acid sequences, e.g., the "Clustal Omega" "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Multiple sequence alignment programs are also available for nucleic acid sequences. Examples of such programs include, "Clustal Omega" "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

II. Expression Cassette and Vectors

In one embodiment, the hSMN genes described herein are engineered into a suitable genetic element (vector) useful for generating viral vectors and/or for delivery to a host cell, e.g., naked DNA, phage, transposon, cosmid, episome, etc., which transfers the hSMN1 sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. In one aspect, an expression cassette comprising the hSMN nucleic acid sequences is provided.

Thus, in one aspect, an adeno-associated viral vector is provided which comprises an AAV capsid and at least one expression cassette, wherein the at least one expression cassette comprises nucleic acid sequences encoding SMN and expression control sequences that direct expression of the SMN sequences in a host cell. The AAV vector also comprises AAV ITR sequences. In one embodiment, the ITRs are from an AAV different than that supplying a capsid. In a preferred embodiment, the ITR sequences from AAV2, or the deleted version thereof (ΔITR), which may be used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, AAV vector genome comprises an AAV 5' ITR, the hSMN coding sequences and any regulatory sequences, and an AAV 3' ITR. However, other configurations of these elements may be suitable. A shortened version of the 5' ITR, termed AITR, has been described in which the D-sequence and terminal resolution site (trs) are deleted. In other embodiments, the full-length AAV 5' and 3' ITRs are used.

In one aspect, a construct is provided which is a DNA molecule (e.g., a plasmid) useful for generating viral vectors. The expression cassette typically contains a promoter sequence as part of the expression control sequences, e.g., located between the selected 5' ITR sequence and the hSMN coding sequence. The illustrative plasmid and vector described herein uses the ubiquitous chicken β-actin promoter (CB) with CMV immediate early enhancer (CMV IE). Alternatively, neuron-specific promoters may be used [see, e.g., the Lockery Lab neuron-specific promoters database, accessed at chinook.uoregon.edu/promoters.html]. Such neuron-specific promoters include, without limitation, e.g., synapsin I (SYN), calcium/calmodulin-dependent protein kinase II, tubulin alpha I, neuron-specific enolase and platelet-derived growth factor beta chain promoters. See, Hioki et al, Gene Therapy, June 2007, 14(11):872-82, which is incorporated herein by reference. Other neuron-specific promoters include the 67 kDa glutamic acid decarboxylase (GAD67), homeobox Dlx5/6, glutamate receptor 1 (GluR1), preprotachykinin 1 (Tac1) promoter, neuron-specific enolase (NSE) and dopaminergic receptor 1 (Drd1a) promoters. See, e.g., Delzor et al, Human Gene Therapy Methods. August 2012, 23(4): 242-254. In another embodiment, the promoter is a GUSb promoter www.jci.org/articles/view/41615#B30.

Other promoters, such as constitutive promoters, regulatable promoters [see, e.g., WO 2011/126808 and WO 2013/04943], or a promoter responsive to physiologic cues may be used may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter.

In addition to a promoter, an expression cassette and/or a vector may contain one or more other appropriate transcription initiation, termination, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. Examples of suitable polyA sequences include, e.g., SV40, SV50, bovine growth hormone (bGH), human growth hormone, and synthetic polyAs. An example of a suitable enhancer is the CMV enhancer. Other suitable enhancers include those that are appropriate for CNS indications. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. Other suitable introns include those known in the art, e.g., such as are described in WO 2011/126808. Optionally, one or more sequences may be selected to stabilize mRNA. An example of such a sequence is a modified WPRE sequence, which may be engineered upstream of the polyA sequence and downstream of the coding sequence [see, e.g., M A Zanta-Boussif, et al, Gene Therapy (2009) 16: 605-619.

These control sequences are "operably linked" to the hSMN gene sequences. As used herein, the term "operably linked" refers to both expression control sequences that are contiguous with the gene of interest and expression control sequences that act in trans or at a distance to control the gene of interest.

In one embodiment, a self-complementary AAV is provided. The abbreviation "sc" in this context refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Methods for generating and isolating AAV viral vectors suitable for delivery to a subject are known in the art. See, e.g. US Published Patent Application No. 2007/0036760 (Feb. 15, 2007), U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

Optionally, the hSMN genes described herein may be engineered into other delivery systems, including viral vectors other than rAAV. Such other viral vectors may include any virus suitable for gene therapy may be used, including but not limited to adenovirus; herpes virus; lentivirus; retrovirus; bocavirus; etc. Suitably, where one of these other vectors is generated, it is produced as a replication-defective viral vector.

In certain embodiments, engineered AAVhu68.SMN vectors are provided. In one embodiment, the vector genome of rAAVhu68SMN has a sequence of SEQ ID NO: 15. In another embodiment, the vector genome of rAAVhu68SMN has a sequence of SEQ ID NO: 25. In certain embodiments, the terms "rAAVhu68.SMN1" and "rAAVhu68.SMN" are used interchangeably.

III. Compositions and Uses

Also provided herein are pharmaceutical compositions. The pharmaceutical compositions described herein are designed for delivery to subjects in need thereof by any suitable route or a combination of different routes.

These delivery means are designed to avoid direct systemic delivery of the suspension containing the AAV composition(s) described herein. Suitably, this may have the benefit of reducing dose as compared to systemic administration, reducing toxicity and/or reducing undesirable immune responses to the AAV and/or transgene product.

Alternatively, other routes of administration may be selected (e.g., oral, inhalation, intranasal, intratracheal, intraarterial, intraocular, intravenous, intramuscular, and other parental routes).

Optionally, an immunosuppressive co-therapy may be used in a subject in need. Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent. In certain embodiments, the immunosuppressive therapy may be started 0, 1, 2, 3, 4, 5, 6, 7, or more days prior to or after the gene therapy administration. Such immunosuppressive therapy may involve administration of one, two or more drugs (e.g., glucocorticoids, prednelisone, micophenolate mofetil (MMF) and/or sirolimus (i.e., rapamycin)). Such immunosuppressive drugs may be administered to a subject in need once, twice or for more times at the same dose or an adjusted dose. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week (7 days), about 60 days, or longer, as needed. In certain embodiments, a tacrolimus-free regimen is selected.

The rAAVhu68.hSMN vectors described herein may be dosed in a single composition or multiple compositions. Optionally, two or more different rAAV may be delivered [see, e.g., WO 2011/126808 and WO 2013/049493]. In another embodiment, such multiple viruses may contain different replication-defective viruses (e.g., AAV, adenovirus, and/or lentivirus). Alternatively, delivery may be mediated by non-viral constructs, e.g., "naked DNA", "naked plasmid DNA", RNA, and mRNA; coupled with various delivery compositions and nano particles, including, e.g., micelles, liposomes, cationic lipid-nucleic acid compositions, poly-glycan compositions and other polymers, lipid and/or cholesterol-based-nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, both of which are incorporated herein by reference, Such non-viral hSMN delivery constructs may be administered by the routes described previously. The viral vectors, or non-viral DNA or RNA transfer moieties, can be formulated with a physiologically acceptable carrier for use in gene transfer and gene therapy applications.

In certain embodiments, the rAAVhu68.SMA is purified from any contaminants associated with production prior to storage and/or formulation for delivery to a subject. A number of suitable purification methods may be selected. Examples of suitable purification methods are described, e.g., International Patent Application No. PCT/US2016/065970, filed Dec. 9, 2016 and its priority documents, US Patent Application Nos. 62/322,071, filed Apr. 13, 2016 and 62/226,357, filed Dec. 11, 2015 and entitled "Scalable Purification Method for AAV9", which is incorporated by reference herein. Purification methods for AAV8, International Patent Application No. PCT/US2016/065976, filed Dec. 9, 2016 and is priority documents US Patent Application Nos. 62/322,098, filed Apr. 13, 2016 and 62/266,341, filed Dec. 11, 2015, and rh10, International Patent Application No. PCT/US16/66013, filed Dec. 9, 2016 and its priority documents, U.S. Patent Application No. 62/322,055, filed Apr. 13, 2016 and 62/266,347, entitled "Scalable Purification Method for AAVrh10", also filed Dec. 11, 2015, and for AAV1, International Patent Application No. PCT/US2016/065974, filed Dec. 9, 2016 and its priority documents U.S. Patent Application No. 62/322,083, filed Apr. 13, 2016 and 62/26,351, for "Scalable Purification Method for AAV1", filed Dec. 11, 2015, are all incorporated by reference herein.

For the rAAVhu68.SMN1 vectors described herein quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate contaminating host DNA from the production process. The DNase resistant particles are then subjected to heat treatment to release the genome from the capsid. The released genomes are then quantitated by real-time PCR using primer/probe sets targeting specific region of the viral genome (for example poly A signal). Another suitable method for determining genome copies are the quantitative-PCR (qPCR), particularly the optimized qPCR or digital droplet PCR [Lock Martin, et al, Human Gene Therapy Methods. April 2014, 25(2): 115-125. doi:10.1089/hgtb.2013.131, published online ahead of editing Dec. 13, 2013]. Alternatively, ViroCyt3100 can be used for particle quantitation, or flow cytometry.

The rAAVhu68.SMN1 compositions can be formulated in dosage units to contain an amount of rAAV that is in the range of about $1.0 \times 10^9$ GC to about $9 \times 10^{15}$ GC (e.g., based on about 2.5 kg to about 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{15}$ GC per dose including all integers or fractional amounts within the range.

In certain embodiments, the dose may be in the range of about $1 \times 10^9$ GC/g brain mass to about $1 \times 10^{12}$ GC/g brain mass. In certain embodiments, the dose may be in the range of about $3 \times 10^{10}$ GC/g brain mass to about $3 \times 10^{11}$ GC/g brain mass. In certain embodiments, the dose may be in the range of about $5 \times 10^{10}$ GC/g brain mass to about $1.85 \times 10^{11}$ GC/g brain mass.

In one embodiment, the rAAVhu68.SMN1 may be delivered in doses of from at least about least $1 \times 10^9$ GCs to about $1 \times 10^{15}$, or about $1 \times 10^{11}$ to $5 \times 10^{13}$ GC. Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

The above-described rAAVhu68.SMN1 may be delivered to host cells according to published methods. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of 6.8 to about 7.2 may be desired. However, other pHs within the broadest ranges and these subranges may be selected for other route of delivery.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate.7H$_2$O), potassium chloride, calcium chloride (e.g., calcium chloride.2H$_2$O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/-article/2093316-overview. Optionally, for intrathecal delivery, a commercially available diluent may be used as a suspending agent, or in combination with another suspending agent and other optional excipients. See, e.g., Elliotts B® solution [Lukare Medical]. Each 10 mL of Elliotts B Solution contains:

Sodium Chloride, USP 73 mg
Sodium Bicarbonate, USP 19 mg
Dextrose, USP 8 mg
Magnesium Sulfate.7H$_2$O, USP 3 mg
Potassium Chloride, USP 3 mg
Calcium Chloride.2H$_2$O, USP 2 mg
Sodium Phosphate, dibasic.7H$_2$O, USP 2 mg
Water for Injection, USP qs 10 mL
Concentration of Electrolytes:

| | |
|---|---|
| Sodium 149 mEq/liter | Bicarbonate 22.6 mEq/liter |
| Potassium 4.0 mEq/liter | Chloride 132 mEq/liter |
| Calcium 2.7 mEq/liter | Sulfate 2.4 mEq/liter |
| Magnesium 2.4 mEq/liter | Phosphate 1.5 mEq/liter |

The formulae and molecular weights of the ingredients are:

| INGREDIENT | MOLECULAR FORMULA | MOLECULAR WEIGHT |
|---|---|---|
| Sodium Chloride | NaCl | 58.44 |
| Sodium Bicarbonate | NaHCO3 | 84.01 |
| Dextrose | C6H12O6 | 180.16 |
| Magnesium Sulfate•7H2O | Mg2SO4•7H2O | 246.48 |
| Potassium Chloride | KCl | 74.55 |
| Calcium Chloride•2H2O | CaCl2•2H2O | 147.01 |
| Sodium Phosphate, dibasic•7H2O | Na2HPO4•7H2O | 268.07 |

The pH of Elliotts B Solution is 6 to 7.5, and the osmolarity is 288 mOsmol per liter (calculated). In certain embodiments, the composition containing the rAAVhu68.SMN1 gene is delivered at a pH in the range of 6.8 to 8, or 7.2 to 7.8, or 7.5 to 8. For intrathecal delivery, a pH above 7.5 may be desired, e.g., 7.5 to 8, or 7.8.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. The aqueous solution may have a pH of 7.2.

In another embodiment, the formulation may contain a buffered saline aqueous solution comprising 1 mM Sodium Phosphate (Na$_3$PO$_4$), 150 mM sodium chloride (NaCl), 3 mM potassium chloride (KCl), 1.4 mM calcium chloride (CaCl$_2$), 0.8 mM magnesium chloride (MgCl$_2$), and 0.001% Kolliphor® 188. See, e.g., harvardapparatus.com/harvard-apparatus-perfusion-fluid.html. In certain embodiments, Harvard's buffer is preferred due to better pH stability observed with Harvard's buffer. The table below provides a comparison of Harvard's buffer and Elliot's B buffer. Cerebrospinal Fluid (CSF) Compositions

| Component | Units | CSF | Elliot's B | Harvard's |
|---|---|---|---|---|
| Na+ | mEq/L | 117-137 | 149 | 150 |
| K+ | mEq/L | 2.3-4.6 | 4.0 | 3.0 |
| Mg+ | mEq/L | 2.2 | 2.4 | 0.8 |
| Ca2+ | mEq/L | 2.2 | 2.7 | 1.4 |
| Cl— | mEq/L | 113-127 | 132 | 155 |
| HCO3— | mEq/L | 22.9 | 22.6 | 0 |
| Phos | mg/dL | 1.2-2.1 | 1.5 | 1.0 |
| Glucose | mg/dL | 45-80 | 80 | — |
| Pluronic | % | — | 0.001% (added) | 0.001% (added) |
| Osmolarity | mOsm/L | 295 | 288 | 290 |
| pH | | 7.31 | 6.0-7.5* Drift to 9+ (8.2+ w/o titratn) | 7.2 (titrated to) |

In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery. In one embodiment, intrathecal delivery encompasses an injection into the spinal canal, e.g., the subarachnoid space.

The viral vectors described herein may be used in preparing a medicament for delivering hSMN to a subject (e.g., a human patient) in need thereof, supplying functional SMN to a subject, and/or for treating spinal muscular atrophy. A course of treatment may optionally involve repeat administration of the same viral vector (e.g., an AAVhu68 vector) or a different viral vector (e.g., an AAVhu68 and an AAVrh10). Still other combinations may be selected using the viral vectors and non-viral delivery systems described herein.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube.

In one embodiment, delivery may be performed using the device described herein.

IV. Apparatus and Method for Delivery of a Pharmaceutical Composition into Cerebrospinal Fluid In one aspect, the vectors provided herein may be administered intrathecally via the method and/or the device provided in this section and described further in the Examples and FIG. 7. Alternatively, other devices and methods may be selected. The method comprises the steps of advancing a spinal needle into the cisterna magna of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient.

In another aspect, a device for intracisternal delivery of a pharmaceutical composition is provided. The device includes a first vessel containing an amount of a pharmaceutical composition, a second vessel containing an isotonic solution, and a spinal needle through which the pharmaceutical composition may be ejected from the device directly into cerebrospinal fluid within the cisterna magna of a patient. The device further includes a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle.

As used herein, the term Computed Tomography (CT) refers to radiography in which a three-dimensional image of a body structure is constructed by computer from a series of plane cross-sectional images made along an axis.

Figure 7:
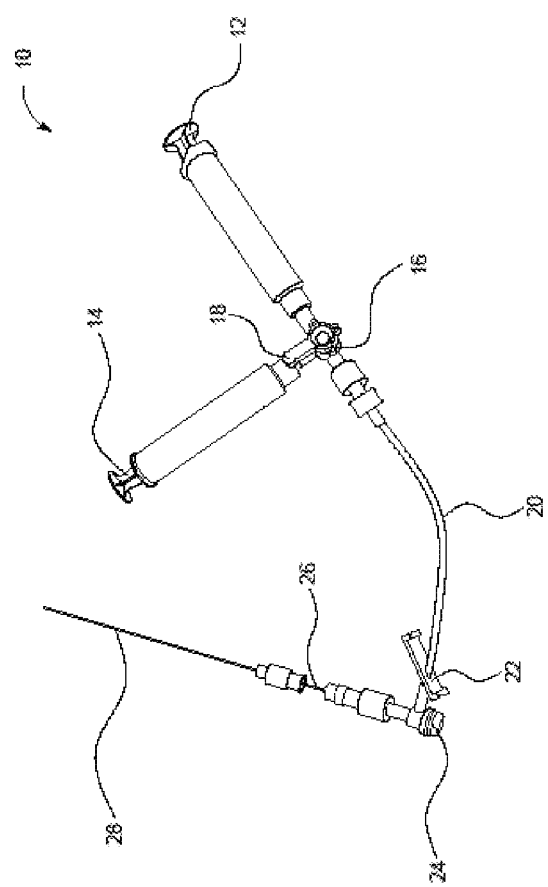
FIG. 7 is an image of an apparatus for intracisternal delivery, including optional introducer needle for coaxial insertion method, which includes a 10 cc vector syringe, a 10 cc prefilled flush syringe, a T-connector extension set, a 22G×5" spinal needle, an optional 18G×3.5" introducer needle.

The apparatus or medical device 10 as shown in FIG. 7 includes one or more vessels, 12 and 14, interconnected via a valve 16. The vessels, 12 and 14, provide a fresh source of a pharmaceutical composition, drug, vector, or like substance and a fresh source of an isotonic solution such as saline, respectively. The vessels, 12 and 14, may be any form of medical device that enables injection of fluids into a patient.

By way of example, each vessel, 12 and 14, may be provided in the form of a syringe, cannula, or the like. For instance, in the illustrated embodiment, the vessel 12 is provided as a separate syringe containing an amount of a pharmaceutical composition and is referred to herein as a "vector syringe". Merely for purposes of example, the vessel 12 may contain about 10 cc of a pharmaceutical composition or the like.

Likewise, the vessel 14 may be provided in the form of a separate syringe, cannula, or the like that contains an amount of saline solution and may be referred to as a "flush syringe". Merely for purposes of example, the vessel 14 may contain about 10 cc of a saline solution.

As an alternative, the vessels 12 and 14 may be provided in forms other than syringes and may be integrated into a single device, such as an integrated medical injection device have a pair of separate chambers, one for the pharmaceutical composition and one for saline solution. Also, the size of the chambers or vessels may be provided as needed to contain a desired amount of fluid.

In the illustrated embodiment, the valve 16 is provided as a 4-way stopcock having a swivel male luer lock 18. The valve 16 interconnects the vessels 12 and 14 (i.e., the vector syringe and flush syringe in the illustrated embodiment), and the swivel male luer lock enables a path through the valve 16 to be closed or opened to each of the vessels 12 and 14. In this way, the path through the valve 16 may be closed to both the vector syringe and flush syringe or may be open to a selected one of the vector syringe and flush syringe. As an alternative to a 4-way stopcock, the valve may be a 3-way stopcock or fluid control device.

In the illustrated embodiment, the valve 16 is connected to one end of a length of extension tubing 20 or the like conduit for fluid. The tubing 20 may be selected based on a desired length or internal volume. Merely by way of example, the tubing may be about 6 to 7 inches in length.

In the illustrated embodiment, an opposite end 22 of the tubing 12 is connected to a T-connector extension set 24 which, in turn, is connected to a spinal needle 26. By way of example, the needle 26 may be a five inch, 22 or 25 gauge spinal needle. In addition, as an option, the spinal needle 26 may be connected to an introducer needle 28, such as a three and a half inch, 18 gauge introducer needle.

In use, the spinal needle 26 and/or optional introducer needle 28 may be advanced into a patient towards the cisterna magna. After needle advancement, Computed Tomography (CT) images may be obtained that permit visualization of the needle 26 and/or 28 and relevant soft tissues (e.g., paraspinal muscles, bone, brainstem, and spinal cord). Correct needle placement is confirmed by observation of Cerebrospinal Fluid (CSF) in the needle hub and visualization of a needle tip within the cisterna magna. Thereafter, the relatively short extension tubing 20 may be attached to the inserted spinal needle 26, and the 4-way stopcock 16 may then be attached to the opposite end of the tubing 20.

The above assembly is permitted to become "self-primed" with the patient's CSF. Thereafter, the prefilled normal saline flush syringe 14 is attached to a flush inlet port of the 4-way stopcock 16 and then the vector syringe 12 containing a pharmaceutical composition is attached to a vector inlet port of the 4-way stopcock 16. Thereafter, the output port of the stopcock 16 is opened to the vector syringe 12, and the contents of the vector syringe may be slowly injected through the valve 16 and assembled apparatus and into the patient over a period of time. Merely for purposes of example, this period of time may be approximately 1-2 minutes and/or any other time of desire.

After the contents of the vector syringe 12 are injected, the swivel lock 18 on the stopcock 16 is turned to a second position so that the stopcock 16 and needle assembly can be flushed with a desired amount of normal saline using the attached prefilled flush syringe 14. Merely by way of example, 1 to 2 cc of normal saline may be used; although greater or lesser amounts may be used as needed. The normal saline ensures that all or most of the pharmaceutical composition is forced to be injected through the assembled device and into the patient and so that little or none of the pharmaceutical composition remains in the assembled device.

After the assembled device has been flushed with the saline, the assembled device in its entirely, including the needle(s), extension tubing, stopcock, and syringes are slowly removed from the subject and placed onto a surgical tray for discarding into a biohazard waste receptacle or hard container (for the needle(s)).

A screening process may be undertaken by a principal investigator which may ultimately lead to an intracisternal (IC) procedure. The principal investigator may describe the process, procedure, the administration procedure itself, and all potential safety risks in order for the subject (or designated caregiver) to be fully informed. Medical history, concomitant medications, physical exam, vital signs, electrocardiogram (ECG), and laboratory testing results are obtained or performed and provided to a neuroradiologist, neurosurgeon, and anesthesiologist for use in screening assessment of subject eligibility for the IC procedure.

To allow adequate time to review eligibility, the following procedures may be performed at any time between the first screening visit and up to one week prior to a study visit. For example, on "Day 0", Head/Neck Magnetic Resonance Imaging (MRI) with and without gadolinium (i.e., eGFR>30 mL/min/1.73 m2) may be obtained. In addition to the Head/Neck MRI, the investigator may determine the need for any further evaluation of the neck via flexion/extension studies. The MRI protocol may include T1, T2, DTI, FLAIR, and CINE protocol images.

In addition, Head/Neck MRA/MRV may be obtained as per institutional protocol (i.e., subjects with a history of intra/transdural operations may be excluded or may need further testing (e.g., radionucleotide cisternography)) that allows for adequate evaluation of CSF flow and identification of possible blockage or lack of communication between CSF spaces.

The neuroradiologist, neurosurgeon, and anesthesiologist ultimately discuss and determine the eligibility of each subject for the IC procedures based on all available information (scans, medical history, physical exam, labs, etc.). An Anesthesia pre-op evaluation may also be obtained from "Day −28" to "Day 1" that provides a detailed assessment of airway, neck (shortened/thickened) and head range-of-motion (degree of neck flexion), keeping in mind the special physiologic needs of a MPS subject.

Prior to an IC procedure, the CT Suite will confirm the following equipment and medications are present: Adult lumbar puncture (LP) kit (supplied per institution); BD (Becton Dickinson) 22 or 25 gauge×3-7" spinal needle (Quincke bevel); Coaxial introducer needle, used at the discretion of the interventionalist (for introduction of spinal needle); 4 way small bore stopcock with swivel (Spin) male luer lock; T-connector extension set (tubing) with female luer lock adapter, approximate length of 6.7 inches; Omnipaque 180 (iohexol), for intrathecal administration; Iodinated contrast for intravenous (IV) administration; 1% lidocaine solution for injection (if not supplied in adult LP kit); Prefilled 10 cc normal saline (sterile) flush syringe; Radiopaque marker(s); Surgical prep equipment/shaving razor; Pillows/supports to allow proper positioning of intubated subject; Endotracheal intubation equipment, general anesthesia machine and mechanical ventilator; Intraoperative neurophysiological monitoring (IONM) equipment (and required personnel); and 10 cc syringe containing vector; prepared and transported to CT/Operating Room (OR) suite in accordance with separate Pharmacy Manual.

Informed Consent for the procedure are confirmed and documented within the medical record and/or study file. Separate consent for the procedure from radiology and anesthesiology staff is obtained as per institutional requirements. Subject has intravenous access placed within the appropriate hospital care unit according to institutional guidelines (e.g., two IV access sites). Intravenous fluids are administered at the discretion of the anesthesiologist. At the discretion of the anesthesiologist and per institutional guidelines, subject may be induced and undergo endotracheal intubation with administration of general anesthesia in an appropriate patient care unit, holding area or the surgical/CT procedure suite.

A lumbar puncture is performed, first to remove 5 cc of cerebrospinal fluid (CSF) and subsequently to inject contrast (Omnipaque 180) intrathecally to aid visualization of the cisterna magna. Appropriate subject positioning maneuvers may be performed to facilitate diffusion of contrast into the cisterna magna.

Intraoperative neurophysiological monitoring (IONM) equipment is attached to the subject. Subject is placed onto the CT scanner table in the prone or lateral decubitus position. Adequate staff must be present to assure subject safety during transport and positioning. If deemed appropriate, subject may be positioned in a manner that provides neck flexion to the degree determined to be safe during pre-operative evaluation and with normal neurophysiologic monitor signals documented after positioning.

The following staff may be confirmed to be present and identified on-site: Interventionalist/neurosurgeon performing the procedure; Anesthesiologist and respiratory technician(s); Nurses and physician assistants; CT (or OR) technicians; Neurophysiology technician; and Site Coordinator. A "time-out" may be completed per Joint Commission/hospital protocol to verify correct subject, procedure, site, positioning, and presence of all necessary equipment in the room. The lead site investigator may then confirm with staff that he/she may proceed with prepping the subject.

The subject's skin under the skull base is shaved as appropriate. CT scout images are performed, followed by a pre-procedure planning CT with IV contrast, if deemed necessary by the interventionalist to localize the target location and to image vasculature. After the target site (cisterna magna) is identified and needle trajectory planned, the skin is prepped and draped using sterile technique as per institutional guidelines. A radiopaque marker is placed on the target skin location as indicated by the interventionalist. The skin under the marker is anesthetized via infiltration with 1% lidocaine. A 22G or 25G spinal needle is than advanced towards the cisterna magna, with the option to use a coaxial introducer needle.

After needle advancement, CT images are obtained using the thinnest CT slice thickness feasible using institutional equipment (ideally≤2.5 mm). Serial CT images using the lowest radiation dose possible that allows for adequate visualization of the needle and relevant soft tissues (e.g., paraspinal muscles, bone, brainstem, and spinal cord) are obtained. Correct needle placement is confirmed by observation of CSF in the needle hub and visualization of needle tip within the cisterna magna.

The interventionalist confirms that the vector syringe is positioned close to, but outside of the sterile field. Prior to handling or administering the pharmaceutical composition in the vector syringe, gloves, mask, and eye protection are donned by staff assisting the procedure within the sterile field.

The extension tubing is attached to the inserted spinal needle, which is then attached to the 4-way stopcock. Once this apparatus is "self-primed" with the subject's CSF, the 10 cc prefilled normal saline flush syringe is attached to a flush inlet port of the 4-way stopcock. The vector syringe is then provided to the interventionalist and attached to a vector inlet port on the 4-way stop cock.

After the outlet port of the stopcock is opened to the vector syringe by placing the swivel lock of the stopcock in a first position, the contents of the vector syringe are injected slowly (over approximately 1-2 minutes), with care taken not to apply excessive force onto the plunger of the syringe during the injection. After the contents of the vector syringe are injected, the swivel lock of stopcock is turned to a second position so that the stopcock and needle assembly can be flushed with 1-2 cc of normal saline using the attached prefilled flush syringe.

When ready, the interventionist then alerts staff that he/she will remove the apparatus from the subject. In a single motion, the needle, extension tubing, stopcock, and syringes are slowly removed from the subject and placed onto a surgical tray for discarding into a biohazard waste receptacle or hard container (for the needle).

The needle insertion site is examined for signs of bleeding or CSF leakage and treated as indicated by the investigator. Site is dressed using gauze, surgical tape and/or Tegaderm dressing, as indicated. Subject is then removed from the CT scanner and placed supine onto a stretcher. Adequate staff is present to assure subject safety during transport and positioning.

Anesthesia is discontinued and subject cared for following institutional guidelines for post-anesthesia care. Neurophysiologic monitors are removed from the subject. The head of the stretcher on which the subject lies should be slightly raised (~30 degrees) during recovery. Subject is transported to a suitable post-anesthesia care unit as per institutional guidelines. After subject has adequately recovered consciousness and is in stable condition, he/she will be admitted to the appropriate floor/unit for protocol mandated assessments. Neurological assessments will be followed as per the protocol and the Primary Investigator oversees subject care in collaboration with hospital and research staff.

In one embodiment, a method for delivery of a composition provided herein comprises the steps of: advancing a spinal needle into the cisterna magna of a patient; connecting a length of flexible tubing to a proximal hub of the spinal needle and an output port of a valve to a proximal end of the flexible tubing; after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve; after connecting said first and second vessels to the valve, opening a path for fluid flow between the vector inlet port and the outlet port of the valve and injecting the pharmaceutical composition into the patient through the spinal needle; and after injecting the pharmaceutical composition, opening a path for fluid flow through the flush inlet port and the outlet port of the valve and injecting the isotonic solution into the spinal needle to flush the pharmaceutical composition into the patient. In certain embodiment, the method further comprises confirming proper placement of a distal tip of the spinal needle within the cisterna magna before connecting the tubing and valve to the hub of the spinal needle. In certain embodiments, the confirming step includes visualizing the distal tip of the spinal needle within the cisterna magna with Computed Tomography (CT) imaging. In certain embodiments, the confirming step includes observing the presence of the patient's cerebrospinal fluid in the hub of the spinal needle.

In the above-described method, the valve may be a stopcock with a swivel luer lock adapted to swivel to a first position permitting flow from the vector inlet port to the outlet port while simultaneously blocking flow through the flush inlet port and to a second position permitting flow from the flush inlet port to the outlet port while simultaneously blocking flow through the vector inlet port, and wherein the swivel luer lock is positioned into said first position when said pharmaceutical composition is injected the patient and is positioned into said second position when said pharmaceutical composition is being flushed into said patient by the isotonic solution. In certain embodiments, after injecting the isotonic solution into the spinal needle to flush the pharmaceutical composition into the patient, the spinal needle is withdrawn from the patient with the tubing, valve, and first and second vessels connected thereto as an assembly. In certain embodiments, the valve is a 4-way stopcock with a swivel male luer lock. In certain embodiments, the first and second vessels are separate syringes. In certain embodiments, a T-connector is located at the hub of the spinal needle and interconnects the tubing to the spinal needle. Optionally, the spinal needle includes an introducer needle at the distal end of the spinal needle. The spinal needle may be a five inch, 22 or 24 gauge spinal needle. In certain embodiments, the introducer needle is a 3.5 inch, 18 gauge introducer needle.

In certain aspects, the method utilizes a device which is composed of, at a minimum, a first vessel for containing an amount of a pharmaceutical composition; a second vessel for containing an isotonic solution; a spinal needle through which the pharmaceutical composition may be ejected from the device directly into cerebrospinal fluid within the cisterna magna of a patient; and a valve having a first inlet port interconnected to the first vessel, a second inlet port interconnected to the second vessel, an outlet port interconnected to the spinal needle, and a luer lock for controlling flow of the pharmaceutical composition and isotonic solution through the spinal needle. In certain embodiments, the valve is a stopcock with a swivel luer lock adapted to swivel to a first position permitting flow from the first inlet port to the outlet port while simultaneously blocking flow through the second inlet port and to a second position permitting flow from the second inlet port to the outlet port while simultaneously blocking flow through the first inlet port. Optionally, the valve is a 4-way stopcock with a swivel male luer lock. In certain embodiments, the first and second vessels are separate syringes. In certain embodiments, the spinal needle is interconnected to the valve via a length of flexible tubing. A T-connector may interconnect the tubing to the spinal needle. In certain embodiments, the spinal needle is a five inch, 22 or 24 gauge spinal needle. In certain embodiments, the device further comprises an introducer needle connected to a distal end of the spinal needle. Optionally, the introducer needle is a 3.5 inch, 18 gauge introducer needle.

This method and this device may each optionally be used for intrathecal delivery of the compositions provided herein. Alternatively, other methods and devices may be used for such intrathecal delivery.

In one embodiment, a single-dose of AAVhu68.SMA as provided herein is administered to adults (at least 18 years of age (≥18)) with genetically confirmed 5q SMA and/or a clinical history of Type 3 SMA. In other embodiments, patients may be younger (e.g., 12 years old to up to 18 years old; 6 years old to 12 years; 3 years to 6 years; 18 months to 3 years; 6 months to 18 months; newborn). The patients may be non-ambulatory or ambulatory patients. Dosing may be via a single dose of vector by ICM (intra-cisterna magna) injection. In one embodiment, the dose ranges from about $3 \times 10^{13}$ GC to a high dose of $1 \times 10^{14}$ GC. However, other suitable ranges are provided herein. Efficacy assessments may include one or more of: motor assessments, such as six-minute walt test (6MWT), 10 meter walk time, RULM score, 4 stair climb, 9 hole peg test; pulmonary function tests such as forced vital capacity (FVC), maximum expiratory pressure (MEP), and maximum inspiratory pressure (MIP); measures of respiratory function, PedsQL (fatigue scale), SMA-FRS (functional rating scale), electrophysiology, such as nerve conduction testing, CMAP (e.g., ulnar and peroneal CMAP amplitude, and sensory testing, SMN protein concentration and other exploratory biomarkers will be evaluated in CSF.

In one embodiment, a syringe containing vector at the appropriate concentration is used. Prior to vector administration, a lumbar puncture is performed to remove a predetermined volume of CSF and then to inject iodinated contrast intrathecally (IC) to aid in visualization of relevant anatomy of the cisterna magna. Intravenous (IV) contrast may be administered prior to or during needle insertion as an alternative to the intrathecal contrast. The decision to used IV or IC contrast is at the discretion of the interventionalist. The patient is anesthetized, intubated, and positioned on the procedure table. Intraoperative neurophysiological monitoring (IONM) equipment is attached to the participant. The injection site is prepped and draped using sterile technique. A spinal needle (22-25 G) is advanced into the cisterna magna under fluoroscopic guidance. A larger introducer needle is used to assist with needle placement. After confirmation of needle placement, the extension set is attached to the spinal needle and allowed to fill with patient CSF. At the discretion of the interventionalist, a syringe containing contrast material may be connected to the extension set and a small amount injected to confirm needle placement in the cisterna magna. After the needle placement is confirmed by CT guidance+/−contrast injection, a syringe containing vector (e.g., 5.6 mL) is connected to the extension set. The syringe contents is slowly injected over 1-2 minutes, delivering a volume of about 5 mL. The needle is slowly removed from the patient.

As used herein, the "subject" is a mammal, e.g., a human, mouse, rat, guinea pig, dog, cat, horse, cow, pig, or non-human primate, such as a monkey, chimpanzee, baboon or gorilla. In one embodiment, the subject is a human patient who has SMA.

The International SMA Consortium classification defines several degrees of severity in the SMA phenotype, depending on the age of onset and motor development milestones. SMA 0 designation is proposed to reflect prenatal onset and severe joint contractures, facial diplegia, and respiratory failure. Type I SMA, Werdnig-Hoffmann I disease, is the most severe post-natal form with onset within 6 months of birth. Patients are unable to sit up and have serious respiratory dysfunction. Type II SMA is the intermediate form with onset within the first 2 years; children can sit up but are unable to walk. The clinical course is variable. Type III (also called Kugelberg-Welander disease) begins after 2 years of age and usually has a chronic evolution. Children can stand and walk unaided at least in infancy. Adult form (type IV) is the mildest, with onset after 30 years of age; few cases have been reported and its prevalence is not accurately known.

In some instances, SMA is detected in a fetus at around 30 to 36 weeks of pregnancy. In this situation, it may be desirable to treat the neonate as soon as possible after delivery. It also may be desirable to treat the fetus in utero. Thus, a method of rescuing and/or treating a neonatal subject having SMA is provided, comprising the step of delivering a hSNM1 gene to the neuronal cells of a newborn subject (e.g., a human patient). A method of rescuing and/or treating a fetus having SMA is provided, comprising the step of delivering a hSMN gene to the neuronal cells of the fetus in utero. In one embodiment, the gene is delivered in a composition described herein via intrathecal injection. This method may utilize any nucleic acid sequence encoding a functional hSMN protein, whether a codon optimized hSMN as described herein or a native hSMN, or an hSMN allele with potentiated activity, as compared to a "wild type" protein, or a combination thereof. In one embodiment, treatment in utero is defined as administering an hSMN construct as described herein after detection of SMA in the fetus. See, e.g., David et al, Recombinant adeno-associated virus-mediated in utero gene transfer gives therapeutic transgene expression in the sheep, Hum Gene Ther. 2011 April; 22(4):419-26. doi: 10.1089/hum.2010.007. Epub 2011 Feb. 2, which is incorporated herein by reference.

In one embodiment, neonatal treatment is defined as being administered an hSMN construct as described herein within 8 hours, the first 12 hours, the first 24 hours, or the first 48 hours of delivery. In another embodiment, particularly for a primate (human or non-human), neonatal delivery is within the period of about 12 hours to about 1 week, 2 weeks, 3 weeks, or about 1 month, or after about 24 hours to about 48 hours. In another embodiment, for late onset SMA, the composition is delivered after onset of symptoms. In one embodiment, treatment of the patient (e.g., a first injection) is initiated prior to the first year of life. In certain embodiments, e.g., with infants, the construct is readministered, e.g., after 1 year of age. Optionally, more than one readministration is permitted. Such readministration may be with the same type of vector, a different viral vector, or via non-viral delivery as described herein. In another embodiment, treatment is initiated after the first 1 year, or after the first 2 to 3 years of age, after 5 years of age, after 11 years of age, or at an older age.

According to the present invention, a "therapeutically effective amount" of the AAV.hSMN is delivered as described herein to achieve a desired result, i.e., treatment of SMA or one or more symptoms thereof. Other desired results include reducing muscle weakness, increasing muscle strength and tone, preventing or reducing scoliosis, or maintaining or increasing respiratory health, or reducing tremors or twitching. Other desired endpoints can be determined by a physician.

In certain embodiments, therapeutic effectiveness of a composition containing the AAV.hSMN as provided herein may be assessed by one or more of the following parameters. Such scores may be at 52 weeks, or at a longer or shorter interval, e.g., 8 weeks, 12 weeks, 36 weeks, 48 weeks, or times therebetween. RULM scores at a predetermined time post-dosing are compared to baseline scores. Motor function may be measured by 6MWT test, and 10 meter walk time in ambulatory subjects. Motor function may be measured by 9 hole peg test (ambulatory and non-ambulatory) and 4 stair climb test (ambulatory only). Pulmonary function may be measured by Forced vital capacity (FVC), maximum expiratory pressure (MEP), maximum inspiratory pressure (MIP). Changes from baseline in ulnar and the peroneal CMAP amplitude may be assessed. PedQLVersion 3.0 multidimensional fatigue scale, adult report module may be assessed. SMA-FRS (functional rating scale) may be assessed. Pharmacokinetics of the vector in DNA and other AAV-based drug components in CSF, serum, and urine may be measured.

As used herein, the 6MWT is a measure of the distance covered by an Ambulatory subject in a 6MWT. The 6MWT will be performed in a long low traffic straight hallway located indoors. A 30-meter distance will be marked with orange cones on either end. A starting line will be marked with brightly colored tape.

RULM: The revised upper limb module consists of 20 motor tasks performed with one upper extremity selected by the subject. Performance on each task is rated on a scale of 0-2 by the evaluator.

9 hole peg test: The 9-HPT is a brief, standardized, quantitative test of upper extremity function. Both the dominant and non-dominant hands are tested twice. The subject is seated at a table with a small, shallow container holding nine pegs and a wood or plastic block containing nine empty holes. On a start command when a stopwatch is started, the subject picks up the nine pegs one at a time as quickly as possible, puts them in the nine holes, and, once they are in the holes, removes them again as quickly as possible one at a time, replacing them into the shallow container. The total time to complete the task is recorded. Two consecutive trials with the dominant hand are immediately followed by two consecutive trials with the non-dominant hand. The score for the 9-HPT is an average of the four trials. The two trials for each hand are averaged, converted to the reciprocals of the mean times for each hand and then the two reciprocals are averaged.

10 meter walk time: The 10-meter walk time is a measure of the time required to walk 10 meter. The test will be performed in a long-low traffic straight hallway located indoors. A 10 meter distance will be marked with orange cones on either end. A starting line will be marked with brightly colored tape.

4 stair climb: The 4 stair climb test evaluates the time required for a subject to ascend and descend 4 stairs. The task will be performed by a trained evaluator who will ensure that the subject is able to safely complete the task. The stairs must have a 16-20 cm rise and a handrail. Subjects are instructed to ascend and descend as quickly as possible in a safe manner. Both the time required to complete the task as well as the need for use of the handrail will be recorded.

Electrophysiology studies are performed to assess the function of motor units. CMAP: Motor nerve conduction studies of the ulnar nerve with be performed preferentially on the right arm unless there is a compelling reason to avoid study of this limb (e.g. premorbid superimposed nerve injury). This involves providing current to the nerve and recording the motor response in the muscle. This response is called a compound muscle action potential. Both the height and area of the CMAP (amplitude and AUC) may be measured.

Functional and fatigue rating scales:
PedsQL fatigue scale, adult report: The PedsQL Multidimensional Fatigue Scale is an 18-item questionnaire assessing general fatigue (6 items), sleep and rest (6 items), and cognitive fatigue (6 items).
SMA-FRS: The SMA-FRS is an easily administered ordinal rating scale based around 10 aspects of activities of daily living. Each subset is scored from 0 (fully dependent) to 5 (fully independent) by the subject or caregiver, with a maximum score of 50.

In one embodiment, the sequence of assessments are performed in the following order for a patient as follows: PedsQL (fatigue scale), SMA-FRS (functional rating scale), 6MWT, 15-min rest (minimum), RULM, 9-hole peg test, 10 meter walk, 15-min rest (minimum), 4 stair climb, PFTs* and Ulnar and peroneal CMAP*. *Can be performed in any order. Tests that cannot be safely performed by the patient will be omitted.

Prior to treatment, the SMA patient can be assessed for neutralizing antibodies (Nab) to the capsid of the rAAV vector used to deliver the hSMN-1 gene. Such Nabs can interfere with transduction efficiency and reduce therapeutic efficacy. SMA patients that have a baseline serum Nab titer≤1:5 to ≤1:20, or ≤1:2.5 to ≤1:10 are good candidates for treatment with the rAAV.hSMN1 gene therapy protocol. Treatment of SMA patients with titers of serum Nab>1:5 may require a combination therapy, such as transient co-treatment with an immunosuppressant before and/or during treatment with rAAV.hSMN vector delivery. Optionally, immunosuppressive co-therapy may be used as a precautionary measure without prior assessment of neutralizing antibodies to the AAV vector capsid and/or other components of the formulation. In certain embodiments, prior immunosuppression therapy may be desirable to prevent potential adverse immune reaction to the hSMN transgene product, especially in patients who have virtually no levels of SMN activity, where the transgene product may be seen as "foreign."

Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, cyclosporin, tacrolimus, sirolimus, IFN-β, IFN-γ, an opioid, or TNF-α (tumor necrosis factor-alpha) binding agent. In certain embodiments, the immunosuppressive therapy may be started prior to the gene therapy administration. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week, about 15 days, about 30 days, about 45 days, 60 days, or longer, as needed. In certain embodiments, a patient receiving the rAAVhu68.SMA gene therapy described herein has received prior treatments with nusinersen. In other embodiments, the patient receives ongoing treatments with nusinersen and is monitored post-gene therapy for a reduction or elimination in the need for such nusinersen treatment. Patients receiving rAAVhu68. SMA may receive other therapies, including, without limitation, pyridostigmine [μm Ultrecht], RO7034067 [Hoffman-LaRoche], celecoxib, CK-2127107 [Astellas Pharma]. In certain embodiments, efficacy of the rAAVhu68.SMA is measured by a decrease in the frequency and/or dose of such co-therapies. In certain embodiments, since AAVhu68-SMN1 therapy although durable may not result in as high a correction as desired for a selected patient, so roll-over to nusinersen (Spinraza™) therapy may be desired as early as 6 months after AAVhu68-SMN1 treatment, administration of nusinersen (Spinraza™) to patients could be considered co-administration of the two agents. See, also, Wang et al, Consensus Statement for Standard of Care in Spinal Muscular Atrophy, which provides a discussion of the present standard of care for SMA and www.ncbi.nlm.nih.gov/books/NBK1352/.

For example, when nutrition is a concern in SMA, placement of a gastrostomy tube is appropriate. As respiratory function deteriorates, tracheotomy or noninvasive respiratory support is offered. Sleep-disordered breathing can be treated with nighttime use of continuous positive airway pressure. Surgery for scoliosis in individuals with SMA II and SMA III can be carried out safely if the forced vital capacity is greater than 30%-40%. A power chair and other equipment may improve quality of life. See also, U.S. Pat. No. 8,211,631, which is incorporated herein by reference.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (±10%) from the reference given, unless otherwise specified.

As used herein, "disease", "disorder" and "condition" are used interchangeably, to indicate an abnormal state in a subject.

The term "expression" is used herein in its broadest meaning and comprises the production of RNA or of RNA and protein. With respect to RNA, the term "expression" or "translation" relates in particular to the production of peptides or proteins. Expression may be transient or may be stable.

The term "translation" relates to a process at the ribosome, wherein an mRNA strand controls the assembly of an amino acid sequence to generate a protein or a peptide.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Example 1—Novel Clade F AAV—AAVhu68

Tissue DNA was extracted from human tissue samples as PCR template with QIAamp columns (Qiagen) following the manufacturer's recommendations with the following modifications. Q5 DNA polymerase (Q5® Hot Start High-Fidelity 2× Master Mix, NEB) was chosen for its extraordinary high fidelity and robust efficiency to recover full length VP1 gene of potential AAVs in the samples with as described by Gao, et al [Proc Natl Acad Sci USA, 2002 Sep. 3, 99(18): 11854-11859 (Epub 2002 Aug. 21)] with the primer set modified as follows: in the place of the AV1NS, primer, prm504, [GCTGCGTCAACTGGACCAAT-GAGAAC, SEQ ID NO: 23] was used and in the place of reverse primer AV2CAS, prm505 [CGCAGAGAC-CAAAGTTCAACTGAAACGA, SEQ ID NO: 24], was used. The PCR conditions were modified as follows:

|  | μL |
|---|---|
| Water | 9 |
| prm504 | 1.25 |
| prm505 | 1.25 |
| template | 1 |
| 2X Q5 | 12.5 |

PCR Program

|  | Time (seconds) | Cycle(s) |
| --- | --- | --- |
| 98 | 30 | 1 |
| 98 | 10 | 50 |
| 59 | 10 |  |
| 72 | 93 |  |
| 72 | 120 | 1 |

The bands of 3 kb from the PCR were cut out from the gel; DNA was extracted with QIAquick Gel Extraction Kit (Qiagen) and cloned into Zero Blunt® TOPO® PCR Cloning Kit (Thermo Fisher Scientific). Plasmids were sequenced to get the full length of AAV VP1 gene. For most of the samples, at least three plasmids were fully sequenced and consensus sequences were drawn as the final AAV sequence for that sample.

The acquired nucleic acid sequence encoding the vp1 capsid protein of AAVhu68 is provided in SEQ ID NO: 7. See, also, FIGS. 8B-8D. The vp1 amino acid sequence of AAVhu68 is provided in FIG. 8A and SEQ ID NO: 8. Compared to AAV9, AAVhu31 and AAVhu32, two mutations (A67E and A157V) were identified critical in AAVhu68 (circled in FIG. 8A).

pAAV2/hu68 trans plasmid was then made by loading the VP1 gene of hu68 into a pAAV2/9 backbone in the place of the AAV9 VP1 gene in order to assess packaging efficiency, yield, and transduction properties. The pAAV2/9 plasmid contains AAV2 5' and 3' ITRs flanking the capsid gene and is available from the Penn Vector Core [University of Pennsylvania, Phila, Pa. US, pennvectorcore.med.upenn.edu].

Example 2—AAVhu68 Vectors

AAVhu68 and AAV9 vectors carrying various tags, such as GFP and LacZ were generated and evaluated. Each of the vectors was generated using the triple transfection technique in 293 cells, as described by Gao et al [Gao, Guang-Ping, et al. "Novel adeno-associated viruses from rhesus monkeys as vectors for human gene therapy." Proceedings of the National Academy of Sciences 99.18 (2002): 11854-11859].

1. Production of pAAVhu68 Trans Plasmid

The nucleic acid sequence encoding the vp1 capsid protein is provided in SEQ ID NO: 7.

pAAV2/hu68 trans plasmid was made by loading the VP1 gene of hu68 into a pAAV2/9 backbone in the place of the AAV9 VP1 gene in order to assess packaging efficiency, yield, and transduction properties. The pAAV2/9 plasmid contains AAV2 5' and 3' ITRs flanking the capsid gene and is available from the Penn Vector Core [University of Pennsylvania, Phila, Pa. US,pennvectorcore.med.upenn.edu].

2. Yield of AAVhu68 Vectors 293 cells were cultured and maintained in DMEM, 1X (Dulbecco's Modification of Eagle's Medium) with 4.5 g/L glucose, L-glutamine & sodium pyruvate supplemented with 10% of fetal bovine serum under the atmosphere with 5% $CO_2$ at 37° C. Transfections were performed as described by Gao et al [Gao, Guang-Ping, et al. "Novel adeno-associated viruses from rhesus monkeys as vectors for human gene therapy." Proceedings of the National Academy of Sciences 99.18 (2002): 11854-11859.] with the vector plasmid replaced by pAAV2/hu68 or pAAV2/9. The transgene cassette utilized was CB7.CI.ffLuciferase.RBG. The transfected cells were further cultured in 6-well plates. Total lysate of the cells as well as the supernatant was collected for virus quantification via TaqMan (Applied Biosystems) analysis by using probes and primers targeting the rabbit beta-globin polyA region of the transgene cassette as described in Gao et al [Gao, Guangping, et al. "Purification of recombinant adeno-associated virus vectors by column chromatography and its performance in vivo." Human gene therapy 11.15 (2000): 2079-2091.]. The yields of six pAAV2/9 plasmids and six pAAV2/hu.68 plasmids were compared in 6-well plate, head to head, in terms of both supernatant titer and the total lysate titer. Each plasmid was from an individual bacteria colony.

The yield of AAVhu68 was found to be similar to that of AAV9 in terms of total lysate. However, in the supernatant, the yield of AAVhu68 was significantly higher than that of AAV9. Thus, AAVhu68 was demonstrated as a better vector compared to AAV9 in terms of production since supernatant is preferred for large scale virus production.

3. In Vivo Transduction of AAVhu68.LacZ

AAVhu68.CB7.nLacZ (also referred as AAVhu68.LacZ) was generated via inserting a sequence encoding nuclear-localized bacterial β-galactosidase (nLacZ) as transgene and then produced as described above. To assess the packaging efficiency, yield, transduction properties, transduction efficiency and tropism of AAVhu68 in vivo, mice were injected with $5 \times 10^{11}$ genome copies of the AAVhu68.LacZ vector via various administration methods, such as intravenous, intramuscular and intranasal administration. Muscle, lung, liver and heart were collected after sacrificing the mice two weeks after vector administration. Frozen sections of each organ were prepared, processed and analyzed as conventional protocol detecting LacZ gene expression [Bell, Peter, et al. "An optimized protocol for detection of E. coli β-galactosidase in lung tissue following gene transfer." Histochemistry and cell biology 124.1 (2005): 77-85.]. These results revealed that AAVhu68 demonstrated high transduction efficiency and a broad tissue/organ tropism.

4. In Vivo Transduction of AAVhu68.GFP Compared to AAV9.GFP

AAVhu68.GFP and AAV9.GFP were generated via inserting a gene encoding green fluorescent protein (GFP) as transgene and then produced as described above. To assess the packaging efficiency, yield, transduction properties, transduction efficiency and tropism of AAVhu68 and AAV9 in vivo, mice were administrated with AAVhu68.GFP or AAV9.GFP at the doses of $1 \times 10^{10}$ GC or $1 \times 10^{11}$ GC. Sections from various brain regions (hippocampus, motor cortex and cerebellum) of mice with intracerebroventricular administration of the vectors were investigated. Transduction of the AAV vectors was observed in all tested hippocampal samples except one from mice injected with $1 \times 10^{10}$ GC of AAV9.GFP. A better transduction of AAVhu68.GFP compared to that of AAV9 was observed in the motor cortex. Furthermore, transduction in cerebellum of AAVhu68.GFP was observed when mice were injected with $1 \times 10^{11}$ GC of the vector only. In these mice, AAVhu68 displayed a higher transduction efficiency as well as a broader tropism in the brain compared to AAV9.

In a further experiment, various organs, such as liver, kidney, heart and pancreas, from mice administrated with AAVhu68.GFP intravenously were prepared and processed as described by Wang et al Mang L, Calcedo R, Bell P, Lin J, Grant R L, Siegel D L, Wilson J M, Hum Gene Ther. 2011 November; 22(11):1389-401; Wang L, Calcedo R, Wang H, Bell P, Grant R, Vandenberghe L H, Sanmiguel J, Morizono H, Batshaw M L, Wilson J M, Mol Ther. 2010 January; 18(1):126-34]. Strong positive signal was observed in liver while kidney, heart and pancreas demonstrated transduction of the vector as well, indicating a broad tissue/organ tropism of AAVhu68 vector.

Example 3—AAV Vectors Containing hSMN

The AAVhu68.CB7.CI.hSMN1co.RBG consists of an external component and internal DNA genome. The external vector component is a serotype hu68, T=1 icosahedral capsid consisting of 60 copies of three AAV viral proteins, VP1, VP2, and VP3, at a ratio of approximately 1:1:8-10. The capsid contains a single-stranded DNA genome consisting of the human Survival of motor neuron 1 (hSMN1) transgene flanked by the two AAV inverted terminal repeats (ITRs). An enhancer, promoter, intron, hSMN1 coding sequence and polyadenylation (polyA) signal comprise the human SMN1 transgene. The ITRs are the genetic elements responsible for the replication and packaging of the genome during vector production and are the only viral cis elements required to generate rAAV. Expression of the hSMN1 coding sequence is driven by a CB7 promoter, a hybrid between a cytomegalovirus (CMV) immediate early enhancer (C4) and the chicken beta actin promoter. Transcription from this promoter is enhanced by the presence of the chicken beta actin intron (CI). A rabbit beta globin polyA signal is included to mediate termination of human hSMN1 mRNA transcripts. A schematic of the AAVhu68.CB7.CI.hSMN1co.RBG vector genome is shown in FIG. 1A.

Description of the Sequence Elements:

1. Inverted terminal repeats (ITR): AAV ITRs (GenBank #NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.

2. CMV immediate-early enhancer (382 bp, GenBank #K03104.1).

3. Chicken β-actin promoter (282 bp; GenBank #X00182.1) promoter and is used to drive high-level human Survival of Motor Neuron 1(hSMN1) expression.

4. Chicken β-actin intron: The 973 bp intron from the chicken β-actin gene (GenBank #X00182.1) is present in the vector expression cassette. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased level of gene expression.

5. Coding sequence: The human SMN1 sequence (www.ncbi.nlm.nih.gov/nuccore/NM_000344.3) was codon-optimized and synthesized (UPenn). Spinal muscular atrophy (SMA) is caused by mutations in the telomeric gene Survival of Motor Neuron 1 (SMN1). Mutations in SMN1 result in selective toxicity to lower motor neurons, leading to progressive neuron loss and associated muscle weakness and degeneration. The transgene we are using is SMN1, isoform D. Isoform D codes for the longest isoform, and this variant is thought to be the predominant transcript/isoform produced by SMN1 in both CNS and ubiquitously.

6. Polyadenylation Signal: The 127 bp rabbit β-globin polyadenylation signal (GenBank #V00882.1) provides cis sequences for efficient polyadenylation of the antibody mRNA. This element functions as a signal for transcriptional termination, a specific cleavage event at the 3' end of the nascent transcript and addition of a long polyadenyl tail.

The vector was prepared using conventional triple transfection techniques in 293 cells as described [Mizukami, Hiroaki, et al. A Protocol for AAV vector production and purification. Diss. Division of Genetic Therapeutics, Center for MolecularMedicine, 1998.]. All vectors were produced by the Vector Core at the University of Pennsylvania as previously described [Lock, M., et al, Hum Gene Ther, 21: 1259-1271 (2010)].

A droplet digital Polymerase Chain Reaction (ddPCR)-based technique was performed for determining the genome copy (GC) titer for AAV vectors as described previously (Lock, Martin, et al. "Absolute determination of single-stranded and self-complementary adeno-associated viral vector genome titers by droplet digital PCR." Human gene therapy methods 25.2 (2013): 115-125). The method is practical, reports equivalent or better titers than qPCR, and does not require a plasmid standard curve. The assay utilized involved digestion with DNase I, followed by digital PCR analysis to measure encapsulated vector genomic copies. DNA detection was accomplished using sequence specific primers targeting the polyA region in combination with a fluorescently tagged probe hybridizing to this same region.

Example 4—AAVhu68.CB7.CI.hSMN.RBG in the Model of SMA

All animal procedures were performed in accordance with protocols approved by the Institutional Animal Care and Use Committee (IACUC) of the University of Pennsylvania. All mice were maintained at the Animal Facility of the Translational Research Laboratories at the University of Pennsylvania.

In mice, there is one SMN gene which is equivalent to human SMN1 (hSMN1). Complete loss of this gene results in an embryonic lethal phenotype (Monani U R, Sendtner M, Coovert D D et al. The human centromeric survival motor neuron gene (SMN2) rescues embryonic lethality in Smn (−/−) mice and results in a mouse with spinal muscular atrophy. Hum Mol Genet 2000; 9:333-9; Schrank B, Gotz R, Gunnersen J M et al. Inactivation of the survival motor neuron gene, a candidate gene for human spinal muscular atrophy, leads to massive cell death in early mouse embryos. Proc Natl Acad Sci USA 1997; 94:9920-5.). One of the most commonly used preclinical models of SMA to evaluate therapeutics is the SMNΔ7 mouse model. The SMNΔ7 mouse model is a transgenic mouse developed on the FVB background that has 2 copies of human SMN2 (hSMN2) and 2 copies of hSMN2 with exon 7 removed (SMNΔ7). Wild-type (WT) SMNΔ7 mice harbor 2 copies of murine SMN (mSMN), heterozygous (HET) mice have 1 copy of mSMN, and knockout (KO) SMNΔ7 mice have no copies of mSMN. KO SMNΔ7 mice have an average lifespan of 13-15 days and display reduced motor neuron counts in the spinal cord, reduced myofiber size, reduced weight, impaired righting and ambulation, and an increase in the number of partially and non-innervated neuro-muscular junctions. A major advantage of the SMNΔ7 mouse model is an increased treatment window relative to severe SMA models with an average lifespan of approximately 5 days, while also displaying a severe enough phenotype to quickly discern if therapeutic interventions are having an impact on disease attenuation. Please see Le T T, Pham L T, Butchbach M E et al. SMNDelta7, the major product of the centromeric survival motor neuron (SMN2) gene, extends survival in mice with spinal muscular atrophy and associates with full-length SMN. Hum Mol Genet 2005; 14:845-57.

In example 4, the mSMN−/− hSMN2+/+SMNΔ7+/+(KO SMNΔ7, also noted as SMNΔ7 in the following examples) mice were utilized. The immunohistochemistry for SMN demonstrated that in cortex, cerebellum and spinal cord, SMNΔ7 pups exhibited no expression of SMN1 (FIG. 2). 23 days after injection of $3 \times 10^{10}$ GC of the AAVhu68.CB7.CI.hSMN1.RBG vectors at birth, SMNΔ7 pups, wild-type and heterozygous littermates were observed with an increase expression of SMN. Administration was performed by intracerebroventricular injection into the left lateral ventricle.

Viral transduction of the tested vector was further evaluated by in-situ hybridization (ISH) for the codon-optimized hSMN1 ribonucleic acid (RNA) in the cortex of AAVhu68.CB7.CI.hSMN1co.RBG treated animals. Wild type and SMNΔ7 animals were provided as controls. Result shown in the bottom panel of FIG. 2 demonstrates a high transduction rate at the test dose.

An analysis to determine the percentage of motor neuron transduction via immunohistochemistry is performed. A further analysis via western blot to detect SMN expression of the homogenates from both brain and spinal cord is performed.

Example 5—AAVhu68.CB7.CI.hSMN1.RBG Increases Survival in a Rodent Model of SMA

Figures 3A, 3B:
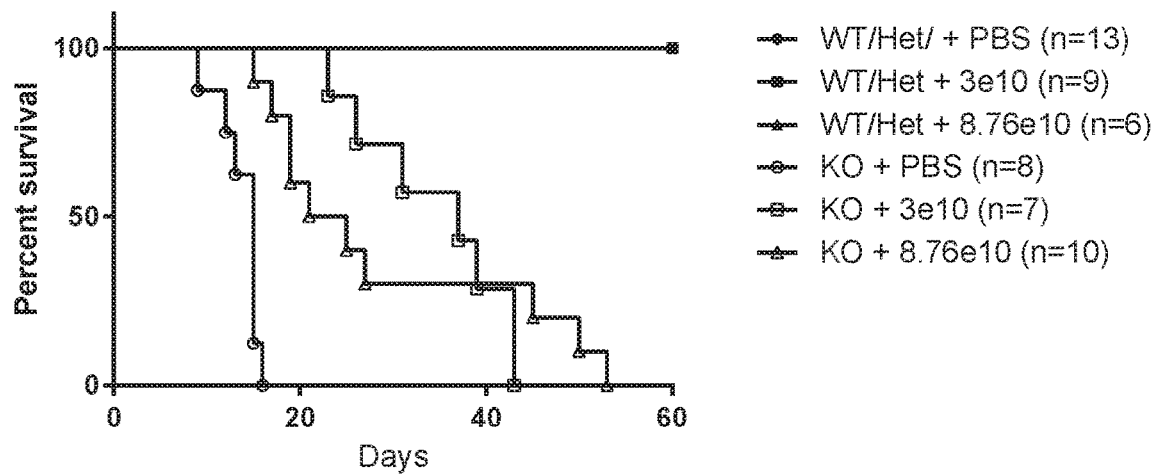
FIG. 3A is a survival curve of SMNΔ7 (KO) mice treated with or without $3 \times 10^{10}$ or $8.76 \times 10^{10}$ GC/pup of AAVhu68.CB7.CI.hSMN1.RBG. Wild-type (WT)/heterozygous (Het) littermates and PBS injected mice served as controls.
FIG. 3B is a table of statistical analysis of the survival curve described in FIG. 3A. Median Survival was calculated and listed.

The efficacy of intracerebroventricular injection of AAVhu68.CB7.CI.hSMN1.RBG was evaluated in newborn mSMN1$^{-/-}$hSMN2$^{+/+}$SMNΔ7$^{+/+}$ (SMNΔ7), heterozygous littermates (HET) and wild type C57BL/6J (WT) pups. The tested mice received a single intracerebroventricular (ICV) injection into the left lateral ventricle with either $3 \times 10^{10}$ or $8.76 \times 10^{10}$ GC of AAVhu68.CB7.CI.hSMN1co.RBG within 24 hours of birth with phosphate-buffered saline (PBS). PBS injected pups were served as controls (FIG. 3A). Mice were monitored daily. Any mice meeting euthanasia criteria (20% weight loss from prior weighing or digital necrosis) or found dead prior to weaning were genotyped, and all mice that survived until weaning were genotyped.

During the two-month observation period, survival rates of the wild type, heterozygous pups injected with PBS, and heterozygous pups injected with the vector were similar, indicating no toxicity related to vector or route of administration (FIG. 3A). No significant differences in righting reflex were observed between PBS treated WT animals and WT mice treated with either $3 \times 10^{10}$ GC or $\sim 9 \times 10^{10}$ GC of AAVhu68.CB7.CI.hSMN1co.RBG (FIG. 3A). The median survival of the SMNΔ7 pups injected with PBS only (n=8) was 15 days. However, upon treatment with a lower dose of the vector ($3 \times 10^{10}$ GC/1.5 g pup), the median survival increased significantly to 37 days (n=7). If the dose of the vector was raised to $8.76 \times 10^{10}$ GC per pup (n=10), the median survival was 23 days (FIG. 3B). This result indicated an intracerebroventricular injection of AAVhu68.CB7.CI.hSMN1.RBG with both doses at birth successfully improved the survival of the SMNΔ7 pups while minimal toxicity was detected.

Example 6—AAVhu68.CB7.CI.hSMN1.RBG Promotes Growth in a Rodent Model of SMA

Figure 4A:
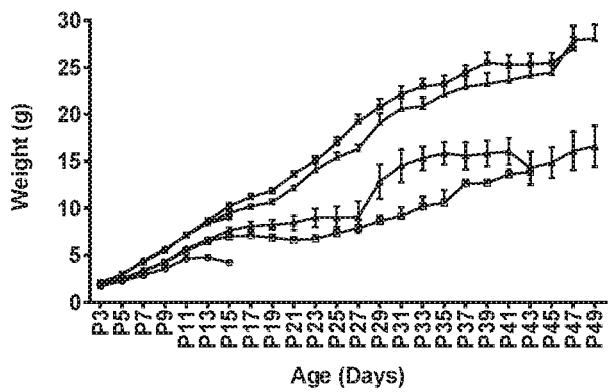
FIG. 4A is a line graph of body weights of SMNΔ7 (KO) mice treated with $3 \times 10^{10}$ or $8.76 \times 10^{10}$ GC/pup of AAVhu68.CB7.CI.hSMN1.RBG vectors. Wild-type (WT)/heterozygous (Het) littermates and PBS injected mice served as controls.

Beginning on Postnatal Day (PND) 3, mice were weighed every 2 days until they met euthanasia criteria or were found dead and the result was plotted in FIG. 4A. The overall change of the variable across all time points was compared between every two groups.

Figure 4B:
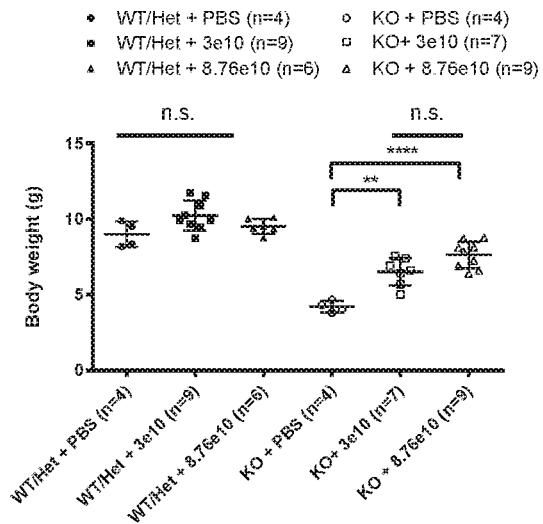
FIG. 4B is a graph of body weights on postnatal day 15 of SMNΔ7 (KO) mice treated with $3 \times 10^{10}$ or $8.76 \times 10^{10}$ GC/pup of AAVhu68.CB7.CI.hSMN1.RBG. Wild-type (WT)/heterozygous (Het) littermates and PBS injected mice served as controls.
Figure 4C:
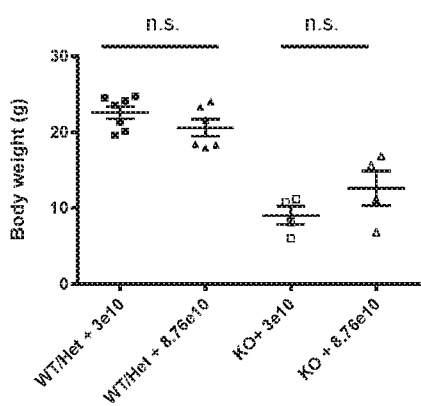
FIG. 4C is a graph of body weights on postnatal day 30 of SMNΔ7 (KO) mice treated with $3 \times 10^{10}$ or $8.76 \times 10^{10}$ GC/pup of AAVhu68.CB7.CI.hSMN1.RBG. Wild-type (WT)/heterozygous (Het) littermates served as controls.

Wild type and heterozygous pups treated with PBS or the vectors at both low and high doses showed a similar growth curve, indicating no toxicity related to vector or route of administration. The SMNΔ7 pups treated with PBS exhibited progressive weight loss and median survival of 15 days. However, when injected with AAVhu68.CB7.CI.hSMN1co.RBG vectors, the body weights of the pups slowly but steadily increased after birth. On postnatal day15 (P15), while the wild type pups from all three groups were comparable in weight, the vector rescued SMNΔ7 pups were significantly heavier compared to the PBS only group (FIG. 4B). On postnatal day 30 (P30), both SMNΔ7 pups and wild-type/heterozygous littermates demonstrated no difference in body weighs between the high dose and low dose of vector treatments (FIG. 4C).

Figure 4D:
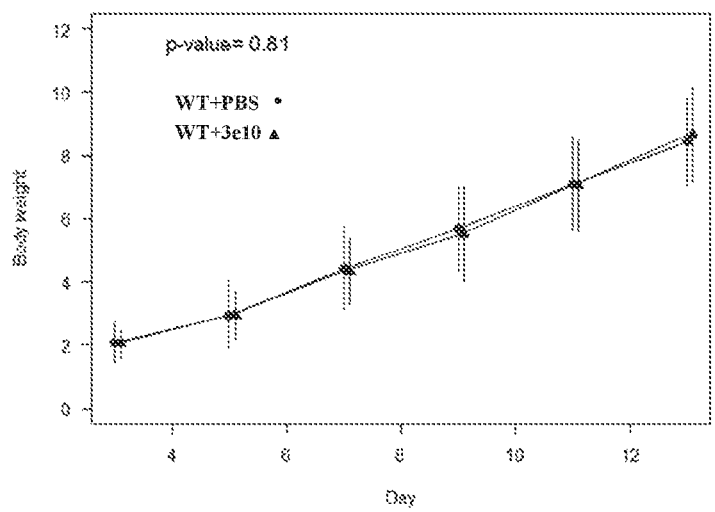
FIGS. 4D-4J are line graphs of body weights after normalization by gender. The experiment was performed every two days from postnatal day 3 to 13 or 15 on SMNΔ7 (KO) mice treated with $3 \times 10^{10}$ or $8.76 \times 10^{10}$ GC of AAVhu68.CB7.CI.hSMN1.RBG per pup. Wild-type/heterozygous littermates (WT) and PBS injected mice served as controls. P value was calculated via statistical analysis and indicated in the figure.
Figure 4E:
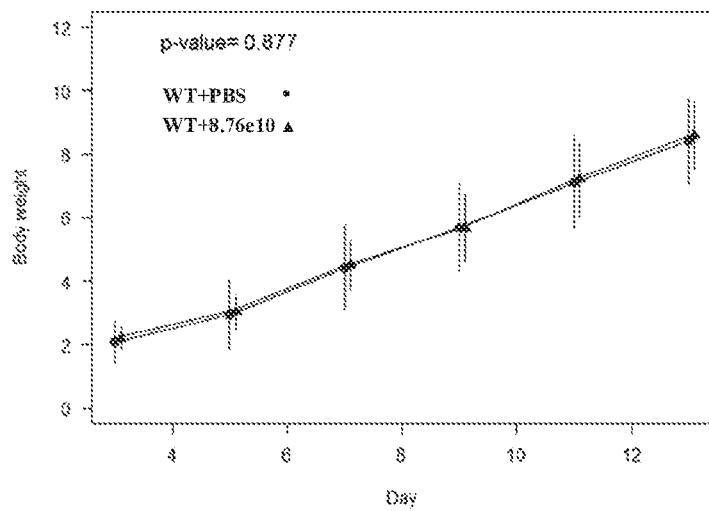
Figure 4F:
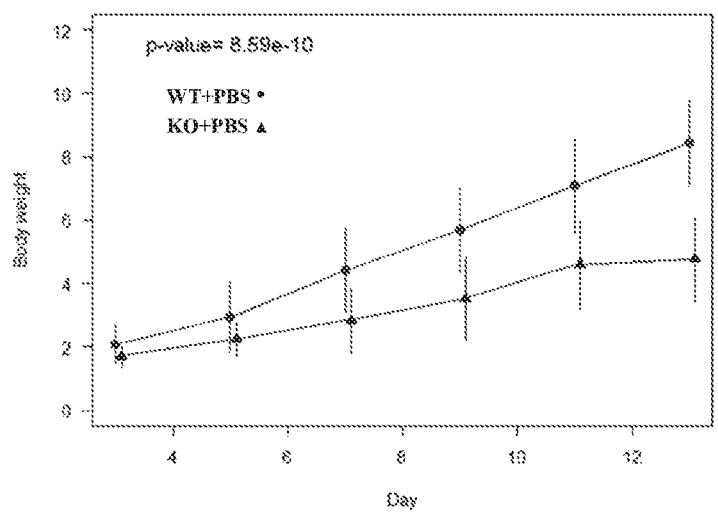
Figure 4G:
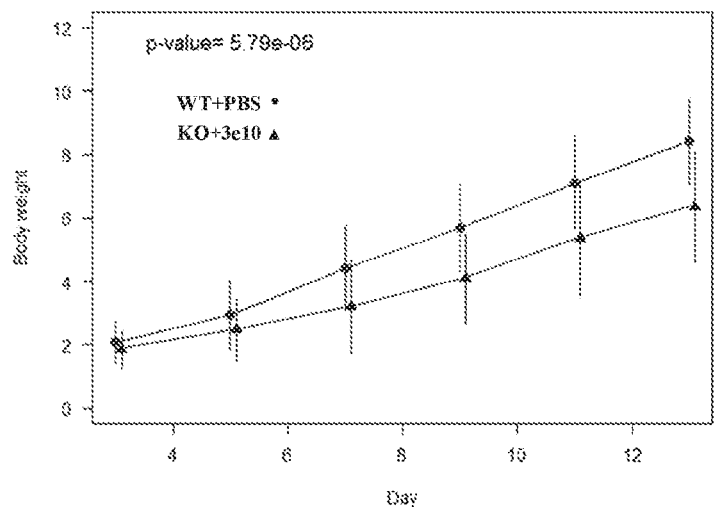
Figure 4H:
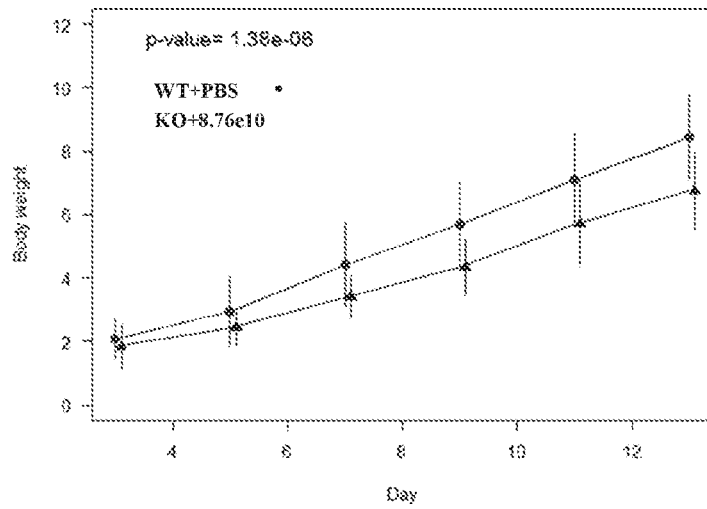
Figure 4I:
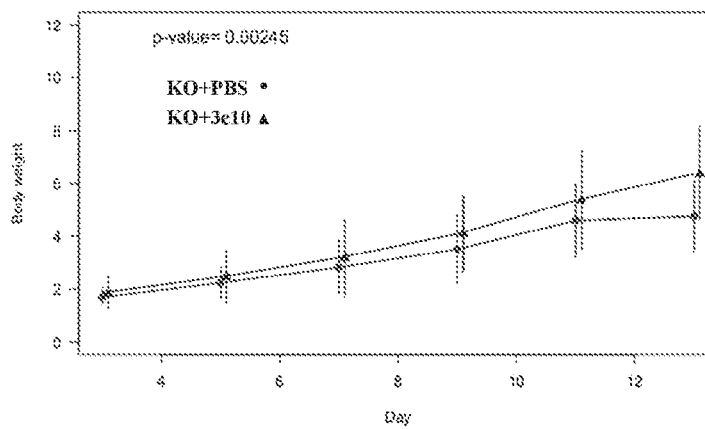
Figure 4J:
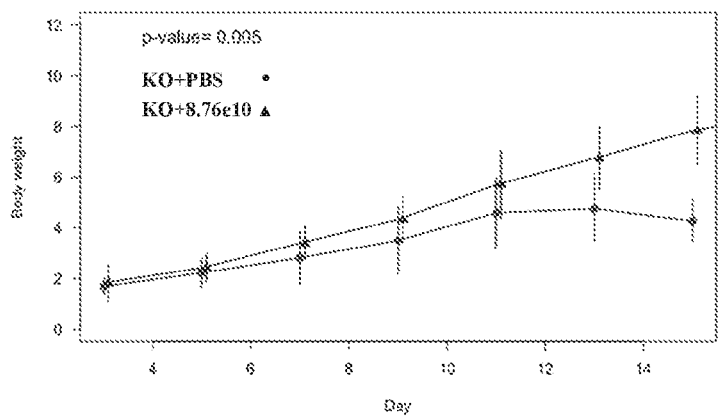

Further comparisons were carried out using linear mixed effect modeling within the R Program (version 3.3.1; cran.r-project.org) using function "lme" in the "nlme" package. Sex was included as a covariate in the analysis. Linear mixed effect model accounts for dependency of observations across different time points within each subject, and is a preferable method for the analysis of time-course data. No significant differences in weight were observed between PBS treated WT animals and WT mice treated with either $3 \times 10^{10}$ GC or $\sim 9 \times 10^{10}$ GC of AAVhu68.CB7.CI.hSMN1co.RBG (FIGS. 4D&4E), indicating no toxicity related to vector or route of administration. Compared to healthy littermates, SMNΔ7 pups demonstrated a slower growth rate of body weights (FIG. 4F), while treatments with $3 \times 10^{10}$ GC/pup or $8.76 \times 10^{10}$ GC/pup of AAVhu68.CB7.CI.hSMN1co.RBG in SMNΔ7 pups increased the gaining of the body weight significantly (FIGS. 4I & 4J).

These results suggested that AAVhu68.CB7.CI.hSMN1co.RBG improved the growth of SMNΔ7 pups indicated by body weights.

Example 7—Functional Evaluations Reveal Positive Effects of AAVhu68.CB7.CI.hSMN1.RBG in a Rodent Model of SMA Two functional evaluations, Hind-Limb Suspension Test and Righting Reflex Test, were performed to evaluate the development and progression of SMA upon treatment of the vector described herein.

To evaluate proximal hind limb muscle strength and fatigue in the neonate mouse model of SMA, the protocol for Hind-Limb Suspension Test was adopted and optimized from Behavior Phenotype for neonates: Hind Limb Suspension Test (a.k.a. Tube Test), SOP #SMA_M.2.2.001 from TREAT-NMD (El-Khodor et al.). Hind Limb Suspension (HLS) Score and Time Spent Hanging (TSH) were included as parameters to measure hind limb muscle strength and fatigue. The test was performed in 2 consecutive trials every 2 days after birth. Each trial was last to a maximum of 60 seconds. Both HLS and TSH were measured in the same trial. The first 15 seconds was used to determine the HLS score. For TSH, the time continued to count until the animal fell or time reached 60 seconds, whichever was the first. In addition, a litter of more than 10 animals was excluded from this study to avoid a bias due to nutrition competition. Litters under 5 pups was excluded from this study as the increased maternal care could cause milder phenotype and led to the bias of the study.

Figure 5A:
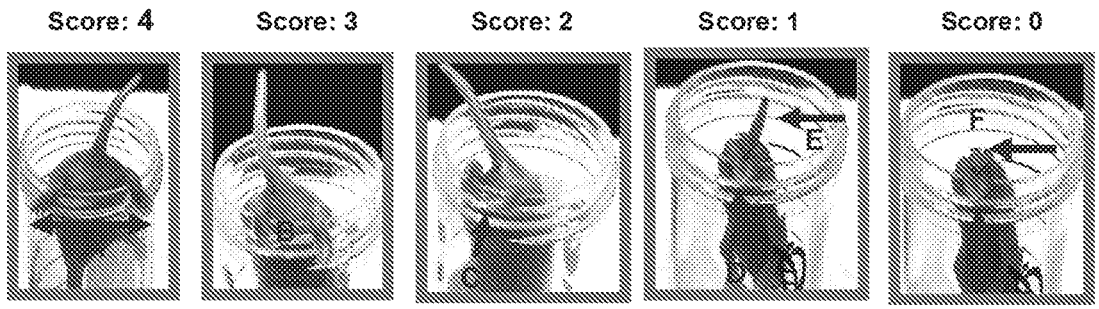
FIG. 5A is an illustration of the scoring system utilized in Hind-Limb Suspension Test.
Figure 5B:
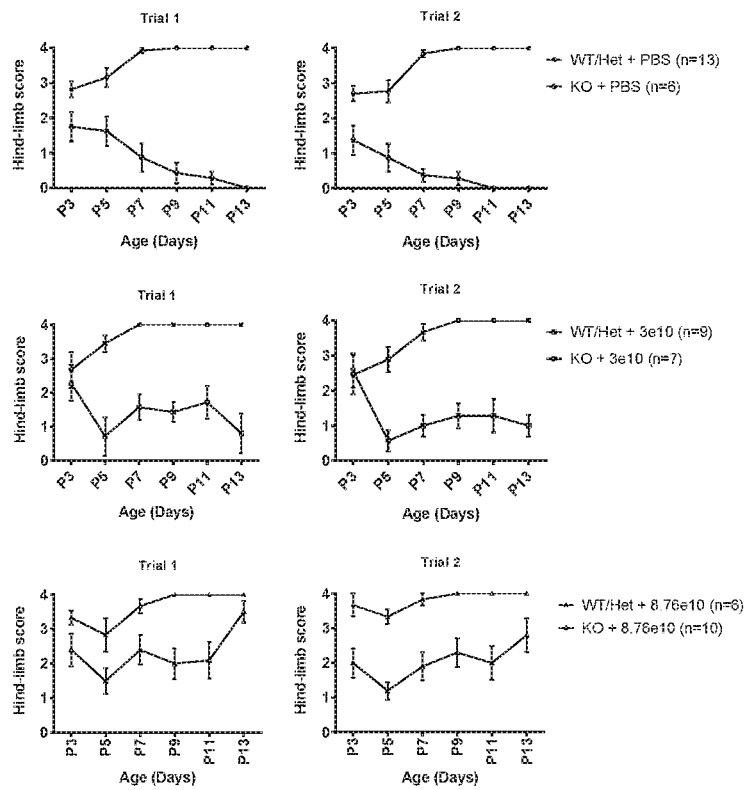
FIG. 5B encloses graphs of Hind-Limb Score recorded every two days from postnatal day 3 to 13 in SMNΔ7 (KO) mice treated with $3 \times 10^{10}$ or $8.76 \times 10^{10}$ GC of AAVhu68.CB7.CI.hSMN1.RBG per pup. Wild-type (WT)/heterozygous (Het) littermates and PBS injected mice served as controls.

Instead of an increasing HLS score upon growth observed in the wild type or heterozygous pups treated with PBS or vector, the SMNΔ7 pups injected with PBS exhibited a decline in HLS score indicating compromised hind limb muscle strength (FIG. 5B). However, with a single injection of AAVhu68.CB7.CI.hSMN1.RBG at the dose of $3 \times 10^{10}$ GC per pup, the HLS score stayed stable during the development of the SMNΔ7 pups. Furthermore, if the dose increased to $8.76 \times 10^{10}$ GC per pup, a slight increase of the HLS score upon time was observed. Those results indicated that the AAVhu68.CB7.CI.hSMN1co.RBG vector improved the functional development of SMNΔ7 pups.

Time Spent Hanging (TSH) was recorded as described above and served as an indicator for latency to fall, with no difference was observed in SMNΔ7 pups and its healthy littermates. This result indicated that TSH failed to reveal the compromised muscle function in SMNΔ7 model thus excluded from further evaluation.

To test the locomotor abilities and evaluate muscle strength in the neonate mouse model of SMA, a protocol of Righting Reflex Test was adopted and optimized from Behavior Phenotype for neonates: Righting Reflex, SOP #MD_M.2.2.002 from TREAT-NMD (Didonato et al.). It examined general body strength, which could be affected by muscle weakness and/or general poor health, by measuring the ability of mice to correct the orientation of body when it was taken out of its normal upright position. Individual animal was removed from its home cage and placed in a supine position so that all 4 paws were facing upwards. A finger was placed on the chest to stabilize the animals in the inverted position. The finger was then removed and a timer started. The timer was stopped once the animal had turned onto its stomach and had all 4 paws flat against the surface it was standing on. After each trial the animal was returned to its home cage and allowed to rest for 5 minutes.

The SMNΔ7 pups were tested every two days from postnatal day 7 to postnatal day 17. Each trial was 60 seconds maximum. The time that an animal took to return to the normal position within this time period was used to quantify muscle strength. If an animal was unable to right within the given time the trial was terminated and the time to right was recorded as 60 seconds.

In addition, a litter of more than 10 animals was excluded from this study to avoid a bias due to nutrition competition. Litters under 5 pups was excluded from this study as the increased maternal care could cause milder phenotype and led to the bias of the study. When the righting reflex test was used in conjugation with hind limb suspension test in the same day, it was always conducted first to prevent the animal with muscle exhausting.

Figure 6A:
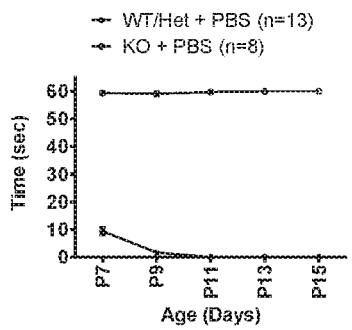
FIGS. 6A-6C enclose graphs showing the time that an animal took to return to its normal position in Righting Reflex Test. The experiment was performed every two days from postnatal day 7 to 17 on SMNΔ7 (KO) mice treated with $3 \times 10^{10}$ or $8.76 \times 10^{10}$ GC of AAVhu68.CB7.CI.hSMN1.RBG per pup. Wild-type (WT)/heterozygous (Het) littermates and PBS injected mice served as controls.
Figure 6B:
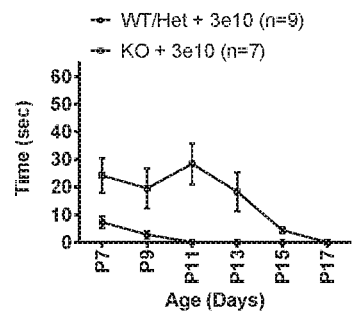
Figure 6C:
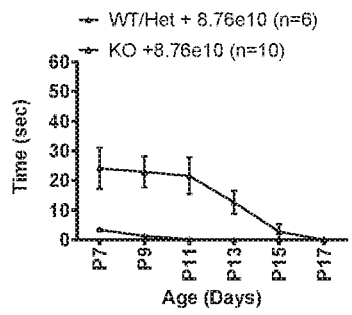
Figure 6D:
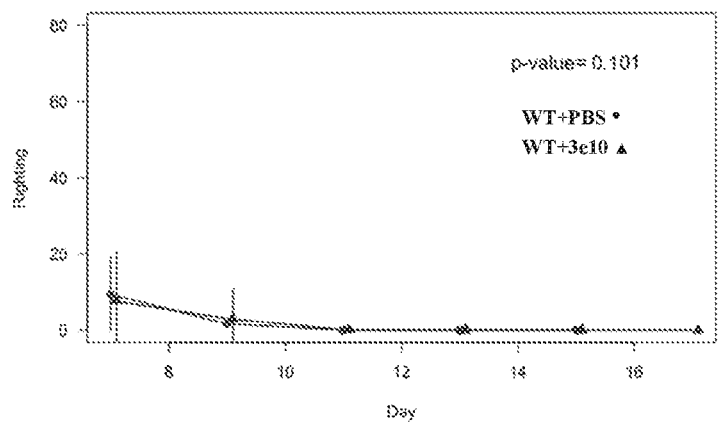
FIGS. 6D-6J are graphs showing the time that an animal took to return to its normal position in Righting Reflex Test after normalization by gender. The experiment was performed every two days from postnatal day 7 to 17 on SMNΔ7 (KO) mice treated with $3 \times 10^{10}$ or $8.76 \times 10^{10}$ GC of AAVhu68.CB7.CI.hSMN1.RBG per pup. Wild-type/heterozygous littermates (WT) littermates and PBS injected mice served as controls. P value was calculated via statistical analysis and indicated in the figure.
Figure 6E:
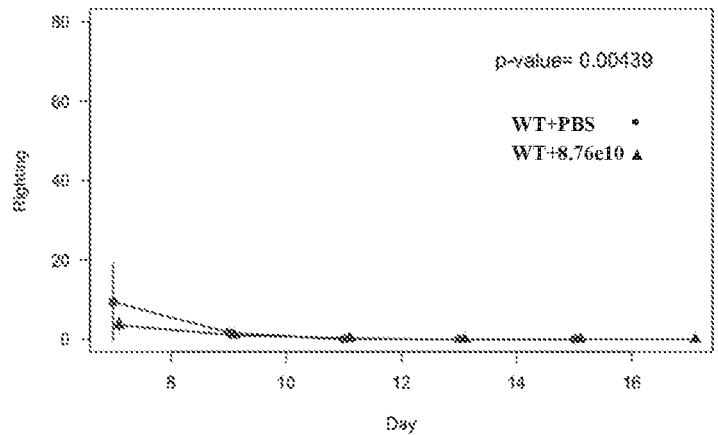
Figure 6F:
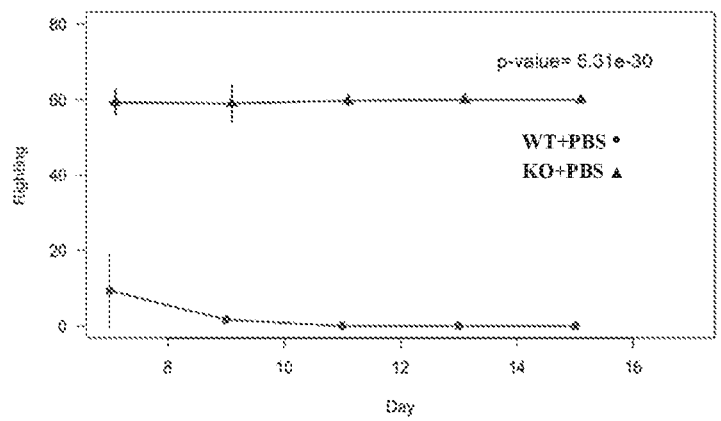
Figure 6G:
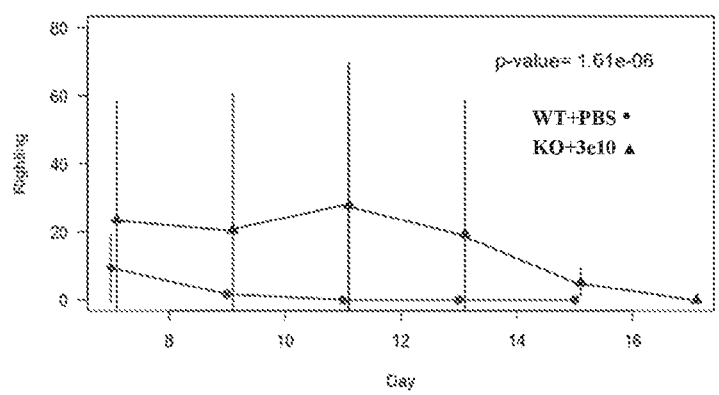
Figure 6H:
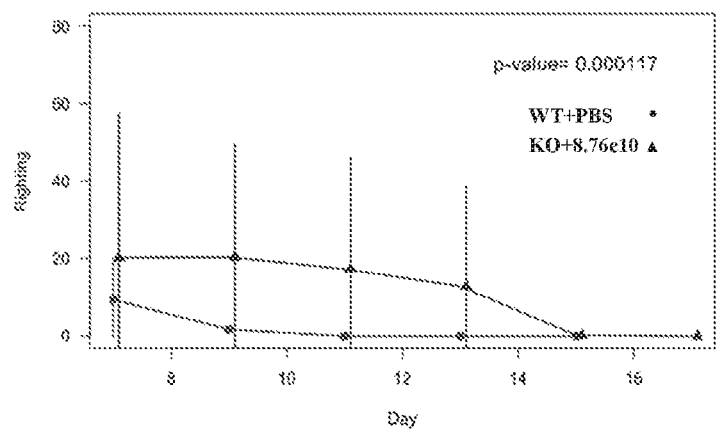
Figure 6I:
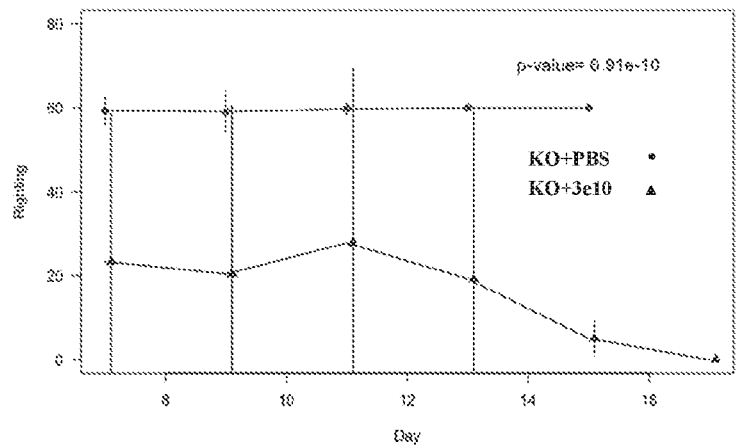
Figure 6J:
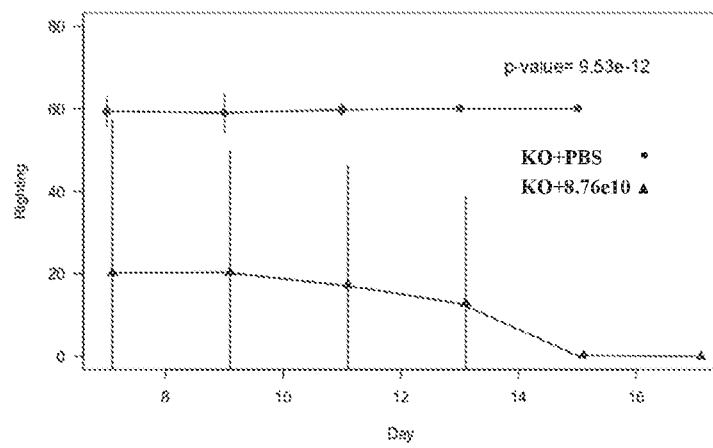

A further analysis was performed to provide detailed comparisons between groups and to reduce the variation caused by gender. The overall change of the variable across all time points was compared between every two groups. Comparisons were carried out using linear mixed effect modeling within the R Program (version 3.3.1; cran.r-project.org) using function "lme" in the "nlme" package. Sex was included as a covariate in the analysis. The recorded time that an animal took to return to the upright position was normalized by gender and the data was plotted in FIG. 6D to 6J. No significant differences in righting reflex were observed between PBS treated WT animals and WT mice treated with either $3 \times 10^{10}$ GC or $\sim 9 \times 10^{10}$ GC of AAVhu68.CB7.CI.hSMN1co.RBG (FIGS. 6D & 6E).

The result demonstrated that wild type or heterozygous pups took limited time to return to the upright position and this time period reduced upon growth, while the SMNΔ7 pups were not able to correct their orientation during the given time (FIG. 6).

With an injection of AAVhu68.CB7.CI.hSMN1.RBG at birth at $3 \times 10^{10}$ GC per pup or $8.76 \times 10^{10}$ GC per pup, the time spent on correcting the position significantly decreased in SMNΔ7 pups and returned to the normal level indicated by wild type and heterozygous pups on postnatal day 17, indicating AAVhu68.CB7.CI.hSMN1.RBG successfully improve the functional development in a rodent model of SMA.

Interestingly, in KOs, median survival and weight gain did not improve in a dose-dependent manner, while righting reflex improved in a dose-dependent manner. Based on these data, it is concluded that $3 \times 10^{10}$ GC and $\sim 9 \times 10^{10}$ GC of AAVhu68.CB7.CI.hSMN1co.RBG are above the minimum effective dose (MED) in SMNΔ7 KOs.

In conclusion, a single intracerebroventricular injection of AAVhu68.CB7.CI.hSMN1.RBG vector resulted in substantial motor neuron transduction and concomitant functional correction when administered intrathecally (intra-cerebroventricular) in neonatal SMNΔ7 mice.

Example 8—Histological Analysis Reveals Positive Effects of AAVhu68.CB7.CI.hSMN1.RBG in a Rodent Model of SMA A further study is performed to evaluate the histological and morphological compromise of myofibers in the SMA model and the recovery due to the injection of AAVhu68.CB7.CI.hSMN1.RBG. The myofiber in tibialis anterior, quadriceps, diaphragm, intercostal, longissimus capitis and tongue are revealed via Hematoxylin and eosin staining and immunohistochemical staining for α-Dystrophin. The cross sectional area (CSA), the fiber diameter and the percentage of centronucleated fibers (CNF) are utilized as parameters. For CSA determination, only round- or polygonal-shaped fibers are taken into consideration.

Example 9—Dose-Ranging and Transduction Efficiency of AAVhu68.CB7.CI.hSMN1.RBG in Wild Type and SMNΔ7 Mice To determine the potential toxicity of the highest dose, the dose-dependent expression of AAVhu68.CB7.CI.hSMN1co.RBG as well as to determine the minimum effective dose (MED) of AAVhu68.CB7.CI.hSMN1co.RBG in SMNΔ7 mice, entire litters produced from HET/HET mating are injected into the left lateral ventricle (intracerebroventricular) (ICV) within 24 hours of birth with phosphate-buffered saline (PBS), $1 \times 10^9$ GC, $3 \times 10^9$ GC, $1 \times 10^{10}$ GC, $3 \times 10^{10}$ GC, or $7 \times 10^{10}$ GC of AAVhu68.CB7.CI.hSMN1co.RBG per mouse. Mice were monitored daily throughout the study. Any mice meeting euthanasia criteria (15% weight loss from prior weighing or inability to nurse) were euthanized. No mice found dead or euthanized before Study Day 13 were necropsied.

On Study Days 3, 5, 7, 9, 11, and 13, mice were weighed. On Study Day 3, mice were tattooed and genotyped. On Study Days 7 and 13, mice underwent 3 rounds of righting reflex testing. On Study Day 9, litters were culled to maintain uniform litter size. Litters were culled to include all KOs and a corresponding number of HETs and WTs so that litter size is equal to 4 animals. On Study Day 13, animals were euthanized and necropsied for analysis of motor neuron transduction and myofiber size.

All doses of AAVhu68.CB7.CI.hSMN1co.RBG were well tolerated in both HET/WT and KO SMNΔ7 mice. The data in FIGS. 9A and 9B represents only 2 liters per dose, so the significantly decreased weight in HET/WT animals treated with $1\times10^9$ GC was thought to be due to the variability in the mothers and litter sizes (FIG. 9B). In addition, the single KO enrolled in the $1\times10^9$ GC group had to be euthanized due to greater than 15% weight loss on Study Day 9. Higher doses of AAVhu68.CB7.CI.hSMN1co.RBG did not alter weight gain in HET/WT animals, and improved weight gain in KO animals relative to PBS treated KO controls (FIGS. 9A and 9B). Based on these data, it is concluded that $1\times10^{10}$ GC represents the MED of AAVhu68.CB7.CI.hSMN1co.RBG in SMNΔ7 mice.

For righting reflex, at Study Day 7 there was appreciable variation between HET/WT animals in the various in the various dose groups (FIG. 10A). Yet, by Study Day 13 HET/WT animals in all dose groups had an average righting time of ~1 second (FIG. 10A). This variation at Study Day 7 was thought to be due to the variability in mothers and litter sizes. Similar to the weight monitoring data, at doses of $1\times10^{10}$ GC and above, AAVhu68.CB7.CI.hSMN1co.RBG treated KOs exhibited significant improvement in righting time on Study Day 13 relative to PBS treated KO controls (FIG. 10B).

Therefore, based on the in-life measurements of weight monitoring and righting reflex, it was concluded that the current MED of AAVhu68.CB7.CI.hSMN1co.RBG in SMNΔ7 mice is $1\times10^{10}$ GC.

Histological measurements of motor neuron transduction and myofiber size are assessed. Additional litters are enrolled in the experiment described above in Example 9.

In addition, in the litters enrolled, no signs of acute toxicity related to any dose of vector were observed, and over the 13 day study period, there were no signs of toxicity related to vector.

To further evaluate the potential toxicity and tolerability of AAVhu68.CB7.CI.hSMN1co.RBG in adult mice following ICV administration, adult C57BL/6J males and females were injected with AAVhu68.CB7.CI.hSMN1co.RBG intrathecally. The total doses used in this study were equivalent to those used in the neonatal experiment described above, while the doses per gram brain mass were 2-fold different due to the estimated brain mass of 0.4 g for an adult mouse, compared to an estimated brain mass of 0.2 g for a neonatal mouse. All doses were included for the Study Day 14 time-point, while only vehicle and $7\times10^{10}$ GC were duplicated for the Study Day 28 time-point.

Weights were monitored on Study Day 0, 7, 14, 21, and 28, as applicable. Clinical chemistry is performed on serum collected at necropsy (Study Day 14 or Study Day 28 as applicable). Brain, spinal cord, heart, lungs, liver, spleen, kidneys, sciatic nerve, and quadriceps femoris were collected for microscopic histopathological evaluation. All parameters were compared to vehicle treated animals.

Figure 14B:
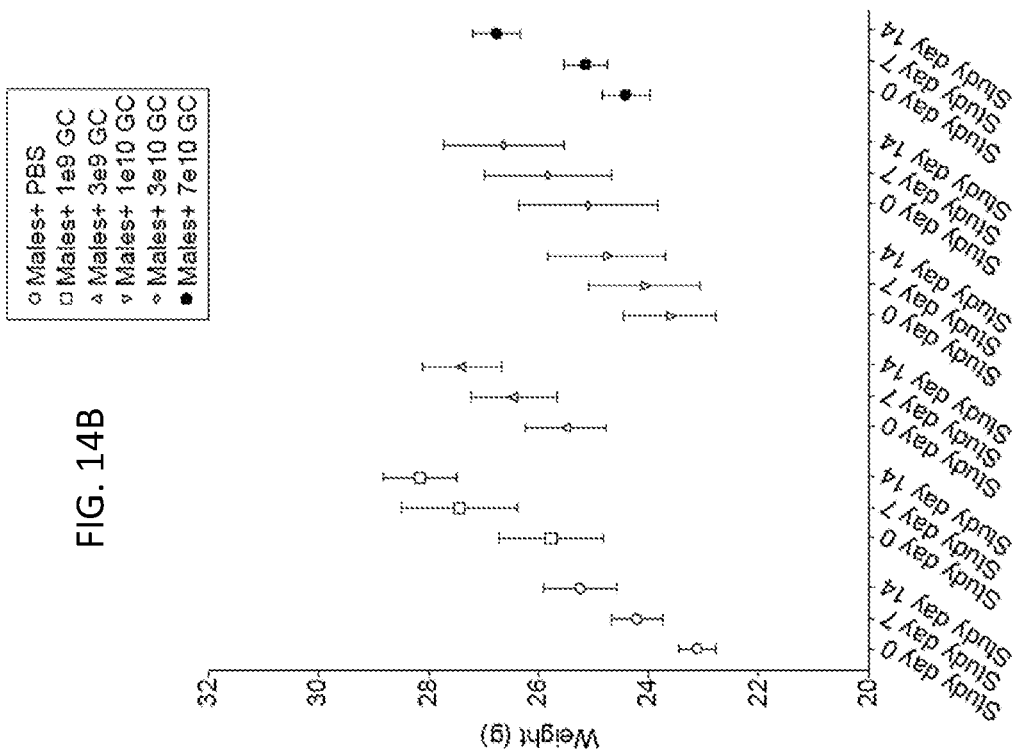
FIGS. 14A-14B provide weight monitoring results in adult C57BL/6J mice treated ICV with AAVhu68.CB7.CI.hSMN1co.RBG as described in Example 9.
Figure 14A:
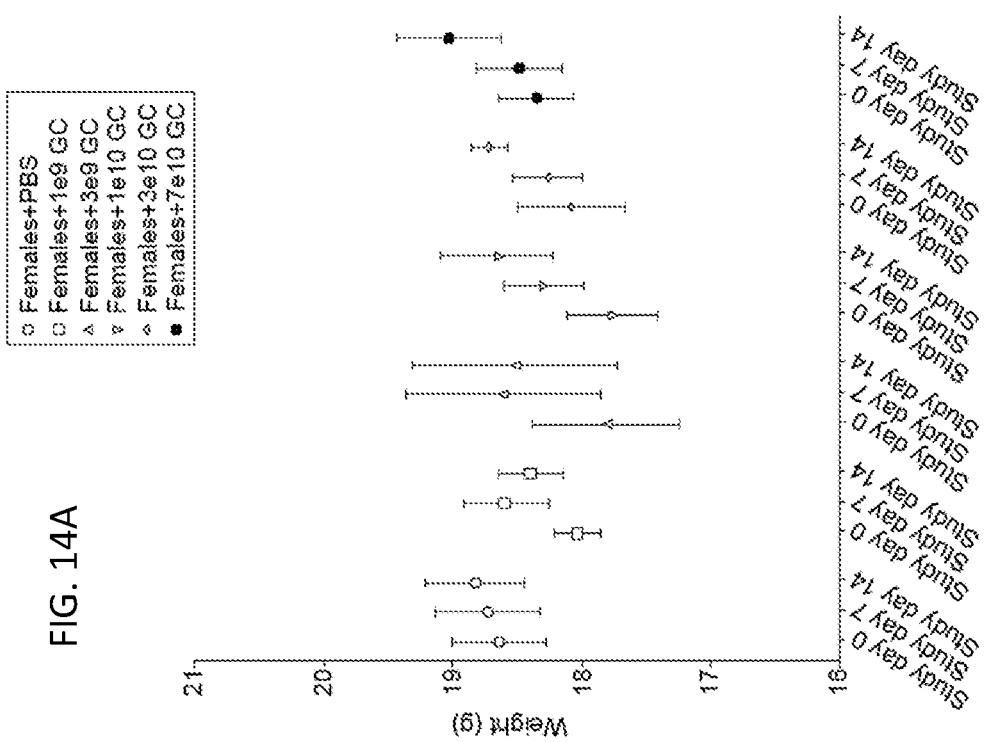

Through Study Day 14, there was no morbidity or mortality in any group. All doses of AAVhu68.CB7.CI.hSMN1co.RBG had no impact on weight trajectory compared to sex-matched vehicle treated control (FIGS. 14A-14B).

A further study is performed to evaluate the histological and morphological compromise of myofibers in the above-described models in Example 9 and the recovery due to the injection of AAVhu68.CB7.CI.hSMN1.RBG. The myofiber in tibialis anterior, quadriceps, diaphragm, intercostal, longissimus capitis and tongue are revealed via Hematoxylin and eosin staining and immunohistochemical staining for α-Dystrophin. The cross sectional area (CSA), the fiber diameter and the percentage of centronucleated fibers (CNF) are utilized as parameters. For CSA determination, only round- or polygonal-shaped fibers are taken into consideration.

Example 10—AAV Vectors Containing hSMN1 in Rhesus Macaques

The purpose of this study was to evaluate different intrathecal routes of administration in rhesus macaques to determine which route results in the most robust spinal cord motor neuron transduction as well as to assess the pharmacokinetic profile and the safety of AAVhu68.CB7.CI.hSMN1co.RBG in Rhesus Macaques. Rhesus macaques were used in this study because their size, and central nervous system anatomy serves as a far better approximation of humans than mice.

Fluoroscopic guidance and contrast material were used to confirm needle placement in the cisterna magna (intracisterna magna) (ICM) or in the lumbar cistern (lumbar puncture) (LP) into the intervertebral space between L4 and L5. The groups were 1.0 mL ICM (n=3), 2.5 mL LP (n=4), and 5.0 mL LP (n=4). Each group contained animals with a range of neutralizing antibody (NAb) titers to AAV9 from undetectable to greater than 1:20. All groups received $3.3\times10^{11}$ GC/g brain ($3\times10^{13}$ GC total) of AAVhu68.CB7.CI.hSMN1co.RBG. There was no vehicle control group included in this study.

Animals were observed daily for abnormal behavior and signs of distress by dedicated personnel during the study. Clinical pathology was performed at baseline, on the day of AAVhu68.CB7.CI.hSMN1co.RBG administration (Study Day 0), Study Day 3, Study Day 7, and weekly thereafter until completion of the study. CSF chemistry and cytology were performed on Study Day 0, Study Day 7, and weekly thereafter until completion of the study. Animals were euthanized and necropsied on Study Day 28 for histological assessment of motor neuron transduction in the spinal cord, biodistribution, and preliminary histopathological evaluation.

Figure 11A:
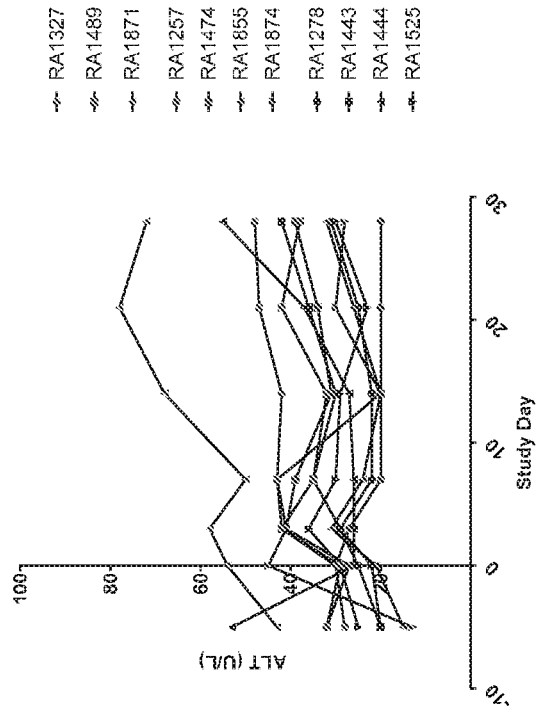
Figure 11B:
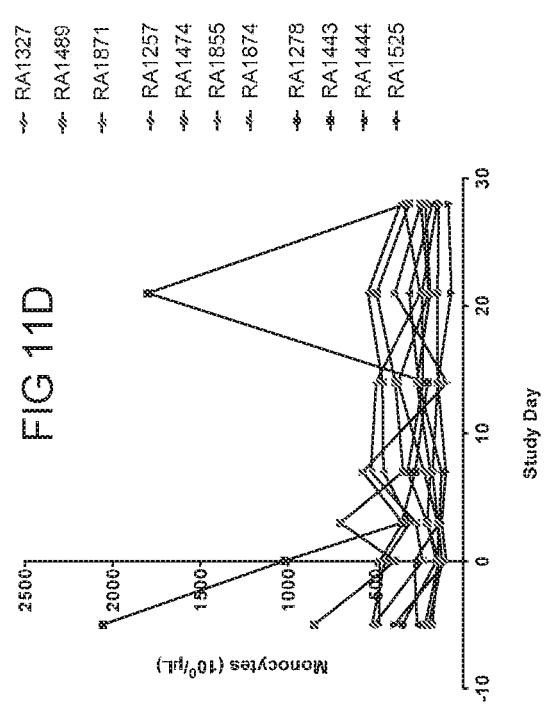
Figure 11C:
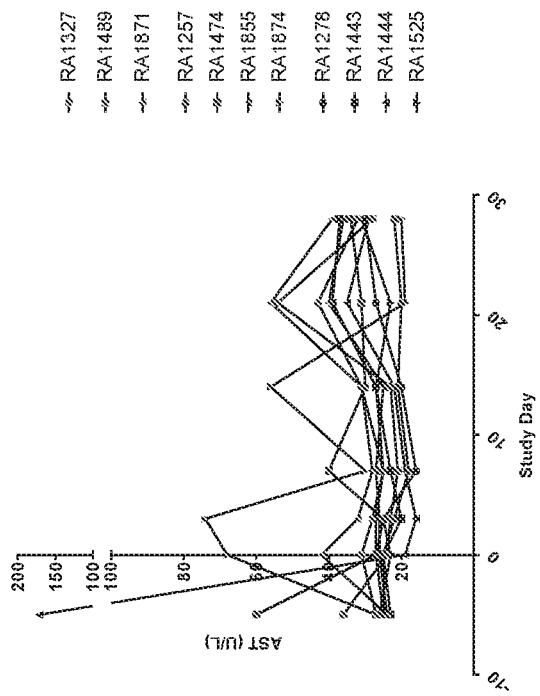
Figure 11D:
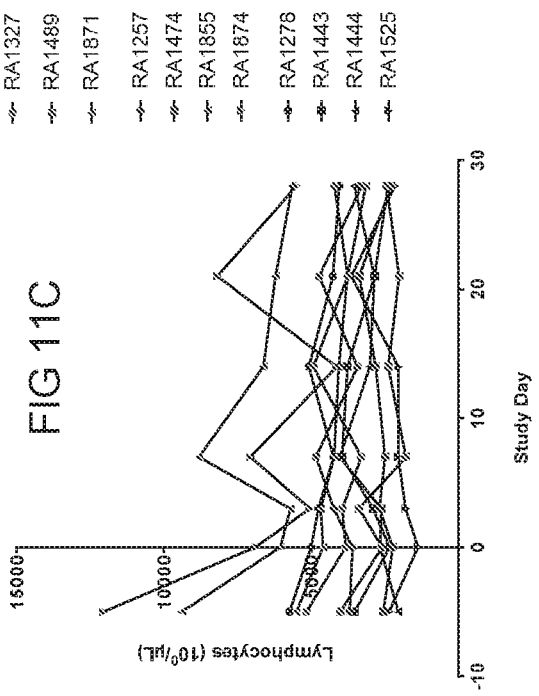

No animals exhibited abnormal behavior or signs of distress throughout the course of the study. 1 animal (RA1871) had an increase in ALT level from 55 U/L to ~80 U/L between Study Day 0 and Study Day 21, although this did not correspond with any clinical signs (FIG. 11B). No other animals exhibited trends of increasing ALT (FIG. 11B), AST (FIG. 11A), lymphocytes (FIG. 11C), or monocytes (FIG. 11D) after AAVhu68.CB7.CI.hSMN1co.RBG administration.

There did not appear to be any trends of altered CSF protein or glucose in any animals throughout the study (FIGS. 11E-11H). On Study Day 28, 1 animal (RA1327) had 17 white blood cells/μL in CSF (FIG. 11E). On gross examination, the CSF did not appear to have blood contamination, but did contain 250 red blood cells/μL. It is unclear if this was true pleocytosis or an unclean CSF tap. CSF cytology from previous intrathecal studies showed a gradual increase in CSF white blood cell counts from single to double digits over the course of weeks (data not shown), leading to conclude that this single occurrence of 17 white blood cells/μL on Study Day 28 (from 0 white blood cells/μL on Study Day 21) was likely due to an unclean CSF tap, as opposed to a true pleocytosis.

At necropsy, each spinal cord was divided into cervical, thoracic, and lumbar sections. Each spinal cord level was subsequently divided into 4 pieces. 1 piece was snap-frozen for biodistribution, 1 piece was placed in formalin for histopathological evaluation, and the 2 remaining pieces were placed in formalin for assessment of motor neuron transduction.

Figure 12A:
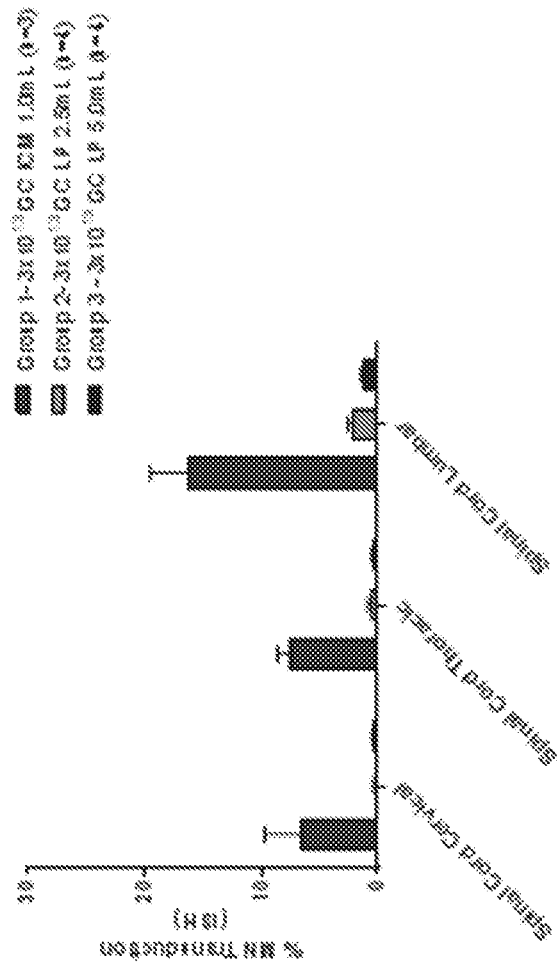
FIGS. 12A-12B provide quantification of motor neuron transduction by ISH (FIG. 12A) and IHC (FIG. 12B) in adult Rhesus Macaques treated intrathecally with AAVhu68.CB7.CI.hSMN1.RBG as described in Example 10. Fluoroscopic guidance and contrast material were used to confirm needle placement in the cisterna magna (intra cisterna magna; ICM) or in the lumbar cistern (lumbar puncture; LP). Total injection volume was 1.0 mL for the ICM group (n=3) and 2.5 mL (n=4) or 5.0 mL (n=4) for the LP groups. One month after injection, animals were sacrificed, and motor neuron transduction was quantified in spinal cord sections by in situ hybridization (ISH) for the transgene mRNA and immunohistochemistry (IHC) for the human SMN protein.
Figure 12B:
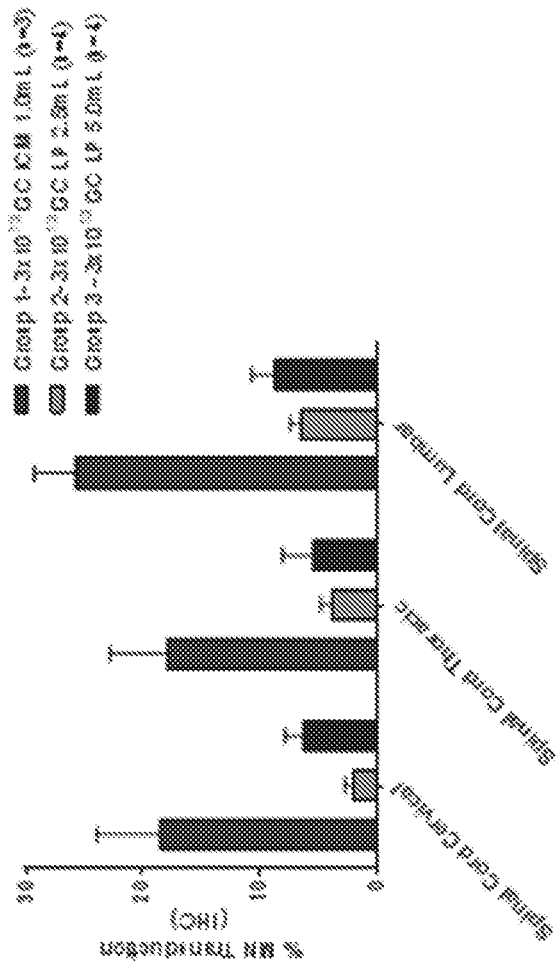

Motor neuron transduction was measured by ISH (3 slides/spinal cord level piece/animal equal to 6 slides/spinal cord level/animal) for the codon-optimized hSMN1 ribonucleic acid (RNA) and IHC (2 slides/spinal cord level piece/animal equal to 4 slides/spinal cord level/animal) for hSMN1 protein. Motor neurons were labeled with a Nissl stain to determine the percent of motor neurons transduced. ICM administration of AAVhu68.CB7.CI.hSMN1co.RBG resulted in significantly higher motor neuron transduction than LP administration of AAVhu68.CB7.CI.hSMN1co.RBG measured by both ISH and IHC at all spinal cord levels (FIGS. 12A & 12B). There was concordance in transduction efficiency between ISH and IHC within each group, although the percent of motor neurons transduced was higher when measured by IHC (FIGS. 12A and 12B). While cross-reactivity of the antibody with rhesus SMN protein might occur, the RNA probe used for ISH was specific for the codon-optimized hSMN1 RNA produced from AAVhu68.CB7.CI.hSMN1co.RBG, which eliminated the possibility of cross-reactivity with rhesus SMN RNA. In agreement with published data, the percent of motor neurons transduced increased in a caudal to rostral (cervical to lumbar) pattern in all groups (Hinderer C, Bell P, Vite C H et al. Widespread gene transfer in the central nervous system of cynomolgus macaques following delivery of AAV9 into the cisterna magna. Molecular therapy Methods & clinical development 2014; 1:14051) (FIGS. 12A & 12B).

Intrathecal AAV delivery can be performed using a variety of routes for CSF access. Lumbar puncture is the most common method for accessing CSF, and was therefore evaluated as a route for AAV administration in nonhuman primates. Remarkably, delivery of an AAV9 vector into the CSF via a lumbar puncture was found to be at least 10-fold less efficient at transducing cells of the brain and spinal cord compared to injection of the vector more superiorly at the level of the cisterna magna [Hinderer C, et al. (2014) Widespread gene transfer in the central nervous system of cynomolgus macaques following delivery of AAV9 into the cisterna magna. Mol Ther Methods Clin Dev 1:14051]. This finding was confirmed in a NHP study using the AAVhu68-SMN1 vector. Adult rhesus macaques injected with the clinical candidate vector via suboccipital puncture into the cisterna magna (n=3) exhibited motor neuron transduction at all levels of the spinal cord, as shown by in situ hybridization (ISH) for transgene mRNA, and immunohistochemical staining (IHC) for the human SMN protein. In contrast, animals receiving vector injection via lumbar puncture showed substantially lower transduction at all levels of the spinal cord, even when injection volume was increased to 5 mL-approximately 40% of the animal's CSF volume-to promote rostral distribution. This study illustrated the necessity of delivering vector at the level of the cisterna magna, and supported the selection of suboccipital puncture as the clinical route of administration.

Figure 13:
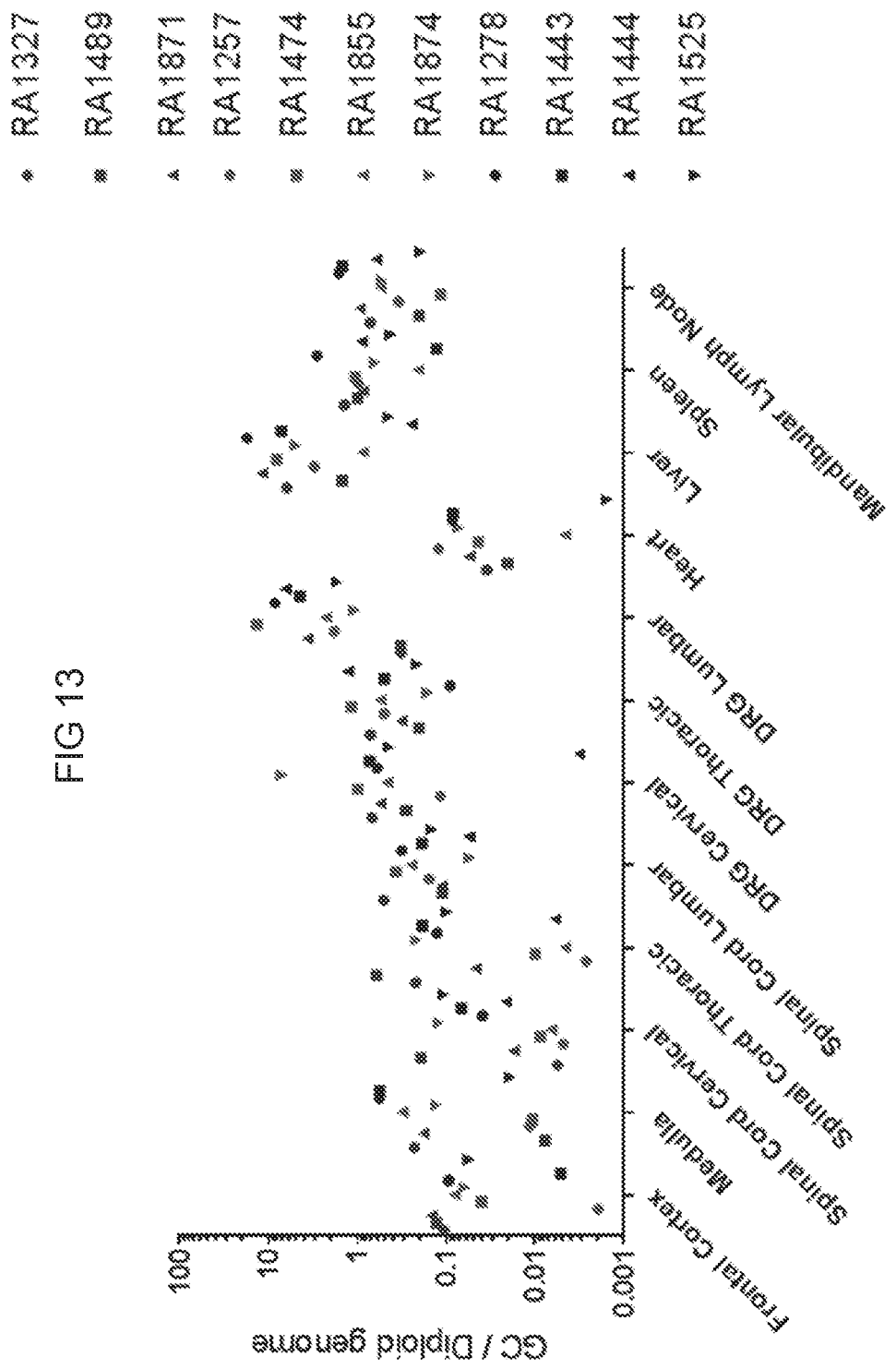
FIG. 13 provides biodistribution in adult Rhesus Macaques treated intrathecally with AAVhu68.CB7.CI.hSMN1.RBG as described in Example 10.

Biodistribution was performed on select tissues from the study to determine transduction following different intrathecal routes of administration. Substantial differences in brain and spinal cord transduction following ICM and LP administration of vector in prior studies could be due to the low volume utilized for LP (Hinderer C, Bell P, Vite C H et al. Widespread gene transfer in the central nervous system of cynomolgus macaques following delivery of AAV9 into the cisterna magna. Molecular therapy Methods & clinical development 2014; 1:14051). In the present study, transduction of brain and spinal cord was equivalent after ICM and LP administration of AAVhu68.CB7.CI.hSMN1co.RBG (FIG. 13).

Interestingly, NAbs did appear to have an impact of transduction of peripheral organs. In each group, the animal with NAbs greater than 1:20 had the lowest transduction in heart, liver, and spleen (FIG. 13).

Preliminary histopathological evaluation was performed on brain, spinal cord, dorsal root ganglia (DRG), sciatic nerve, and liver. In brain, the primary findings were minimal to mild mononuclear cell infiltration and gliosis. These findings were equally distributed within all groups. In the spinal cord, findings were present primarily in the ICM group, with an increased frequency of findings in the lumbar spinal cord. The most common findings were minimal to mild axonal degeneration in the dorsal funiculi and minimal to mild mononuclear cell and histiocyte infiltration. In cervical, thoracic, and lumbar DRG, the primary findings were minimal to mild mononuclear cell infiltration, minimal to mild neuronal vacuolation, and minimal to moderate axonal degeneration. These findings were present at a higher prevalence in the ICM group compared to both LP groups. In sciatic nerve, there was minimal to moderate axonal degeneration and minimal macrophage infiltration. These findings were primarily present in the ICM group. In liver, there was minimal to mild mononuclear cell infiltration and minimal micro-granulomas in all groups.

In addition, adrenal gland, ascending aorta, bone marrow, brain, cecum, cervix epididimides, esophagus, eye, gall bladder, heart, kidney, large intestine, lung, lacrimal gland, lymph node, muscle, ovaries, pancreas, prostate, rectum, salivary gland, seminal vesicle, skin, small intestine, spinal cord, spleen, stomach, testes, urinary bladder, uterus, pituitary, thymus, thyroid gland, trachea, vagina, and gross lesions (if any) were collected for histopathological analysis. The tissues are stained with hematoxylin and eosin (H&E) and/or other immunohistochemical stainings to identify/clarify histologic features.

Example 11—Toxicity and Biodistribution Studies of AAV Vectors Containing hSMN1 in Rhesus Macaques A 180 day GLP study is conducted in rhesus macaques to investigate the pharmacology and toxicology of AAVhu68.CB7.CI.hSMN1co.RBG following ICM administration. Rhesus macaques receive one of three doses, $1.85 \times 10^{10}$ GC/g brain, $5.56 \times 10^{10}$ GC/g brain, or $1.85 \times 10^{11}$ GC/g brain (n=3/group/time-point–both sexes) or vehicle (Elliot's Formulation Buffer, EFB) (n=1/group/time-point–either sex). Baseline clinical pathology (cell counts with differentials, clinical chemistries, and coagulation panel), CSF chemistry, and CSF cytology are performed. After AAVhu68.CB7.CI.hSMN1co.RBG or vehicle administration, the animals are monitored daily for signs of distress and abnormal behavior. Clinical pathology is performed on a weekly basis following AAVhu68.CB7.CI.hSMN1co.RBG or vehicle administration. CSF chemistry and cytology are performed on a weekly basis for the first 30 days following AAVhu68.CB7.CI.hSMN1co.RBG or vehicle administration, and monthly thereafter. At baseline, and on a monthly basis thereafter, neutralizing antibodies to AAVhu68 and cytotoxic T lymphocyte (CTL) responses to AAVhu68 and the hSMN1 transgene are assessed by IFN-γ ELISPOT assay.

14 days, 90 days, and 180 days after AAVhu68.CB7.CI.hSMN1co.RBG or vehicle administration, animals are euthanized, and tissues are harvested for a comprehensive microscopic histopathological examination. The histopathological examination is particularly focused on central nervous system tissues (brain, spinal cord, and dorsal root ganglia) as these are the most heavily transduced following intrathecal administration of AAVhu68.CB7.CI.hSMN1co.RBG. In addition, lymphocytes are harvested from the liver, spleen, and bone marrow to examine the presence of CTLs in these organs at the time of necropsy.

A GLP toxicology study performed using the ICM administration of AAVhu68.CB7.CI.hSMN1co.RBG in 30 nonhuman primates identified transient neurological deficits in 1/30 animals after vector administration, which was attributed to direct puncture of the brainstem during the procedure caused by spontaneous movement of the animal while under anesthesia. There were no other clinical adverse events in this study through the 180 day follow up period, and standardized neurological exams performed throughout the study identified no abnormalities. Histopathology revealed dose-dependent sensory neuron axonopathy that was not associated with clinical sequelae. Quantification of spinal motor neuron transduction indicated that a dose of X GC achieved transduction of X % of spinal motor neurons, a level of transduction that was associated with improved motor function in the SMNΔ7 mouse model. This dose was therefore selected as the MED (Update with final tox results).

In a nonclinical study in juvenile rhesus macaques, intravenous administration of AAVhu68.CB7.CI.hSMN1co.RBG at an extremely high dose ($2\times10^{14}$ GC/kg) resulted in acute hepatic toxicity in 3/3 animals, with one animal requiring euthanasia 5 days after vector administration. Similar toxicity has not been observed in 9 adult and 5 juvenile rhesus macaques treated by intrathecal injection at doses up to $3\times10^{13}$ GC, the highest dose evaluated using this route of administration, or in the 27 adult rhesus macaques treated with AAVhu68.CB7.CI.hSMN1co.RBG by ICM injection in the GLP toxicology study.

Example 12—Clinical Study

A. Newborns

A first-in-human trial is initiated corresponding to the MED dose of $5\times10^{10}$ GC/g brain mass, which translates to $\sim5\times10^{13}$ GC total for a human, and is 3-fold above the low dose proposed for the toxicology study shown in Example 11 but still 3-fold below the high dose (Dekaban A S. Changes in brain weights during the span of human life: relation of brain weights to body heights and body weights. Ann Neurol 1978; 4:345-56.). The maximum dose to administer in the first-in-human trial would be equivalent to the highest dose in toxicology study described in Example 11, $1.85\times10^{11}$ GC/g brain, corresponding to $1.85\times10^{14}$ GC total.

To determine the safety of 2 doses of AAVhu68.CB7.CI.hSMN1co.RBG in participants with DNA-verified spinal muscular atrophy (SMA), two different single dose administrations of the said AAV vector in a pharmaceutical suitable carrier/solution are investigated.

Subsequent development includes expanded population groups and doses to establish an efficacious dose.

Primary Objective is assessment by any study-related Grade III or higher treatment-related toxicity.

Secondary Objectives include

Incidence of adverse events (AEs) and/or serious adverse events (SAEs)

Assessment of attainment of Hammersmith Infant Neurological Examination (HINE) developmental motor milestones Change from baseline in the Children's Hospital of Philadelphia Infant Test of Neuromuscular Disorders (CHOP-INTEND) motor function scale Percentage of participants developing clinically manifested spinal muscular atrophy Percentage of participants alive at noted time points Change from baseline in physical measurements:

Weight for age/length; head, chest, and arm circumferences, head-to-chest circumference ratio Change from baseline in resting vital signs:

Pulse, blood pressure, respirations, temperature, pulse oximetry, and transcutaneous carbon dioxide Change from baseline in clinical laboratory parameters:

Assessed by the following laboratory tests: Hematology: red blood cells, hemoglobin, hematocrit, platelets, white blood cells, white blood cell differential, Blood chemistry: total protein, albumin, creatinine, cystatin C, creatine phosphokinase, blood urea nitrogen, total bilirubin (direct and indirect), alkaline phosphatase, alanine aminotransferase, aspartate aminotransferase, glucose, calcium, phosphorous, chloride, sodium, potassium. Urinalysis: specific gravity, pH, protein, glucose, ketones, bilirubin, red blood cells, white blood cells, epithelial cells, bacteria, casts, crystals Change in baseline in Ulnar compound muscle action potential (CMAP)

Cerebrospinal fluid (CSF) and plasma SMN protein concentrations

Target population is infants<6 weeks of age with pre-symptomatic, genetically documented SMA and 2 copies of survival motor neuron 2 (SMN2) gene.

Inclusion Criteria is listed below.

1. Birth age: <6 weeks, with a gestational age of 37 to 42 weeks for singleton births; gestational age of 34 to 42 weeks for twins.

2. Pre-symptomatic SMA with genetic documentation of 5q spinal motor neuron 1 (SMN1) homozygous gene deletion or mutation or compound heterozygous mutation.

3. Genetic documentation of 2 copies of survival motor neuron 2 (SMN2).

4. Post-procedure follow-up with neurologist with SMA trial experience.

Exclusion Criteria is listed below.

1. Treatment with any marketed or investigational drug, biologic agent, or device given for SMA, including a history of gene therapy, prior antisense oligonucleotide (ASO) treatment, or cell transplantation.

2. Any clinical signs or symptoms at screening or immediately prior to the first dosing (Day 1) that are, in the opinion of the Investigator, strongly suggestive of SMA.

3. Abnormal laboratory values considered clinically significant (GGT>3XULN, bilirubin≥[X] mg/dL, creatinine≥[Y] mg/dL, Hgb<[Z] or >[A] g/Dl; WBC>[B] per cmm)

4. Major medical illness

5. Concomitant illness that in the opinion of the Investigator creates unnecessary risks for gene transfer 6. Family does not want to disclose patient's study participation with primary care physician and other medical providers.

Two doses of the AAV vector are tested, with each dosing cohort to include 6 participants.

Cohort 1: Low dose: $3\times10^{13}$ GC
Cohort 2: High dose: $1\times10^{14}$ GC Six participants are enrolled into the low dose cohort ($3\times10^{13}$ GC). Participant dosing is done in serial fashion with a 4-week safety observation period between the enrollment of each participant. Safety is assessed by an Internal Safety Committee (ISC). If no safety review triggers (SRTs) are observed, then 4 weeks after dosing the sixth participant in the low-dose cohort, all available safety data is evaluated by an Independent Data Monitoring Committee (IDMC) prior to advancing to the enrollment of high-dose cohort 2.

In one embodiment, a syringe containing 5.6 mL of the vector at the appropriate concentration will be delivered to the procedure room. The following personnel is present for study drug administration: interventionalist performing the procedure; anesthesiologist and respiratory technician(s); nurses and physician assistants; CT (or operating room) technicians; neurophysiology technician; site research coordinator.

Prior to study drug administration, a lumbar puncture is performed to remove a predetermined volume of CSF and then to inject iodinated contrast intrathecally (IC) to aid in visualization of relevant anatomy of the cisterna magna. Intravenous (IV) contrast may be administered prior to or during needle insertion as an alternative to the intrathecal contrast. The decision to used IV or IC contrast is at the discretion of the interventionalist. The patient is anesthetized, intubated, and positioned on the procedure table. Intraoperative neurophysiological monitoring (IONM) equipment is attached to the participant. The injection site is prepped and draped using sterile technique. A spinal needle (22-25 G) is advanced into the cisterna magna under fluoroscopic guidance. A larger introducer needle may be used to assist with needle placement. After confirmation of needle placement, the extension set is attached to the spinal needle and allowed to fill with patient CSF. At the discretion of the interventionalist, a syringe containing contrast material may be connected to the extension set and a small amount injected to confirm needle placement in the cisterna magna. After the needle placement is confirmed by CT guidance+/− contrast injection, a syringe containing 5.6 mL of GTP-201 is connected to the extension set. The syringe contents are slowly injected over 1-2 minutes, delivering a volume of 5.0 mL. The needle is slowly removed from the patient.

After study drug administration, participants are transported to a suitable post-anesthesia care unit as per institutional guidelines. After the participant has adequately recovered consciousness and is in stable condition, s/he is admitted to the appropriate unit for protocol-mandated clinical monitoring. Vital signs and neurological function are monitored frequently, including assessments every 15 minutes for 3 hours and then hourly for the 24-hour period immediately post-procedure. Following the initial 24-hour post-procedure period, assessments are performed daily for two days after which participants are discharged and return weekly for 4 weeks, then every 4 weeks for an additional two visits, followed by the primary endpoint assessment visit on week 24.

Blood is drawn for safety testing and participants are assessed clinically. Participants undergo a lumbar puncture to collect CSF in order to monitor for signs of inflammation and measure biomarkers at the time of dosing, week 4, 12 and 24. During the follow-up period participants are assessed every three months until 1 year post-procedure. Participants are followed by annual visits for a total of 5 years. At 3 and 6 months after vector administration, participants undergo a repeat MRI and CSF collection.

Evidence of CNS inflammation following AAV vector administration is assessed in CSF samples using standard techniques, including nucleated cell count and differential and total protein. Exploratory measures of treatment associated inflammation include multiplex cytokine analysis of CSF for inflammatory markers.

To validate CSF SMN protein levels as a biomarker for the successful transduction of the AAV hSMN1 vector, assay is under development for the proposed phase 1/2 interventional study.

Compound Muscle Action Potential (CMAP) represents the electrophysiological output from a muscle following supramaximal stimulation of a peripheral nerve and serves as an objective and highly sensitive indicator of the health of motor neurons (Garcia A, Calleja J, Antolin F M, Berciano J. Peripheral motor and sensory nerve conduction studies in normal infants and children. Clin Neurophysiol 2000; 111: 513-20). In particular, natural history studies among patients with Type I SMA demonstrate that CMAP amplitude is abnormally low and does not improve after symptom onset (Finkel R S, McDermott M P, Kaufmann P et al. Observational study of spinal muscular atrophy type I and implications for clinical trials. Neurology 2014; 83:810-7; Swoboda K J, Prior T W, Scott C B et al. Natural history of denervation in SMA: relation to age, SMN2 copy number, and function. Ann Neurol 2005; 57:704-12 and Finkel R S. Electrophysiological and motor function scale association in a pre-symptomatic infant with spinal muscular atrophy type I. Neuromuscul Disord 2013; 23:112-5). Additionally, a study of SMA in a pig knock-out model, which exhibits electrophysiologic findings similar to SMA patients, showed that early restoration of SMN in pre-symptomatic animals resulted in CMAP correction (Duque S I, Arnold W D, Odermatt P et al. A large animal model of spinal muscular atrophy and correction of phenotype. Ann Neurol 2015; 77:399-414). For above noted reasons, CMAP is investigated as an exploratory biomarker.

Events that qualify for study stopping criteria include:
- Any death that is possibly, probably or definitely related to investigational product
- Elevated liver function testing:
- ALT or AST 3× greater than upper limit of normal
- Associated elevation of total serum bilirubin (in the age group for this study, that is defined as a level of
- More than 1 participant experiences a grade 3 or higher AE that is possibly, probably or definitely related to investigational product or injection procedure
- CNS hemorrhage, stroke, or acute paralysis that is possibly, probably or definitely related to investigational product or injection procedure.

Hepatic function abnormality is defined as any increase in alanine aminotransferase (ALT) or aspartate aminotransferase (AST) to greater than 3× upper limit of normal (ULN). Concurrent findings are those that derive from a single blood draw or from separate blood draws taken within 8 days of each other. Follow-up investigations and inquiries are initiated promptly by the investigational site to determine whether the findings are reproducible and/or whether there is objective evidence that clearly supports causation by a disease (e.g., cholelithiasis and bile duct obstruction with distended gallbladder) or an agent other than the investigational agent.

B. Adults

This open label phase 1/2 dose-escalation clinical trial evaluates the safety of a single administration of AAVhu68.SMA in adults with genetically confirmed 5q SMA and a clinical history of Type 3 SMA. This study enrolls both non-ambulatory and ambulatory patients. Subjects receive a single dose of AAVhu68.SMA by ICM (intra-cisterna magna) injection. Cohort 1 (n=3, low dose, $3 \times 10^{13}$ GC) or Cohort 2 (n=6; high dose, $1 \times 10^{14}$ GC). The two doses evaluated in this study were selected based on nonclinical pharmacology and toxicology studies. Both doses to be evaluated in this study were well tolerated in nonhuman primates and achieved levels of spinal motor neuron SMN expression sufficient to improve motor deficits in a murine disease model, and are therefore anticipated to be safe in humans. In addition, the doses have the possibility to offer a benefit to study participants. The first three eligible subjects will be enrolled in Cohort 1. Following the dosing of each subject, there is a 4 week observation period during which the internal safety committee reviews safety data before the dosing of the next subject. If no safety review triggers (SRTs) are observed within the 4 week observation period for the third participant in Cohort 1, all available safety data is evaluated by a Data Safety Monitoring Board (DSMB) prior to advancing to enrollment of Cohort 2. If no safety SRTs are observed, then 4 weeks after dosing the third participant in Cohort 2, all available safety data is evaluated by a DSMB prior to advancing to the enrollment of the remaining 3 patients in Cohort 2.

Subjects are screened from days −35 to −1 prior to dosing. Those who meet the selection criteria are admitted to the hospital on the day of injection (day 1). After receiving an ICM injection of AAVhu68.CB7.CI.hSMN1co.rBG, subjects are monitored as inpatients for 2 days. One site, outpatient follow up and phone assessments occur as specified time points for the remainder of the 52 week primary evaluation period.

The safety and tolerability of AAVhu68.CB7.CI.hSMN1co.rBG are assessed based on the incidence of AEs and SAEs, clinical and laboratory assessments, physical examination and vital signs Immunogenicity of the vector and transgene product are also evaluated.

Efficacy assessments include 6MWT, 10 meter walk time, RULM score, 4 stair climb, 9 hole peg test, measures of pulmonary function, PedsQL (fatigue scale), SMA-FRS (functional rating scale), and ulnar and peroneal CMAP amplitude. SMN protein concentration and other exploratory biomarkers are evaluated in CSF.

Inclusion Criteria
Be a male or female≥18 years of age.
Genetic documentation of 5q SMA homozygous gene deletion or mutation or compound heterozygous mutation and at least 2 copies of SMN2 at screening.
Clinical history of type3 SMA.
Be willing and able to provide written, signed informed consent
Assessment by internal team of Neurointerventionalists and Site Principal Investigator that the subject's anatomical and physical status would not prevent administration of the investigational product.
Non-Ambulatory Subjects
Unable to walk≥15 feet unassisted.
RULM score of 5-30 at screening.
Ambulatory Subjects
Ambulatory (Able to walk≥15 feet unassisted).
Able to safely perform 6MWT with a 6 MW distance of no greater than 530 m.
Exclusion Criteria
Has a contraindication for an ICM injection.
Has any contraindication to lumbar puncture.
Has received treatment with any marketed or investigational drug or biologic agent for SMA, including a history of gene therapy, prior ASO treatment, or cell transplantation (OR) Participation in any other investigational drug or therapy study within the 3-months before screening.
Respiratory insufficiency, defined by the medical necessity for invasive or noninvasive ventilation for >8 hours during a 24 hour period at screening.
Concomitant illness that, according to the Investigator, would interfere with the conduct and assessments of the study or create unnecessary risks for gene transfer.
Has an abnormal coagulation status (Prothrombin Time (PT)>1.5×normal, Partial Thromboplastin Time (aPTT)>1.5×normal).
Has a thrombocytopenia (e.g. platelet count<150)
Has hepatic abnormality (Bilirubin>1.5×ULN, ALT, AST, and alkaline phosphatase>2.0×ULN).
Has uncontrolled hypertension (systolic blood pressure [SBP]>180 mmHg, diastolic blood pressure [DBP]>100 mmHg).
Has a clinically significant ECG abnormality that, in the opinion of the Investigator, would compromise the subject's safety.
History of solid organ transplantation or chronic immunosuppression.
Has a serious or unstable medical or psychological condition that, in the opinion of the Investigator, would compromise the subject's safety or successful participation in the study or interpretation of the study results.
Use of medications intended for the treatment of SMA including riluzole, valproic acid, hydroxyurea, sodium phenylbutyrate, butyrate derivatives, creatine, carnitine, growth hormone, anabolic steroids, probenecid, oral or parenteral use of corticosteroids at entry, agents anticipated to increase or decrease muscle strength or agents with known or presumed histone deacetylase (HDAC) inhibition, within the 30 days prior to screening. Subjects who use a nebulizer or require an inhaler for steroids are allowed in the study; however, oral use of steroids is prohibited. The oral use of salbutamol is permitted with the following restrictions: subjects should have been on salbutamol for at least 6 months before inclusion in the trial, with good tolerance. The dose of salbutamol should remain constant for the duration of the trial. The use of inhaled beta-agonists (for the treatment of asthma crisis for example) is allowed.
Primary Study Endpoints
The primary endpoints of this study are safety and tolerability of AAVhu68.CB7.CI.hSMN1co.rBG through 52 weeks. These endpoints will be assessed based on the frequency of AEs and SAEs, and any changes in vital signs, physical examination or clinical laboratory assessments deemed clinically significant through 52 weeks post study drug administration.
Secondary Study Endpoints
To assess the impact of AAVhu68.CB7.CI.hSMN1co.rBG on motor function measured by RULM non-ambulatory subjects
RULM scores will be compared to baseline scores through 52 weeks post study drug administration.
To assess the impact of AAVhu68.CB7.CI.hSMN1co.rBG on motor function measured by 6MWT test, and 10 meter walk time in ambulatory subjects 6MWT and 10 meter walk times will be compared to baseline values through 52 weeks post study drug administration.

Exploratory Endpoints

To assess the impact of AAVhu68.CB7.CI.hSMN1co.rBG on motor function measured by 9 hole peg test (ambulatory and non-ambulatory) and 4 stair climb test (ambulatory only)

9 hole peg test and 4 stair climb test scores will be compared to baseline scores through 52 weeks post study drug administration.

To assess the impact of Product on pulmonary function measured by Forced vital capacity (FVC), maximum expiratory pressure (MEP), maximum inspiratory pressure (MIP)

Change from baseline in ulnar and the peroneal CMAP amplitude

PedQLVersion 3.0 multidimensional fatigue scale, adult report module

SMA-FRS (functional rating scale)

Pharmacokinetics of vector in DNA and other AAV-based drug components in CSF, serum, and urine Example 13—Manufacturing An AAVhu68.SMN vector is produced by triple plasmid transfection of human HEK293 cells with: 1) the vector genome plasmid, 2) an AAV helper plasmid termed pAAVhu68.KanR containing the AAV rep2 and cap hu68 wild-type (WT) genes, and 3) a helper adenovirus plasmid termed pAdΔF6(Kan). The size of the AAVhu68.CB7.CI.hSMN1co.rBG packaged vector genome is 3257 bp.

1. AAV Vector Genome Plasmid: pENN.AAV.CB7.CI.hSMNco.rBG.KanR (p4342)

The AAV-hSMN1 vector genome plasmid pENN.AAV.CB7.CI.hSMN1co.rBG (p3246) is 6077 bp in size. The vector genome derived from this plasmid is a single-stranded DNA genome with AAV2 derived ITRs flanking the hSMN1 expression cassette. Expression from the transgene cassette is driven by a CB7 promoter, a hybrid between a CMV immediate early enhancer (C4) and the chicken beta actin promoter, while transcription from this promoter is enhanced by the presence of the CI. The polyA signal for the expression cassette is the rBG polyA. The plasmid was constructed by codon-optimizing and synthesizing the hSMN1 sequence (GeneArt) and the resulting construct was cloned into the plasmid pENN.AAV.CB7.CI.rBG (p1044), an AAV2 ITR-flanked expression cassette containing CB7, CI, and rBG expression elements to give pAAV.CB7.CI.hSMN1co.rBG (p3246). The KanR plasmid is pENN.AAV.CB7.CI.hSMN1co.rBG.KanR (p4342). P4342 was constructed by swapping the ampicillin resistant backbone in pAAV.CB7.CI.hSMN1co.rBG (p3246) with the kanamycin resistant backbone from pENN.AAV.TBG.PI.hLDLr.rBG.KanR (p2017) at two PacI sites.

Description of the Sequence Elements:

ITR: AAV ITRs (GenBank #NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.

CMV immediate-early enhancer (382 bp, GenBank #K03104.1).

Chicken β-actin promoter (282 bp; GenBank #X00182.1) is used to drive a high-level hSMN1 expression.

Chicken β-actin intron: the 973 bp intron from the chicken β-actin gene (GenBank #X00182.1) is present in the vector expression cassette. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation.

Coding sequence: the hSMN1 sequence: (www.ncbi.nlm.nih.gov/nuccore/NM_000344.3) was codon-optimized and synthesized. SMA is caused by mutations in the telomeric gene SMN1. Mutations in SMN1 result in selective toxicity to lower motor neurons, leading to progressive neuron loss and associated muscle weakness and degeneration. The transgene is SMN1, isoform D. Isoform D codes for the longest isoform, and this variant is thought to be the predominant transcript/isoform produced by SMN1 in both CNS and ubiquitously.

Polyadenylation Signal: the 127 bp rabbit β-globin polyadenylation signal (GenBank #V00882.1) provides cis sequences for efficient polyadenylation of the antibody mRNA. This element functions as a signal for transcriptional termination, a specific cleavage event at the 3' end of the nascent transcript and addition of a long polyadenyl tail.

2. AAVhu68 Helper Plasmid: pAAV2/hu68n.KanR (p0068)

The AAV2/hu68 helper plasmid pAAV2/hu.68 (Lot #p0065; 7329 bp) is an AAV helper plasmid that encodes the 4 WT AAV2 rep proteins and the 3 WT AAV VP capsid proteins from AAV serotype hu68. A novel AAV sequence was obtained from human heart tissue DNA and designated AAV serotype hu68. To create the chimeric packaging construct, the AAV2 cap gene from plasmid pAAV2/9n (p0061-2), containing the wild type AAV2 rep and AAV9 cap genes, was removed and replaced with the fragment of the AAVhu68 cap gene plasmid pAAV2/hu68 (p0065). The AAV p5 promoter, which normally drives rep expression, is moved in this construct from the 5' end of rep to the 3' end of cap. This arrangement serves to introduce a spacer between the promoter and the rep gene (i.e., the plasmid backbone), down-regulate expression of rep and increase the ability to support vector production. The plasmid backbone in pAAV2/9n is from pBluescript KS. All component parts of the plasmid have been verified by direct sequencing. The ampicillin resistance gene was then replaced by the kanamycin resistance gene to give pAAV2/hu68n.KanR (p0068).

3. pAdDeltaF6(Kan) Adenovirus Helper Plasmid

Plasmid pAdDeltaF6(Kan) is 15,774 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 Kb to 12 kb. Finally, the ampicillin resistance gene was replaced by the kanamycin resistance gene to give pAdeltaF6(Kan). The E2, E4 and VAI adenoviral genes which remain in this plasmid, along with E1, which is present in HEK293 cells, are necessary for AAV vector production.

4. Master Cell Banks

HEK293 cells were originally generated by transforming HEK cells with sheared adenovirus type 5 DNA as described by [Graham F L, et al, (1977) Characteristics of a human cell line transformed by DNA from human adenovirus type 5. J Gen Virol 36(1):59-741. The cells express the E1A and E1B gene products required for high-titer rAAV production. HEK293 cells are adherent and highly transfectable, yielding high-titers of rAAV upon DNA plasmid transfection. Bacterial master cell bank (BMCB) glycerol stocks are made by mixing 1 mL from a 1 L overnight bacterial culture used for plasmid DNA amplification with an equal volume of sterile, 50% glycerol. Two 0.5 mL aliquots of the BMCB glycerol stocks per construct are prepared from the mixture and stored in Nalgene cryogenic vials in −80° C. To verify BMCB glycerol stocks, amplified plasmid DNA is subjected to in-house structure analysis involving restriction enzyme digestion followed by gel electrophoresis, and full-plasmid sequence analysis by Sanger sequencing at Qiagen. To prepare bacterial working cell bank (BWCB) glycerol stock aliquots for shipping to the plasmid DNA manufacturer (Puresyn Inc.), a 3 mL culture is inoculated from a BMCB glycerol stock and grown overnight. One mL of the overnight culture is used to prepare BWCB glycerol stock aliquots as described above.

5. Overview of Manufacturing Process

Figure 15A:
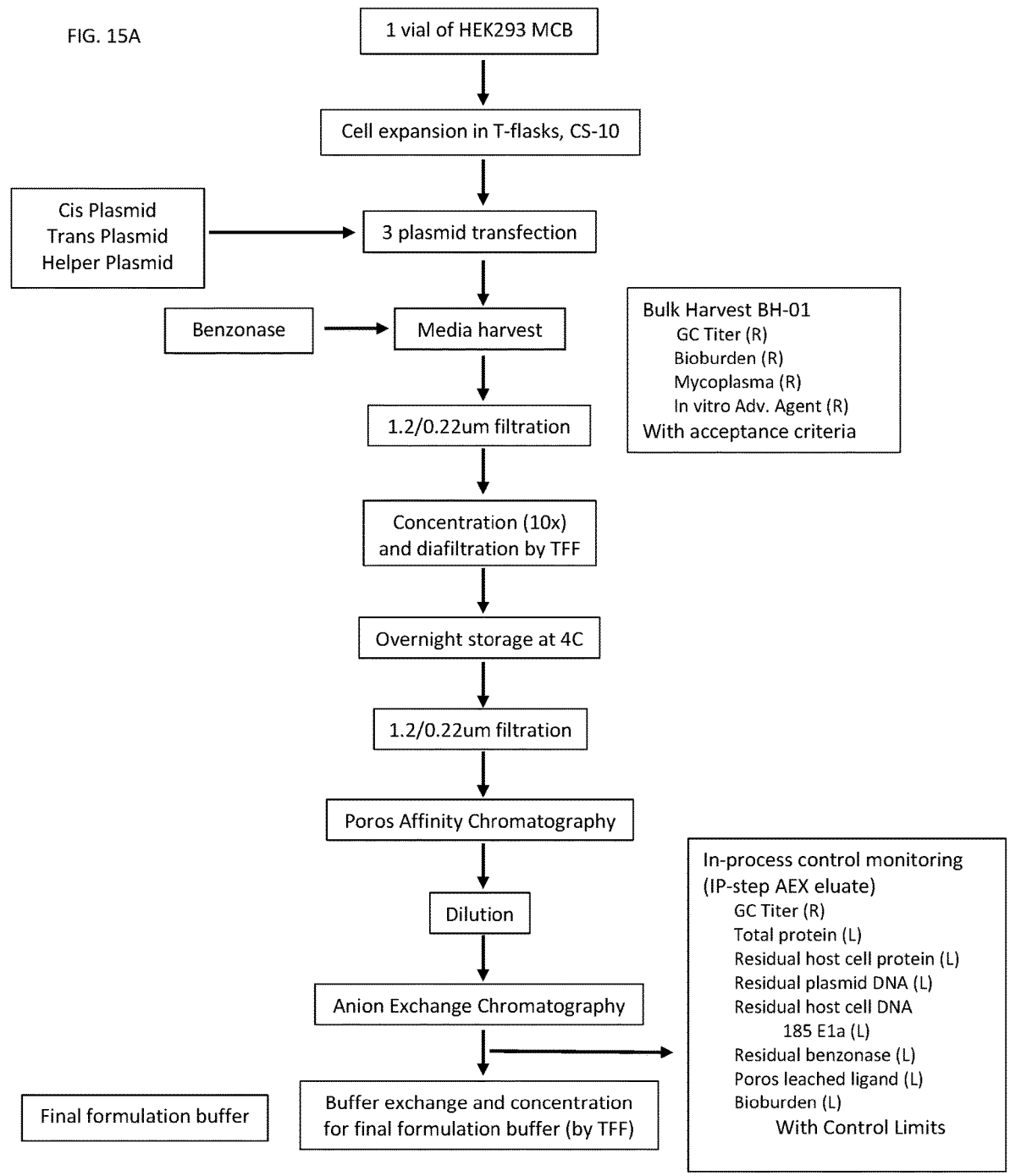
FIGS. 15A-15B are a manufacturing flow diagram for a AAVhu68.SMN vector.
Figure 15B:
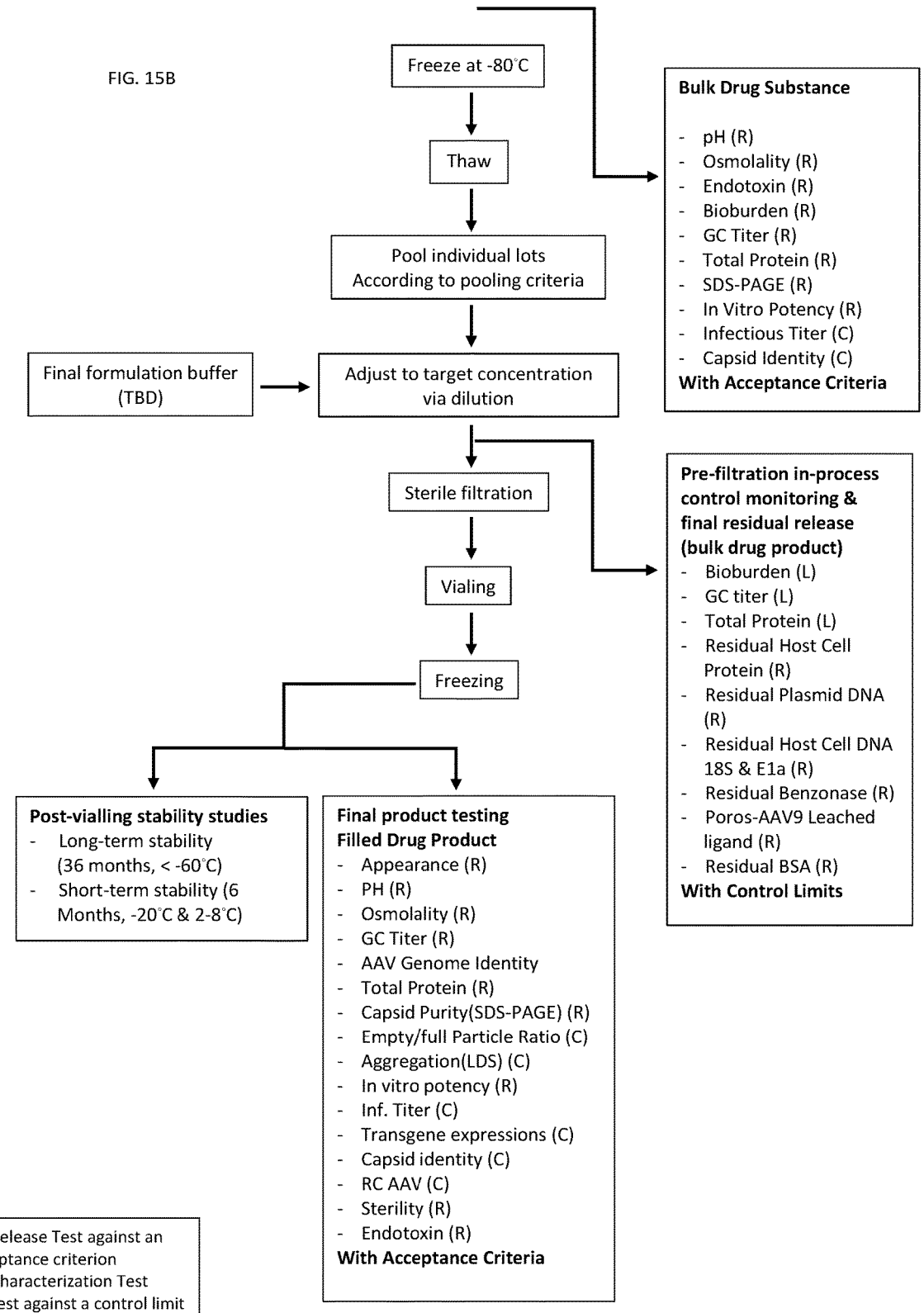
Figure 16E:
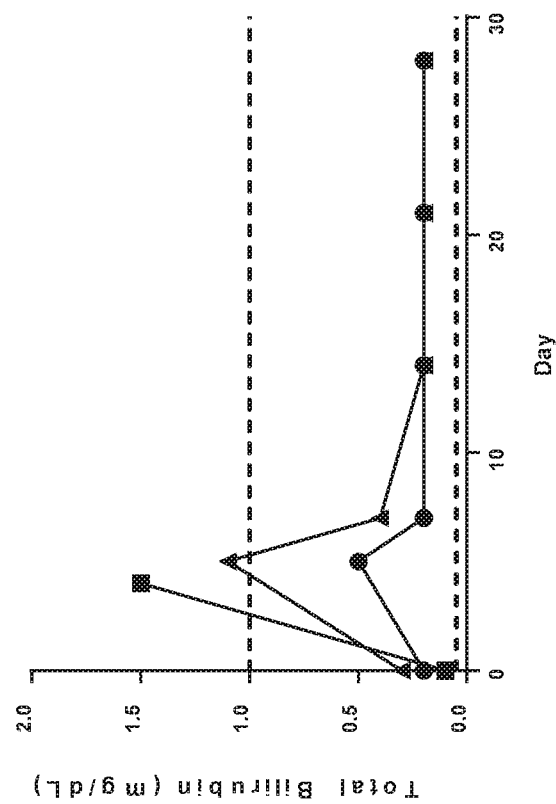
Figure 16D:
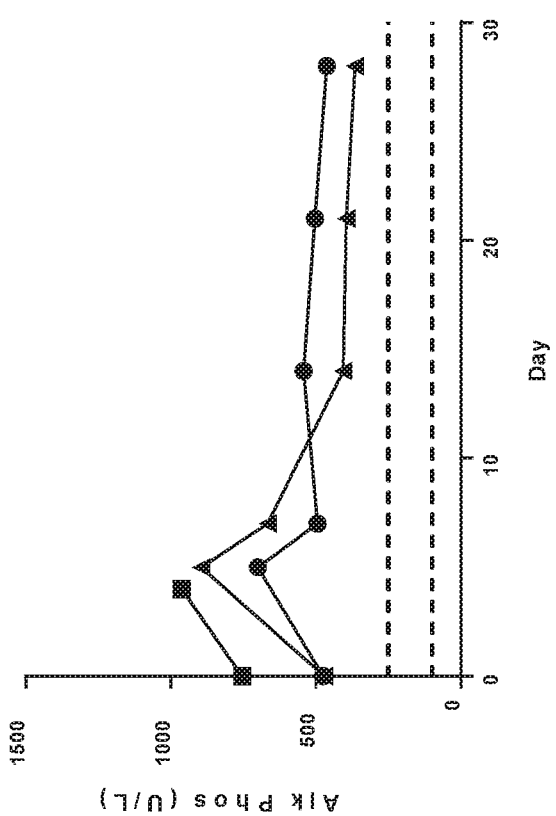

The AAVhu68.CB7.CI.hSMN1co.rBG vector production process is illustrated in the manufacturing process flow diagram of FIG. 15A-15B. The major reagents entering into the preparation of the product are indicated on the left side of the diagram and in-process quality assessments are depicted on the right side of the diagram. A description of each production and purification step is also provided. Product manufacturing follows a linear flow of unit operations and utilizes disposable, closed bioprocessing systems unless otherwise specified. All steps of the production process involving cell culture, from cell seeding to supernatant collection, are performed aseptically using sterile, single-use disposable tubing and bag assemblies. Cells are cultivated in Corning 10-layer CellSTACKs® (CS-10) and HS-36 and all open manipulations. The purification process is performed in a closed system where possible; however, column chromatography manipulations are considered to be sanitary operations and not viewed as a completely closed system.

6. Description of the Manufacturing Process a. Cell Seeding

A qualified HEK293 cell line is used for the production process. A WCB has been produced at Charles River Laboratories from MCB-2 described in 5.2.6 and will be characterized in the IND submission. Cell culture used for vector production will be initiated from a single thawed WCB vial, and expanded as per a Master Batch Record Document (MBR). Cells are expanded to $5 \times 10^9$ to $5 \times 10^{10}$ cells using Corning T-flasks and CS-10, which allow sufficient cell mass to be generated for seeding up to 48 HS-36 for vector production per BDS batch. Cells are be cultivated in medium composed of Dulbecco's Modified Eagle Medium (DMEM) supplemented with 10% gamma irradiated, US-sourced and NZ-sourced, fetal bovine serum (FBS). The cells are anchorage dependent and cell disassociation will be accomplished using TrypLE™ Select, an animal product-free cell disso-ciation reagent. Cell seeding will be accomplished using sterile, single-use disposable bioprocess bags and tubing sets. The cells will be maintained at 37° C. (±2° C.), in 5% (±0.5%) $CO_2$ atmosphere.

b. Transient Transfection

Following approximately 3 days of growth (DMEM media+10% FBS), HS-36 cell culture media will be replaced with fresh, serum-free DMEM media and transfected with the 3 production plasmids using an optimized polyethylenimine (PEI)-based transfection method. Sufficient plasmid DNA transfection complex will be prepared in the BSC to transfect 48 HS-36 (per BDS batch). Initially, a DNA/PEI mixture will be prepared containing cis (vector genome) plasmid, trans (capsid and rep genes) plasmid, and helper (Ad) plasmid in a 0.1:1:2 ratio and GMP grade PEI (PEIPro, PolyPlus Transfection SA). This plasmid ratio was determined to be optimal for AAV production in small scale optimization studies. After mixing well, the solution will be allowed to sit at room temperature for 25 minutes, then added to serum-free media to quench the reaction, and finally added to the HS-36's. The transfection mixture will be equalized between all 36 layers of the HS-36 and the cells will be incubated at 37° C. (±2° C.) in a 5% (±0.5%) $CO_2$ atmosphere for 5 days.

c. Cell Media Harvesting

Transfected cells and media will be harvested from each HS-36 using disposable bioprocess bags by aseptically draining the medium out of the units. Following the harvest of media, approximately 200 liter volume will be supplemented with $MgCl_2$ to a final concentration of 2 mM (co-factor for Benzonase) and Benzonase nuclease will be added to a final concentration of 25 units/mL. The product (in a disposable bioprocess bag) will be incubated at 37° C. for 2 hours in an incubator to provide sufficient time for enzymatic digestion of residual cellular and plasmid DNA present in the harvest as a result of the transfection procedure. This step is performed to minimize the amount of residual DNA in the final vector DP. Following incubation, NaCl will be added to a final concentration of 500 mM to aid in the recovery of the product during filtration and downstream tangential flow filtration.

d. Clarification

Cells and cellular debris will be removed from the product using a depth filter capsule (1.2/0.22 μm) connected in series as a sterile, closed tubing and bag set that is driven by a peristaltic pump. Clarification assures that downstream filters and chromatography columns will be protected from fouling and bioburden reduction filtration ensures that, at the end of the filter train, any bioburden potentially introduced during the upstream production process will be removed before downstream purification. The harvest material will be passed through a Sartorius Sartoguard PES capsule filter (1.2/0.22 μm) (Sartorius Stedim Biotech Inc.).

e. Large-Scale Tangential Flow Filtration

Volume reduction (10-fold) of the clarified product will be achieved by Tangential Flow Filtration (TFF) using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface, preventing membrane pore fouling and product loss through binding to the membrane. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, we utilize a 100 kDa, PES membrane for concentration that is then diafiltered with a minimum of 4 diavolumes of a buffer composed of 20 mM Tris pH 7.5 and 400 mM NaCl. The diafiltered product will be stored overnight at 4° C. and then further clarified with a 1.2/0.22 µm depth filter capsule to remove any precipitated material.

f. Affinity Chromatography

The diafiltered product will be applied to a Poros™ Capture Select™ AAV9 affinity resin (Life Technologies) that efficiently captures the AAVhu68 serotype. Under these ionic conditions, a significant percentage of residual cellular DNA and proteins flow through the column, while AAV particles are efficiently captured. Following application, the column is treated with 5 volumes of a low salt Benzonase solution (2500 U/mL Benzonase, 20 mM Tris pH 7.5 and 40 mM NaCl, 1.5 mM $MgCl_2$) to remove any remaining host cell and plasmid nucleic acid. The column is washed to remove additional feed impurities followed by a low pH step elution (400 mM NaCl, 20 mM Sodium Citrate, pH 2.5) that is immediately neutralized by collection into a 1/10th volume of a neutralization buffer (200 mM Bis Tris Propane, pH 10.2).

g. Anion Exchange Chromatography

To achieve further reduction of in-process impurities including empty AAV particles, the Poros-AAV9 elution pool is diluted 50-fold (20 mM Bis Tris Propane, 0.001% Pluronic F68, pH 10.2) to reduce ionic strength and enable binding to a CIMultus™ QA monolith matrix (BIA Separations). Following a low-salt wash, vector product is eluted using a 60 column volume (CV) NaCl linear salt gradient (10-180 mM NaCl). This shallow salt gradient effectively separates capsid particles without a vector genome (empty particles) from particles containing vector genome (full particles) and results in a preparation enriched for full capsids. Fractions will be collected into tubes containing $1/100^{th}$ volume of 0.1% pluronic F68 and $1/27^{th}$ volume of Bis Tris pH 6.3 to minimize non-specific binding to tubes and the length of exposure to high pH, respectively. The pooled full particle peak factions are diluted 20-fold in 20 mM Bis Tris Propane, 0.001% Pluronic F68, pH 10.2 and reapplied to the same column, which has been cleaned in place. The 10-180 mM NaCl salt gradient is reapplied and the appropriate full particle peak fractions will be collected. The peak area is assessed and compared to previous data for determination of the approximate vector yield.

h. Final Formulation and Bioburden Reduction Filtration to Yield the BDS

TFF is used to achieve final formulation on the pooled anion exchange (AEX) fractions with a 100 kDa membrane. This will be accomplished by diafiltration of final formulation buffer and concentrated to yield the BDS at a desired target concentration. Samples will be removed for BDS testing (described in the section below). The BDS is sterile filtered (0.22 µm), stored in sterile polypropylene tubes, and frozen at ≤−60° C. in a quarantine location until release for Final Fill.

i. Final Fill

The frozen BDS will be thawed, pooled, and adjusted to the target concentration (dilution or concentrating step via TFF) using the final formulation buffer. The product will then be terminally filtered through a 0.22 µm filter and filled into sterile West Pharmaceutical's Crystal Zenith (polymer) vials and stoppers with crimp seals at a fill volume to be determined. Vials will be individually labeled according to the specifications below. Labeled vials are stored at ≤−60° C.

j. Vector Genome Identity: DNA and NGS Sequencing

Viral Vector genomic DNA is isolated and the sequence determined by 2-fold sequencing coverage using primer walking. Sequence alignment is performed and compared to the expected sequence. In certain embodiments, next-generation sequencing (also known as high through-put sequencing) is performed, e.g., using Illumina® machines.

k. Vector Capsid Identity: AAV Capsid Mass Spectrometry of VP1

Confirmation of the AAVhu68 serotype of the vector is achieved by an assay which has been developed based upon analysis of peptides of the AAV capsid protein. The method involves trypsin digestion of the VP followed by tandem mass spectrometry characterization on a Q-Exactive Orbitrap mass spectrometer to sequence the capsid protein peptides. A spectral library from the tandem mass spectra sequenced and a targeted mass spectrometry method is used to assay for signature peptides which can uniquely identify specific AAV viral particles serotypes. A bank of signature peptides specific for eight AAVs (AAVhu68, AAV1, AAV2, AAV6, AAV8, AAV9, AAVrh10, AAVhu37) are screened against the tandem mass spectra produced by digestion of the test article. For a positive identification, signature peptide(s) from a single serotype only will be detected.

l. Genomic Copy Titer

A digital droplet polymerase chain reaction (ddPCR)-based technique for determining the GC titer for AAV vectors has recently been developed [Lock M, Alvira M R, Chen S J, & Wilson J M (2014) Absolute determination of single-stranded and self-complementary adeno-associated viral vector genome titers by droplet digital PCR. Hum Gene Ther Methods 25(2):115-125.] The method is practical, reports equivalent or better titers than qPCR, and does not require a plasmid standard curve. The assay utilized involves digestion with DNase I, followed by digital PCR analysis to measure encapsulated vector genomic copies. DNA detection is accomplished using sequence specific primers targeting the polyA region in combination with a fluorescently tagged probe hybridizing to this same region. A number of standards, validation samples and controls (for background and DNA contamination) have been introduced into the assay.

m. Infectious Unit Titer

The infectious unit (IU) assay is used to determine the productive uptake and replication of rAAV vector in RC32 cells (rep2 expressing HeLa cells). A 96-well end-point format has been employed similar to that previously published. Briefly, RC32 cells are co-infected by serial dilutions of rAAV BDS and a uniform dilution of Ad5 with 12 replicates at each dilution of rAAV. Seventy-two hours after infection the cells are lysed, and qPCR performed to detect rAAV vector amplification over input. An end-point dilution 50% tissue culture infectious dose (TCID50) calculation (Spearman-Karber) is performed to determine a replicative titer expressed as IU/mL. Since "infectivity" values are dependent on particles contact with cells, receptor binding, internalization, transport to the nucleus and genome replication, they are influenced by assay geometry and the presence of appropriate receptors and post-binding pathways in the cell line used. Receptors and post-binding pathways are not usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot.

n. Empty to Full Particle Ratio

Sedimentation velocity, as measured in an analytical ultracentrifuge (AUC), can detect aggregates, other minor components, as well as providing good quantitation of relative amounts of different particle species based upon their different sedimentation coefficients. This is an absolute method based on fundamental units of length and time, requiring no standard molecules as references. Vector samples are loaded into cells with 2-channel charcoal-epon centerpieces with 12 mm optical path length. The supplied dilution buffer is loaded into the reference channel of each cell. The loaded cells are then placed into an AN-60Ti analytical rotor and loaded into a Beckman-Coulter ProteomeLab XL-I analytical ultracentrifuge equipped with both absorbance and RI detectors. After full temperature equilibration at 20° C., the rotor is brought to the final run speed of 12,000 rpm. Absorbance at 280 nm scans are recorded approximately every 3 minutes for approximately 5.5 hours (110 total scans for each sample). The raw data is analyzed using the c(s) method and implemented in the analysis program SEDFIT. The resultant size distributions are graphed and the peaks integrated. The percentage values associated with each peak represent the peak area fraction of the total area under all peaks and are based upon the raw data generated at 280 nm; many labs use these values to calculate empty: full particle ratios. However, because empty and full particles have different extinction coefficients at this wavelength, the raw data can be adjusted accordingly. The ratio of the empty particle and full monomer peak values both before and after extinction coefficient-adjustment is used to determine the empty-full particle ratio and both ratios are recorded on certificates of analysis.

o. Host Cell DNA

A qPCR assay is used to detect residual human 293 DNA. After spiking with a "non-relevant DNA", total DNA (non-relevant, vector and residual genomic) is extracted from approximately 1 mL of product. The host cell DNA is quantified using qPCR targeting the 18S rDNA gene. The quantities of DNA detected are normalized based on the recovery of the spiked non-relevant DNA. Three different amplicon sizes are tested to establish the size spectrum of residual host cell DNA.

p. Host Cell Protein

An ELISA is performed to measure levels of contaminating host HEK293 cell proteins. The Cygnus Technologies HEK293 Host Cell Proteins 2nd Generation ELISA kit is used according to the instructions provided by the vendor.

q. Replication-Competent AAV Assay

A sample is analyzed for the presence of replication competent AAV2/hu68 (rcAAV) that could potentially arise during the production process. A 3-passage assay has been developed a consisting of cell-based amplification and passage followed by detection of rcAAV DNA by real-time qPCR (caphu68 target). The cell-based component consists of inoculating monolayers of HEK293 cells (P1) with dilutions of the test sample and WT human adenovirus type 5 (Ad5). The maximal amount of the product tested will be $1 \times 10^{10}$ GC of the vector product. Due to the presence of adenovirus, rcAAV will amplify in the cell culture. After 2 days, a cell lysate is generated and Ad5 heat inactivated. The clarified lysate is then passed onto a second round of cells (P2) to enhance sensitivity (again in the presence of Ad5). After 2 days, a cell lysate is generated and Ad5 heat inactivated. The clarified lysate is then passed onto a third round of cells (P3) to maximize sensitivity (again in the presence of Ad5). After 2 days, cells are lysed to release DNA, which is then subjected to qPCR to detect AAVhu68 cap sequences. Amplification of AAVu68 cap sequences in an Ad5 dependent manner indicates the presence of rcAAV. The use of a AAV2/hu68 surrogate positive control containing AAV2 rep and AAVhu68 cap genes enables the limit of detection (LOD) of the assay to be determined (0.1, 1, 10, and 100 IU) and using a serial dilution of rAAV ($1 \times 10^{10}$, $1 \times 10^{9}$, $1 \times 10^{8}$, and $1 \times 10^{7}$ GC) the approximate level of rcAAV present in the test sample can be quantitated.

r. In Vitro Potency

To relate the qPCR GC titer to gene expression, an in vitro bioassay is performed. Briefly, cells are plated per well in a 96-well plate and are incubated at 37° C./5% $CO_2$ overnight. The next day, cells are infected with serially diluted AAV vector and are incubated at 37° C./5% $CO_2$ for two days. Cells are then fixed with 4% paraformaldehyde, followed by washes with PBS containing 0.1% Triton-100, then incubated with blocking buffer. After blocking, cells are incubated with a 1:200 dilution of the primary antibody (GenTex monoclonal α-Smn1, CAT #GTX60451), washed, and incubated with 1:500 α-mouse-488 (Thermo Fisher). Before imaging, cells are treated with PBS containing DAPI to visualize nuclei. Plates are imaged using the Cell Insight Cx5 high content imager (Thermo Fisher). The current method for data capture is screening 2,500 objects (i.e., cells) per well and using a modified SpotID protocol to count the number of Gemini of Cajal bodies per nucleus. Nuclear Gemini of Cajal body formation is dependent on functional Smn1 protein. Log Vector MOI is plotted on the x-axis versus instrument read-out on the y-axis. Optimization of the assay is ongoing.

s. Total Protein, Capsid Protein, Protein Purity, and Capsid Protein Ratio

Vector samples are first quantified for total protein against a bovine serum albumin (BSA) protein standard curve using a bicinchoninic acid (BCA) assay. The determination is made by mixing equal parts of sample with a Micro-BCA reagent provided in the kit. The same procedure is applied to dilutions of a BSA Standard. The mixtures are incubated at 60° C. and absorbance measured at 562 nm. A standard curve is generated from the standard absorbance of the known concentrations using a 4-Parameter fit. Unknown samples are quantified according to the 4-parameter regression. To provide a semi-quantitative determination of rAAV purity, the samples will be normalized for genome titer and $5 \times 10^{9}$ GC separated on a sodium dodecyl sulfate polyacrylamide gel electrophoresis (SDS-PAGE) gel under reducing conditions. The gel is then stained with SYPRO Ruby dye. Any impurity bands are quantified by densitometry. Stained bands that appear in addition to the 3 AAV specific proteins VP1, VP2, and VP3 are considered protein impurities. The impurity mass percent as well as approximate molecular weight of contaminant bands are reported. The SDS-PAGE gels will also be used to quantify the VP1, VP2, and VP3 proteins and determine their ratio.

t. BSA Protein

This assay is performed using the bovine albumin ELISA kit obtained from Bethyl Laboratories according to the protocol provided with the assay kit.

u. Benzonase Endonuclease

Benzonase is used in the production process to degrade nucleic acids to facilitate vector purification and as such represents a process impurity. A commercial ELISA (Millipore) is used to measure the concentration of residual benzonase. Since the amount of benzonase is likely to be in trace amounts if at all, it is necessary to perform an ELISA with a range of standards that includes concentrations<1 ng/mL.

v. Ratio of GC to IU

The GC/IU ratio is a measure of product consistency. The ddPCR titer (GC/mL) is divided by the "infectious unit (IU/mL) to give the calculated GC/IU ratio.

w. Osmolarity, pH, and Appearance Testing

Osmolality and pH are determined according to USP<785> and USP<791>, respectively. Appearance of the product is determined by visual inspection for transparency, color, and the absence/presence of foreign particles. The product is inspected against white and black backgrounds.

Example 14—Severe Toxicity in Nonhuman Primates and Piglets Following High-Dose Intravenous Administration of an AAV Vector Expressing Human SMN Neurotropic AAV serotypes such as AAV9 have been demonstrated to transduce spinal alpha motor neurons when administered intravenously at high doses. This observation led to the recent successful application of intravenous AAV9 delivery to treat infants with spinal muscular atrophy, an inherited deficiency of the survival of motor neuron (SMN) protein characterized by selective death of lower motor neurons.

To evaluate the efficiency of motor neuron transduction using this approach, three juvenile nonhuman primates (NHPs; age 13-14 months) and three neonatal piglets (age 7-30 days) were treated with an intravenous injection of an AAV vector carrying a human SMN transgene closely related to AAV serotype 9 (AAVhu68) carrying a human SMN expression cassette at a dose similar to that employed in the SMA clinical trial. Animals were evaluated for transduction of spinal motor neurons as well as evidence of toxicity. Administration of $2\times10^{14}$ genome copies per kilogram body weight resulted in widespread transduction of spinal motor neurons in both species. However, severe toxicity occurred in both NHPs and piglets. All three NHPs exhibited marked transaminase elevations, and one animal was euthanized 5 days post injection with clinical and histologic signs of acute liver failure and shock. Degeneration of dorsal root ganglia (DRG) sensory neurons was also observed, although NHPs exhibited no clinically apparent sensory deficits. There was no correlation between clinical findings and T-cell responses to the vector capsid or transgene product in NHPs. Piglets demonstrated no evidence of hepatic toxicity, but within 14 days of vector injection all three animals exhibited proprioceptive deficits and ataxia which profoundly impaired ambulation and necessitated euthanasia. These clinical findings correlated with more severe DRG sensory neuron lesions than those observed in NHPs. The liver and sensory neuron findings in these species appear to be a direct consequence of AAV transduction independent of an immune response to the capsid or transgene product. Preclinical and clinical studies involving high systemic exposure to AAV vectors should include careful monitoring for similar toxicity.

A. Results:

1. Nonhuman primate study:

Three 13-14-month-old rhesus macaques were administered an intravenous (IV) dose of $2\times10^{14}$ GC/kg AAVhu68 vector expressing human SMN under control of a chicken beta actin promoter with a cytomegalovirus immediate early enhancer (Table 1).

TABLE 1

Rhesus macaques treated with AAVhu68.CB7.hSMN1 included in Example 14

| Animal ID | Age (months) | Weight (kg) | Baseline AAVhu68 nAb Titer | Dose | Route of Administration |
|---|---|---|---|---|---|
| 16C116 | 13 | 2.52 | <1:5 | $2 \times 10^{14}$ GC/kg | IV |
| 16C176 | 14 | 2.22 | <1:5 | $2 \times 10^{14}$ GC/kg | IV |
| 16C215 | 14 | 2.40 | <1:5 | $2 \times 10^{14}$ GC/kg | IV |

All animals exhibited stable vital signs during vector infusion and recovered uneventfully from anesthesia. On study Day 5, animal 16C176 became acutely nonresponsive. Physical exam revealed pale mucous membranes, an approximate 15% decrease in body weight from the time of vector administration, hepatomegaly, and a palpable abdominal fluid wave. Abnormalities on bloodwork included a packed cell volume of 22%, glucose of <20 mg/dL, BUN of 75 mg/dL and creatinine of 2 mg/dL. This animal's condition rapidly declined and it was subsequently euthanized. A complete necropsy was performed.

Blood was collected at the time of euthanasia and a full serum chemistry panel performed. Remarkable findings included hypoproteinemia, markedly elevated liver enzymes (AST, ALT, GGTP, ALP), hyperbilirubinemia, increased blood urea nitrogen (BUN), elevated BUN/creatinine ratio, hyperphosphatemia, hypoglycemia, hypocalcemia, hypochloremia, hypocholesterolemia, hypertriglyceridemia and elevated creatinine phosphokinase (CPK) (FIGS. 16A-16E). These findings were suggestive of hepatic failure with renal insufficiency likely secondary to hypoperfusion. The sample collected at necropsy was severely hemolyzed and therefore a complete blood count (CBC) and coagulation panel were not reported.

At necropsy the abdominal cavity contained approximately 44 mL of red serosanguineous fluid. Cytologic evaluation of the abdominal fluid was consistent with transudate with acute hemorrhage. The liver was diffusely enlarged, firm, and mottled tan to red, which corresponded histologically to massive hepatocellular necrosis and degeneration affecting ~95% of the hepatic parenchyma with only rare clusters of relatively normal hepatocytes remaining (FIGS. 17A-17D). The centrilobular to midzonal regions were severely congested with hepatocyte loss, degeneration and necrosis. Additionally, there were small foci of fibrin which occasionally formed plugs within sinusoids and filled the lumen of portal veins (acute fibrin thrombi).

Immunohistochemistry (IHC) for fibrinogen confirmed the presence of sinusoidal fibrin plugs. Fibrinogen staining was strongly positive within periportal to midzonal regions, which were the areas of active hepatocellular necrosis in the hepatic parenchyma that remained. Fibrinogen staining frequently highlighted sinusoids in these regions. The necrotic hepatocytes and associated debris were also strongly positive.

The spleen was diffusely enlarged, firm and congested. The congestion was confirmed histologically and germinal centers within the white pulp were depleted of lymphocytes with extensive cellular debris (lymphocytolysis) and had prominent, occasionally hyalinized, high endothelial venules (HEV). Similarly, the cortex of the thymus exhibited mild lymphocytolysis with prominent tingible body macrophages.

Grossly, the mesenteric lymph nodes were diffusely enlarged and congested. Histologically the follicles exhibited germinal center depletion with lymphocytolysis. Similar histologic findings were observed in other lymphoid tissues, including other lymph nodes (submandibular, rectal), bronchial-associated lymphoid tissue (BALT) in the lung and gut-associated lymphoid tissue (GALT) in the colon and cecum. Lymph nodes associated with the rectum, assumed to be mesorectal lymph nodes, had subcapsular and medullary sinus erythrocytosis, consistent with drainage of red blood cells. The histologic findings within lymphoid follicles were suggestive of severe systemic stress.

Histologically, acute hemorrhage and edema was evident in the lung, adventitia of the gall bladder, heart, perirectal adipose tissue and subcutis near the mammary gland. The superficial mucosa of the small intestines, cecum and rectum were congested with occasional hemorrhage as well as superficial aggregates of hemosiderin-laden macrophages. The presence of hemorrhage and edema in the lung, gastrointestinal tract and liver are suggestive of shock as these are known shock organs in nonhuman primates. Acinar cell degeneration in the pancreas was observed which has also been reported in cases of shock in nonhuman primates (Khan, N. A., et al. Mitigation of septic shock in mice and rhesus monkeys by human chorionic gonadotrophin-related oligopeptides. *Clinical and Experimental Immunology* 160, 466-478 (2010)) Minimal adrenocortical single cell degeneration and necrosis was present in the zona fasciculata of the adrenal glands also likely attributable to systemic disease, such as systemic stress, ischemia, hemorrhage and inflammation. No gross or histologic findings were noted in the brain, spinal cord, cranial nerves and peripheral nerves of this animal No significant findings were observed in the kidneys.

The remaining two primates (16C116 and 16C215) were clinically normal throughout the study and necropsied as planned on Day 28. Bloodwork performed at specified time points throughout the study revealed a dramatic transaminase elevation on Day 5, which was decreasing by Day 7 and normalized by Day 14 (FIGS. 16A-16E). One of the two remaining primates exhibited transient thrombocytopenia (platelet count 24,000/μL) on Day 5; platelets could not be quantified in the other animal due to clumping but appeared to be normal in number on the peripheral smear. Bloodwork was otherwise unremarkable throughout the study. At the time of necropsy, the liver of one animal (16C116) was mottled tan to red with an accentuated lobular pattern; no other significant abnormalities were observed in either of these two primates.

Histologically, the liver of both primates exhibited minimal multifocal single hepatocellular necrosis which was most prominent in the periportal region (FIGS. 17A-17D). Additionally, animal 16C215 had multifocal aggregates of irregularly arranged hepatocytes with cytoplasmic basophilia, vesicular nuclei and occasional mitotic figures, indicative of regeneration. These hepatocyte clusters generally surrounded portal areas with interspersed mononuclear cell infiltrates and proliferating fibroblasts (fibroplasia).

Histologic findings in the two terminally necropsied primates (16C215 and 16C116) were observed in the nervous system, predominately in the spinal cord, trigeminal ganglia and dorsal root ganglia as well as the peripheral nerves, including the median, radial, sciatic, tibial and peroneal nerves (FIGS. 18A-18D, Tables 2-4). The histologic lesions within the central and peripheral nervous system were often variable, with severity differing between tissue sections within the same segment as well as between segments of spinal cord and peripheral nerves in the same animal. The dorsal root ganglia (DRG) exhibited minimal to mild neuronal cell body degeneration characterized by central chromatolysis and mononuclear cell infiltrates surrounding (satellitosis) and infiltrating neuronal cell bodies (neuronophagia). Based on immunohistochemistry (IHC), the mononuclear cell infiltrates were composed of CD3-positive T cells with few CD20-positive B cells. In both primates, the dorsal white matter tracts of the cervical, thoracic and lumbar spinal cord exhibited bilateral, minimal to moderate axonopathy characterized by dilated myelin sheaths with and without myelomacrophages indicating axonal degeneration. Occasionally, minimal to marked axonopathy was observed in the dorsal nerve roots of the spinal cord. The peripheral nerves (median, radial, sciatic, peroneal and tibial) exhibited a similar axonopathy that ranged from mild to marked along with variable mononuclear cell infiltrates and periaxonal fibrosis. Peripheral axonopathy was observed bilaterally; however, severity varied between sections and even within some nerve sections.

TABLE 2

Incidence and severity of axonopathy in dorsal white matter tracts of the spinal cord in infant nonhuman primates and piglets that received AAVhu68 expressing human SMN intravenously. Excluding the NHP necropsied on Day 5, the incidence and severity of the dorsal axonopathy in the spinal cord was relatively similar between the NHPs and piglets.

| Species | Infant NHP | Piglets |
|---|---|---|
| Number of animals evaluated per group | 3 | 3 |
| Number Examined | 3 | 3 |
| Spinal Cord, Cervical (C2) | | |
| Axonopathy, dorsal white matter tracts | | |
| Not Present | 1* | — |
| Grade 1 | 1 | 1 |
| Grade 2 | — | 1 |
| Grade 3 | 1 | 1 |
| Spinal Cord, Thoracic (T2) | | |
| Axonopathy, dorsal white matter tracts | | |
| Not Present | 1* | — |
| Grade 1 | 1 | 1 |
| Grade 2 | 1 | 2 |
| Spinal Cord, Lumbar (L2) | | |
| Axonopathy, dorsal white matter tracts | | |
| Not Present | 1* | — |
| Grade 1 | 1 | 2 |
| Grade 2 | — | 1 |
| Grade 3 | 1 | — |

*Denotes unscheduled necropsy animal 16C176 (Day 5)

TABLE 3

Incidence and severity of neuronal degeneration of dorsal root and trigeminal ganglia in infant nonhuman primates and piglets that received AAVhu68 expressing human SMN intravenously. Excluding the NHP necropsied on Day 5, the incidence of the neuronal cell body degeneration was similar between the NHPs and piglets; however the severity was slightly increased in the piglets compared to the NHPs.

| Species | Infant NHP | Piglets |
|---|---|---|
| Number of animals evaluated per group | 3 | 3 |
| *Dorsal root ganglia, Cervical* | | |
| Number examined | 3 | 3 |
| Neuronal cell body degeneration with mononuclear cell infiltrate | | |
| Not Present | 1* | — |
| Grade 1 | 2 | — |
| Grade 2 | — | 1 |
| Grade 4 | — | 2 |
| *Dorsal root ganglia, Thoracic* | | |
| Number examined | 2 | 3 |
| Neuronal cell body degeneration with mononuclear cell infiltrate | | |
| Not Present | — | — |
| Grade 1 | 1 | — |
| Grade 2 | 1 | 3 |
| *Dorsal root ganglia, Lumbar* | | |
| Number examined | 3 | 3 |
| Neuronal cell body degeneration with mononuclear cell infiltrate | | |
| Not Present | 1* | — |
| Grade 1 | 1 | — |
| Grade 2 | 1 | 1 |
| Grade 3 | — | 2 |
| *Trigeminal ganglia* | | |
| Number examined | 2 | 3 |
| Neuronal cell body degeneration with mononuclear cell infiltrate | | |
| Not Present | — | — |
| Grade 1 | 2 | 1 |
| Grade 2 | — | 1 |
| Grade 3 | — | 1 |

*Denotes unscheduled necropsy animal 16C176 (Day 5)

TABLE 4

Incidence and severity of axonopathy of peripheral nerves in infant nonhuman primates and piglets that received AAVhu68 expressing human SMN intravenously. Excluding the NHP necropsied on Day 5, the incidence of the peripheral axonopathy was similar between the NHPs and piglets; however the severity was slightly increased in the NHPs compared to the piglets.

| Species | Infant NHP | Piglets |
|---|---|---|
| Number of animals evaluated per group | 3 | 3 |
| Number examined | 3 | 3 |
| *Median nerve* | | |
| Axonopathy | | |
| Not Present | 1* | 1 |
| Grade 1 | — | 1 |
| Grade 2 | 1 | 1 |
| Grade 3 | 1 | — |
| *Peroneal nerve* | | |
| Axonopathy | | |
| Not Present | 1* | 2 |
| Grade 1 | — | — |
| Grade 2 | 1 | — |
| Grade 4 | 1 | 1 |
| *Radial nerve* | | |
| Axonopathy | | |
| Not Present | 2* | 1 |
| Grade 1 | — | 1 |
| Grade 2 | — | 1 |
| Grade 3 | 1 | — |
| *Sciatic nerve* | | |
| Axonopathy | | |
| Not Present | 1* | 1 |
| Grade 1 | — | 1 |
| Grade 3 | 1 | 1 |
| Grade 4 | 1 | — |
| *Tibial nerve* | | |
| Axonopathy | | |
| Not Present | 1* | 1 |
| Grade 1 | — | 1 |
| Grade 3 | 1 | 1 |
| Grade 4 | 1 | — |

*Denotes unscheduled necropsy animal 16C176 (Day 5)

Figure 19:
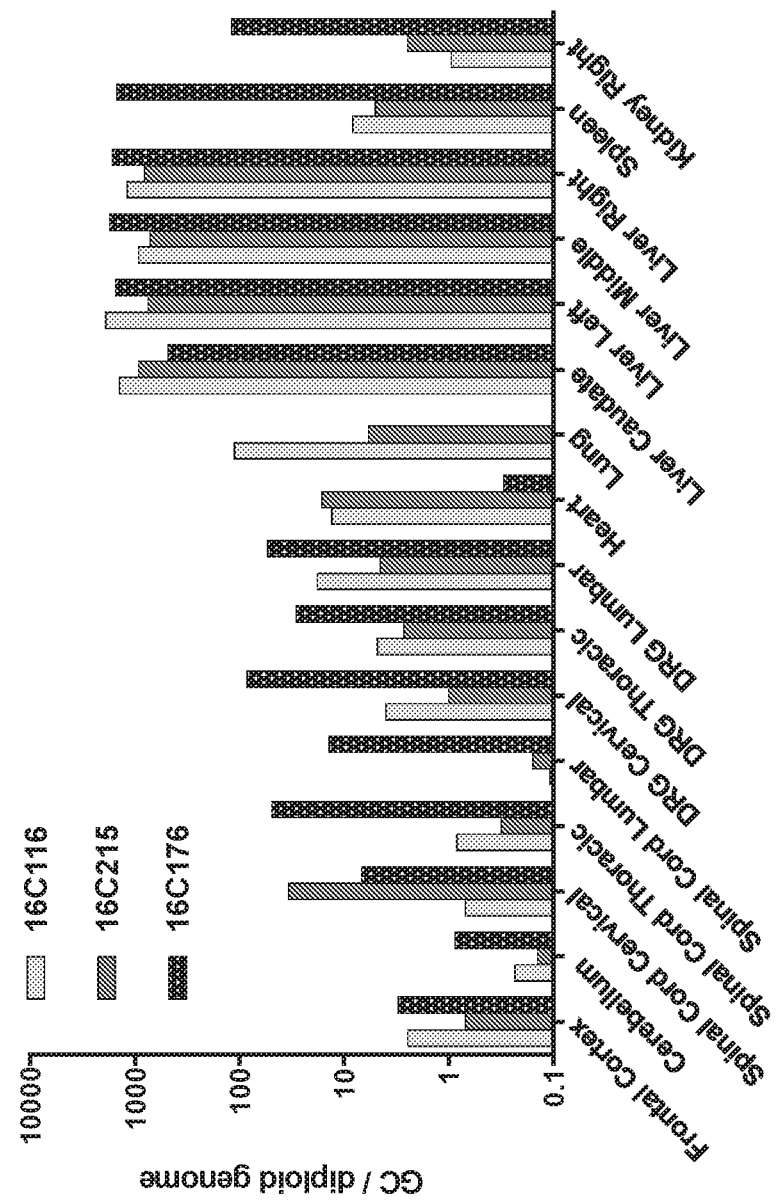
FIG. 19 provides vector biodistribution in rhesus macaques. Rhesus macaques treated with intravenous AAVhu68 expressing human SMN were euthanized 28 days after injection except for animal 16C176, developed liver failure and shock and was euthanized 5 days after vector administration. Vector genomes were detected in tissue DNA samples by quantitative PCR. Values are expressed as vector genome copies (GC) per host diploid genome. DRG=dorsal root ganglia. Data are shown for four liver lobes (caudate, left, middle and right).

Analysis of vector biodistribution demonstrated gene transfer to all tissues evaluated, including the brain and spinal cord (FIG. 19). Notably dorsal root ganglia (DRG) were heavily targeted with more than 10 vector genomes per cell in many samples. Extremely high liver transduction was also evident with more than 1000 vector genome copies (GC) per cell. Vector genome copies were detected at higher levels in the animal necropsied on day 5 than those necropsied on day 28, suggesting that some of the vector genomes detected in tissues early after injection do not represent stable transduction.

SMN expression was evaluated by in-situ hybridization (FIGS. 20A-20G). There was marked expression of human SMN mRNA in the liver of the animal necropsied on day 5, but no detectable expression in spinal cord or brain. The two animals necropsied 28 days after vector injection exhibited robust SMN expression in spinal motor neurons, with approximately 30-90% of cells transduced on average at each level of spinal cord evaluated. There were also scattered patches of transduced neurons and ependymal cells in the brain.

T cell responses to the vector capsid and human SMN transgene product were evaluated by interferon gamma ELISPOT (Table 5). Peripheral blood mononuclear cells were collected for ELISPOT analysis prior to vector administration and at the time of necropsy for all three animals. Mononuclear cells were also harvested from liver at necropsy. All samples exhibited a robust interferon gamma response to a positive control stimulation with PHA with the exception of liver lymphocytes collected from animal 16C215, which exhibited no response to PHA stimulation and were excluded from subsequent analysis. No T cell response to AAVhu68 capsid or hSMN was detectable at either timepoint for animals 16C176 or 16C215. Animal 16C116 exhibited no T cell response in PBMCs at either timepoint, but had a detectable interferon gamma response to both the vector capsid and transgene product at the time of necropsy.

TABLE 5

IFN gamma ELISPOT detection of T cell responses to AAVhu68 capsid and hSMN transgene in peripheral blood and liver lymphocytes. T cell responses were measured against pooled overlapping 15-mer peptides comprising the AAVhu68 VP1 sequence (3 peptide pools) or the human SMN sequence (2 peptide pools). Values are expressed as spot forming units (SFU) per million PBMCs. Asterisk indicates a detectable T cell response (>50 SFU and 3-fold greater than unstimulated control). Hepatic lymphocytes isolated from 16C215 exhibited inadequate response to PHA stimulation and were excluded from analysis.

| Animal ID | Lymphocyte source | Time Point | Unstimulated | PHA | AAVhu68 Pool A | AAVhu68 Pool B | AAVhu68 Pool C | hSMN Pool A | hSMN Pool B |
|---|---|---|---|---|---|---|---|---|---|
| 16C116 | Peripheral blood | Baseline | 8 | TNTC | 5 | 8 | 8 | 8 | 5 |
|  | Peripheral blood | Necropsy | 3 | TNTC | 13 | 8 | 8 | 13 | 3 |
|  | Liver | Necropsy | 0 | TNTC | 28 | 40 | 80* | 123* | 48 |
| 16C215 | Peripheral blood | Baseline | 0 | TNTC | 30 | 13 | 8 | 23 | 15 |
|  | Peripheral blood | Necropsy | 10 | TNTC | 8 | 23 | 18 | 13 | 18 |
| 16C176 | Peripheral blood | Baseline | 25 | TNTC | 8 | 18 | 8 | 28 | 18 |
|  | Peripheral blood | Necropsy | 13 | 1043 | 8 | 5 | 0 | 20 | 0 |
|  | Liver | Necropsy | 5 | 1023 | 5 | 5 | 0 | 3 | 0 |

PHA: phytohemaglutinin, TNTC: too numerous to count.

2. Piglet study

Three micro Yucatan piglets were administered an intravenous dose of $2\times10^{14}$ GC/kg AAVhu68.hSMN at 7 (n=1; Piglet A) or 30 (n=2; Piglets B and C) days of age (Table 6). All animals recovered uneventfully after vector administration. On study Day 14 post vector administration, Piglet A developed hindlimb ataxia. The ataxia was characterized by a swaying gait with intermittent knuckling and crossing over of the hindlimbs. When the hind feet were placed on their dorsal surface, the piglet failed to correct positioning of the hoof (placement test), indicating a deficit in conscious proprioception. This ataxia progressed to the forelimbs over the course of 6 hours. This piglet also developed dyspnea, but auscultation of all lung fields was within normal limits. Given progression of clinical signs, the piglet was euthanized on day 14 post-vector administration and a full necropsy was performed.

TABLE 6

Micro Yucatan piglets treated with AAVhu68.CB7.hSMN1 included in this study

| Animal ID | Age (Days) | Weight (kg) | Dose | Route of Administration |
|---|---|---|---|---|
| Piglet A | 7 | 1.56 | $2 \times 10^{14}$ GC/kg | IV |
| Piglet B | 30 | 3.35 | $2 \times 10^{14}$ GC/kg | IV |
| Piglet C | 30 | 4.30 | $2 \times 10^{14}$ GC/kg | IV |

On day 13 post vector administration, the piglets injected at 30 days of age developed similar neurologic signs, albeit less severe. No dyspnea was observed in these animals. The piglets were euthanized, and a full necropsy was performed.

No significant gross abnormalities were observed in piglets of either age group. The 7-day-old injected piglet was in fair to poor nutritional condition at the time of necropsy and had a clinical history of diarrhea on study Day 7, which resolved on study Day 9 following treatment with intramuscular (IM) ceftiofur. The 30-day-old injected piglets were in adequate nutritional condition. A complete blood count (CBC) from blood taken prior to euthanasia on the 7-day-old injected piglet (piglet A) revealed a marked neutrophilia (22,468/µL; reference range: 2,300-11,900/µl). No other significant abnormalities were noted on bloodwork. The neutrophilia likely corresponded to histologic evidence of bacterial bronchopneumonia. No significant bloodwork abnormalities were noted in the 30-day-old injected piglets.

The cervical, thoracic and lumbar dorsal root ganglia (DRG) from all animals exhibited mild to marked neuronal cell body degeneration with mononuclear cell infiltrates (FIGS. 21A-21D, Tables 2-4). The histologic lesions of neuronal degeneration ranged from cytoplasmic eosinophilia with bright eosinophilic cytoplasmic globules and central chromatolysis to complete effacement with infiltrating mononuclear cells (neuronophagia). Similar, albeit less severe, lesions were observed in the trigeminal ganglia of all animals as well, ranging from minimal to moderate. In all piglets, the dorsal white matter tracts of the cervical, thoracic and lumbar spinal cord exhibited minimal to moderate axonopathy characterized by dilated myelin sheaths with and without myelomacrophages, consistent with axonal degeneration. The incidence of these lesions was the same across all animals; however, the severity was slightly decreased in one of the 30-day-old injected piglets (piglet C).

In 7-day-old inject piglet (piglet A), the peripheral nerves (median, radial, sciatic, peroneal and tibial) contained a similar axonopathy to the spinal cord that ranged from mild to severe bilaterally. Interestingly, the axonopathy in the peripheral nerves of the hindlimbs (moderate to marked)

was more severe than the forelimbs (mild). In the 30-day-old injected piglets, only 1 animal (piglet B) had a minimal peripheral axonopathy in majority of nerves, except the peroneal nerve. The peripheral nerves of the other 30-day-old injected piglet (piglet C) were histologically unremarkable. The histologic lesions within the central and peripheral nervous system were often variable, as severity often differed between and within tissue sections of the same animal, as well as between different segments of spinal cord. No histologic abnormalities were noted in the brain or liver.

In general, the incidence and severity of the peripheral nerve lesions were decreased in the 30-day-old injected piglets compared with the 7-day-old injected piglet which coincided with the less severe antemortem neurologic signs observed in older animals. Additionally, severity of spinal cord lesions and incidence of peripheral nerve lesions were lowest in one of the 30-day-old injected piglets (piglet C) which also had the least severe neurologic signs of piglets in both age groups.

Figure 22:
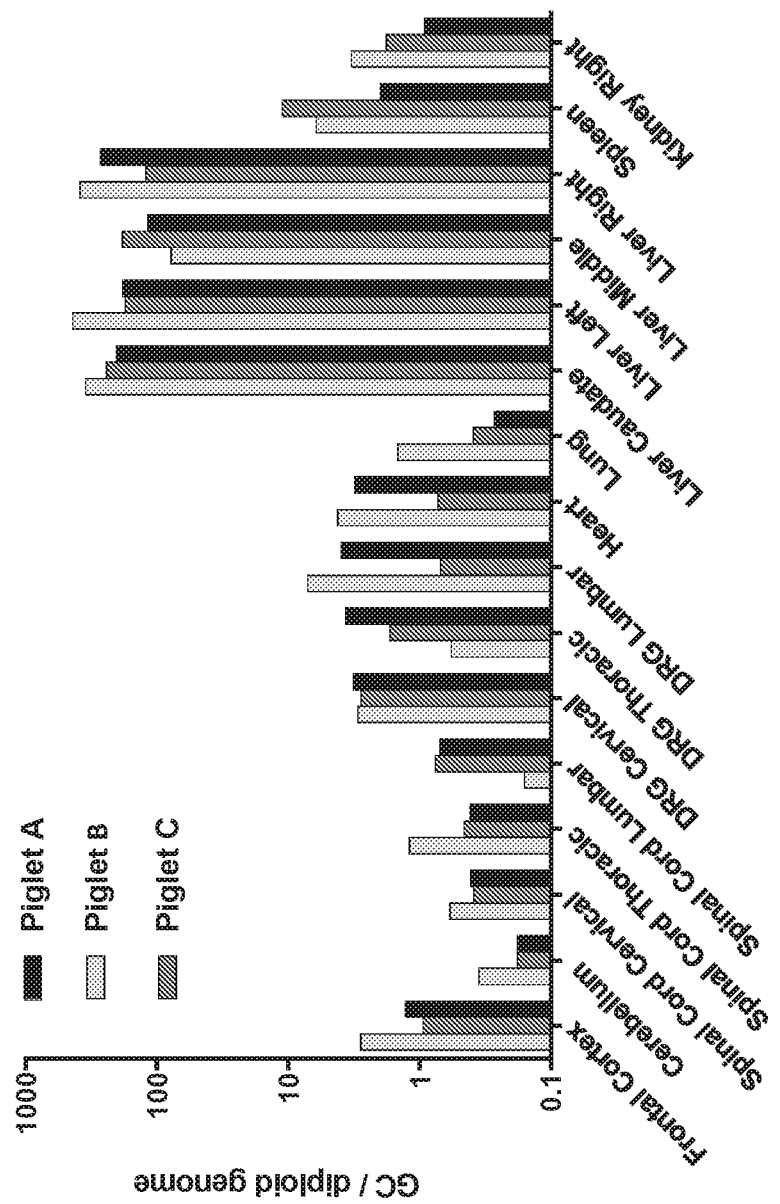
FIG. 22 provides vector biodistribution in piglets. Newborn piglets treated with intravenous AAVhu68 expressing human SMN were euthanized 13-14 days after injection. Vector genomes were detected in tissue DNA samples by quantitative PCR. Values are expressed as vector genome copies (GC) per host diploid genome. DRG=dorsal root ganglia. Data are shown for four liver lobes (caudate, left, middle and right).

Vector genomes were detectable in all tissues analyzed including brain and spinal cord (FIG. 22). Gene transfer to DRG was generally higher than that to spinal cord, often with more than 1 vector GC per host diploid genome (dg). The highest vector genome copy numbers were found in liver, with approximately 200 GC/dg in liver samples from all three animals. There was no apparent impact of age at injection of the efficiency of gene transfer to the tissues evaluated.

Expression of human SMN mRNA was detected by ISH in motor neurons throughout the spinal cord of all three animals (FIGS. 23A-23). The majority of motor neurons appeared to be transduced in all animals, with no apparent difference in transduction between the 7 and 30-day-old piglets.

B. Discussion:

In this example, intravenous administration of an AAV vector expressing human SMN at a high dose resulted in unexpected toxicity in piglets and juvenile NHPs. Hepatic toxicity which was limited to NHPs, whereas sensory neuron degeneration occurred in both species. The approximately 5-fold lower gene transfer to liver in piglets treated with the same vector dose suggests that a lesser hepatic tropism of AAV in this species may explain the absence of the liver toxicity observed in NHPs. All three NHPs developed a rapid elevation of liver enzymes and bilirubin after vector administration. The animal with the most pronounced transaminase elevation also exhibited evidence of coagulopathy, with extensive fibrin deposition in liver, widespread hemorrhage, and apparent spontaneous hemoperitoneum, though coagulation studies could not be performed at the time of necropsy, limiting the interpretation of these findings. The presence of fibrin deposition in liver associated with widespread hemorrhage was suggestive of disseminated intravascular coagulation (DIC). However, fibrin deposition was not noted outside the liver, inconsistent with true DIC. The findings appear similar to those described in acute liver failure caused by acetaminophen toxicity, which is characterized by rapid hepatocellular degeneration and tissue factor presentation in liver which leads to intrahepatic coagulation. See, e.g., Ganey, P. E., et al. Role of the coagulation system in acetaminophen-induced hepatotoxicity in mice. Hepatology 46, 1177-1186 (2007); Kerr, R. New insights into haemostasis in liver failure. Blood coagulation & fibrinolysis: an international journal in haemostasis and thrombosis 14 Suppl 1, S43-45 (2003); Payen, C., Dachraoui, A., Pulce, C. & Descotes, J. Prothrombin time prolongation in paracetamol poisoning: a relevant marker of hepatic failure? Human & experimental toxicology 22, 617-621 (2003); and James, L. P., Wells, E., Beard, R. H. & Farrar, H. C. Predictors of outcome after acetaminophen poisoning in children and adolescents. The Journal of pediatrics 140, 522-526 (2002). This is often associated with coagulopathy, which may be related to clotting factor consumption caused by intrahepatic coagulation, decreased clotting factor synthesis due to liver failure, or a combination of these. See Ganey et al, 2007 and Kerr, 2003 as cited above. Transient thrombocytopenia in one animal at day 5 could also be related to intrahepatic coagulation. Another possible explanation could be activation of a systemic inflammatory response by high dose AAV, with platelet activation, intravascular coagulation, shock and liver dysfunction as secondary consequences. Investigations are performed to determine whether liver injury is the initial cause of this cascade or a secondary consequence, as attempts to reduce the hepatic tropism of AAV vectors may be beneficial in the former case, but not in the latter. Insufficient data are available from this example to distinguish between these possibilities, and additional studies are under investigation to fully elucidate the pathophysiology of hepatic toxicity following high systemic exposure to AAV vectors.

DRG degeneration following AAV administration has not been reported, although a strong tropism for DRG has been noted in some studies. See, e.g., Gray, S. J., Kalburgi, S. N., McCown, T. J. & Samulski, R. J. Global CNS gene delivery and evasion of anti-AAV-neutralizing antibodies by intrathecal AAV administration in non-human primates. Gene therapy 20, 450-459 (2013). The lesions observed in the present example consisted of degeneration of DRG sensory neuron cell bodies as well as their central and peripheral axons. These lesions likely appear more than 5 days after gene transfer, as they were absent from the NHP sacrificed 5 days after treatment, and clinical signs first presented in piglets 13-14 days after vector administration. DRG lesions were slightly more severe in pigs than NHPs, whereas the degeneration of sensory axons in the spinal cord and peripheral nerves was similar to or even milder in the pigs compared to the NHPs, an observation which could be explained by the earlier necropsy timepoint in the pigs which may not have allowed for degeneration of all axons associated with the dying cells. Sensory deficits were apparent in pigs but not NHPs, suggesting that the extent of the DRG lesions in NHPs fell below a threshold at which clinical signs appear. The type of sensory fibers affected in either species was not characterized. Proprioception appeared to be impacted based on the deficits noted in piglets; impact on other sensory fibers was not clear, and is further characterized in subsequent studies.

T cell responses to a neoantigen are a theoretical cause of toxicity in any study evaluating delivery of a xenogenic human transgene to an animal model, or in clinical studies of gene therapy for recessive diseases. In addition, capsid derived peptides cross-presented on MHC class I by transduced cells have been identified as potential targets for cytotoxic T cell responses following AAV-mediated gene transfer. See, e.g., Manno, C. S., et al. Successful transduction of liver in hemophilia by AAV-Factor IX and limitations imposed by the host immune response. Nat Med 12, 342-347 (2006); and Martino, A. T., et al. Engineered AAV vector minimizes in vivo targeting of transduced hepatocytes by capsid-specific CD8+ T cells. Blood 121, 2224-2233 (2013). This latter mechanism has been proposed to be responsible for the transaminase elevations observed in some clinical trials of systemic AAV delivery, and administration of glucocorticoids to suppress T cell responses has been employed to mitigate this risk. See, e.g., Manno et al, 2006 as cited above and George, L. A., et al. Hemophilia B Gene Therapy with a High-Specific-Activity Factor IX Variant. New England Journal of Medicine 377, 2215-2227 (2017). In this example, transaminase elevations in NHPs appeared to have no correlation with T cell responses to the capsid or transgene product. T cell responses to the vector capsid and transgene product were detected in lymphocytes harvested from liver but not peripheral blood of one animal, demonstrating that responses can occur to both antigens, and that responses measured in peripheral blood may not always reflect those occurring within the target organ. However, the animal with the most severe toxicity had no detectable T cell response in either peripheral blood or liver lymphocytes, and another animal exhibiting marked transaminase elevation exhibited no T cell response in peripheral blood. Moreover, the rapid onset of liver toxicity (less than 5 days) is not consistent with a T cell response in a naïve host. The finding of hepatic toxicity in the absence of a T cell response suggests that an alternative mechanism is responsible for liver injury. Possibilities may include toxicity caused by massive accumulation of vector capsid within the endosomal pathway, induction of the DNA damage response by delivery of large numbers of vector genomes, toxicity of the transgene product expressed at extremely high levels, or impairment of normal transcription and translation of host genes caused by high levels of transgene expression. Whether this toxicity is specific to the SMN transgene can be readily tested in preclinical studies; evaluating the other possibilities requires more extensive research. It was observed that severe liver toxicity, coagulation abnormalities, thrombocytopenia and shock in an adult NHP treated with the same dose of a different AAV serotype carrying a green fluorescent protein transgene, demonstrating that these findings are not unique to AAVhu68 vectors nor to the SMN transgene (data not shown). Importantly, if there are non-immune mediated mechanisms of hepatic toxicity that occur in humans, the glucocorticoid administration protocols currently being incorporated into clinical trials may be ineffective for mitigating this risk.

A critical question for the field of AAV gene therapy is whether the toxicity observed in this study translates to humans, and if so, which animal models are sufficiently predictive of toxicity to allow for informative preclinical safety studies. Some SMA patients treated with a similar dose of a closely related AAV9 vector did exhibit marked hepatic toxicity, suggesting that the liver findings in the present study may be applicable to humans, and that macaques may be a predictive model. It is more difficult to determine whether the DRG toxicity observed in this example translates to humans. Sensory symptoms have not been reported in the SMA clinical trial, though subclinical lesions similar to those in NHPs may not be noted on routine evaluations.

The present findings raise important questions about the safety of systemic administration of AAV vectors at extremely high doses. Results shown in this example support the potential for high dose AAV to effectively transduce critical target cells such as lower motor neurons, but demonstrate that the doses required may be associated with significant toxicity. An adult NHP with a 10-fold lower dose of an AAV9 vector was previously treated and neither significant motor neuron transduction nor toxicity was observed, demonstrating that the therapeutic index for systemic AAV targeting motor neurons may be quite narrow. See, e.g., Hinderer, C., et al. Widespread gene transfer in the central nervous system of cynomolgus macaques following delivery of AAV9 into the cisterna magna. Molecular therapy. Methods & clinical development 1, 14051 (2014). Similar to the reported transaminase elevations in the SMA clinical trial, NHPs treated with the same vector dose in this study exhibited inter-subject variation in the severity of liver toxicity, and 2/3 NHPs demonstrated effective gene transfer with only asymptomatic laboratory abnormalities. This suggests that high dose systemic AAV may be safe and effective in some patients, although the narrow therapeutic index and severity of findings in outliers could mean that cases of severe toxicity emerges as larger numbers of patients are treated.

Studies are under investigation to understand the mechanism of the hepatic and sensory neuron toxicity observed in this example, and the relevance of each to humans. At present, nonhuman primate experiments may be informative for evaluating hepatic and neurologic toxicity associated with high-dose systemic AAV administration, and these studies should be performed before advancing into the clinic. In clinical trials, hepatic toxicity should be carefully evaluated, as should symptoms of sensory neuropathy. Objective assessments of toxicity to sensory neurons including somatosensory evoked potentials and nerve conduction studies may also be valuable. When transaminase elevations or other signs of toxicity are encountered in AAV clinical trials, investigators should maintain a broad differential diagnosis, as both immune and non-immune mechanisms may be responsible.

C. Materials and Methods:

Animal Procedures: All animal procedures were approved by the Institutional Animal Care and Use Committee of the University of Pennsylvania. For intravenous vector administration, vector was diluted in sterile phosphate buffered saline and infused via the saphenous vein (NHPs) or an ear vein (piglets) over 10 minutes. Euthanasia was performed with pentobarbital overdose.

Histology: Tissues were fixed in formalin, paraffin embedded, sectioned, and stained with hematoxylin and eosin according to conventional protocols. The fibrinogen IHC were also performed according to conventional methods.

In situ hybridization (ISH) was performed on formalin-fixed paraffin-embedded tissues not exceeding a fixation time of 24 h using the ViewRNA ISH Tissue Assay Kit (Thermo Fisher) according to the manufacturer's protocol. Probes consisting of Z-shaped probe pairs were synthesized by the kit manufacturer. Probes specific for codon-optimized human SMN were either used alone or in combination with probes for rhesus or pig CHAT as markers for motor neurons. Bound SMN probes were detected by the formation of Fast Red precipitates imaged with a rhodamin filter set. CHAT probes were detected via Fast Blue deposits imaged with a custom filter set (AVR Optics, Rochester, N.Y.) made according to the specifications of the kit manufacturer. Sections were counterstained with DAPI to show nuclei.

Vector production: The AAVhu68 vector was produced by triple transfection of adherent HEK293 cells. The vector was purified from cell supernatant by affinity chromatography using a POROS™ CaptureSelect™ AAV9 resin, followed by anion exchange chromatography to remove empty capsids and other impurities.

Vector biodistribution: At the time of necropsy tissues were frozen on dry ice for vector biodistribution analysis. DNA was extracted, and vector genomes quantified by TaqMan PCR as previously described. See, Wang, L., et al. Impact of pre-existing immunity on gene transfer to nonhuman primate liver with adeno-associated virus 8 vectors. Human gene therapy 22, 1389-1401 (2011).

ELISPOT: interferon gamma ELISPOT was performed as previously described. See, Brandy, M. L., et al. Sustained transgene expression despite T lymphocyte responses in a clinical trial of rAAV1-AAT gene therapy. Proceedings of the National Academy of Sciences of the United States of America 106, 16363-16368 (2009). The human SMN and AAVhu68 VP1 peptide libraries consisted of 15mer peptides overlapping by 5 amino acids divided into 2 (SMN) or 3 (AAVhu68) pools.

All published documents cited in this specification are incorporated herein by reference, as are U.S. Provisional Patent Application No. 62/618,437, filed Jan. 17, 2018, U.S. Provisional Patent Application No. 62/515,902, filed Jun. 6, 2017 and U.S. Provisional Patent Application No. 62/464,756, filed Feb. 28, 2017. Similarly, the SEQ ID NOs which are referenced herein and which appear in the appended Sequence Listing (file named 17-7988PCT ST25.txt) are incorporated by reference. While the invention has been described with reference to particular embodiments, it will be appreciated that modifications can be made without departing from the spirit of the invention. Such modifications are intended to fall within the scope of the appended claims.

(Sequence Listing Free Text)
The following information is provided for sequences containing free text under numeric identifier <223>.

| SEQ ID NO: (containing free text) | Free text under <223> |
|---|---|
| 1 | <223>engineered sequence encoding human SMN variant D protein<br><220><br><221> CDS<br><222> (1) . . . (882) |
| 2 | <223>Synthetic Construct |
| 4 | <223>Engineered hSMN transgene G2 |
| 5 | <223> Engineered SMN transgene G3 |
| 6 | <223> Engineered SMN transgene G4 |
| 7 | <223> AAVhu68 vp1 coding sequence<br><220><br><221> CDS<br><222> (1) . . . (2211)<br><223> AAVhu68 vp1 |
| 8 | <223> Synthetic Construct |
| 9 | <223> AAVhu68 rep coding sequence<br><220><br><221> CDS<br><222> (1) . . . (1866) |
| 10 | <223> Synthetic Construct |
| 15 | <223> AAV.CB7.CI.hSMN vector genome<br><220><br><221> repeat_region<br><222> (1) . . . (130)<br><223> AAV2- 5'ITR<br><br><220><br><221> promoter<br><222> (197) . . . (579)<br><223> CMV IE promoter<br><br><220><br><221> promoter<br><222> (582) . . . (863)<br><223> CB promoter<br><br><220><br><221> Intron<br><222> (958) . . . (1930)<br><223> CMV IE promoter<br><br><220><br><221> misc_feature<br><222> (1948) . . . (2829)<br><220> hSMN coding sequence |

-continued (Sequence Listing Free Text)
The following information is provided for sequences containing free text under numeric identifier <223>.

| SEQ ID NO:<br>(containing free text) | Free text under <223> |
|---|---|
| | <221> polyA_signal<br><222> (2914) ... (3040)<br><br><220><br><221> repeat_region<br><222> (3129) ... (3258)<br><223> AAV2- 3'ITR |
| 16 | <223> Encoded AAV9 vp1 amino acid sequence<br><220><br><221> MISC_FEATURE<br><222> (1) ... (137)<br><223> encoded vp1-unique region<br><br><220><br><221> MISC_FEATURE<br><222> (1) ... (736)<br><223> encoded vp1 amino acid sequence<br><br><220><br><221> MISC_FEATURE<br><222> (138) ... (736)<br><223> encoded amino acid sequence of alternative splice variant vp2 protein<br><br><220><br><221> MISC_FEATURE<br><222> (203) ... (736)<br><223> encoded amino acid sequence of alternative splice variant vp3 protein |
| 17 | <223> Encoded AAVrh10 vp1 amino acid sequence |
| 18 | <223> Encoded AAVhu31 vp1 amino acid sequence |
| 19 | <223> Encoded AAVhu32 vp1 amino acid sequence |
| 20 | <223> AAVhu31 vp1 coding sequence |
| 21 | <223> AAVhu32 vp1 coding sequence |
| 22 | <223> AAV9 vp1 coding sequence |
| 23 | <223> Primer prm504 |
| 24 | <223> Primer prm505 |
| 25 | <223> AAV.CB7.CI.hSMN vector genome<br><220><br><221> repeat_region<br><222> (1) ... (130)<br><223> 5'ITR<br><br><220><br><221> promoter<br><222> (198) ... (579)<br><223> CMV IE promoter<br><br><220><br><221> promoter<br><222> (582) ... (862)<br><223> CB promoter<br><br><220><br><221> TATA_signal<br><222> (836) ... (839)<br><br><220><br><221> Intron<br><222> (956) ... (1928)<br><223> Chicken beta-actin intron |

-continued

| | (Sequence Listing Free Text) |
|---|---|
| | The following information is provided for sequences containing free text under numeric identifier <223>. |

| SEQ ID NO: (containing free text) | Free text under <223> |
|---|---|
| | <220><br><221> misc_feature<br><222> (1946) . . . (2827)<br><223> hSMN coding sequence<br><br><220><br><221> polyA_signal<br><222> (2912) . . . (3038)<br><223> Rabbit globin polyA<br><br><220><br><221> repeat_region<br><222> (3127) . . . (3256)<br><223> 3'ITR |
| 26 | <223> modified hu68vp1<br><220><br><221> MISC_FEATURE<br><222> (23) . . . (23)<br><223> Xaa may be W (Trp, tryptophan), or oxidated W.<br><br><220><br><221> MISC_FEATURE<br><222> (35) . . . (35)<br><223> Xaa may be Asn, or deamidated to Asp, isoAsp, or Asp/isoAsp<br><br><220><br><221> MISC_FEATURE<br><222> (57) . . . (57)<br><223> Xaa may be Asn, or deamidated to Asp, isoAsp, or Asp/isoAsp<br><br><220><br><221> MISC_FEATURE<br><222> (66) . . . (66)<br><223> Xaa may be Asn, or deamidated to Asp, isoAsp, or Asp/isoAsp<br><br><220><br><221> MISC_FEATURE<br><222> (94) . . . (94)<br><223> Xaa may be Asn, or deamidated to Asp, isoAsp, or Asp/isoAsp<br><br><220><br><221> MISC_FEATURE<br><222> (97) . . . (97)<br><223> Xaa may be D (asp, aspartic acid), or isomerized D.<br><br><220><br><221> MISC_FEATURE<br><222> (107) . . . (107)<br><223> Xaa may be D (asp, aspartic acid), or isomerized D.<br><br><220><br><221> misc_feature<br><222> (113) . . . (113)<br><223> Xaa can be any naturally occurring amino acid<br><br><220><br><221> MISC_FEATURE<br><222> (149) . . . (149)<br><223> Xaa may be S (Ser, serine), or Phosphorilated S |

-continued (Sequence Listing Free Text)
The following information is provided for sequences containing free text under numeric identifier <223>.

| SEQ ID NO: (containing free text) | Free text under <223> |
|---|---|
| | <220><br><221> MISC_FEATURE<br><222> (149) . . . (149)<br><223> Xaa may be S (Ser, serine), or Phosphorylated S<br><br><220><br><221> MISC_FEATURE<br><222> (247) . . . (247)<br><223> Xaa may be W (Trp, tryptophan), or oxidated W (e.g., kynurenine).<br><br><220><br><221> MISC_FEATURE<br><222> (253) . . . (253)<br><223> Xaa may be Asn, or deamidated to Asp, isoAsp, or Asp/isoAsp<br><br><220><br><221> MISC_FEATURE<br><222> (259) . . . (259)<br><223> Xaa represents Q, or Q deamidated to glutamic acid (alpha-glutamic acid), gamma-glutamic acid (Glu), or a blend of<br>alpha- and gamma-glutamic acid<br><br><220><br><221> MISC_FEATURE<br><222> (270) . . . (270)<br><223> Xaa may be Asn, or deamidated to Asp, isoAsp, or Asp/isoAsp<br><br><220><br><221> MISC_FEATURE<br><222> (297) . . . (297)<br><223> Xaa represents D (Asp, aspartic acid) or amindated D to N (Asn,<br>asparagine)<br><br><220><br><221> MISC_FEATURE<br><222> (304) . . . (304)<br><223> Xaa may be Asn, or deamidated to Asp, isoAsp, or Asp/isoAsp<br><br><220><br><221> MISC_FEATURE<br><222> (306) . . . (306)<br><223> Xaa may be W (Trp, tryptophan), or oxidated W (e.g., kynurenine).<br><br><220><br><221> MISC_FEATURE<br><222> (314) . . . (314)<br><223> Xaa may be Asn, or deamidated to Asp, isoAsp, or Asp/isoAsp<br><br><220><br><221> MISC_FEATURE<br><222> (319) . . . (319)<br><223> Xaa may be Asn, or deamidated to Asp, isoAsp, or Asp/isoAsp<br><br><220><br><221> MISC_FEATURE<br><222> (329) . . . (329)<br><223> Xaa may be Asn, or deamidated to Asp, isoAsp, or Asp/isoAsp |

-continued (Sequence Listing Free Text)
The following information is provided for sequences containing free text under numeric identifier <223>.

| SEQ ID NO: (containing free text) | Free text under <223> |
|---|---|

```
<220>
<221> MISC_FEATURE
<222> (332) . . . (332)
<223> Xaa may be K (lys, lysine), or acetylated K <220>
<221> MISC_FEATURE
<222> (336) . . . (336)
<223> Xaa may be Asn, or deamidated to Asp, isoAsp, or
Asp/isoAsp <220>
<221> MISC_FEATURE
<222> (384) . . . (384)
<223> Xaa may be D (asp, aspartic acid), or isomerized D.

<220>
<221> MISC_FEATURE
<222> (404) . . . (404)
<223> Xaa may be M (Met, Methionine), or oxidated M.

<220>
<221> MISC_FEATURE
<222> (409) . . . (409)
<223> Xaa may be Asn, or deamidated to Asp, isoAsp, or
Asp/isoAsp <220>
<221> MISC_FEATURE
<222> (436) . . . (436)
<223> Xaa may be M (Met, Methionine), or oxidated M.

<220>
<221> MISC_FEATURE
<222> (452) . . . (452)
<223> Xaa may be Asn, or deamidated to Asp, isoAsp, or
Asp/isoAsp <220>
<221> MISC_FEATURE
<222> (477) . . . (477)
<223> Xaa may be Asn, or deamidated to Asp, isoAsp, or
Asp/isoAsp <220>
<221> MISC_FEATURE
<222> (499) . . . (499)
<223> Xaa may be S (Ser, serine), or Phosphorylated S <220>
<221> MISC_FEATURE
<222> (512) . . . (512)
<223> Xaa may be Asn, or deamidated to Asp, isoAsp, or
Asp/isoAsp <220>
<221> MISC_FEATURE
<222> (515) . . . (515)
<223> Xaa may be Asn, or deamidated to Asp, isoAsp, or
Asp/isoAsp <220>
<221> MISC_FEATURE
<222> (518) . . . (518)
<223> Xaa may be M (Met, Methionine), or oxidated M.

<220>
<221> MISC_FEATURE
<222> (524) . . . (524)
<223> Xaa may be M (Met, Methionine), or oxidated M.
```

-continued (Sequence Listing Free Text)
The following information is provided for sequences containing free text under numeric identifier <223>.

| SEQ ID NO: (containing free text) | Free text under <223> |
|---|---|

<220>
<221> MISC_FEATURE
<222> (559) . . . (559)
<223> Xaa may be M (Met, Methionine), or oxidated M.

<220>
<221> MISC_FEATURE
<222> (569) . . . (569)
<223> Xaa may be T (Thr, threonine), or Phosphorylated T <220>
<221> MISC_FEATURE
<222> (586) . . . (586)
<223> Xaa may be S (Ser, serine), or Phosphorylated S <220>
<221> MISC_FEATURE
<222> (599) . . . (599)
<223> Xaa represents Q, or Q deamidated to glutamic acid
(alpha-glutamic acid), gamma-glutamic acid (Glu), or a
blend of
alpha- and gamma-glutamic acid <220>
<221> MISC_FEATURE
<222> (605) . . . (605)
<223> Xaa may be M (Met, Methionine), or oxidated M.

<220>
<221> MISC_FEATURE
<222> (619) . . . (619)
<223> Xaa may be W (Trp, tryptophan), or oxidated W (e.g.,
kynurenine).

<220>
<221> MISC_FEATURE
<222> (628) . . . (628)
<223> Xaa may be Asn, or deamidated to Asp, isoAsp, or
Asp/isoAsp <220>
<221> MISC_FEATURE
<222> (640) . . . (640)
<223> Xaa may be M (Met, Methionine), or oxidated M.

<220>
<221> MISC_FEATURE
<222> (651) . . . (651)
<223> Xaa may be Asn, or deamidated to Asp, isoAsp, or
Asp/isoAsp <220>
<221> MISC_FEATURE
<222> (663) . . . (663)
<223> Xaa may be Asn, or deamidated to Asp, isoAsp, or
Asp/isoAsp <220>
<221> MISC_FEATURE
<222> (666) . . . (666)
<223> Xaa may be K (lys, lysine), or acetylated K <220>
<221> MISC_FEATURE
<222> (689) . . . (689)
<223> Xaa may be K (lys, lysine), or acetylated K -continued (Sequence Listing Free Text)
The following information is provided for sequences containing free text under numeric identifier <223>.

| SEQ ID NO: (containing free text) | Free text under <223> |
|---|---|
| | <220> <br> <221> MISC_FEATURE <br> <222> (693)...(693) <br> <223> Xaa may be K (lys, lysine), or acetylated K <br><br> <220> <br> <221> MISC_FEATURE <br> <222> (695)...(695) <br> <223> Xaa may be W (Trp, tryptophan), or oxidated W. <br><br> <220> <br> <221> MISC_FEATURE <br> <222> (709)...(709) <br> <223> Xaa may be Asn, or deamidated to Asp, isoAsp, or Asp/isoAsp <br><br> <220> <br> <221> MISC_FEATURE <br> <222> (735)...(735) <br> <223> Xaa may be Asn, or deamidated to Asp, isoAsp, or Asp/isoAsp |

What is claimed is:

1. A recombinant adeno-associated viral (rAAV) vector comprising an AAVhu68 capsid and at least one expression cassette, wherein the at least one expression cassette comprises a nucleic acid sequences encoding a functional survival of motor neuron (SMN) 1 protein and expression control sequences that direct expression of the SMN1 protein in a host cell, wherein the rAAV has an AAVhu68 capsid comprising: AAVhu68 VP1 proteins, AAVhu68 VP2 proteins and AAVhu68 VP3 proteins expressed from a nucleic acid sequence encoding SEQ ID NO: 8 (amino acids 1 to 736).

2. The rAAV vector of claim 1, wherein the encoded SMN1 protein is an SMN1 isoform D protein.

3. The rAAV vector of claim 2, wherein the encoded SMN1 isoform D protein has the amino acid sequence of SEQ ID NO: 2.

4. The rAAV vector of claim 1, wherein the nucleic acid sequence is encoding SMN1 isoform D is selected from:
   (a) SEQ ID NO: 1 or a sequence at least 70% identity therewith which encodes an SMN1 protein having the amino acid sequence of SEQ ID NO:2;
   (b) SEQ ID NO: 4;
   (c) SEQ ID NO: 5,
   (d) SEQ ID NO: 6, or
   (e) SEQ ID NO: 3 or a sequence at least 99% identical to SEQ ID NO: 3 which encodes functional SMN1 isoform D protein.

5. The rAAV vector of claim 1, wherein the expression control sequences comprise a promoter.

6. The rAAV vector of claim 5, wherein the promoter is a chicken β-actin (CB) promoter.

7. The rAAV vector of claim 1, wherein the promoter is a CB7 promoter comprising a cytomegalovirus enhancer and a chicken beta actin promoter.

8. The rAAV vector of claim 1, further comprising one or more of an enhancer, an intron, a Kozak sequence, a polyA, a post-transcriptional regulatory element.

9. The AAV vector of claim 1, further comprising AAV inverted terminal repeat (ITRs) sequences from an AAV different from the AAV supplying the capsid.

10. The AAV vector of claim 9, wherein the ITRs are from AAV2.

11. A recombinant adeno-associated virus (rAAV) vector comprising an AAVhu68 capsid which has packaged therein a vector genome comprising an AAV 5' ITR, a CB7 promoter which comprises a cytomegalovirus enhancer and a chicken beta actin promoter, an intron, a nucleic acid sequences of SEQ ID NO:1, a polyA, and an AAV 3' inverted terminal repeat sequence, wherein the AAVhu68 capsid comprises AAVhu68 VP1 proteins, AAVhu68 VP2 proteins and AAVhu68 VP3 proteins expressed from a nucleic acid sequence encoding SEQ ID NO: 8 (amino acids 1 to 736).

12. The rAAV of claim 11, wherein the vector genome has the sequence of SEQ ID NO: 15 or SEQ ID NO: 25.

13. A pharmaceutical composition comprising a pharmaceutically acceptable carrier, excipient and/or preservative and the rAAV vector of claim 1.

14. A pharmaceutical composition comprising a pharmaceutically acceptable carrier, excipient and/or preservative and the rAAV vector of claim 11.

\* \* \* \* \*

SEQUENCE LISTING

<160> NUMBER OF SEQ ID NOS: 26

<210> SEQ ID NO 1
<211> LENGTH: 882
<212> TYPE: DNA
<213> ORGANISM: Artificial Sequence
<220> FEATURE:
<223> OTHER INFORMATION: engineered sequence encoding human SMN variant
      D protein
<220> FEATURE:
<221> NAME/KEY: CDS
<222> LOCATION: (1)..(882)

<400> SEQUENCE: 1

```
atg gcc atg tcg agt ggg ggc agt gga ggg gga gtg cca gaa cag gaa        48
Met Ala Met Ser Ser Gly Gly Ser Gly Gly Gly Val Pro Glu Gln Glu
1               5                   10                  15 gat tcc gtg ctg ttc agg cga gga acc ggg cag agt gac gac agt gac        96
Asp Ser Val Leu Phe Arg Arg Gly Thr Gly Gln Ser Asp Asp Ser Asp
                20                  25                  30 att tgg gac gac acg gcc ctg atc aag gcc tat gac aaa gcc gtg gcc       144
Ile Trp Asp Asp Thr Ala Leu Ile Lys Ala Tyr Asp Lys Ala Val Ala
            35                  40                  45 tcc ttc aag cac gcg ctg aag aac ggc gac att tgc gaa acc agc ggc       192
Ser Phe Lys His Ala Leu Lys Asn Gly Asp Ile Cys Glu Thr Ser Gly
        50                  55                  60 aag cct aag acc acc cct aaa cgg aag ccc gcc aag aaa aat aag tcc       240
Lys Pro Lys Thr Thr Pro Lys Arg Lys Pro Ala Lys Lys Asn Lys Ser
65                  70                  75                  80 cag aaa aag aac aca gcc gca agt ctt cag caa tgg aag gtg ggg gat       288
Gln Lys Lys Asn Thr Ala Ala Ser Leu Gln Gln Trp Lys Val Gly Asp
                85                  90                  95 aag tgc tcc gcg ata tgg agt gaa gac ggg tgc atc tat cct gcc acc       336
Lys Cys Ser Ala Ile Trp Ser Glu Asp Gly Cys Ile Tyr Pro Ala Thr
                100                 105                 110
```

| | | | | | | | | | | | | | | | |
|---|---|---|---|---|---|---|---|---|---|---|---|---|---|---|---|
| atc | gcc | agc | ata | gac | ttc | aag | cgc | gaa | acc | tgc | gtg | gtg | gtg | tac | act | 384
| Ile | Ala | Ser | Ile | Asp | Phe | Lys | Arg | Glu | Thr | Cys | Val | Val | Val | Tyr | Thr |
| | | 115 | | | | 120 | | | | 125 | | | | | |

```
atc gcc agc ata gac ttc aag cgc gaa acc tgc gtg gtg gtg tac act      384
Ile Ala Ser Ile Asp Phe Lys Arg Glu Thr Cys Val Val Val Tyr Thr
        115                 120                 125 gga tac ggg aac cgg gag gag cag aac ctg agc gac ctg ttg agc cct      432
Gly Tyr Gly Asn Arg Glu Glu Gln Asn Leu Ser Asp Leu Leu Ser Pro
130                 135                 140 att tgt gag gtg gcc aac aac atc gag cag aat gcg caa gaa aat gaa      480
Ile Cys Glu Val Ala Asn Asn Ile Glu Gln Asn Ala Gln Glu Asn Glu
145                 150                 155                 160 aac gag agt cag gtg tcc acc gat gag agt gaa aac agt agg agc ccc      528
Asn Glu Ser Gln Val Ser Thr Asp Glu Ser Glu Asn Ser Arg Ser Pro
        165                 170                 175 ggc aac aaa tcc gac aat atc aag ccc aaa agc gca ccc tgg aat agc      576
Gly Asn Lys Ser Asp Asn Ile Lys Pro Lys Ser Ala Pro Trp Asn Ser
        180                 185                 190 ttc ctt cca ccc ccc ccc cca atg ccc gga cct cga ctg ggc ccc gga      624
Phe Leu Pro Pro Pro Pro Pro Met Pro Gly Pro Arg Leu Gly Pro Gly
        195                 200                 205 aag cct ggc ctg aag ttc aac ggc ccc cct cct cct ccc cct cct           672
Lys Pro Gly Leu Lys Phe Asn Gly Pro Pro Pro Pro Pro Pro Pro
210                 215                 220 ccc ccc cac ctg ctg agc tgc tgg ttg ccc cct ttc cct tcg gga ccc      720
Pro Pro His Leu Leu Ser Cys Trp Leu Pro Pro Phe Pro Ser Gly Pro
225                 230                 235                 240 cct atc ata cct ccc ccc ccc cct att tgc cct gac tcc ctg gac gac      768
Pro Ile Ile Pro Pro Pro Pro Pro Ile Cys Pro Asp Ser Leu Asp Asp
        245                 250                 255 gcg gac gcg ctg ggc agt atg ctc atc tcg tgg tac atg tca gga tac      816
Ala Asp Ala Leu Gly Ser Met Leu Ile Ser Trp Tyr Met Ser Gly Tyr
        260                 265                 270 cac acc ggg tac tac atg ggc ttc aga caa aat cag aag gaa gga cga      864
His Thr Gly Tyr Tyr Met Gly Phe Arg Gln Asn Gln Lys Glu Gly Arg
    275                 280                 285 tgt agt cac tcc ctg aat                                                882
Cys Ser His Ser Leu Asn
    290
```

<210> SEQ ID NO 2
<211> LENGTH: 294
<212> TYPE: PRT
<213> ORGANISM: Artificial Sequence
<220> FEATURE:
<223> OTHER INFORMATION: Synthetic Construct

<400> SEQUENCE: 2

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110
```

Ile Ala Ser Ile Asp Phe Lys Arg Glu Thr Cys Val Val Tyr Thr
            115                 120                 125

Gly Tyr Gly Asn Arg Glu Glu Gln Asn Leu Ser Asp Leu Leu Ser Pro
        130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro
210                 215                 220

Pro Pro His Leu Leu Ser Cys Trp Leu Pro Phe Pro Ser Gly Pro
225                 230                 235                 240

Pro Ile Ile Pro Pro Pro Pro Ile Cys Pro Asp Ser Leu Asp Asp
            245                 250                 255

Ala Asp Ala Leu Gly Ser Met Leu Ile Ser Trp Tyr Met Ser Gly Tyr
        260                 265                 270

His Thr Gly Tyr Tyr Met Gly Phe Arg Gln Asn Gln Lys Glu Gly Arg
        275                 280                 285

Cys Ser His Ser Leu Asn
        290

<210> SEQ ID NO 3
<211> LENGTH: 874
<212> TYPE: DNA
<213> ORGANISM: Homo sapiens

<400> SEQUENCE: 3
cagcggcggc agtggtggcg gcgtcccgga gcaggaggat tccgtgctgt tccggcgcgg      60
cacaggccag agcgatgatt ctgacatttg ggatgataca gcactgataa aagcatatga     120
taaagctgtg gcttcattta agcatgctct aaagaatggt gacatttgtg aaacttcggg     180
taaaccaaaa accacaccta aaagaaaacc tgctaagaag aataaaagcc aaagaagaa      240 tactgcagct tccttacaac agtggaaagt tggggacaaa tgttctgcca tttggtcaga     300
agacggttgc atttacccag ctaccattgc ttcaattgat tttaagagag aaacctgtgt     360
tgtggtttac actggatatg gaatagaga ggagcaaaat ctgtccgatc tactttcccc      420
aatctgtgaa gtagctaata atatagaaca gaatgctcaa gagaatgaaa atgaaagcca     480
agtttcaaca gatgaaagtg agaactccag gtctcctgga aataaatcag ataacatcaa     540
gcccaaatct gctccatgga actctttcct ccctccacca ccccccatgc cagggccaag     600
actgggacca ggaaagccag gtctaaaatt caatggccca ccaccgccac cgccaccacc     660
accaccccac ttactatcat gctggctgcc tccatttcct tctggaccac caataattcc     720
cccaccacct cccatatgtc cagattctct tgatgatgct gatgctttgg gaagtatgtt     780
aatttcatgg tacatgagtg gctatcatac tggctattat atgggtttca gacaaaatca     840
aaaagaagga aggtgctcac attccttaaa ttaa     874

<210> SEQ ID NO 4
<211> LENGTH: 885
<212> TYPE: DNA

```
<213> ORGANISM: Artificial Sequence
<220> FEATURE:
<223> OTHER INFORMATION: Engineered hSMN transgene G2

<400> SEQUENCE: 4
atggcgatga gcagcggcgg cagtggtggc ggcgtcccgg agcaggagga ttccgtgctg        60
ttccggcgcg gcacaggcca gagcgatgat tctgacattt gggatgatac agcactgata       120
aaagcatatg ataaagctgt ggcttcattt aagcatgctc taagaatgg tgacatttgt        180 gaaacttcgg gtaaaccaaa aaccacacct aaaagaaaac ctgctaagaa aataaaagc        240 caaaagaaga atactgcagc ttccttacaa cagtggaaag ttggggacaa atgttctgcc       300
atttggtcag aagacggttg catttaccca gctaccattg cttcaattga ttttaagaga       360
gaaacctgtg ttgtggttta cactggatat ggaaatagag aggagcaaaa tctgtccgat       420
ctactttccc caatctgtga agtagctaat aatatagaac agaatgctca agagaatgaa       480
aatgaaagcc aagtttcaac agatgaaagt gagaactcca ggtctcctgg aaataaatca       540
gataacatca agcccaaatc tgctccatgg aactcttttc tccctccacc acccccccatg      600 ccagggccaa gactgggacc aggaaagcca ggtctaaaat tcaatggccc accaccgcca       660
ccgccaccac caccacccca cttactatca tgctggctgc ctccatttcc ttctggacca       720
ccaataattc ccccaccacc tcccatatgt ccagattctc ttgatgatgc tgatgctttg       780
ggaagtatgt taatttcatg gtacatgagt ggctatcata ctggctatta tatgggtttc       840
agacaaaatc aaaagaagg aaggtgctca cattccttaa attaa                        885

<210> SEQ ID NO 5
<211> LENGTH: 885
<212> TYPE: DNA
<213> ORGANISM: Artificial Sequence
<220> FEATURE:
<223> OTHER INFORMATION: Engineered SMN transgene G3

<400> SEQUENCE: 5
atggctatga gcagtggcgg ctctggcggc ggagtgcctg agcaggaaga tagcgtgctg        60
ttcagacggg gcaccggcca gagcgacgac agcgacatct gggatgacac cgccctgatc       120
aaggcctacg acaaggccgt ggccagcttc aagcacgccc tgaagaacgg cgatatctgc       180
gagacaagcg gcaagcccaa gaccacccc aagagaaagc cgccaagaa gaacaagagc         240 cagaagaaga ataccgccgc ctccctgcag cagtggaaag tgggcgataa gtgcagcgcc       300
atttggagcg aggacggctg catctacccc gccacaatcg ccagcatcga cttcaagcgg       360
gaaacctgcg tggtggtgta cacaggctac ggcaacagag aggaacagaa cctgagcgac       420
ctgctgagcc ccatctgcga ggtggccaac aacatcgagc agaacgccca ggaaaacgag       480
aacgagtccc aggtgtccac cgacgagagc gagaacagca agcccggg caacaagagc         540 gacaacatca gcctaagag cgcccctgg aacagcttcc tgcctccccc tccaccaatg         600
cctggcccta gactgggacc tggcaagccc ggcctgaagt tcaatggccc cctcccccca       660
cctccaccac caccccctca tctgctgagc tgttggctgc ccccattccc tagcggccct       720
cccatcattc ctccaccccc cccaatctgc ccgacagcc tggatgatgc tgatgccctg       780
ggctccatgc tgatctcttg gtacatgagc ggctaccaca ccggctacta catgggcttc       840
cggcagaacc agaaagaggg ccgctgtagc cacagcctga actga                       885

<210> SEQ ID NO 6
<211> LENGTH: 885
```

```
<212> TYPE: DNA
<213> ORGANISM: Artificial Sequence
<220> FEATURE:
<223> OTHER INFORMATION: Engineered SMN transgene G4

<400> SEQUENCE: 6
atggcgatga gcagcggtgg ttccggagga ggggtgccgg agcaggagga ttccgtcctt    60
ttcagacggg gaaccggcca gtcggacgac tcggacatct gggatgacac cgcactgatc   120
aaagcatacg ataaagcagt ggcatcgttc aagcacgccc ttaagaatgg agacatttgc   180
gaaaccagcg ggaagccaaa aactactccg aagcgcaagc ccgccaagaa gaataagtca   240
cagaagaaaa acaccgccgc ttcgctgcaa cagtggaaag tgggcgacaa gtgctccgcg   300
atctggtcag aggatggctg catctacccg ccacgatcg cctccatcga cttcaagcgg    360
gaaacttgtg tggtcgtcta cactggctac ggaaaccgcg aggaacagaa tctcagcgat   420
ctcctcagcc cgatttgtga ggtggccaac aatatcgaac gaacgcgca gaaaacgag    480 aacgagtccc aagtgtcgac tgacgaatcg gaaaattcgc gctcaccagg aaacaagtca   540
gataacatca agcccaaaag cgcgccatgg aacagctttt tgccgccacc accacctatg   600
cctggaccga ggctgggacc gggaaagccg ggactcaaat tcaacggccc accgcctccg   660
ccacctccgc ctccacccca cttgctgtcc tgctggctgc cgccatttcc gtcgggtccg   720
cctatcatcc ctcctccacc gccgatttgc cccgactcac tcgacgatgc tgacgccctg   780
gggtcaatgc tgatctcctg gtatatgtcc ggctaccata ccggatacta catgggattc   840
cggcagaacc aaaaggaagg gagatgctcc cattcgctga attga                   885

<210> SEQ ID NO 7
<211> LENGTH: 2211
<212> TYPE: DNA
<213> ORGANISM: Artificial Sequence
<220> FEATURE:
<223> OTHER INFORMATION: AAVhu68 vp1 coding sequence
<220> FEATURE:
<221> NAME/KEY: CDS
<222> LOCATION: (1)..(2211)
<223> OTHER INFORMATION: AAVhu68 vp1

<400> SEQUENCE: 7 atg gct gcc gat ggt tat ctt cca gat tgg ctc gag gac aac ctc agt    48
Met Ala Ala Asp Gly Tyr Leu Pro Asp Trp Leu Glu Asp Asn Leu Ser
1               5                   10                  15 gaa ggc att cgc gag tgg tgg gct ttg aaa cct gga gcc cct caa ccc    96
Glu Gly Ile Arg Glu Trp Trp Ala Leu Lys Pro Gly Ala Pro Gln Pro
            20                  25                  30 aag gca aat caa caa cat caa gac aac gct cgg ggt ctt gtg ctt ccg   144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg   192
Gly Tyr Lys Tyr Leu Gly Pro Gly Asn Gly Leu Asp Lys Gly Glu Pro
    50                  55                  60 gtc aac gaa gca gac gcg gcg gcc ctc gag cac gac aag gcc tac gac   240
Val Asn Glu Ala Asp Ala Ala Ala Leu Glu His Asp Lys Ala Tyr Asp
65                  70                  75                  80 cag cag ctc aag gcc gga gac aac ccg tac ctc aag tac aac cac gcc   288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc   336
Asp Ala Glu Phe Gln Glu Arg Leu Lys Glu Asp Thr Ser Phe Gly Gly
            100                 105                 110
```

```
aac ctc ggg cga gca gtc ttc cag gcc aaa aag agg ctt ctt gaa cct      384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg      432
Leu Gly Leu Val Glu Glu Ala Ala Lys Thr Ala Pro Gly Lys Lys Arg
130                 135                 140 cct gta gag cag tct cct cag gaa ccg gac tcc tcc gtg ggt att ggc      480
Pro Val Glu Gln Ser Pro Gln Glu Pro Asp Ser Ser Val Gly Ile Gly
145                 150                 155                 160 aaa tcg ggt gca cag ccc gct aaa aag aga ctc aat ttc ggt cag act      528
Lys Ser Gly Ala Gln Pro Ala Lys Lys Arg Leu Asn Phe Gly Gln Thr
                165                 170                 175 ggc gac aca gag tca gtc ccc gac cct caa cca atc gga gaa cct ccc      576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc      624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc      672
Ala Pro Val Ala Asp Asn Asn Glu Gly Ala Asp Gly Val Gly Ser Ser
210                 215                 220 tcg gga aat tgg cat tgc gat tcc caa tgg ctg ggg gac aga gtc atc      720
Ser Gly Asn Trp His Cys Asp Ser Gln Trp Leu Gly Asp Arg Val Ile
225                 230                 235                 240 acc acc agc acc cga acc tgg gcc ctg ccc acc tac aat aac cac ctc      768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac      816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga      864
Ala Tyr Phe Gly Tyr Ser Thr Pro Trp Gly Tyr Phe Asp Phe Asn Arg
        275                 280                 285 ttc cac tgc cac ttc tca cca cgt gac tgg caa aga ctc atc aac aac      912
Phe His Cys His Phe Ser Pro Arg Asp Trp Gln Arg Leu Ile Asn Asn
290                 295                 300 aac tgg gga ttc cgg cct aag cga ctc aac ttc aag ctc ttc aac att      960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gct aat     1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc     1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca     1104
Pro Tyr Val Leu Gly Ser Ala His Glu Gly Cys Leu Pro Pro Phe Pro
        355                 360                 365 gcg gac gtt ttc atg att cct cag tac ggg tat cta acg ctt aat gat     1152
Ala Asp Val Phe Met Ile Pro Gln Tyr Gly Tyr Leu Thr Leu Asn Asp
370                 375                 380 gga agc caa gcc gtg ggt cgt tcg tcc ttt tac tgc ctg gaa tat ttc     1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag     1248
Pro Ser Gln Met Leu Arg Thr Gly Asn Asn Phe Gln Phe Ser Tyr Glu
                405                 410                 415 ttt gag aac gta cct ttc cat agc agc tat gct cac agc caa agc ctg     1296
Phe Glu Asn Val Pro Phe His Ser Ser Tyr Ala His Ser Gln Ser Leu
            420                 425                 430
```

```
gac cga ctc atg aat cca ctc atc gac caa tac ttg tac tat ctc tca      1344
Asp Arg Leu Met Asn Pro Leu Ile Asp Gln Tyr Leu Tyr Tyr Leu Ser
        435                 440                 445 aag act att aac ggt tct gga cag aat caa caa acg cta aaa ttc agt      1392
Lys Thr Ile Asn Gly Ser Gly Gln Asn Gln Gln Thr Leu Lys Phe Ser
450                 455                 460 gtg gcc gga ccc agc aac atg gct gtc cag gga aga aac tac ata cct      1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac      1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat      1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa      1584
Gly Arg Asn Ser Leu Met Asn Pro Gly Pro Ala Met Ala Ser His Lys
        515                 520                 525 gaa gga gag gac cgt ttc ttt cct ttg tct gga tct tta att ttt ggc      1632
Glu Gly Glu Asp Arg Phe Phe Pro Leu Ser Gly Ser Leu Ile Phe Gly
530                 535                 540 aaa caa gga act gga aga gac aac gtg gat gcg gac aaa gtc atg ata      1680
Lys Gln Gly Thr Gly Arg Asp Asn Val Asp Ala Asp Lys Val Met Ile
545                 550                 555                 560 acc aac gaa gaa gaa att aaa act acc aac cca gta gca acg gag tcc      1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag      1776
Tyr Gly Gln Val Ala Thr Asn His Gln Ser Ala Gln Ala Gln Ala Gln
            580                 585                 590 acc ggc tgg gtt caa aac caa gga ata ctt ccg ggt atg gtt tgg cag      1824
Thr Gly Trp Val Gln Asn Gln Gly Ile Leu Pro Gly Met Val Trp Gln
        595                 600                 605 gac aga gat gtg tac ctg caa gga ccc att tgg gcc aaa att cct cac      1872
Asp Arg Asp Val Tyr Leu Gln Gly Pro Ile Trp Ala Lys Ile Pro His
610                 615                 620 acg gac ggc aac ttt cac cct tct ccg ctg atg gga ggg ttt gga atg      1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg      1968
Lys His Pro Pro Pro Gln Ile Leu Ile Lys Asn Thr Pro Val Pro Ala
                645                 650                 655 gat cct cca acg gct ttc aac aag gac aag ctg aac tct ttc atc acc      2016
Asp Pro Pro Thr Ala Phe Asn Lys Asp Lys Leu Asn Ser Phe Ile Thr
            660                 665                 670 cag tat tct act ggc caa gtc agc gtg gag att gag tgg gag ctg cag      2064
Gln Tyr Ser Thr Gly Gln Val Ser Val Glu Ile Glu Trp Glu Leu Gln
        675                 680                 685 aag gaa aac agc aag cgc tgg aac ccg gag atc cag tac act tcc aac      2112
Lys Glu Asn Ser Lys Arg Trp Asn Pro Glu Ile Gln Tyr Thr Ser Asn
690                 695                 700 tat tac aag tct aat aat gtt gaa ttt gct gtt aat act gaa ggt gtt      2160
Tyr Tyr Lys Ser Asn Asn Val Glu Phe Ala Val Asn Thr Glu Gly Val
705                 710                 715                 720 tat tct gaa ccc cgc ccc att ggc acc aga tac ctg act cgt aat ctg      2208
Tyr Ser Glu Pro Arg Pro Ile Gly Thr Arg Tyr Leu Thr Arg Asn Leu
                725                 730                 735 taa                                                                  2211
```

<210> SEQ ID NO 8
<211> LENGTH: 736
<212> TYPE: PRT
<213> ORGANISM: Artificial Sequence
<220> FEATURE:
<223> OTHER INFORMATION: Synthetic Construct

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365
```

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 1866
<212> TYPE: DNA
<213> ORGANISM: Artificial Sequence
<220> FEATURE:
<223> OTHER INFORMATION: AAVhu68 rep coding sequence
<220> FEATURE:
<221> NAME/KEY: CDS
<222> LOCATION: (1)..(1866)

```
<400> SEQUENCE: 9 atg ccg ggg ttt tac gag att gtg att aag gtc ccc agc gac ctt gac      48
Met Pro Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag      96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att     144
Lys Glu Trp Glu Leu Pro Pro Asp Ser Asp Met Asp Leu Asn Leu Ile
        35                  40                  45 gag cag gca ccc ctg acc gtg gcc gag aag ctg cag cgc gac ttt ctg     192
Glu Gln Ala Pro Leu Thr Val Ala Glu Lys Leu Gln Arg Asp Phe Leu
    50                  55                  60 acg gaa tgg cgc cgt gtg agt aag gcc ccg gag gct ctt ttc ttt gtg     240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa     288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att     336
Thr Thr Gly Val Lys Ser Met Val Leu Gly Arg Phe Leu Ser Gln Ile
            100                 105                 110 cgc gaa aaa ctg att cag aga att tac cgc ggg atc gag ccg act ttg     384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg     432
Pro Asn Trp Phe Ala Val Thr Lys Thr Arg Asn Gly Ala Gly Gly Gly
    130                 135                 140 aac aag gtg gtg gat gag tgc tac atc ccc aat tac ttg ctc ccc aaa     480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta     528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat     576
Ser Ala Cys Leu Asn Leu Thr Glu Arg Lys Arg Leu Val Ala Gln His
            180                 185                 190 ctg acg cac gtg tcg cag acg cag gag cag aac aaa gag aat cag aat     624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac     672
Pro Asn Ser Asp Ala Pro Val Ile Arg Ser Lys Thr Ser Ala Arg Tyr
    210                 215                 220 atg gag ctg gtc ggg tgg ctc gtg gac aag ggg att acc tcg gag aag     720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc     768
Gln Trp Ile Gln Glu Asp Gln Ala Ser Tyr Ile Ser Phe Asn Ala Ala
                245                 250                 255 tcc aac tcg cgg tcc caa atc aag gtc gcc ttg gac aat gcg gga aag     816
Ser Asn Ser Arg Ser Gln Ile Lys Val Ala Leu Asp Asn Ala Gly Lys
            260                 265                 270 att atg agc ctg act aaa acc gcc ccc gac tac ctg gtg ggc cag cag     864
Ile Met Ser Leu Thr Lys Thr Ala Pro Asp Tyr Leu Val Gly Gln Gln
        275                 280                 285 ccc gtg gag gac att tcc agc aat cgg att tat aaa att ttg gaa cta     912
Pro Val Glu Asp Ile Ser Ser Asn Arg Ile Tyr Lys Ile Leu Glu Leu
    290                 295                 300
```

```
                                    -continued aac ggg tac gat ccc caa tat gcg gct tcc gtc ttt ctg gga tgg gcc      960
Asn Gly Tyr Asp Pro Gln Tyr Ala Ala Ser Val Phe Leu Gly Trp Ala
305                 310                 315                 320 acg aaa aag ttc ggc aag agg aac acc atc tgg ctg ttt ggg cct gca     1008
Thr Lys Lys Phe Gly Lys Arg Asn Thr Ile Trp Leu Phe Gly Pro Ala
            325                 330                 335 act acc ggg aag acc aac atc gcg gag gcc ata gcc cac act gtg ccc     1056
Thr Thr Gly Lys Thr Asn Ile Ala Glu Ala Ile Ala His Thr Val Pro
340                 345                 350 ttc tac ggg tgc gta aac tgg acc aat gag aac ttt ccc ttc aac gac     1104
Phe Tyr Gly Cys Val Asn Trp Thr Asn Glu Asn Phe Pro Phe Asn Asp
        355                 360                 365 tgt gtc gac aag atg gtg atc tgg tgg gag gag ggg aag atg acc gcc     1152
Cys Val Asp Lys Met Val Ile Trp Trp Glu Glu Gly Lys Met Thr Ala
370                 375                 380 aag gtc gtg gag tcg gcc aaa gcc att ctc gga gga agc aag gtg cgc     1200
Lys Val Val Glu Ser Ala Lys Ala Ile Leu Gly Gly Ser Lys Val Arg
385                 390                 395                 400 gtg gac cag aaa tgc aag tcc tcg gcc cag ata gac ccg act ccc gtg     1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac tca     1296
Ile Val Thr Ser Asn Thr Asn Met Cys Ala Val Ile Asp Gly Asn Ser
            420                 425                 430 acg acc ttc gaa cac cag cag ccg ttg caa gac cgg atg ttc aaa ttt     1344
Thr Thr Phe Glu His Gln Gln Pro Leu Gln Asp Arg Met Phe Lys Phe
        435                 440                 445 gaa ctc acc cgc cgt ctg gat cat gac ttt ggg aag gtc acc aag cag     1392
Glu Leu Thr Arg Arg Leu Asp His Asp Phe Gly Lys Val Thr Lys Gln
450                 455                 460 gaa gtc aaa gac ttt ttc cgg tgg gca aag gat cac gtg gtt gag gtg     1440
Glu Val Lys Asp Phe Phe Arg Trp Ala Lys Asp His Val Val Glu Val
465                 470                 475                 480 gag cat gaa ttc tac gtc aaa aag ggt gga gcc aag aaa aga ccc gcc     1488
Glu His Glu Phe Tyr Val Lys Lys Gly Gly Ala Lys Lys Arg Pro Ala
                485                 490                 495 ccc agt gac gca gat ata agt gag ccc aaa cgg gtg cgc gag tca gtt     1536
Pro Ser Asp Ala Asp Ile Ser Glu Pro Lys Arg Val Arg Glu Ser Val
            500                 505                 510 gcg cag cca tcg acg tca gac gcg gaa gct tcg atc aac tac gcg gac     1584
Ala Gln Pro Ser Thr Ser Asp Ala Glu Ala Ser Ile Asn Tyr Ala Asp
        515                 520                 525 agg tac caa aac aaa tgt tct cgt cac gtg ggc atg aat ctg atg ctg     1632
Arg Tyr Gln Asn Lys Cys Ser Arg His Val Gly Met Asn Leu Met Leu
530                 535                 540 ttt ccc tgc aga caa tgc gag aga ctg aat cag aat tca aat atc tgc     1680
Phe Pro Cys Arg Gln Cys Glu Arg Leu Asn Gln Asn Ser Asn Ile Cys
545                 550                 555                 560 ttc act cac ggt gtc aaa gac tgt tta gag tgc ttt ccc gtg tca gaa     1728
Phe Thr His Gly Val Lys Asp Cys Leu Glu Cys Phe Pro Val Ser Glu
                565                 570                 575 tct caa ccc gtt tct gtc gtc aaa aag gcg tat cag aaa ctg tgc tac     1776
Ser Gln Pro Val Ser Val Val Lys Lys Ala Tyr Gln Lys Leu Cys Tyr
            580                 585                 590 att cat cac atc atg gga aag gtg cca gac gct tgc act gct tgc gac     1824
Ile His His Ile Met Gly Lys Val Pro Asp Ala Cys Thr Ala Cys Asp
        595                 600                 605 ctg gtc aat gtg gac ttg gat gac tgt gtt tct gaa caa taa              1866
Leu Val Asn Val Asp Leu Asp Asp Cys Val Ser Glu Gln
610                 615                 620
```

```
<210> SEQ ID NO 10
<211> LENGTH: 621
<212> TYPE: PRT
<213> ORGANISM: Artificial Sequence
<220> FEATURE:
<223> OTHER INFORMATION: Synthetic Construct

<400> SEQUENCE: 10

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Val Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365
```

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Leu Asn Gln Asn Ser Asn Ile Cys
545                 550                 555                 560

Phe Thr His Gly Val Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
                580                 585                 590

Ile His His Ile Met Gly Lys Val Pro Asp Ala Cys Thr Ala Cys Asp
            595                 600                 605

Leu Val Asn Val Asp Leu Asp Asp Cys Val Ser Glu Gln
610                 615                 620

<210> SEQ ID NO 11
<211> LENGTH: 1545
<212> TYPE: DNA
<213> ORGANISM: Homo sapiens

<400> SEQUENCE: 11
ccacaaatgt gggagggcga taaccactcg tagaaagcgt gagaagttac tacaagcggt      60
cctcccggcc accgtactgt tccgctccca gaagccccgg gcggcggaag tcgtcactct     120
taagaaggga cggggcccca cgctgcgcac ccgcgggttt gctatggcga tgagcagcgg     180
cggcagtggt ggcggcgtcc cggagcagga ggattccgtg ctgttccggc gcggcacagg     240
ccagagcgat gattctgaca tttgggatga tacagcactg ataaaagcat atgataaagc     300
tgtggcttca tttaagcatg ctctaaagaa tggtgacatt tgtgaaactt cgggtaaacc     360
aaaaaccaca cctaaaagaa aacctgctaa gaagaataaa agccaaaaga agaatactgc     420
agcttcctta caacagtgga agttgggga caatgttct gccatttggt cagaagacgg      480
ttgcatttac ccagctacca ttgcttcaat tgattttaag agagaaacct gtgttgtggt     540
ttacactgga tatggaaata gagaggagca aaatctgtcc gatctacttt ccccaatctg     600
tgaagtagct aataatatag aacaaaatgc tcaagagaat gaaaatgaaa gccaagtttc     660

```
aacagatgaa agtgagaact ccaggtctcc tggaaataaa tcagataaca tcaagcccaa    720
atctgctcca tggaactctt ttctccctcc accaccccc atgccagggc caagactggg     780
accaggaaag ataattcccc caccacctcc catatgtcca gattctcttg atgatgctga    840
tgctttggga agtatgttaa tttcatggta catgagtggc tatcatactg gctattatat   900
gggtttcaga caaaatcaaa agaaggaag gtgctcacat tccttaaatt aaggagaaat    960
gctggcatag agcagcacta atgacacca ctaaagaaac gatcagacag atctggaatg   1020
tgaagcgtta tagaagataa ctggcctcat ttcttcaaaa tatcaagtgt tgggaaagaa  1080
aaaaggaagt ggaatgggta actcttcttg attaaaagtt atgtaataac caaatgcaat  1140
gtgaaatatt ttactggact ctattttgaa aaaccatctg taaaagactg gggtggggt   1200
gggaggccag cacggtggtg aggcagttga gaaaatttga atgtggatta gattttgaat  1260
gatattggat aattattggt aatttttatga gctgtgagaa gggtgttgta gtttataaaa 1320
gactgtctta atttgcatac ttaagcattt aggaatgaag tgttagagtg tcttaaaatg  1380
tttcaaatgg tttaacaaaa tgtatgtgag gcgtatgtgg caaaatgtta cagaatctaa  1440
ctggtggaca tggctgttca ttgtactgtt tttttctatc ttctatatgt ttaaaagtat  1500
ataataaaaa tatttaattt tttttttaaaa aaaaaaaaaa aaaaa                  1545
```

```
<210> SEQ ID NO 12
<211> LENGTH: 262
<212> TYPE: PRT
<213> ORGANISM: Homo sapiens

<400> SEQUENCE: 12

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Ile Ile Pro Pro Pro Pro Ile Cys Pro Asp Ser Leu Asp Asp
    210                 215                 220
```

Ala Asp Ala Leu Gly Ser Met Leu Ile Ser Trp Tyr Met Ser Gly Tyr
225                 230                 235                 240

His Thr Gly Tyr Tyr Met Gly Phe Arg Gln Asn Gln Lys Glu Gly Arg
            245                 250                 255

Cys Ser His Ser Leu Asn
            260

<210> SEQ ID NO 13
<211> LENGTH: 1571
<212> TYPE: DNA
<213> ORGANISM: Homo sapiens

<400> SEQUENCE: 13

| | | | | | | |
|---|---|---|---|---|---|---|
| ccacaaatgt | gggagggcga | taaccactcg | tagaaagcgt | gagaagttac | tacaagcggt | 60 |
| cctcccggcc | accgtactgt | tccgctccca | gaagccccgg | gcggcggaag | tcgtcactct | 120 |
| taagaaggga | cggggcccca | cgctgcgcac | ccgcgggttt | gctatggcga | tgagcagcgg | 180 |
| cggcagtggt | ggcggcgtcc | cggagcagga | ggattccgtg | ctgttccggc | gcggcacagg | 240 |
| ccagagcgat | gattctgaca | tttgggatga | tacagcactg | ataaaagcat | atgataaagc | 300 |
| tgtggcttca | tttaagcatg | ctctaaagaa | tggtgacatt | tgtgaaactt | cgggtaaacc | 360 |
| aaaaaccaca | cctaaaagaa | aacctgctaa | gaagaataaa | agccaaaaga | agaatactgc | 420 |
| agcttcctta | caacagtgga | aagttgggga | caaatgttct | gccatttggt | cagaagacgg | 480 |
| ttgcatttac | ccagctacca | ttgcttcaat | tgattttaag | agagaaacct | gtgttgtggt | 540 |
| ttacactgga | tatggaaata | gagaggagca | aaatctgtcc | gatctacttt | ccccaatctg | 600 |
| tgaagtagct | aataatatag | aacaaaatgc | tcaagagaat | gaaaatgaaa | gccaagtttc | 660 |
| aacagatgaa | agtgagaact | ccaggtctcc | tggaaataaa | tcagataaca | tcaagcccaa | 720 |
| atctgctcca | tggaactctt | ttctccctcc | accaccccc | atgccagggc | caagactggg | 780 |
| accaggaaag | ccaggtctaa | aattcaatgg | cccaccaccg | ccaccgccac | caccaccacc | 840 |
| ccacttacta | tcatgctggc | tgcctccatt | tccttctgga | ccaccaataa | ttcccccacc | 900 |
| acctcccata | tgtccagatt | ctcttgatga | tgctgatgct | tgggaagta | tgttaatttc | 960 |
| atggtacatg | agtggctatc | atactggcta | ttatatggaa | atgctggcat | agagcagcac | 1020 |
| taaatgacac | cactaaagaa | acgatcagac | agatctggaa | tgtgaagcgt | tatagaagat | 1080 |
| aactggcctc | atttcttcaa | aatatcaagt | gttgggaaag | aaaaaaggaa | gtggaatggg | 1140 |
| taactcttct | tgattaaaag | ttatgtaata | accaaatgca | atgtgaaata | ttttactgga | 1200 |
| ctctattttg | aaaaaccatc | tgtaaaagac | tggggtgggg | gtgggaggcc | agcacggtgg | 1260 |
| tgaggcagtt | gagaaaattt | gaatgtggat | tagattttga | atgatattgg | ataattattg | 1320 |
| gtaattttat | gagctgtgag | aagggtgttg | tagtttataa | aagactgtct | taatttgcat | 1380 |
| acttaagcat | ttaggaatga | agtgttagag | tgtcttaaaa | tgtttcaaat | ggtttaacaa | 1440 |
| aatgtatgtg | aggcgtatgt | ggcaaaatgt | tacagaatct | aactggtgga | catggctgtt | 1500 |
| cattgtactg | ttttttttcta | tcttctatat | gtttaaaagt | atataataaa | aatatttaat | 1560 |
| ttttttttaa | a | | | | | 1571 |

<210> SEQ ID NO 14
<211> LENGTH: 282
<212> TYPE: PRT
<213> ORGANISM: Homo sapiens

<400> SEQUENCE: 14

```
Met Ala Met Ser Ser Gly Gly Ser Gly Gly Val Pro Glu Gln Glu
1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
            35                  40                  45

Ser Phe Lys His Ala Leu Lys Asn Gly Asp Ile Cys Glu Thr Ser Gly
50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
                100                 105                 110

Ile Ala Ser Ile Asp Phe Lys Arg Glu Thr Cys Val Val Val Tyr Thr
            115                 120                 125

Gly Tyr Gly Asn Arg Glu Glu Gln Asn Leu Ser Asp Leu Leu Ser Pro
130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
            195                 200                 205

Lys Pro Gly Leu Lys Phe Asn Gly Pro Pro Pro Pro Pro Pro Pro Pro
210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala
            275                 280

<210> SEQ ID NO 15
<211> LENGTH: 3258
<212> TYPE: DNA
<213> ORGANISM: Artificial Sequence
<220> FEATURE:
<223> OTHER INFORMATION: AAV.CB7.CI.hSMN vector genome
<220> FEATURE:
<221> NAME/KEY: repeat_region
<222> LOCATION: (1)..(130)
<223> OTHER INFORMATION: AAV2- 5'ITR
<220> FEATURE:
<221> NAME/KEY: promoter
<222> LOCATION: (197)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: Intron
<222> LOCATION: (958)..(1930)
<223> OTHER INFORMATION: CMV IE promoter
<220> FEATURE:
```

```
<221> NAME/KEY: misc_feature
<222> LOCATION: (1948)..(2829)
<223> OTHER INFORMATION: hSMN coding sequence
<220> FEATURE:
<221> NAME/KEY: polyA_signal
<222> LOCATION: (2914)..(3040)
<220> FEATURE:
<221> NAME/KEY: repeat_region
<222> LOCATION: (3129)..(3258)
<223> OTHER INFORMATION: AAV2- 3'ITR

<400> SEQUENCE: 15
```

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctaccag | ggtaatgggg | 180 |
| atcctctaga | actatagcta | gtcgacattg | attattgact | agttattaat | agtaatcaat | 240 |
| tacggggtca | ttagttcata | gcccatatat | ggagttccgc | gttacataac | ttacggtaaa | 300 |
| tggcccgcct | ggctgaccgc | ccaacgaccc | ccgcccattg | acgtcaataa | tgacgtatgt | 360 |
| tcccatagta | acgccaatag | ggactttcca | ttgacgtcaa | tgggtggact | atttacggta | 420 |
| aactgcccac | ttggcagtac | atcaagtgta | tcatatgcca | agtacgcccc | ctattgacgt | 480 |
| caatgacggt | aaatggcccg | cctggcatta | tgcccagtac | atgaccttat | gggactttcc | 540 |
| tacttggcag | tacatctacg | tattagtcat | cgctattacc | atggtcgagg | tgagccccac | 600 |
| gttctgcttc | actctcccca | tctccccccc | ctccccaccc | ccaattttgt | atttatttat | 660 |
| tttttaatta | ttttgtgcag | cgatgggggc | ggggggggg | ggggggcgcg | cgccaggcgg | 720 |
| ggcggggcgg | ggcgaggggc | ggggcgggc | gaggcggaga | ggtgcggcgg | cagccaatca | 780 |
| gagcggcgcg | ctccgaaagt | ttccttttat | ggcgaggcgg | cggcggcggc | ggccctataa | 840 |
| aaagcgaagc | gcgcggcggg | cggggagtcg | ctgcgacgct | gccttcgccc | cgtgccccgc | 900 |
| tccgccgccg | cctcgcgccg | cccgccccgg | ctctgactga | ccgcgttact | cccacaggtg | 960 |
| agcgggcggg | acggcccttc | tcctccgggc | tgtaattagc | gcttggttta | atgacggctt | 1020 |
| gtttcttttc | tgtggctgcg | tgaaagcctt | gaggggctcc | gggagggccc | tttgtgcggg | 1080 |
| gggagcggct | cggggggtgc | gtgcgtgtgt | gtgtgcgtgg | ggagcgccgc | gtgcggctcc | 1140 |
| gcgctgcccg | gcggctgtga | gcgctgcggg | cgcggcgcgg | ggctttgtgc | gctccgcagt | 1200 |
| gtgcgcgagg | ggagcgcggc | cgggggcggt | gccccgcggt | gcggggggg | ctgcgagggg | 1260 |
| aacaaaggct | gcgtgcgggg | tgtgtgcgtg | gggggtgag | caggggtgt | gggcgcgtcg | 1320 |
| gtcgggctgc | aaccccccct | gcacccccct | ccccgagttg | ctgagcacgg | cccggcttcg | 1380 |
| ggtgcggggc | tccgtacggg | gcgtggcgcg | ggctcgccg | tgccgggcgg | ggggtggcgg | 1440 |
| caggtggggg | tgccgggcgg | ggcggggccg | cctcggccg | ggagggctc | ggggagggg | 1500 |
| cgcggcggcc | cccggagcgc | cggcggctgt | cgaggcgcgg | cgagccgcag | ccattgcctt | 1560 |
| ttatggtaat | cgtgcgagag | ggcgcaggga | cttcctttgt | cccaaatctg | tgcggagccg | 1620 |
| aaatctggga | ggcgccgccg | cacccctct | agcgggcgcg | gggcgaagcg | gtgcggcgcc | 1680 |
| ggcaggaagg | aaatgggcgg | ggagggcctt | cgtgcgtcgc | cgcgccgccg | tccccttctc | 1740 |
| cctctccagc | ctcggggctg | tccgcggggg | gacggctgcc | ttcggggggg | acggggcagg | 1800 |
| gcggggttcg | gcttctggcg | tgtgaccggc | ggctctagag | cctctgctaa | ccatgttcat | 1860 |
| gccttcttct | ttttcctaca | gctcctgggc | aacgtgctgg | ttattgtgct | gtctcatcat | 1920 |
| tttggcaaag | aattctagct | tgccaccatg | gccatgtcga | gtgggggcag | tggagggga | 1980 |

-continued

```
gtgccagaac aggaagattc cgtgctgttc aggcgaggaa ccgggcagag tgacgacagt    2040
gacatttggg acgacacggc cctgatcaag gcctatgaca agccgtggc ctccttcaag    2100 cacgcgctga agaacggcga catttgcgaa accagcggca agcctaagac cacccctaaa    2160
cggaagcccg ccaagaaaaa taagtcccag aaaaagaaca cagccgcaag tcttcagcaa    2220
tggaaggtgg gggataagtg ctccgcgata tggagtgaag acgggtgcat ctatcctgcc    2280
accatcgcca gcatagactt caagcgcgaa acctgcgtgg tggtgtacac tggatacggg    2340
aaccgggagg agcagaacct gagcgacctg ttgagccta tttgtgaggt ggccaacaac    2400
atcgagcaga atgcgcaaga aaatgaaaac gagagtcagg tgtccaccga tgagagtgaa    2460
aacagtagga gccccggcaa caaatccgac aatatcaagc ccaaaagcgc accctggaat    2520
agcttccttc cacccccccc cccaatgccc ggacctcgac tgggcccggg aaagcctggc    2580
ctgaagttca acggcccccc tcctcctcct ccccctcctc cccccacct gctgagctgc    2640 tggttgcccc ctttcccttc gggacccct atcatacctc cccccccccc tatttgccct    2700
gactccctgg acgacgcgga cgcgctgggc agtatgctca tctcgtggta catgtcagga    2760
taccacaccg ggtactacat gggcttcaga caaaatcaga aggaaggacg atgtagtcac    2820
tccctgaatt aatgatagct agaattcacg cgtggtacct ctagagtcga cccgggcggc    2880
ctcgaggacg gggtgaacta cgcctgagga tccgatcttt ttccctctgc caaaaattat    2940
ggggacatca tgaagcccct tgagcatctg acttctggct aataaaggaa atttattttc    3000
attgcaatag tgtgttggaa ttttttgtgt ctctcactcg gaagcaattc gttgatctga    3060
atttcgacca cccataatac ccattaccct ggtagataag tagcatggcg ggttaatcat    3120
taactacaag gaacccctag tgatggagtt ggccactccc tctctgcgcg ctcgctcgct    3180
cactgaggcc gggcgaccaa aggtcgcccg acgcccgggc tttgcccggg cggcctcagt    3240
gagcgagcga gcgcgcag                                                  3258
```

<210> SEQ ID NO 16
<211> LENGTH: 736
<212> TYPE: PRT
<213> ORGANISM: Artificial Sequence
<220> FEATURE:
<223> OTHER INFORMATION: Encoded AAV9 vp1 amino acid sequence
<220> FEATURE:
<221> NAME/KEY: MISC_FEATURE
<222> LOCATION: (1)..(137)
<223> OTHER INFORMATION: encoded vp1-unique region
<220> FEATURE:
<221> NAME/KEY: MISC_FEATURE
<222> LOCATION: (1)..(736)
<223> OTHER INFORMATION: encoded vp1 amino acid sequence
<220> FEATURE:
<221> NAME/KEY: MISC_FEATURE
<222> LOCATION: (1)..(736)
<223> OTHER INFORMATION: encoded vp1 amino acid sequence
<220> FEATURE:
<221> NAME/KEY: MISC_FEATURE
<222> LOCATION: (138)..(736)
<223> OTHER INFORMATION: encoded amino acid sequence of alternative
      splice variant vp2 protein
<220> FEATURE:
<221> NAME/KEY: MISC_FEATURE
<222> LOCATION: (203)..(736)
<223> OTHER INFORMATION: encoded amino acid sequence of alternative
      splice variant vp3 protein

<400> SEQUENCE: 16

```
Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
```

435                 440                 445
Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 17
<211> LENGTH: 738
<212> TYPE: PRT
<213> ORGANISM: Artificial Sequence
<220> FEATURE:
<223> OTHER INFORMATION: Encoded AAVrh10 vp1 amino acid sequence

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp

-continued

```
                65                  70                  75                  80
        Gln Gln Leu Lys Ala Gly Asp Asn Pro Tyr Leu Arg Tyr Asn His Ala
                        85                  90                  95

Asp Ala Glu Phe Gln Glu Arg Leu Gln Glu Asp Thr Ser Phe Gly Gly
                        100                 105                 110

Asn Leu Gly Arg Ala Val Phe Gln Ala Lys Lys Arg Val Leu Glu Pro
                        115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
        145                 150                 155                 160

Gly Lys Lys Gly Gln Gln Pro Ala Lys Lys Arg Leu Asn Phe Gly Gln
                        165                 170                 175

Thr Gly Asp Ser Glu Ser Val Pro Asp Pro Gln Pro Ile Gly Glu Pro
                        180                 185                 190

Pro Ala Gly Pro Ser Gly Leu Gly Ser Gly Thr Met Ala Ala Gly Gly
                        195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
        225                 230                 235                 240

Ile Thr Thr Ser Thr Arg Thr Trp Ala Leu Pro Thr Tyr Asn Asn His
                        245                 250                 255

Leu Tyr Lys Gln Ile Ser Asn Gly Thr Ser Gly Gly Ser Thr Asn Asp
                        260                 265                 270

Asn Thr Tyr Phe Gly Tyr Ser Thr Pro Trp Gly Tyr Phe Asp Phe Asn
                        275                 280                 285

Arg Phe His Cys His Phe Ser Pro Arg Asp Trp Gln Arg Leu Ile Asn
                        290                 295                 300

Asn Asn Trp Gly Phe Arg Pro Lys Arg Leu Asn Phe Lys Leu Phe Asn
        305                 310                 315                 320

Ile Gln Val Lys Glu Val Thr Gln Asn Glu Gly Thr Lys Thr Ile Ala
                        325                 330                 335

Asn Asn Leu Thr Ser Thr Ile Gln Val Phe Thr Asp Ser Glu Tyr Gln
                        340                 345                 350

Leu Pro Tyr Val Leu Gly Ser Ala His Gln Gly Cys Leu Pro Pro Phe
                        355                 360                 365

Pro Ala Asp Val Phe Met Ile Pro Gln Tyr Gly Tyr Leu Thr Leu Asn
                        370                 375                 380

Asn Gly Ser Gln Ala Val Gly Arg Ser Ser Phe Tyr Cys Leu Glu Tyr
        385                 390                 395                 400

Phe Pro Ser Gln Met Leu Arg Thr Gly Asn Asn Phe Glu Phe Ser Tyr
                        405                 410                 415

Gln Phe Glu Asp Val Pro Phe His Ser Ser Tyr Ala His Ser Gln Ser
                        420                 425                 430

Leu Asp Arg Leu Met Asn Pro Leu Ile Asp Gln Tyr Leu Tyr Tyr Leu
                        435                 440                 445

Ser Arg Thr Gln Ser Thr Gly Gly Thr Ala Gly Thr Gln Gln Leu Leu
            450                 455                 460

Phe Ser Gln Ala Gly Pro Asn Asn Met Ser Ala Gln Ala Lys Asn Trp
        465                 470                 475                 480

Leu Pro Gly Pro Cys Tyr Arg Gln Gln Arg Val Ser Thr Thr Leu Ser
                        485                 490                 495
```

-continued

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 18
<211> LENGTH: 736
<212> TYPE: PRT
<213> ORGANISM: Artificial Sequence
<220> FEATURE:
<223> OTHER INFORMATION: Encoded AAVhu31 vp1 amino acid sequence

<400> SEQUENCE: 18

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

-continued

Asn Leu Gly Arg Ala Val Phe Gln Ala Lys Lys Arg Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Gly Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly

```
                530             535             540
Lys Gln Gly Thr Gly Arg Asp Asn Val Asp Ala Asp Lys Val Met Ile
545                 550             555                 560

Thr Asn Glu Glu Glu Ile Lys Thr Thr Asn Pro Val Ala Thr Glu Ser
                565             570             575

Tyr Gly Gln Val Ala Thr Asn His Gln Ser Ala Gln Ala Gln Ala Gln
                580             585             590

Thr Gly Trp Val Gln Asn Gln Gly Ile Leu Pro Gly Met Val Trp Gln
                595             600             605

Asp Arg Asp Val Tyr Leu Gln Gly Pro Ile Trp Ala Lys Ile Pro His
610                 615             620

Thr Asp Gly Asn Phe His Pro Ser Pro Leu Met Gly Gly Phe Gly Met
625                 630             635             640

Lys His Pro Pro Pro Gln Ile Leu Ile Lys Asn Thr Pro Val Pro Ala
                645             650             655

Asp Pro Pro Thr Ala Phe Asn Lys Asp Lys Leu Asn Ser Phe Ile Thr
                660             665             670

Gln Tyr Ser Thr Gly Gln Val Ser Val Glu Ile Glu Trp Glu Leu Gln
                675             680             685

Lys Glu Asn Ser Lys Arg Trp Asn Pro Glu Ile Gln Tyr Thr Ser Asn
                690             695             700

Tyr Tyr Lys Ser Asn Asn Val Glu Phe Ala Val Ser Thr Glu Gly Val
705                 710             715                 720

Tyr Ser Glu Pro Arg Pro Ile Gly Thr Arg Tyr Leu Thr Arg Asn Leu
                725             730             735
```

<210> SEQ ID NO 19
<211> LENGTH: 736
<212> TYPE: PRT
<213> ORGANISM: Artificial Sequence
<220> FEATURE:
<223> OTHER INFORMATION: Encoded AAVhu32 vp1 amino acid sequence

<400> SEQUENCE: 19

```
Met Ala Ala Asp Gly Tyr Leu Pro Asp Trp Leu Glu Asp Thr Leu Ser
1               5               10              15

Glu Gly Ile Arg Gln Trp Trp Lys Leu Lys Pro Gly Pro Pro Pro Pro
                20              25              30

Lys Pro Ala Glu Arg His Lys Asp Asp Ser Arg Gly Leu Val Leu Pro
                35              40              45

Gly Tyr Lys Tyr Leu Gly Pro Gly Asn Gly Leu Asp Lys Gly Glu Pro
50              55              60

Val Asn Ala Ala Asp Ala Ala Ala Leu Glu His Asp Lys Ala Tyr Asp
65              70              75              80

Gln Gln Leu Lys Ala Gly Asp Asn Pro Tyr Leu Lys Tyr Asn His Ala
                85              90              95

Asp Ala Glu Phe Gln Glu Arg Leu Lys Glu Asp Thr Ser Phe Gly Gly
                100             105             110

Asn Leu Gly Arg Ala Val Phe Gln Ala Lys Lys Arg Leu Leu Glu Pro
                115             120             125

Leu Gly Leu Val Glu Glu Ala Ala Lys Thr Ala Pro Gly Lys Lys Arg
                130             135             140

Pro Val Glu Gln Ser Pro Gln Glu Pro Asp Ser Ser Ala Gly Ile Gly
145                 150             155                 160

Lys Ser Gly Ser Gln Pro Ala Lys Lys Lys Leu Asn Phe Gly Gln Thr
```

```
                165                 170                 175
Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590
```

```
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Gln Ile Leu Ile Lys Asn Thr Pro Val Pro Ala
            645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
            725                 730                 735

<210> SEQ ID NO 20
<211> LENGTH: 2211
<212> TYPE: DNA
<213> ORGANISM: Artificial Sequence
<220> FEATURE:
<223> OTHER INFORMATION: AAVhu31 vp1 coding sequence

<400> SEQUENCE: 20
atggctgccg atggttatct tccagattgg ctcgaggaca accttagtga aggaattcgc      60
gagtggtggg cttttgaaacc tggagcccct caacccaagg caaatcaaca acatcaagac    120
aacgctcgag gtcttgtgct tccgggttac aaataccttg acccggcaa cggactcgac      180 aagggggagc cggtcaacgc agcagacgcg gcggccctcg agcacgacaa ggcctacgac    240
cagcagctca aggccggaga caaccccgtac ctcaagtaca ccacgccga cgccgagttc    300 caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctccccgcag ccccctcagg tgtgggatct    600
cttacaatgg cttcaggtgg tggcgcacca gtggcagaca taacgaagg tgccgatgga    660 gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840 tggggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca cgccaataa ccttaccagc   1020 acggtccagg tcttcacgga ctcagactat cagctcccgt acgtgctcgg tcggctcac    1080 gagggctgcc tccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta   1260
```

```
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaaggga ggaccgtt tctttccttt gtctggatct   1620 ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag cgcagaccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acagcaagc gctggaaccc ggagatccag   2100
tacacttcca actattacaa gtctaataat gttgaatttg ctgttaatac tgaaggtgta   2160
tatagtgaac cccgcccat tggcaccaga tacctgactc gtaatctgta a             2211

<210> SEQ ID NO 21
<211> LENGTH: 2211
<212> TYPE: DNA
<213> ORGANISM: Artificial Sequence
<220> FEATURE:
<223> OTHER INFORMATION: AAVhu32 vp1 coding sequence

<400> SEQUENCE: 21
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg acccggcaa cggactcgac     180 aagggggagc cggtcaacgc agcagacgcg gcggcccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtt cacagcccgc taaaaagaaa ctcaatttcg gtcagactgg cgacacagag    540
tcagtccccg accctcaacc aatcggagaa cctcccgcag ccccctcagg tgtgggatct    600
cttacaatgg cttcaggtgg tggcgcacca gtggcagaca taacgaaggc tgccgatgga    660
gtgggtagtt cctcgggaaa ttggcattgc gattcccaat ggctgggga cagagtcatc    720 accaccagca cccgaacctg ggccctgccc acctacaaca tcacctcta caagcaaatc    780 tccaacagca catctggagg atcttcaaat gacaacgcct acttcggcta cagcacccc    840 tgggggtatt ttgacttcaa cagattccac tgccactct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
```

```
gagggctgcc tcccgccgtt cccagcggac gttttcatga ttcctcagta cgggtatctg    1140
acgcttaatg atgggagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gcgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaaggaa gaggaccgtt tctttccttt gtctggatct    1620 ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc caagcacacg gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc taatgggagg gtttggaatg    1920
aagcacccgc ctcctcagat cctcatcaaa acacacctg tacctgcgga tcctccaacg    1980
gctttcaata aggacaagct gaactctttc atcacccagt attctactgg ccaagtcagc    2040
gtggagattg agtgggagct gcagaaggaa acagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a            2211
```

<210> SEQ ID NO 22
<211> LENGTH: 2211
<212> TYPE: DNA
<213> ORGANISM: Artificial Sequence
<220> FEATURE:
<223> OTHER INFORMATION: AAV9 vp1 coding sequence

<400> SEQUENCE: 22

```
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccgggttac aaataccttg acccggcaa cggactcgac     180 aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtcttt ggggggcaacc tcgggcgagc agtcttccag    360
gccaaaaaga ggcttcttga acctcttggt ctggttgagg aagcggctaa cacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca taacgaaggt gccgatgga    660 gtgggtagtt cctcgggaaa ttggcattgc gattcccaat ggctggggga cagagtcatc    720
accaccagca cccgaacctg ggccctgccc acctacaaca tcacctcta caagcaaatc    780 tccaacagca catctggagg atcttcaaat gacaacgcct acttcggcta cagcacccc    840 tgggggtatt ttgacttcaa cagattccac tgccacttct caccacgtga ctggcagcga    900
ctcatcaaca caaactgggg attccggcct aagcgactca acttcaagct cttcaacatt    960
```

```
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaaggga gaggaccgtt tctttccttt gtctggatct    1620 ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat ggcaccaga tacctgactc gtaatctgta a              2211
```

<210> SEQ ID NO 23
<211> LENGTH: 26
<212> TYPE: DNA
<213> ORGANISM: Artificial Sequence
<220> FEATURE:
<223> OTHER INFORMATION: Primer prm504

<400> SEQUENCE: 23
gctgcgtcaa ctggaccaat gagaac                                          26

<210> SEQ ID NO 24
<211> LENGTH: 28
<212> TYPE: DNA
<213> ORGANISM: Artificial Sequence
<220> FEATURE:
<223> OTHER INFORMATION: Primer prm505

<400> SEQUENCE: 24
cgcagagacc aaagttcaac tgaaacga                                        28

<210> SEQ ID NO 25
<211> LENGTH: 3256
<212> TYPE: DNA
<213> ORGANISM: Artificial Sequence
<220> FEATURE:
<223> OTHER INFORMATION: AAV.CB7.CI.hSMN vector genome
<220> FEATURE:
<221> NAME/KEY: repeat_region
<222> LOCATION: (1)..(130)
<223> OTHER INFORMATION: 5'ITR
<220> FEATURE:

```
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: Chicken beta-actin intron
<220> FEATURE:
<221> NAME/KEY: misc_feature
<222> LOCATION: (1946)..(2827)
<223> OTHER INFORMATION: hSMN coding sequence
<220> FEATURE:
<221> NAME/KEY: polyA_signal
<222> LOCATION: (2912)..(3038)
<223> OTHER INFORMATION: Rabbit globin polyA
<220> FEATURE:
<221> NAME/KEY: repeat_region
<222> LOCATION: (3127)..(3256)
<223> OTHER INFORMATION: 3'ITR

<400> SEQUENCE: 25
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca gtacgccccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc ccaattttgt atttatttat    660
tttttaatta ttttgtgcag cgatgggggc ggggggggg gggggcgcg cgccaggcgg      720 ggcggggcgg ggcgagggc ggggcgggc gaggcggaga ggtgcggcgg cagccaatca    780
gagcggcgcg ctccgaaagt tcctttttat ggcgaggcgg cggcggcgg ggccctataa    840 aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggcccct tgtgcggggg   1080
gagcggctcg ggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc ggggggggct gcgaggggaa   1260
caaaggctgc gtgcggggtg tgtgcgtggg ggggtgagca ggggtgtgg gcgcgtcggt   1320 cgggctgcaa ccccccctgc accccctcc ccgagttgct gagcacggcc cggcttcggg   1380 tgcgggctc cgtacgggc gtggcgcggg gctcgccgtg ccgggcgggg ggtggcggca   1440 ggtggggtg ccgggcgggg cggggccgcc tcgggccggg gagggctcgg gggagggcg   1500
```

```
cggcggcccc cggagcgccg gcggctgtcg aggcgcggcg agccgcagcc attgcctttt    1560
atggtaatcg tgcgagaggg cgcagggact tcctttgtcc caaatctgtg cggagccgaa    1620
atctgggagg cgccgccgca ccccctctag cgggcgcggg gcgaagcggt gcggcgccgg    1680
caggaaggaa atgggcgggg agggccttcg tgcgtcgccg cgccgccgtc cccttctccc    1740
tctccagcct cggggctgtc cgcggggggga cggctgcctt cggggggggac ggggcagggc    1800 ggggttcggc ttctgcgtg tgaccggcgg ctctagagcc tctgctaacc atgttcatgc    1860
cttcttcttt ttcctacagc tcctgggcaa cgtgctggtt attgtgctgt ctcatcattt    1920
tggcaaagaa ttctagcttg ccaccatggc catgtcgagt gggggcagtg gagggggagt    1980
gccagaacag gaagattccg tgctgttcag gcgaggaacc gggcagagtg acgacagtga    2040
catttgggac gacacggccc tgatcaaggc ctatgacaaa gccgtggcct ccttcaagca    2100
cgcgctgaag aacggcgaca tttgcgaaac cagcggcaag cctaagacca cccctaaacg    2160
gaagcccgcc aagaaaaata gtcccgaaa aagaacaca gccgcaagtc ttcagcaatg    2220
gaaggtgggg gataagtgct ccgcgatatg gagtgaagac gggtgcatct atcctgccac    2280
catcgccagc atagacttca agcgcgaaac ctgcgtggtg gtgtacactg gatacgggaa    2340
ccgggaggag cagaacctga gcgacctgtt gagccctatt tgtgaggtgg ccaacaacat    2400
cgagcagaat gcgcaagaaa atgaaaacga gagtcaggtg tccaccgatg agagtgaaaa    2460
cagtaggagc cccggcaaca aatccgacaa tatcaagccc aaaagcgcac ctggaatag    2520 cttccttcca ccccccccc caatgcccgg acctcgactg ggccccggaa agcctggcct    2580
gaagttcaac ggccccctc ctcctcctcc ccctcctccc cccacctgc tgagctgctg    2640 gttgccccct ttcccttcgg gaccccctat catacctccc cccccccta tttgccctga    2700 ctccctggac gacgcggacg cgctgggcag tatgctcatc tcgtggtaca tgtcaggata    2760
ccacaccggg tactacatgg gcttcagaca aaatcagaag gaaggacgat gtagtcactc    2820
cctgaattaa tgatagctag aattcacgcg tggtacctct agagtcgacc cgggcggcct    2880
cgaggacggg gtgaactacg cctgaggatc cgatcttttt ccctctgcca aaaattatgg    2940
ggacatcatg aagccccttg agcatctgac ttctggctaa taaaggaaat ttattttcat    3000
tgcaatagtg tgttggaatt ttttgtgtct ctcactcgga agcaattcgt tgatctgaat    3060
ttcgaccacc cataataccc attaccctgg tagataagta gcatggcggg ttaatcatta    3120
actacaagga acccctagtg atggagttgg ccactccctc tctgcgcgct cgctcgctca    3180
ctgaggccgg gcgaccaaag gtcgcccgac gcccgggctt tgcccgggcg gcctcagtga    3240
gcgagcgagc gcgcag                                                     3256
```

<210> SEQ ID NO 26
<211> LENGTH: 736
<212> TYPE: PRT
<213> ORGANISM: Artificial Sequence
<220> FEATURE:
<223> OTHER INFORMATION: modified hu68vp1
<220> FEATURE:
<221> NAME/KEY: MISC_FEATURE
<222> LOCATION: (23)..(23)
<223> OTHER INFORMATION: Xaa may be W (Trp, tryptophan), or oxidated W.
<220> FEATURE:
<221> NAME/KEY: MISC_FEATURE
<222> LOCATION: (35)..(35)
<223> OTHER INFORMATION: Xaa may be Asn, or deamidated to Asp, isoAsp,
    or Asp/isoAsp
<220> FEATURE:
<221> NAME/KEY: MISC_FEATURE
<222> LOCATION: (57)..(57)

```
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (66)..(66)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (94)..(94)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (97)..(97)
<223> OTHER INFORMATION: Xaa may be D (asp, aspartic acid), or
      isomerized D.
<220> FEATURE:
<221> NAME/KEY: MISC_FEATURE
<222> LOCATION: (107)..(107)
<223> OTHER INFORMATION: Xaa may be D (asp, aspartic acid), or
      isomerized D.
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: MISC_FEATURE
<222> LOCATION: (149)..(149)
<223> OTHER INFORMATION: Xaa may be S (Ser, serine), or Phosphorilated S
<220> FEATURE:
<221> NAME/KEY: MISC_FEATURE
<222> LOCATION: (149)..(149)
<223> OTHER INFORMATION: Xaa may be S (Ser, serine), or Phosphorylated S
<220> FEATURE:
<221> NAME/KEY: MISC_FEATURE
<222> LOCATION: (247)..(247)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (253)..(253)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (259)..(259)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (270)..(270)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (297)..(297)
<223> OTHER INFORMATION: Xaa represents D (Asp, aspartic acid) or
      amindated D to N (Asn, asparagine)
<220> FEATURE:
<221> NAME/KEY: MISC_FEATURE
<222> LOCATION: (304)..(304)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (306)..(306)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (314)..(314)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (319)..(319)
<223> OTHER INFORMATION: Xaa may be Asn, or deamidated to Asp, isoAsp,
```

```
            or Asp/isoAsp
<220> FEATURE:
<221> NAME/KEY: MISC_FEATURE
<222> LOCATION: (329)..(329)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (332)..(332)
<223> OTHER INFORMATION: Xaa may be K (lys, lysine), or acetylated K
<220> FEATURE:
<221> NAME/KEY: MISC_FEATURE
<222> LOCATION: (336)..(336)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (384)..(384)
<223> OTHER INFORMATION: Xaa may be D (asp, aspartic acid), or
      isomerized D.
<220> FEATURE:
<221> NAME/KEY: MISC_FEATURE
<222> LOCATION: (404)..(404)
<223> OTHER INFORMATION: Xaa may be M (Met, Methionine), or oxidated M.
<220> FEATURE:
<221> NAME/KEY: MISC_FEATURE
<222> LOCATION: (409)..(409)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (436)..(436)
<223> OTHER INFORMATION: Xaa may be M (Met, Methionine), or oxidated M.
<220> FEATURE:
<221> NAME/KEY: MISC_FEATURE
<222> LOCATION: (452)..(452)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (477)..(477)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (499)..(499)
<223> OTHER INFORMATION: Xaa may be S (Ser, serine), or Phosphorylated S
<220> FEATURE:
<221> NAME/KEY: MISC_FEATURE
<222> LOCATION: (512)..(512)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (515)..(515)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (518)..(518)
<223> OTHER INFORMATION: Xaa may be M (Met, Methionine), or oxidated M.
<220> FEATURE:
<221> NAME/KEY: MISC_FEATURE
<222> LOCATION: (524)..(524)
<223> OTHER INFORMATION: Xaa may be M (Met, Methionine), or oxidated M.
<220> FEATURE:
<221> NAME/KEY: MISC_FEATURE
<222> LOCATION: (559)..(559)
<223> OTHER INFORMATION: Xaa may be M (Met, Methionine), or oxidated M.
<220> FEATURE:
<221> NAME/KEY: MISC_FEATURE
<222> LOCATION: (569)..(569)
<223> OTHER INFORMATION: Xaa may be T (Thr, threonine), or
      Phosphorylated T
<220> FEATURE:
<221> NAME/KEY: MISC_FEATURE
<222> LOCATION: (586)..(586)
<223> OTHER INFORMATION: Xaa may be S (Ser, serine), or Phosphorylated S
<220> FEATURE:
```

```
<221> NAME/KEY: MISC_FEATURE
<222> LOCATION: (599)..(599)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (605)..(605)
<223> OTHER INFORMATION: Xaa may be M (Met, Methionine), or oxidated M.
<220> FEATURE:
<221> NAME/KEY: MISC_FEATURE
<222> LOCATION: (619)..(619)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (628)..(628)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (640)..(640)
<223> OTHER INFORMATION: Xaa may be M (Met, Methionine), or oxidated M.
<220> FEATURE:
<221> NAME/KEY: MISC_FEATURE
<222> LOCATION: (651)..(651)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (663)..(663)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (666)..(666)
<223> OTHER INFORMATION: Xaa may be K (lys, lysine), or acetylated K
<220> FEATURE:
<221> NAME/KEY: MISC_FEATURE
<222> LOCATION: (689)..(689)
<223> OTHER INFORMATION: Xaa may be K (lys, lysine), or acetylated K
<220> FEATURE:
<221> NAME/KEY: MISC_FEATURE
<222> LOCATION: (693)..(693)
<223> OTHER INFORMATION: Xaa may be K (lys, lysine), or acetylated K
<220> FEATURE:
<221> NAME/KEY: MISC_FEATURE
<222> LOCATION: (695)..(695)
<223> OTHER INFORMATION: Xaa may be W (Trp, tryptophan), or oxidated W.
<220> FEATURE:
<221> NAME/KEY: MISC_FEATURE
<222> LOCATION: (709)..(709)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (735)..(735)
<223> OTHER INFORMATION: Xaa may be Asn, or deamidated to Asp, isoAsp,
      or Asp/isoAsp

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Xaa Ala Leu Lys Pro Gly Ala Pro Gln Pro
            20                  25                  30

Lys Ala Xaa Gln Gln His Gln Asp Asn Ala Arg Gly Leu Val Leu Pro
        35                  40                  45

Gly Tyr Lys Tyr Leu Gly Pro Gly Xaa Gly Leu Asp Lys Gly Glu Pro
    50                  55                  60

Val Xaa Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Xaa His Ala
                85                  90                  95
```

```
Xaa Ala Glu Phe Gln Glu Arg Leu Lys Glu Xaa Thr Ser Phe Gly Gly
            100                 105                 110

Xaa Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Xaa Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Xaa Ala Leu Pro Thr Tyr Xaa Asn His Leu
            245                 250                 255

Tyr Lys Xaa Ile Ser Asn Ser Thr Ser Gly Gly Ser Ser Xaa Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Xaa Trp Gln Arg Leu Ile Asn Xaa
            290                 295                 300

Asn Xaa Gly Phe Arg Pro Lys Arg Leu Xaa Phe Lys Leu Phe Xaa Ile
305                 310                 315                 320

Gln Val Lys Glu Val Thr Asp Asn Xaa Gly Val Xaa Thr Ile Ala Xaa
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Xaa
370                 375                 380

Gly Ser Gln Ala Val Gly Arg Ser Ser Phe Tyr Cys Leu Glu Tyr Phe
385                 390                 395                 400

Pro Ser Gln Xaa Leu Arg Thr Gly Xaa Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Xaa Asn Pro Leu Ile Asp Gln Tyr Leu Tyr Tyr Leu Ser
            435                 440                 445

Lys Thr Ile Xaa Gly Ser Gly Gln Asn Gln Gln Thr Leu Lys Phe Ser
            450                 455                 460

Val Ala Gly Pro Ser Asn Met Ala Val Gln Gly Arg Xaa Tyr Ile Pro
465                 470                 475                 480

Gly Pro Ser Tyr Arg Gln Gln Arg Val Ser Thr Thr Val Thr Gln Asn
                485                 490                 495

Asn Asn Xaa Glu Phe Ala Trp Pro Gly Ala Ser Ser Trp Ala Leu Xaa
            500                 505                 510
```

-continued

```
Gly Arg Xaa Ser Leu Xaa Asn Pro Gly Pro Ala Xaa Ala Ser His Lys
        515             520             525

Glu Gly Glu Asp Arg Phe Phe Pro Leu Ser Gly Ser Leu Ile Phe Gly
    530             535             540

Lys Gln Gly Thr Gly Arg Asp Asn Val Asp Ala Asp Lys Val Xaa Ile
545             550             555             560

Thr Asn Glu Glu Glu Ile Lys Thr Xaa Asn Pro Val Ala Thr Glu Ser
            565             570             575

Tyr Gly Gln Val Ala Thr Asn His Gln Xaa Ala Gln Ala Gln Ala Gln
            580             585             590

Thr Gly Trp Val Gln Asn Gln Gly Ile Leu Pro Gly Xaa Val Trp Gln
            595             600             605

Asp Arg Asp Val Tyr Leu Gln Gly Pro Ile Xaa Ala Lys Ile Pro His
        610             615             620

Thr Asp Gly Xaa Phe His Pro Ser Pro Leu Met Gly Gly Phe Gly Xaa
625             630             635             640

Lys His Pro Pro Gln Ile Leu Ile Lys Xaa Thr Pro Val Pro Ala
            645             650             655

Asp Pro Pro Thr Ala Phe Xaa Lys Asp Xaa Leu Asn Ser Phe Ile Thr
            660             665             670

Gln Tyr Ser Thr Gly Gln Val Ser Val Glu Ile Glu Trp Glu Leu Gln
        675             680             685

Xaa Glu Asn Ser Xaa Arg Xaa Asn Pro Glu Ile Gln Tyr Thr Ser Asn
        690             695             700

Tyr Tyr Lys Ser Xaa Asn Val Glu Phe Ala Val Asn Thr Glu Gly Val
705             710             715             720

Tyr Ser Glu Pro Arg Pro Ile Gly Thr Arg Tyr Leu Thr Arg Xaa Leu
            725             730             735
```